US009517250B2

(12) United States Patent
Srivastava et al.

(10) Patent No.: US 9,517,250 B2
(45) Date of Patent: Dec. 13, 2016

(54) METHODS FOR GENERATING CARDIOMYOCYTES

(75) Inventors: Deepak Srivastava, San Francisco, CA (US); Masaki Ieda, Tokyo (JP)

(73) Assignee: The J. David Gladstone Institutes, San Francisco, CA (US)

( * ) Notice: Subject to any disclaimer, the term of this patent is extended or adjusted under 35 U.S.C. 154(b) by 0 days.

(21) Appl. No.: 13/642,391

(22) PCT Filed: Apr. 26, 2011

(86) PCT No.: PCT/US2011/033938
§ 371 (c)(1),
(2), (4) Date: Apr. 15, 2013

(87) PCT Pub. No.: WO2011/139688
PCT Pub. Date: Nov. 10, 2011

(65) Prior Publication Data
US 2013/0216503 A1    Aug. 22, 2013

Related U.S. Application Data

(60) Provisional application No. 61/328,988, filed on Apr. 28, 2010, provisional application No. 61/364,295, filed on Jul. 14, 2010.

(51) Int. Cl.
| | | |
|---|---|---|
| *C12N 5/00* | (2006.01) | |
| *C12N 5/06* | (2006.01) | |
| *C12N 15/63* | (2006.01) | |
| *A01N 63/00* | (2006.01) | |
| *A61K 38/02* | (2006.01) | |
| *C12N 5/077* | (2010.01) | |
| *A61K 35/34* | (2015.01) | |
| *A61K 38/17* | (2006.01) | |
| *C12N 15/85* | (2006.01) | |
| *A01K 67/00* | (2006.01) | |

(52) U.S. Cl.
CPC .............. *A61K 38/02* (2013.01); *A61K 35/34* (2013.01); *A61K 38/1709* (2013.01); *C12N 5/0657* (2013.01); *C12N 15/85* (2013.01); *C12N 2501/60* (2013.01); *C12N 2506/1307* (2013.01); *C12N 2510/00* (2013.01); *C12N 2740/13043* (2013.01)

(58) Field of Classification Search
CPC ............. C12N 5/0657; C12N 2501/60; C12N 2506/1307; C12N 2510/00; C12N 2740/13043; A61K 35/34; A61K 38/1709
USPC ...................... 435/377, 352, 455; 424/93.21
See application file for complete search history.

(56) References Cited

U.S. PATENT DOCUMENTS

| | | | |
|---|---|---|---|
| 7,682,828 B2 | 3/2010 | Jaenisch et al. | |
| 2005/0043260 A1* | 2/2005 | Schneider et al. | 514/44 |
| 2009/0081170 A1 | 3/2009 | Riley et al. | |
| 2009/0163994 A1 | 6/2009 | Quigley et al. | |
| 2009/0208245 A1 | 8/2009 | Okano et al. | |
| 2009/0253203 A1 | 10/2009 | Eilertsen et al. | |
| 2009/0275032 A1 | 11/2009 | Eilertsen et al. | |
| 2010/0075421 A1 | 3/2010 | Yamanaka et al. | |
| 2010/0150879 A1* | 6/2010 | Wary | 424/93.21 |
| 2010/0330044 A1 | 12/2010 | Blanpain et al. | |
| 2011/0165570 A1 | 7/2011 | Feng et al. | |
| 2014/0235526 A1 | 8/2014 | Srivastava et al. | |
| 2014/0301991 A1 | 10/2014 | Srivastava et al. | |

FOREIGN PATENT DOCUMENTS

| | | | |
|---|---|---|---|
| WO | WO 2008/088882 | * | 7/2008 |
| WO | WO 2008/151387 | | 12/2008 |
| WO | 2009152484 | | 12/2009 |
| WO | 2009152485 | | 12/2009 |
| WO | 2010124143 | | 10/2010 |
| WO | 2011109695 | | 9/2011 |
| WO | 2011139688 | | 11/2011 |
| WO | 2011163531 | | 12/2011 |

OTHER PUBLICATIONS

Choi; et al. "MyoD converts primary dermal fibroblasts, chondroblasts, smooth muscle, and retinal pigmented epithelial cells into striated mononucleated myoblasts and multinucleated myotubes", Proc Natl Acad Sci U S A (Oct. 1990), 87(20): 7988-7992.
Min; et al. "Significant improvement of heart function by cotransplantation of human mesenchymal stem cells and fetal cardiomyocytes in postinfarcted pigs", Ann Thorac Surg (Nov. 2002), Abstract.
Potthoff; et al. "MEF2; a ceniral regulator of diverse developmental programs", Development (Dec. 2007), 134(23):4131-4140.
Qian; et al. "In vivo reprogramming of murine cardiac fibroblasts into induced cardiomyocytes", Nature (May 2012), 485(7400):593-598.
Takeuchi; et al. Directed transdifferentiation of mouse mesoderm to heart tissue by defined factors, Nature (Jun. 2009), 459(7247):708-711.
Teng; et al. "A Role for Tbx2 in the Regulation of the alpha2(1) Collagen Gene in Human Fibroblasts", J Cell Biochem (Oct. 2007), 102(3):618-625.
Zhou; et al. "Generation of induced pluripotent stem cells using recombinant proteins" Cell Stem Cell (May 2009), 4(5):381-384.
Ieda, et al., Direct Reprogramming of Fibroblasts into Functional Cardiomyocytes by Defined Factors, Cell, 2010, 142(3):375-386.
Yamada et al., "Single-Cell-Derived Mesenchymal Stem Cells Overexpressing Csx/Nkx2.5 and GATA4 Undergo the Stochastic Cardiomyogenic Fate and Behave like Transient Amplifying Cells", Experimental Cell Research, Academic Press, US, 2007, 313(4):698-706.

(Continued)

*Primary Examiner* — Quang Nguyen
(74) *Attorney, Agent, or Firm* — Michael B. Rubin; Bozicevic, Field & Francis LLP

(57) ABSTRACT

The present disclosure provides method of generating cardiomyocytes from post-natal fibroblasts. The present disclosure further provides cells and compositions for use in generating cardiomyocytes.

10 Claims, 18 Drawing Sheets

(56) References Cited

OTHER PUBLICATIONS

Shiojima, Ichiro and Komuro Issei; "The heart development and regeneration"; (2005), *The Medical Frontline 60*, 8, pp. 1781-1786.
Vierbuchen, et al.; "Direct conversion of fibroblasts to functional neurons by defined factors"; *Nature*, vol. 463, pp. 1035-1041 (Feb. 25, 2010).
Xu, et al.; "GATA-4 plays an important role in bone marrow stem cell transdifferentiation into myocytes"; *Circulation*; vol. 110, No. 17, Supplement III, III-280, pp. 1339 (Oct. 26, 2004).
Zeng, Junyi; et al, Co-culture with cardiomycytes induces mesenchymal stem cells to differentiate into cardiomycyte-like cells and express heart development-associated genes; Cell Research (2008) 18:s62; 1 page.
Alaynick, "Phenotypic characterization of estrogen-related receptor gamma mutant mice" Jan. 1, 2006, pp. 123, para 3, Fig 4.9, 168 pages total [retrieved from http://escholarship.org/uc/item/6w80b6st on Oct. 7, 2012].
Alaynick et al; "ERRγ Directs and Maintains the Transition to Oxidative Metabolism in the Postnatal Heart"; Cell Metabolism 6: (2007); pp. 13-24.
Feng et al; "Reprogramming of fibroblasts into induced pluripotent stem cells with orphan nuclear receptor Esrrb"; Nature Cell Biol. 11; (2009); pp. 197-203.
Fu, Ji-Dong et al; "Direct Reprogramming of Human Fibroblasts toward a Cardiomyocyte-like State"; Stem Cell Reports, vol. 1, No. 3; Sep. 1, 2013; pp. 235-247, ISSN: 2213-6711, DOI: 10.1016/j.stemcr.2013.07.005.
Takahashi et al.; "Induction of pluripotent stem cells from mouse embryonic and adult fibroblast cultures by defined factors", Cell, 126; (2006); pp. 663-676.

\* cited by examiner

METHODS FOR GENERATING CARDIOMYOCYTES

CROSS-REFERENCE

This application claims the benefit of U.S. Provisional Patent Application No. 61/328,988, filed Apr. 28, 2010, and of U.S. Provisional Patent Application No. 61/364,295, filed Jul. 14, 2010, which applications are incorporated herein by reference in their entirety.

BACKGROUND

Heart disease is a leading cause of adult and childhood mortality in the western world. The underlying pathology is typically loss of cardiomyocytes that leads to heart failure, or improper development of cardiomyocytes during embryogenesis that leads to congenital heart malformations. Because cardiomyocytes have little or no regenerative capacity, current therapeutic approaches are limited. Embryonic stem cells possess clear cardiogenic potential, but efficiency of cardiac differentiation, risk of tumor formation, and issues of cellular rejection must be overcome.

There is a need in the art for methods of generating cardiomyocytes.

LITERATURE

U.S. Patent Publication No. 2009/0208465; U.S. Pat. No. 7,682,828; U.S. Patent Publication No. 2010/0075421; WO 2009/152484; WO 2009/152485; Takahashi and Yamanaka (2006) *Cell* 126:663.

SUMMARY OF THE INVENTION

The present disclosure provides method of generating cardiomyocytes from post-natal fibroblasts. The present disclosure further provides cells and compositions for use in generating cardiomyocytes.

DEFINITIONS

Figure 1:
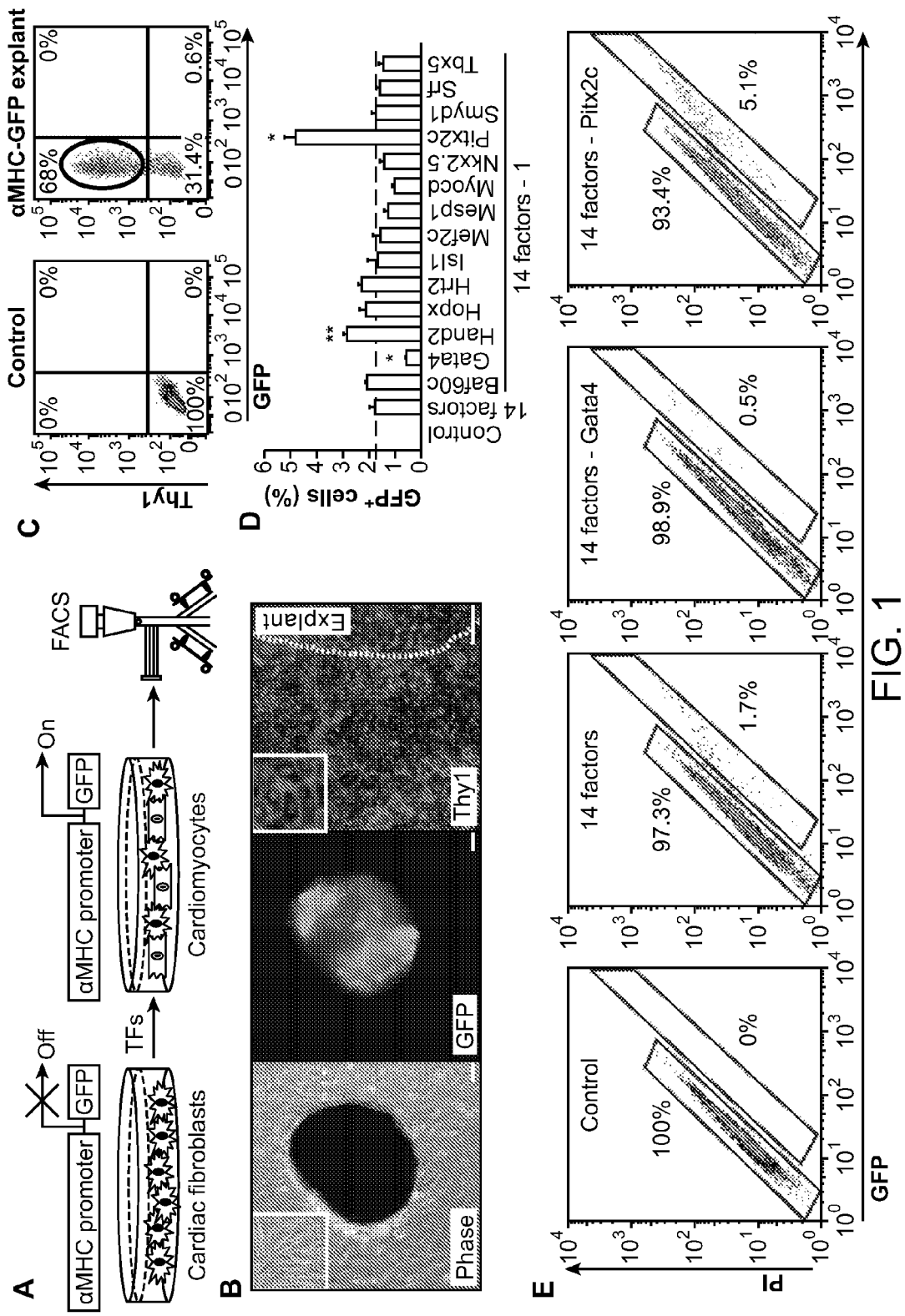
FIGS. 1A-I depict the results of screening for cardiomyocyte-inducing factors.
Figure 1:
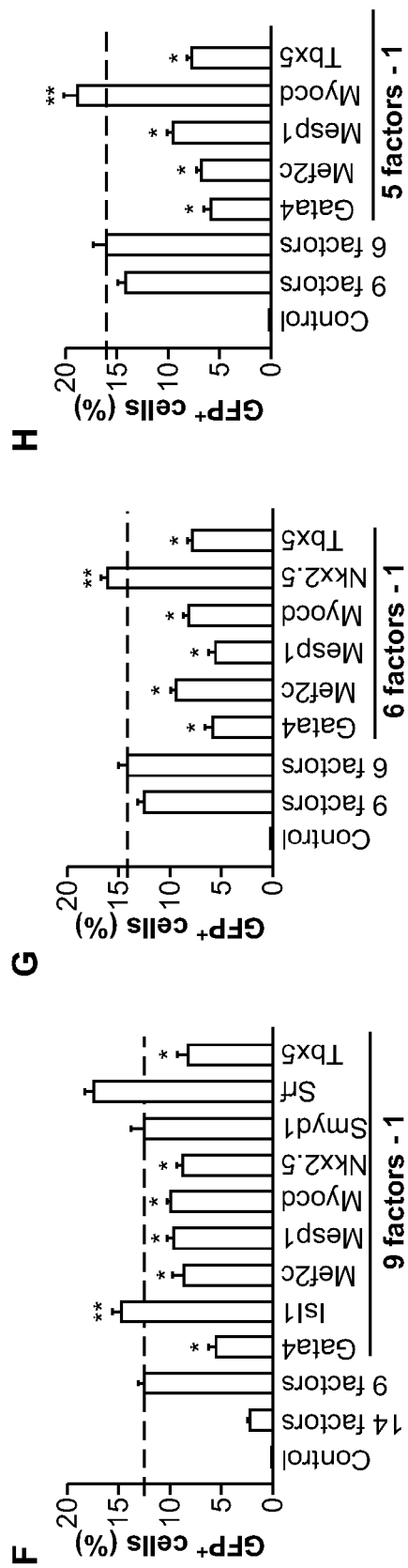
Figure 1:
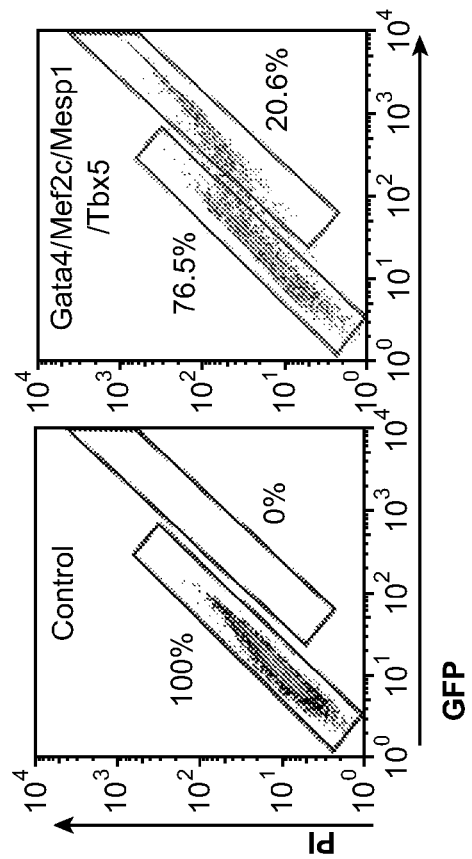

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

The terms "nucleic acid" and "polynucleotide" are used interchangeably herein and refer to a polymeric form of nucleotides of any length, either deoxyribonucleotides or ribonucleotides, or analogs thereof. Non-limiting examples of polynucleotides include linear and circular nucleic acids, messenger RNA (mRNA), cDNA, recombinant polynucleotides, vectors, probes, and primers.

The term "operably linked" refers to functional linkage between molecules to provide a desired function. For example, "operably linked" in the context of nucleic acids refers to a functional linkage between nucleic acids to provide a desired function such as transcription, translation, and the like, e.g., a functional linkage between a nucleic acid expression control sequence (such as a promoter, signal sequence, or array of transcription factor binding sites) and a second polynucleotide, wherein the expression control sequence affects transcription and/or translation of the second polynucleotide.

As used herein the term "isolated" with reference to a cell, refers to a cell that is in an environment different from that in which the cell naturally occurs, e.g., where the cell naturally occurs in a multicellular organism, and the cell is removed from the multicellular organism, the cell is "isolated." An isolated genetically modified host cell can be present in a mixed population of genetically modified host cells, or in a mixed population comprising genetically modified host cells and host cells that are not genetically modified. For example, an isolated genetically modified host cell can be present in a mixed population of genetically modified host cells in vitro, or in a mixed in vitro population comprising genetically modified host cells and host cells that are not genetically modified.

A "host cell," as used herein, denotes an in vivo or in vitro cell (e.g., a eukaryotic cell cultured as a unicellular entity), which eukaryotic cell can be, or has been, used as recipients for a nucleic acid (e.g., an exogenous nucleic acid) or an exogenous polypeptide(s), and include the progeny of the original cell which has been modified by introduction of the exogenous polypeptide(s) or genetically modified by the nucleic acid. It is understood that the progeny of a single cell may not necessarily be completely identical in morphology or in genomic or total DNA complement as the original parent, due to natural, accidental, or deliberate mutation.

The term "genetic modification" and refers to a permanent or transient genetic change induced in a cell following introduction of new nucleic acid (i.e., nucleic acid exogenous to the cell). Genetic change ("modification") can be accomplished by incorporation of the new nucleic acid into the genome of the host cell, or by transient or stable maintenance of the new nucleic acid as an extrachromosomal element. Where the cell is a eukaryotic cell, a permanent genetic change can be achieved by introduction of the nucleic acid into the genome of the cell. Suitable methods of genetic modification include viral infection, transfection, conjugation, protoplast fusion, electroporation, particle gun technology, calcium phosphate precipitation, direct microinjection, and the like.

As used herein, the term "exogenous nucleic acid" refers to a nucleic acid that is not normally or naturally found in and/or produced by a cell in nature, and/or that is introduced into the cell (e.g., by electroporation, transfection, infection, lipofection, or any other means of introducing a nucleic acid into a cell).

The terms "individual," "subject," "host," and "patient," used interchangeably herein, refer to a mammal, including, but not limited to, murines (rats, mice), non-human primates, humans, canines, felines, ungulates (e.g., equines, bovines, ovines, porcines, caprines), etc. In some embodiments, the individual is a human. In some embodiments, the individual is a murine.

A "therapeutically effective amount" or "efficacious amount" means the amount of a compound or a number of cells that, when administered to a mammal or other subject for treating a disease, is sufficient to effect such treatment for the disease. The "therapeutically effective amount" will vary depending on the compound or the cell, the disease and its severity and the age, weight, etc., of the subject to be treated.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an induced cardiomyocyte" includes a plurality of such cardiomyocytes and reference to "the post-natal fibroblast" includes reference to one or more post-natal fibroblasts and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides method of generating cardiomyocytes from post-natal fibroblasts. The present disclosure further provides cells and compositions for use in generating cardiomyocytes.

Methods of Generating Cardiomyocytes

The present disclosure provides method of generating cardiomyocytes from post-natal fibroblasts. The methods generally involve introducing into a post-natal fibroblast one or more reprogramming factors. In some cases, the polypeptides themselves are introduced into a post-natal fibroblast. In other cases, the post-natal fibroblast is genetically modified with one or more nucleic acids comprising nucleotide sequences encoding the re-programming factors.

In some embodiments, the methods involve introducing into a post-natal fibroblast one or more reprogramming factors selected from Gata4, Mef2c, Tbx5, Mesp1, Nkx2-5, Isl-1, Myocd, Smyd1, and Srf polypeptides. In some cases, the polypeptides themselves are introduced into a post-natal fibroblast. In other cases, the post-natal fibroblast is genetically modified with one or more nucleic acids comprising nucleotide sequences encoding Gata4, Mef2c, and Tbx5 polypeptides.

In some embodiments, the methods involve introducing into a post-natal fibroblast three (and only three) reprogramming factors: Gata4, Mef2c, and Tbx5 polypeptides. In some cases, the polypeptides themselves are introduced into a post-natal fibroblast. In other cases, the post-natal fibroblast is genetically modified with one or more nucleic acids comprising nucleotide sequences encoding Gata4, Mef2c, and Tbx5 polypeptides.

Cardiomyocytes generated directly from post-natal fibroblasts using a subject method are referred to herein as "induced cardiomyocytes." Polypeptides such as Gata4, Mef2c, Tbx5, Mesp1, Nkx2-5, Isl-1, Myocd, Smyd1, and Srf are also referred to collectively herein as "reprogramming factors," or "reprogramming transcription factors." A post-natal fibroblast into one or more reprogramming factors are introduced is reprogrammed directly into a differentiated cardiomyocyte, without first becoming a stem cell or a progenitor cell.

As noted above, in some cases, a subject method of generating a cardiomyocyte involves genetically modifying a post-natal fibroblast with one or more nucleic acids comprising nucleotide sequences encoding one or more of Gata4, Mef2c, Tbx5, Mesp1, Nkx2-5, Isl-1, Myocd, Smyd1, and Srf polypeptides. The reprogramming factors encoded by the nucleotide sequences are produced in the post-natal fibroblast and, as a result of the production of the one or more reprogramming factors, the genetically modified fibroblast is reprogrammed directly into a differentiated cardiomyocyte. The genetically modified fibroblast is reprogrammed directly into a differentiated cardiomyocyte, without first becoming a stem cell or progenitor cell.

As noted above, in some cases, a subject method of generating a cardiomyocyte involves genetically modifying a post-natal fibroblast with one or more nucleic acids comprising nucleotide sequences encoding Gata4, Mef2c, and Tbx5 polypeptides. The Gata4, Mef2c, and Tbx5 polypeptides are produced in the post-natal fibroblast and, as a result of the production of the Gata4, Mef2c, and Tbx5 polypeptides, the genetically modified fibroblast is reprogrammed directly into a differentiated cardiomyocyte. The genetically modified fibroblast is reprogrammed directly into a differentiated cardiomyocyte, without first becoming a stem cell or progenitor cell.

In some cases, a post-natal fibroblast is modified by introducing one or more of Gata4, Mef2c, Tbx5, Mesp1, Nkx2-5, Isl-1, Myocd, Smyd1, and Srf polypeptides themselves into a host post-natal fibroblast. A post-natal fibroblast into which one or more of Gata4, Mef2c, Tbx5, Mesp1, Nkx2-5, Isl-1, Myocd, Smyd1, and Srf polypeptides has been introduced (either by introducing the polypeptides themselves or by introducing one or more nucleic acids comprising nucleotide sequence encoding the one or more polypeptides) is referred to as a "modified fibroblast" or a "modified post-natal fibroblast." A post-natal fibroblast into which one or more nucleic acids comprising nucleotide sequence encoding one or more of Gata4, Mef2c, Tbx5, Mesp1, Nkx2-5, Isl-1, Myocd, Smyd1, and Srf polypeptides has been introduced is referred to as a "genetically modified fibroblast" or a "genetically modified post-natal fibroblast."

In some cases, a post-natal fibroblast is modified by introducing Gata4, Mef2c, and Tbx5 polypeptides themselves into a host post-natal fibroblast. A post-natal fibroblast into which Gata4, Mef2c, and Tbx5 polypeptides have been introduced (either by introducing the polypeptides themselves or by introducing one or more nucleic acids comprising nucleotide sequence encoding Gata4, Mef2c, and Tbx5 polypeptides) is referred to as a "modified fibroblast" or a "modified post-natal fibroblast." A post-natal fibroblast into which one or more nucleic acids comprising nucleotide sequence encoding Gata4, Mef2c, and Tbx5 polypeptides have been introduced is referred to as a "genetically modified fibroblast" or a "genetically modified post-natal fibroblast."

As noted above, using a subject method, one or more reprogramming factors (e.g., one or more of Gata4, Mef2c, Tbx5, Mesp1, Nkx2-5, Isl-1, Myocd, Smyd1, and Srf; or a subset of reprogramming factors comprising Gata4, Mef2c, and Tbx5 polypeptides) are introduced into a post-natal fibroblast (e.g., the reprogramming factor polypeptide(s) themselves are introduced into a post-natal fibroblast; or a post-natal fibroblast is genetically modified with one or more nucleic acids comprising nucleotide sequences encoding reprogramming factor polypeptide(s)), and as a result, the modified fibroblast is reprogrammed directly into a differentiated cardiomyocyte, without first becoming a stem cell or progenitor cell. Thus, for example, the modified or genetically modified fibroblast does not produce detectable levels of an early cardiac progenitor marker. For example, the modified or genetically modified fibroblast does not produce detectable levels of Isl1, an early cardiac progenitor marker that is transiently expressed before cardiac differentiation.

In some embodiments, a post-natal fibroblast is genetically modified in vitro with one or more nucleic acids comprising nucleotide sequences encoding one or more reprogramming factors (e.g., one or more of Gata4, Mef2c, Tbx5, Mesp1, Nkx2-5, Isl-1, Myocd, Smyd1, and Srf; or a subset of reprogramming factors comprising Gata4, Mef2c, and Tbx5 polypeptides); or one or more reprogramming factor polypeptides themselves (e.g., one or more of Gata4, Mef2c, Tbx5, Mesp1, Nkx2-5, Isl-1, Myocd, Smyd1, and Srf; or a subset of reprogramming factors comprising Gata4, Mef2c, and Tbx5 polypeptides) are introduced in vitro into a post-natal fibroblast; where the modified or genetically modified fibroblasts become cardiomyocytes in vitro. Once the fibroblasts are reprogrammed directly into cardiomyocytes in vitro, generating induced cardiomyocytes, the induced cardiomyocytes can be introduced into an individual.

For example, in some embodiments, a subject method involves: a) genetically modifying a post-natal fibroblast in vitro with one or more nucleic acids comprising nucleotide sequences encoding one or more of Gata4, Mef2c, Tbx5, Mesp1, Nkx2-5, Isl-1, Myocd, Smyd1, and Srf polypeptides, where production of the encoded polypeptides in the genetically modified fibroblasts results in reprogramming of the genetically modified fibroblast directly into a cardiomyocyte in vitro, thereby generating an induced cardiomyocyte; and b) introducing the induced cardiomyocyte(s) into an individual. In other embodiments, a subject method involves: a) introducing one or more of Gata4, Mef2c, Tbx5, Mesp1, Nkx2-5, Isl-1, Myocd, Smyd1, and Srf polypeptides into a post-natal fibroblast in vitro, generating a modified fibroblast, where the modified fibroblast, as a result of introduction of the one or more of Gata4, Mef2c, Tbx5, Mesp1, Nkx2-5, Isl-1, Myocd, Smyd1, and Srf polypeptides, is reprogrammed directly into a cardiomyocyte in vitro, thereby generating an induced cardiomyocyte; and b) introducing the induced cardiomyocyte into an individual.

As another example, in some embodiments, a subject method involves: a) genetically modifying a post-natal fibroblast in vitro with one or more nucleic acids comprising nucleotide sequences encoding Gata4, Mef2c, and Tbx5 polypeptides, where production of the Gata4, Mef2c, and Tbx5 polypeptides in the genetically modified fibroblasts results in reprogramming of the genetically modified fibroblast directly into a cardiomyocyte in vitro, thereby generating an induced cardiomyocyte; and b) introducing the induced cardiomyocyte(s) into an individual. In other embodiments, a subject method involves: a) introducing Gata4, Mef2c, and Tbx5 polypeptides into a post-natal fibroblast in vitro, generating a modified fibroblast, where the modified fibroblast, as a result of introduction of the Gata4, Mef2c, and Tbx5 polypeptides, is reprogrammed directly into a cardiomyocyte in vitro, thereby generating an induced cardiomyocyte; and b) introducing the induced cardiomyocyte into an individual.

In other embodiments, a post-natal fibroblast is genetically modified in vitro with one or more nucleic acids comprising nucleotide sequences encoding one or more reprogramming factors (e.g., one or more of Gata4, Mef2c, Tbx5, Mesp1, Nkx2-5, Isl-1, Myocd, Smyd1, and Srf; or a subset of reprogramming factors comprising Gata4, Mef2c, and Tbx5 polypeptides); or one or more reprogramming factor polypeptides themselves (e.g., one or more of Gata4, Mef2c, Tbx5, Mesp1, Nkx2-5, Isl-1, Myocd, Smyd1, and Srf; or a subset of reprogramming factors comprising Gata4, Mef2c, and Tbx5 polypeptides) are introduced in vitro into a post-natal fibroblast; and the modified or genetically modified fibroblasts are introduced into an individual, where the modified or genetically modified fibroblasts are reprogrammed directly into cardiomyocytes in vivo.

Thus, for example, in some embodiments, a subject method involves: a) genetically modifying a post-natal fibroblast in vitro with one or more nucleic acids comprising nucleotide sequences encoding one or more of Gata4, Mef2c, Tbx5, Mesp1, Nkx2-5, Isl-1, Myocd, Smyd1, and Srf; polypeptides; and b) introducing the genetically modified fibroblasts into an individual, where production of the one or more of Gata4, Mef2c, Tbx5, Mesp1, Nkx2-5, Isl-1, Myocd, Smyd1, and Srf; polypeptides in the genetically modified fibroblasts results in reprogramming of the genetically modified fibroblast directly into a cardiomyocyte in vivo, thereby generating an induced cardiomyocyte in the individual. In other embodiments, a subject method involves: a) introducing one or more of Gata4, Mef2c, Tbx5, Mesp1, Nkx2-5, Isl-1, Myocd, Smyd1, and Srf; polypeptides into a post-natal fibroblast in vitro, generating a modified fibroblast; and b) introducing the modified fibroblast(s) into an individual, where the modified fibroblasts, as a result of introduction of the one or more of Gata4, Mef2c, Tbx5, Mesp1, Nkx2-5, Isl-1, Myocd, Smyd1, and Srf; polypeptides, are reprogrammed directly into a cardiomyocyte in vivo, thereby generating an induced cardiomyocyte in the individual.

As another example, in some embodiments, a subject method involves: a) genetically modifying a post-natal fibroblast in vitro with one or more nucleic acids comprising nucleotide sequences encoding Gata4, Mef2c, and Tbx5 polypeptides; and b) introducing the genetically modified fibroblasts into an individual, where production of the Gata4, Mef2c, and Tbx5 polypeptides in the genetically modified fibroblasts results in reprogramming of the genetically modified fibroblast directly into a cardiomyocyte in vivo, thereby generating an induced cardiomyocyte in the individual. In other embodiments, a subject method involves: a) introducing Gata4, Mef2c, and Tbx5 polypeptides into a post-natal fibroblast in vitro, generating a modified fibroblast; and b) introducing the modified fibroblast(s) into an individual, where the modified fibroblasts, as a result of introduction of the Gata4, Mef2c, and Tbx5 polypeptides, are reprogrammed directly into a cardiomyocyte in vivo, thereby generating an induced cardiomyocyte in the individual.

In other embodiments, a post-natal fibroblast is genetically modified in vivo with one or more nucleic acids comprising nucleotide sequences encoding one or more reprogramming factors (e.g., one or more of Gata4, Mef2c, Tbx5, Mesp1, Nkx2-5, Isl-1, Myocd, Smyd1, and Srf; or a subset of reprogramming factors comprising Gata4, Mef2c, and Tbx5 polypeptides), or one or more reprogramming factor polypeptides themselves (e.g., one or more of Gata4, Mef2c, Tbx5, Mesp1, Nkx2-5, Isl-1, Myocd, Smyd1, and Srf; or a subset of reprogramming factors comprising Gata4, Mef2c, and Tbx5 polypeptides) are introduced in vivo into a post-natal fibroblast; and the modified or genetically modified fibroblasts are reprogrammed directly into cardiomyocytes in vivo.

A post-natal fibroblast that is genetically modified with one or more nucleic acids comprising nucleotide sequences encoding one or more reprogramming factors (e.g., one or more of Gata4, Mef2c, Tbx5, Mesp1, Nkx2-5, Isl-1, Myocd, Smyd1, and Srf; or a subset of reprogramming factors comprising Gata4, Mef2c, and Tbx5 polypeptides), or that is modified with one or more reprogramming factor polypeptides themselves (e.g., one or more of Gata4, Mef2c, Tbx5, Mesp1, Nkx2-5, Isl-1, Myocd, Smyd1, and Srf; or a subset of reprogramming factors comprising Gata4, Mef2c, and Tbx5 polypeptides), is reprogrammed into a differentiated cardiomyocyte in a time period of from about 5 days to about 7 days, or from about 7 days to about 14 days. For example, where a population of post-natal fibroblasts is genetically modified or modified by introducing reprogramming factor polypeptides, as described above, at least about 10%, at least about 15%, at least about 20%, at least about 25%, at least about 30%, at least about 50%, at least about 75%, or more than 75% (e.g., at least about 80%, at least about 85%, at least about 90%, at least about 95%, at least about 98%, or more than 98%), of the population is reprogrammed into differentiated cardiomyocytes (induced cardiomyocytes) in a time period of from about 5 days to about 7 days, from about 7 days to about 14 days, or from about 2 weeks to about 4 weeks.

In some embodiments, where a population of post-natal fibroblasts is genetically modified with one or more nucleic acids comprising nucleotide sequences encoding one or more reprogramming factors (e.g., one or more of Gata4, Mef2c, Tbx5, Mesp1, Nkx2-5, Isl-1, Myocd, Smyd1, and Srf; or a subset of reprogramming factors comprising Gata4, Mef2c, and Tbx5 polypeptides), or where a population of post-natal fibroblasts is modified by introducing one or more reprogramming factors themselves (e.g., one or more of Gata4, Mef2c, Tbx5, Mesp1, Nkx2-5, Isl-1, Myocd, Smyd1, and Srf; or a subset of reprogramming factors comprising Gata4, Mef2c, and Tbx5 polypeptides) into the fibroblasts, at least about 10%, at least about 15%, at least about 20%, at least about 25%, at least about 30%, at least about 50%, at least about 75%, or more than 75% (e.g., at least about 80%, at least about 85%, at least about 90%, at least about 95%, at least about 98%, or more than 98%), of the population is cTnT$^+$ (i.e., expresses cardiac troponin T) in a time period of from about 5 days to about 7 days, from about 7 days to about 14 days, or from about 2 weeks to about 4 weeks.

In some embodiments, a subject method of generating induced cardiomyocytes involves genetically modifying a host post-natal fibroblast (or a population of host post-natal fibroblasts) with one or more nucleic acids comprising nucleotide sequences encoding one or more reprogramming factors (e.g., one or more of Gata4, Mef2c, Tbx5, Mesp1, Nkx2-5, Isl-1, Myocd, Smyd1, and Srf; or a subset of reprogramming factors comprising Gata4, Mef2c, and Tbx5 polypeptides); generating a population of genetically modified post-natal fibroblasts, and, after a time (e.g., 5 days to 7 days, 1 week to 2 weeks, or 2 weeks to 4 weeks), sorting the population of genetically modified post-natal fibroblasts to enrich for cardiomyocytes. The population of genetically modified post-natal fibroblasts can be sorted for expression of a fibroblast-specific marker, to remove any remaining fibroblasts. The population of genetically modified post-natal fibroblasts can be sorted for expression of a cardiomyocyte-specific marker.

In some embodiments, a subject method of generating induced cardiomyocytes involves modifying a host post-natal fibroblast (or a population of host post-natal fibroblasts) by introducing one or more reprogramming factor polypeptides (e.g., one or more of Gata4, Mef2c, Tbx5, Mesp1, Nkx2-5, Isl-1, Myocd, Smyd1, and Srf; or a subset of reprogramming factors comprising Gata4, Mef2c, and Tbx5 polypeptides) into host post-natal fibroblasts; generating a population of modified post-natal fibroblasts, and, after a time (e.g., 5 days to 7 days, 1 week to 2 weeks, or 2 weeks to 4 weeks), sorting the population of modified post-natal fibroblasts to enrich for cardiomyocytes. The population of modified post-natal fibroblasts can be sorted for expression of a fibroblast-specific marker, to remove any remaining fibroblasts. The population of modified post-natal fibroblasts can be sorted for expression of a cardiomyocyte-specific marker.

In some embodiments, a host post-natal fibroblast is genetically modified with one or more nucleic acids comprising nucleotide sequences encoding one or more reprogramming factors (e.g., one or more of Gata4, Mef2c, Tbx5, Mesp1, Nkx2-5, Isl-1, Myocd, Smyd1, and Srf; or a subset of reprogramming factors comprising Gata4, Mef2c, and Tbx5 polypeptides), or is modified by introducing one or more reprogramming factor polypeptides (e.g., one or more of Gata4, Mef2c, Tbx5, Mesp1, Nkx2-5, Isl-1, Myocd, Smyd1, and Srf; or a subset of reprogramming factors comprising Gata4, Mef2c, and Tbx5 polypeptides) into host post-natal fibroblasts); and is also genetically modified with a nucleic acid comprising a nucleotide sequence encoding a detectable marker (e.g., a polypeptide that directly produces a detectable signal; an enzyme that produces a detectable signal upon acting on a substrate), where the detectable marker-encoding nucleotide sequence is operably linked to a cardiomyocyte-specific promoter. Suitable polypeptides that provide a direct detectable signal include a fluorescent protein such as a green fluorescent protein, a yellow fluorescent protein, a blue fluorescent protein, etc. Suitable enzymes that produce a detectable signal upon acting on a substrate include, e.g., luciferase (acting on the substrate luciferin), alkaline phosphatase, and the like. Cardiomyocyte-specific promoters include, e.g., an α-myosin heavy chain promoter; a cTnT promoter; and the like. Expression of the detectable marker can provide for detection of an induced cardiomyocyte; and can provide a means of sorting for induced cardiomyocytes.

The post-natal fibroblasts that serve as host cells for modification or genetic modification, as described above, can be from any of a variety of sources. Mammalian fibroblasts, e.g., human fibroblasts, murine (e.g., mouse) fibroblasts, rat fibroblasts, porcine fibroblasts, etc., can be used. In some embodiments, the fibroblasts are human fibroblasts. In other embodiments, the fibroblasts are mouse fibroblasts. In other embodiments, the fibroblasts are rat fibroblasts. Thus, a "post-natal fibroblast" refers to a fibroblast obtained from a post-natal mammal, or the progeny of a fibroblast obtained from a post-natal mammal.

The post-natal fibroblasts can be from any of a variety of tissue sources. For example, cardiac fibroblasts, foreskin fibroblasts, dermal fibroblasts, lung fibroblasts, etc.

The fibroblasts can be obtained from a living individual. The fibroblasts can be obtained from tissue taken from a living individual. The fibroblasts can be obtained from a recently deceased individual who is considered a suitable organ donor. In some embodiments, the individual is screened for various genetic disorders, viral infections, etc., to determine whether the individual is a suitable source of fibroblasts, where individuals may be excluded on the basis of one or more of a genetic disorder, a viral infection, etc.

Suitable fibroblasts express markers characteristic of fibroblasts, where such markers include, e.g., vimentin, prolyl-4-hydroxylase (an intracellular enzyme involved in collagen synthesis), fibroblast-specific protein-1 (see, e.g., Strutz et al. (1995) J. Cell Biol. 130:393), fibroblast surface antigen, and collagen type 1. In some embodiments, the fibroblasts used as host cells are cardiac fibroblasts, where cardiac fibroblasts can be characterized as Thy1$^+$, vimentin$^+$, and are also negative for c-kit or equivalent of c-kit.

In general, a fibroblast that is suitable for use as a host cell for modification or genetic modification in accordance with a subject method is non-transformed (e.g., exhibits normal cell proliferation), and is otherwise normal.

Where the host cells for modification or genetic modification is a population of fibroblasts, the population of fibroblasts are isolated, e.g., the population of fibroblasts is composed of at least about 75% fibroblasts, at least about 80% fibroblasts, at least about 85% fibroblasts, at least about 90% fibroblasts, at least about 95% fibroblasts, at least about 98% fibroblasts, at least about 99% fibroblasts, or greater than 99% fibroblasts.

Post-natal fibroblasts can be derived from tissue of a non-embryonic subject, a neonatal infant, a child, or an adult. Post-natal fibroblasts can be derived from neonatal or post-natal tissue collected from a subject within the period from birth, including cesarean birth, to death. For example, the post-natal fibroblasts used to generate induced cardiomyocytes can be from a subject who is greater than about 10 minutes old, greater than about 1 hour old, greater than about 1 day old, greater than about 1 month old, greater than about 2 months old, greater than about 6 months old, greater than about 1 year old, greater than about 2 years old, greater than about 5 years old, greater than about 10 years old, greater than about 15 years old, greater than about 18 years old, greater than about 25 years old, greater than about 35 years old, >45 years old, >55 years old, >65 years old, >80 years old, <80 years old, <70 years old, <60 years old, <50 years old, <40 years old, <30 years old, <20 years old or <10 years old.

Methods of isolating fibroblasts from tissues are known in the art, and any known method can be used. As a non-limiting example, cardiac fibroblasts can be obtained using the method of Ieda et al. (2009) Dev. Cell 16:233, or as described in Example 1. Foreskin fibroblasts can be obtained from foreskin tissue (i.e., the skin tissue covering the glans penis; preputium penis) of a male individual, e.g., from an 8-14 day old male individual. The fibroblasts can be obtained by mincing the foreskin tissue, then dissociating the tissue to single cells. Foreskin cell clamps can be dissociated by any means known in the art including physical de-clamping or enzymatic digestion using, for example trypsin.

As noted above, a post-natal fibroblast is genetically modified with one or more nucleic acids comprising nucleotide sequences encoding one or more reprogramming factors (e.g., one or more of Gata4, Mef2c, Tbx5, Mesp1, Nkx2-5, Isl-1, Myocd, Smyd1, and Srf; or a subset of reprogramming factors comprising Gata4, Mef2c, and Tbx5 polypeptides), or is modified by introducing one or more reprogramming factor polypeptides themselves (e.g., one or more of Gata4, Mef2c, Tbx5, Mesp1, Nkx2-5, Isl-1, Myocd, Smyd1, and Srf; or a subset of reprogramming factors comprising Gata4, Mef2c, and Tbx5 polypeptides) into the post-natal fibroblast. Amino acid sequences of such reprogramming factors are known in the art. Nucleotide sequences encoding reprogramming factors are known in the art.

Reprogramming Factors

As discussed above, a post-natal fibroblast is genetically modified with one or more nucleic acids comprising nucleotide sequences encoding one or more reprogramming factors (e.g., one or more of Gata4, Mef2c, Tbx5, Mesp1, Nkx2-5, Isl-1, Myocd, Smyd1, and Srf; or a subset of reprogramming factors comprising Gata4, Mef2c, and Tbx5 polypeptides), or a post-natal fibroblast is modified by introducing one or more reprogramming factor polypeptides themselves (e.g., one or more of Gata4, Mef2c, Tbx5, Mesp1, Nkx2-5, Isl-1, Myocd, Smyd1, and Srf; or a subset of reprogramming factors comprising Gata4, Mef2c, and Tbx5 polypeptides) into the post-natal fibroblast.

In some embodiments, the one or more reprogramming factors includes 1, 2, 3, 4, 5, 6, 7, 8, or 9 of Gata4, Mef2c, Tbx5, Mesp1, Nkx2-5, Isl-1, Myocd, Smyd1, and Srf. In some embodiments, the one or more reprogramming factors includes all of Gata4, Mef2c, Tbx5, Mesp1, Nkx2-5, Isl-1, Myocd, Smyd1, and Srf. In some embodiments, the one or more reprogramming factors a subset of Gata4, Mef2c, Tbx5, Mesp1, Nkx2-5, Isl-1, Myocd, Smyd1, and Srf. Exemplary subsets include:

1) Mef2c, Tbx5, Mesp1, Nkx2-5, Isl-1, Myocd, Smyd1, and Srf;
2) Gata4, Tbx5, Mesp1, Nkx2-5, Isl-1, Myocd, Smyd1, and Srf;
3) Gata4, Mef2c, Mesp1, Nkx2-5, Isl-1, Myocd, Smyd1, and Srf;
4) Gata4, Mef2c, Tbx5, Nkx2-5, Isl-1, Myocd, Smyd1, and Srf;
5) Gata4, Mef2c, Tbx5, Mesp1, Isl-1, Myocd, Smyd1, and Srf;
6) Gata4, Mef2c, Tbx5, Mesp1, Nkx2-5, Myocd, Smyd1, and Srf;
7) Gata4, Mef2c, Tbx5, Mesp1, Nkx2-5, Isl-1, Smyd1, and Srf;
8) Gata4, Mef2c, Tbx5, Mesp1, Nkx2-5, Isl-1, Myocd, and Srf;
9) Gata4, Mef2c, Tbx5, Mesp1, Nkx2-5, Isl-1, Myocd, and Smyd1;
10) Gata4, Mef2c, Mesp1, Myocd, Nkx2-5, and Tbx5;
11) Mef2c, Mesp1, Myocd, Nkx2-5, and Tbx5;
12) Gata4, Mesp1, Myocd, Nkx2-5, and Tbx5;
13) Gata4, Mef2c, Myocd, Nkx2-5, and Tbx5;
14) Gata4, Mef2c, Mesp1, Nkx2-5, and Tbx5;
15) Gata4, Mef2c, Mesp1, Myocd, and Tbx5;
16) Gata4, Mef2c, Mesp1, Myocd, and Nkx2-5;
17) Mef2c, Mesp1, Myocd, and Tbx5;
18) Gata4, Mesp1, Myocd, and Tbx5;
19) Gata4, Mef2c, Myocd, and Tbx5;
20) Gata4, Mef2c, Mesp1, and Tbx5;
21) Gata4, Mef2c, Mesp1, and Myocd;
22) Mef2c, Mesp1, and Tbx5;
23) Gata4, Mef2c, and Tbx5.

As indicated above, in some embodiments, the subset of reprogramming factors is Gata4, Mef2c, and Tbx5.

Gata4

A Gata4 polypeptide is a member of the GATA family zinc-finger transcription factor that recognizes and binds a GATA motif (e.g., recognizes and binds the consensus sequence 5'-AGATAG-3') present in the promoter region of many genes. See, e.g., Huang et al. (1995) *Gene* 155:219. Amino acid sequences for Gata4 polypeptides, and nucleotide sequences encoding Gata4 polypeptides, from a variety of species are known in the art. See, e.g.: 1) GenBank Accession No. NP_002043.2 (*Homo sapiens* Gata4 amino acid sequence; and GenBank Accession No. NM_002052 (*Homo sapiens* Gata4-encoding nucleotide sequence; 2) GenBank Accession No. NP_0032118 (*Mus musculus* Gata4 amino acid sequence); and GenBank Accession No. NM_008092 (*Mus musculus* Gata4-encoding nucleotide sequence); 3) GenBank Accession No. NP_653331 (*Rattus norvegicus* Gata4 amino acid sequence); and GenBank Accession No. NM_144730 (*Rattus norvegicus* Gata4-encoding nucleotide sequence); 4) GenBank Accession No. ABI63575 (*Danio rerio* Gata4 amino acid sequence; and GenBank Accession No. DQ886664 (*Danio rerio* Gata4-encoding nucleotide sequence; and 5) GenBank Accession No. AAH71101.1 (*Xenopus laevis* Gata4 amino acid sequence); and GenBank Accession No. BC071107 (*Xenopus laevis* Gata4-encoding nucleotide sequence).

In some embodiments, a suitable Gata4 nucleic acid comprises a nucleotide sequence having at least about 80%, at least about 85%, at least about 90%, at least about 95%, at least about 98%, at least about 99%, or 100%, nucleotide sequence identity to a contiguous stretch of from about 900 nucleotides to about 1000 nucleotides (nt), from about 1000 nt to about 1100 nt, from about 1100 nt to about 1200 nt, or from about 1200 nt to 1329 nt, of the nucleotide sequence depicted in SEQ ID NO:14. In some embodiments, a suitable Gata4 nucleic acid comprises a nucleotide sequence having at least about 80%, at least about 85%, at least about 90%, at least about 95%, at least about 98%, at least about 99%, or 100%, nucleotide sequence identity to a contiguous stretch of from about 900 nucleotides to about 1000 nucleotides (nt), from about 1000 nt to about 1100 nt, from about 1100 nt to about 1200 nt, or from about 1200 nt to 1323 nt, of the nucleotide sequence depicted in SEQ ID NO:28.

A suitable Gata4 nucleic acid comprises a nucleotide sequence encoding a Gata4 polypeptide, where in some embodiments, a suitable Gata4 polypeptide comprises an amino acid sequence having at least about 80%, at least about 85%, at least about 90%, at least about 95%, at least about 98%, at least about 99%, or 100%, amino acid sequence identity to a contiguous stretch of from about 350 amino acids (aa) to about 400 aa, or from about 400 aa to 442 aa, of the amino acid sequence depicted in SEQ ID NO:13. In some embodiments, a suitable Gata4 polypeptide comprises an amino acid sequence having at least about 80%, at least about 85%, at least about 90%, at least about 95%, at least about 98%, at least about 99%, or 100%, amino acid sequence identity to a contiguous stretch of from about 350 amino acids (aa) to about 400 aa, or from about 400 aa to 441 aa, of the amino acid sequence depicted in SEQ ID NO:27. The encoded Gata4 polypeptide is biologically active, e.g., recognizes and binds a GATA motif (e.g., recognizes and binds the consensus sequence 5'-AGATAG-3') present in a promoter; and activates transcription of a gene operably linked to the promoter comprising the GATA motif.

In some embodiments, a polypeptide that is functionally equivalent to a Gata4 polypeptide (or a nucleotide sequence encoding such functional equivalent) is used. For example, in some embodiments, a Gata5 polypeptide (or a nucleotide sequence encoding a Gata5 polypeptide) is used. In other embodiments, a Gata6 polypeptide (or a nucleotide sequence encoding a Gata6 polypeptide) is used.

Amino acid sequences of Gata5 polypeptides, and nucleotide sequences encoding Gata5 polypeptides, are known in the art. See, e.g., GenBank Accession Nos.: 1) NP_536721 (*Homo sapiens* Gata5 amino acid sequence), and NM_080473 (nucleotide sequence encoding the NP_536721 amino acid sequence); 2) NP_032119 (*Mus musculus* Gata5 amino acid sequence), and NM_008093 (nucleotide sequence encoding the NP_032119 amino acid sequence); and 3) NP_001019487 (*Rattus norvegicus* Gata5 amino acid sequence), and NM_001024316 (nucleotide sequence encoding the NP_001019487 amino acid sequence).

Amino acid sequences of Gata6 polypeptides, and nucleotide sequences encoding Gata6 polypeptides, are known in the art. See, e.g., GenBank Accession Nos.: 1) NP_005248 (*Homo sapiens* Gata6 amino acid sequence), and NM_005257 (nucleotide sequence encoding the NP_005248 amino acid sequence); 2) NP_062058 (*Rattus norvegicus* Gata6 amino acid sequence) and NM_019185 (nucleotide sequence encoding the NP_062058 amino acid sequence); 3) NP_034388 (*Mus musculus* Gata6 amino acid sequence), and NM_010258 (nucleotide sequence encoding the NP_034388 amino acid sequence).

In some embodiments, a suitable functional equivalent of a Gata4 polypeptide is a polypeptide having at least about 80%, at least about 85%, at least about 90%, at least about 95%, at least about 98%, at least about 99%, or 100%, amino acid sequence identity to an amino acid sequence of a Gata5 polypeptide or a Gata6 polypeptide.

In some embodiments, a suitable nucleotide sequence encoding a functional equivalent of a Gata4 polypeptide comprises a nucleotide sequence having at least about 80%, at least about 85%, at least about 90%, at least about 95%, at least about 98%, at least about 99%, or 100%, nucleotide sequence identity to a nucleotide sequence encoding a Gata5 polypeptide or a Gata6 polypeptide.

Mef2c

Mef2c (myocyte-specific enhancer factor 2c) is a transcription activator that binds specifically to the MEF2 element (e.g., the consensus sequence: 5'-CT(A/t)(a/t)AAATAG-3') (SEQ ID NO:10) present in the regulatory regions of many muscle-specific genes. See, e.g., Andrés et al. (1995) *J. Biol. Chem.* 270:23246. Mef2c can include one or more post-translational modifications, e.g., phosphorylation on Ser-59 and Ser-396; sumoylation on Lys-391; and acetylation on Lys-4.

Amino acid sequences of Mef2c polypeptides, and nucleotide sequences encoding Mef2c polypeptides, from a variety of species are known in the art. See, e.g.: 1) GenBank Accession No. XP_001056692 (*Rattus norvegicus* Mef2c amino acid sequence); and GenBank Accession No. XM_001056692 (*Rattus norvegicus* Mef2c-encoding nucleotide sequence); 2) GenBank Accession No. NP_079558.1 (*Mus musculus* Mef2c isoform 2 amino acid sequence); and GenBank Accession No. NM_025282 (*Mus musculus* Mef2c isoform 2-encoding nucleotide sequence); 3) GenBank Accession No. NP_001164008 (*Mus musculus* Mef2c isoform 1 amino acid sequence); and GenBank Accession No. NM_001170537 (*Mus musculus* Mef2c isoform 1-encoding nucleotide sequence); 4) GenBank Accession No. NP_001124477 (*Homo sapiens* Mef2c isoform 2 amino acid sequence); and GenBank Accession No. NM_001131005 (*Homo sapiens* Mef2c isoform 2-encoding nucleotide sequence); 5) GenBank Accession No. NP_002388 (*Homo sapiens* Mef2c isoform 1 amino acid sequence); and GenBank Accession No. NM_002397 (*Homo sapiens* Mef2c isoform 1-encoding nucleotide sequence).

In some embodiments, a suitable Mef2c nucleic acid comprises a nucleotide sequence having at least about 80%, at least about 85%, at least about 90%, at least about 95%, at least about 98%, at least about 99%, or 100%, nucleotide sequence identity to a contiguous stretch of from about 900 nucleotides to about 1000 nucleotides (nt), from about 1000 nt to about 1100 nt, from about 1100 nt to about 1200 nt, from about 1200 nt to 1300 nt, or from about 1300 nt to 1392 nt, of the nucleotide sequence depicted in SEQ ID NO:16.

In some embodiments, a suitable Mef2c nucleic acid comprises a nucleotide sequence having at least about 80%, at least about 85%, at least about 90%, at least about 95%, at least about 98%, at least about 99%, or 100%, nucleotide sequence identity to a contiguous stretch of from about 900 nucleotides to about 1000 nucleotides (nt), from about 1000 nt to about 1100 nt, from about 1100 nt to about 1200 nt, from about 1200 nt to 1300 nt, or from about 1300 nt to 1422 nt, of the nucleotide sequence depicted in SEQ ID NO:18. In some embodiments, a suitable Mef2c nucleic acid comprises a nucleotide sequence having at least about 80%, at least about 85%, at least about 90%, at least about 95%, at least about 98%, at least about 99%, or 100%, nucleotide sequence identity to a contiguous stretch of from about 900 nucleotides to about 1000 nucleotides (nt), from about 1000 nt to about 1100 nt, from about 1100 nt to about 1200 nt, or from about 1200 nt to 1296 nt, of the nucleotide sequence depicted in SEQ ID NO:23.

A suitable Mef2c nucleic acid comprises a nucleotide sequence encoding a Mef2c polypeptide, where in some embodiments a suitable Mef2c polypeptide comprises an amino acid sequence having at least about 80%, at least about 85%, at least about 90%, at least about 95%, at least about 98%, at least about 99%, or 100%, amino acid sequence identity to a contiguous stretch of from about 350 amino acids (aa) to about 400 aa, or from about 400 aa to 463 aa, of the amino acid sequence depicted in SEQ ID NO:15. The encoded Mef2c polypeptide is biologically active, e.g., recognizes and binds a MEF2C element in a promoter; and activates transcription of a gene operably linked to the promoter.

In some embodiments, a suitable Mef2c polypeptide comprises an amino acid sequence having at least about 80%, at least about 85%, at least about 90%, at least about 95%, at least about 98%, at least about 99%, or 100%, amino acid sequence identity to a contiguous stretch of from about 350 amino acids (aa) to about 400 aa, or from about 400 aa to 432 aa, of the amino acid sequence depicted in SEQ ID NO:24. The encoded Mef2c polypeptide is biologically active, e.g., recognizes and binds a MEF2C element in a promoter; and activates transcription of a gene operably linked to the promoter.

A suitable Mef2c nucleic acid comprises a nucleotide sequence encoding a Mef2c polypeptide, where a suitable Mef2c polypeptide comprises an amino acid sequence having at least about 80%, at least about 85%, at least about 90%, at least about 95%, at least about 98%, at least about 99%, or 100%, amino acid sequence identity to a contiguous stretch of from about 350 amino acids (aa) to about 400 aa, or from about 400 aa to 473 aa, of the amino acid sequence depicted in SEQ ID NO:17. The encoded Mef2c polypeptide is biologically active, e.g., recognizes and binds a MEF2C element in a promoter; and activates transcription of a gene operably linked to the promoter.

In some embodiments, a polypeptide that is functionally equivalent to a Mef2c polypeptide (or a nucleotide sequence encoding such functional equivalent) is used. For example, in some embodiments, a Mef2a polypeptide (or a nucleotide sequence encoding a Mef2a polypeptide) is used. In other embodiments, a Mef2b polypeptide (or a nucleotide sequence encoding a Mef2b polypeptide) is used. In other embodiments, a Mef2d polypeptide (or a nucleotide sequence encoding a Mef2d polypeptide) is used.

Amino acid sequences of Mef2a, Me2b, and Mef2d polypeptides are known, as are nucleotide sequences encoding Mef2a, Me2b, and Mef2d polypeptides. See, e.g., GenBank Accession Nos.: 1) NP_005578.2 (*Homo sapiens* Mef2a isoform 1 amino acid sequence), and NM_005587 (nucleotide sequence encoding the NP_005578.2 amino acid sequence); 2) NP_001124398.1 (*Homo sapiens* Mef2a isoform 2 amino acid sequence), and NM_001130926 (nucleotide sequence encoding the NP_001124398.1 amino acid sequence); 3) NP_001124399.1 (*Homo sapiens* Mef2a isoform 3 amino acid sequence), and NM_001130927 (nucleotide sequence encoding the NP_001124399.1 amino acid sequence); 4) NP_001124400.1 (*Homo sapiens* Mef2a isoform 4 amino acid sequence), and NM_001130928 (nucleotide sequence encoding the NP_001124400.1 amino acid sequence); 5) NP_001139257.1 (*Homo sapiens* Mef2b isoform a amino acid sequence), and NM_001145785 (nucleotide sequence encoding the NP_001139257.1 amino acid sequence); 6) NP_005910.1 (*Homo sapiens* Mef2b isoform b amino acid sequence), and NM_005919 (nucleotide sequence encoding the NP_005910.1 amino acid sequence); 7) NP_032604.2 (*Mus musculus* Mef2b isoform 1 amino acid sequence), and NM_008578 (nucleotide sequence encoding the NP_032604.2 amino acid sequence); 8) NP_001038949.1 (*Mus musculus* Mef2b isoform 2 amino acid sequence), and NM_001045484 (nucleotide sequence encoding the NP_001038949.1 amino acid sequence); 9) NP_005911.1 (*Homo sapiens* Mef2d amino acid sequence), and NM_005920 (nucleotide sequence encoding the NP_005911.1 amino acid sequence); and 10) NP_598426.1 (*Mus musculus* Mef2d amino acid sequence), and NM_133665 (nucleotide sequence encoding the NP_598426.1 amino acid sequence).

In some embodiments, a suitable functional equivalent of a Mef2c polypeptide is a polypeptide having at least about 80%, at least about 85%, at least about 90%, at least about 95%, at least about 98%, at least about 99%, or 100%, amino acid sequence identity to an amino acid sequence of a Mef2a polypeptide, a Mef2b polypeptide, or a Mef2d polypeptide.

In some embodiments, a suitable nucleotide sequence encoding a functional equivalent of a Mef2c polypeptide comprises a nucleotide sequence having at least about 80%, at least about 85%, at least about 90%, at least about 95%, at least about 98%, at least about 99%, or 100%, nucleotide sequence identity to a nucleotide sequence encoding a Mef2a polypeptide, a Mef2b polypeptide, or a Mef2d polypeptide.

Tbx5

Tbx5 (T-box transcription factor 5) is a transcription factor that binds to an recognizes a T-box (e.g., an element having the consensus sequence 5'-(A/G)GGTGT-3') in the promoter region of some genes; and activates transcription of genes operably linked to such promoters.

Amino acid sequences for Tbx5 polypeptides, and nucleotide sequences encoding Tbx5 polypeptides, from a variety of species are known in the art. See, e.g.: 1) GenBank Accession No. CAA70592.1 (*Homo sapiens* Tbx5 amino acid sequence); and GenBank Accession No. Y09445 (*Homo sapiens* Tbx5-encoding nucleotide sequence); 2) GenBank Accession No. NP_000183 (*Homo sapiens* Tbx5 amino acid sequence); and GenBank Accession No. NM_000192 (*Homo sapiens* Tbx5-encoding nucleotide sequence); 3) GenBank Accession No. NP_001009964.1 (*Rattus norvegicus* Tbx5 amino acid sequence); and GenBank Accession No. NM_001009964 (*Rattus norvegicus* Tbx5-encoding nucleotide sequence; 4) GenBank Accession No. NP_035667 (*Mus musculus* Tbx5 amino acid sequence); and NM_011537 (*Mus musculus* Tbx5-encoding nucleotide sequence); 5) GenBank Accession No. NP_001079170 (*Xenopus laevis* Tbx5 amino acid sequence); and GenBank Accession No. NM_001085701 (*Xenopus laevis* Tbx5-encoding nucleotide sequence).

In some embodiments, a suitable Tbx5 nucleic acid comprises a nucleotide sequence having at least about 80%, at least about 85%, at least about 90%, at least about 95%, at least about 98%, at least about 99%, or 100%, nucleotide sequence identity to a contiguous stretch of from about 900 nucleotides to about 1000 nucleotides (nt), from about 1200 nt to 1300 nt, from about 1300 nt to about 1400 nt, or from about 1400 nt to about 1500 nt, or from about 1500 nt to 1542 nt of the nucleotide sequence depicted in SEQ ID NO:20. In some embodiments, a suitable Tbx5 nucleic acid comprises a nucleotide sequence having at least about 80%, at least about 85%, at least about 90%, at least about 95%, at least about 98%, at least about 99%, or 100%, nucleotide sequence identity to a contiguous stretch of from about 900 nucleotides to about 1000 nucleotides (nt), from about 1200 nt to 1300 nt, from about 1300 nt to about 1400 nt, or from about 1400 nt to about 1500 nt, or from about 1500 nt to 1560 nt of the nucleotide sequence depicted in SEQ ID NO:25.

In some embodiments, a suitable Tbx5 nucleic acid comprises a nucleotide sequence having at least about 80%, at least about 85%, at least about 90%, at least about 95%, at least about 98%, at least about 99%, or 100%, nucleotide sequence identity to a contiguous stretch of from about 900 nucleotides to about 1000 nucleotides (nt), from about 1200 nt to 1300 nt, from about 1300 nt to about 1400 nt, or from about 1400 nt to about 1500 nt, or from about 1500 nt to 1557, of the nucleotide sequence depicted in SEQ ID NO:22.

A suitable Tbx5 nucleic acid comprises a nucleotide sequence encoding a Tbx5 polypeptide. In some embodiments, a suitable Tbx5 polypeptide comprises an amino acid sequence having at least about 80%, at least about 85%, at least about 90%, at least about 95%, at least about 98%, at least about 99%, or 100%, amino acid sequence identity to a contiguous stretch of from about 350 amino acids (aa) to about 400 aa, from about 400 aa to about 500 aa, or from about 500 aa to 513 aa, of the amino acid sequence depicted in SEQ ID NO:19. In some embodiments, a suitable Tbx5 polypeptide comprises an amino acid sequence having at least about 80%, at least about 85%, at least about 90%, at least about 95%, at least about 98%, at least about 99%, or 100%, amino acid sequence identity to a contiguous stretch of from about 350 amino acids (aa) to about 400 aa, from about 400 aa to about 500 aa, or from about 500 aa to 518 aa, of the amino acid sequence depicted in SEQ ID NO:26. The encoded Tbx5 polypeptide is biologically active, e.g., recognizes and binds a Tbx5 binding site (e.g., an element having the consensus sequence 5'-(A/G)GGTGT-3') in a promoter; and activates transcription of a gene operably linked to the promoter.

A suitable Tbx5 nucleic acid comprises a nucleotide sequence encoding a Tbx5 polypeptide, where in some embodiments a suitable Tbx5 polypeptide comprises an amino acid sequence having at least about 80%, at least about 85%, at least about 90%, at least about 95%, at least about 98%, at least about 99%, or 100%, amino acid sequence identity to a contiguous stretch of from about 350 amino acids (aa) to about 400 aa, from about 400 aa to about 500 aa, or from about 500 aa to 518 aa, of the amino acid sequence depicted in SEQ ID NO:21. The encoded Tbx5 polypeptide is biologically active, e.g., recognizes and binds a Tbx5 binding site (e.g., an element having the consensus sequence 5'-(A/G)GGTGT-3') in a promoter; and activates transcription of a gene operably linked to the promoter.

Mesp1

In some embodiments, a suitable mesoderm posterior protein 1 (Mesp1) nucleic acid comprises a nucleotide sequence having at least about 80%, at least about 85%, at least about 90%, at least about 95%, at least about 98%, at least about 99%, or 100%, nucleotide sequence identity to a contiguous stretch of from about 600 nucleotides to about 800 nucleotides (nt), or 804 nt, of the nucleotide sequence depicted in SEQ ID NO:30.

A suitable Mesp1 nucleic acid comprises a nucleotide sequence encoding a Mesp1 polypeptide, where in some embodiments, a suitable Mesp1 polypeptide comprises an amino acid sequence having at least about 80%, at least about 85%, at least about 90%, at least about 95%, at least about 98%, at least about 99%, or 100%, amino acid sequence identity to a contiguous stretch of from about 200 amino acids (aa) to about 250 aa, or from about 250 aa to 268 aa, of the amino acid sequence depicted in SEQ ID NO:29. The encoded Mesp1 polypeptide is biologically active.

Nkx2-5

In some embodiments, a suitable Nkx2-5 nucleic acid comprises a nucleotide sequence having at least about 80%, at least about 85%, at least about 90%, at least about 95%, at least about 98%, at least about 99%, or 100%, nucleotide sequence identity to a contiguous stretch of from about 350 nucleotides to about 450 nucleotides (nt), or 456 nt, of the nucleotide sequence depicted in SEQ ID NO:32. In some embodiments, a suitable Nkx2-5 nucleic acid comprises a nucleotide sequence having at least about 80%, at least about 85%, at least about 90%, at least about 95%, at least about 98%, at least about 99%, or 100%, nucleotide sequence identity to a contiguous stretch of from about 850 nucleotides to about 950 nucleotides (nt), or 975 nt, of the nucleotide sequence depicted in SEQ ID NO:34. In some embodiments, a suitable Nkx2-5 nucleic acid comprises a nucleotide sequence having at least about 80%, at least about 85%, at least about 90%, at least about 95%, at least about 98%, at least about 99%, or 100%, nucleotide sequence identity to a contiguous stretch of from about 230 nucleotides to about 330 nucleotides (nt), or 339 nt, of the nucleotide sequence depicted in SEQ ID NO:36.

A suitable Nkx2-5 nucleic acid comprises a nucleotide sequence encoding a Nkx2-5 polypeptide, where in some embodiments, a suitable Nkx2-5 polypeptide comprises an amino acid sequence having at least about 80%, at least about 85%, at least about 90%, at least about 95%, at least about 98%, at least about 99%, or 100%, amino acid sequence identity to a contiguous stretch of from about 125 amino acids (aa) to about 150 aa, of the amino acid sequence depicted in SEQ ID NO:31. In some embodiments, a suitable Nkx2-5 polypeptide comprises an amino acid sequence having at least about 80%, at least about 85%, at least about 90%, at least about 95%, at least about 98%, at least about 99%, or 100%, amino acid sequence identity to a contiguous stretch of from about 275 amino acids (aa) to about 300 aa, or from about 300 aa to about 324 aa, of the amino acid sequence depicted in SEQ ID NO:33. In some embodiments, a suitable Nkx2-5 polypeptide comprises an amino acid sequence having at least about 80%, at least about 85%, at least about 90%, at least about 95%, at least about 98%, at least about 99%, or 100%, amino acid sequence identity to a contiguous stretch of from about 75 amino acids (aa) to about 100 aa, or from about 100 aa to about 112 aa, of the amino acid sequence depicted in SEQ ID NO:35. The encoded Nkx2-5 polypeptide is biologically active.

Isl-1

In some embodiments, a suitable islet-1 (Isl-1) nucleic acid comprises a nucleotide sequence having at least about 80%, at least about 85%, at least about 90%, at least about 95%, at least about 98%, at least about 99%, or 100%, nucleotide sequence identity to a contiguous stretch of from about 900 nucleotides to about 1000 nucleotides (nt), or 1050 nt, of the nucleotide sequence depicted in SEQ ID NO:38.

A suitable Isl-1 nucleic acid comprises a nucleotide sequence encoding a Isl-1 polypeptide, where in some embodiments, a suitable Isl-1 polypeptide comprises an amino acid sequence having at least about 80%, at least about 85%, at least about 90%, at least about 95%, at least about 98%, at least about 99%, or 100%, amino acid sequence identity to a contiguous stretch of from about 300 amino acids (aa) to about 325 aa, or from about 325 aa to 346 aa, of the amino acid sequence depicted in SEQ ID NO:37. The encoded Isl-1 polypeptide is biologically active.

Myocd

In some embodiments, a suitable myocardin (Myocd) nucleic acid comprises a nucleotide sequence having at least about 80%, at least about 85%, at least about 90%, at least about 95%, at least about 98%, at least about 99%, or 100%, nucleotide sequence identity to a contiguous stretch of from about 1500 nucleotides to about 2000 nucleotides (nt), or 2055 nt, of the nucleotide sequence depicted in SEQ ID NO:40. In some embodiments, a suitable Myocd nucleic acid comprises a nucleotide sequence having at least about 80%, at least about 85%, at least about 90%, at least about 95%, at least about 98%, at least about 99%, or 100%, nucleotide sequence identity to a contiguous stretch of from about 2500 nucleotides to about 2900 nucleotides (nt), or 2961 nt, of the nucleotide sequence depicted in SEQ ID NO:42. In some embodiments, a suitable Myocd nucleic acid comprises a nucleotide sequence having at least about 80%, at least about 85%, at least about 90%, at least about 95%, at least about 98%, at least about 99%, or 100%, nucleotide sequence identity to a contiguous stretch of from about 2500 nucleotides to about 2800 nucleotides (nt), or 2871 nt, of the nucleotide sequence depicted in SEQ ID NO:44.

A suitable Myocd nucleic acid comprises a nucleotide sequence encoding a Myocd polypeptide, where in some embodiments, a suitable Myocd polypeptide comprises an amino acid sequence having at least about 80%, at least about 85%, at least about 90%, at least about 95%, at least about 98%, at least about 99%, or 100%, amino acid sequence identity to a contiguous stretch of from about 600 amino acids (aa) to about 650 aa, or from about 650 aa to 684 aa, of the amino acid sequence depicted in SEQ ID NO:39. In some embodiments, a suitable Myocd polypeptide comprises an amino acid sequence having at least about 80%, at least about 85%, at least about 90%, at least about 95%, at least about 98%, at least about 99%, or 100%, amino acid sequence identity to a contiguous stretch of from about 900 amino acids (aa) to about 950 aa, or from about 950 aa to 986 aa, of the amino acid sequence depicted in SEQ ID NO:41. In some embodiments, a suitable Myocd polypeptide comprises an amino acid sequence having at least about 80%, at least about 85%, at least about 90%, at least about 95%, at least about 98%, at least about 99%, or 100%, amino acid sequence identity to a contiguous stretch of from about 900 amino acids (aa) to about 925 aa, or from about 925 aa to 938 aa, of the amino acid sequence depicted in SEQ ID NO:43. The encoded Myocd polypeptide is biologically active.

Smyd1

In some embodiments, a suitable Smyd1 nucleic acid comprises a nucleotide sequence having at least about 80%, at least about 85%, at least about 90%, at least about 95%, at least about 98%, at least about 99%, or 100%, nucleotide sequence identity to a contiguous stretch of from about 1400 nucleotides to about 1450 nucleotides (nt), or from about 1450 nt to 1473 nt, of the nucleotide sequence depicted in SEQ ID NO:46.

A suitable Smyd1 nucleic acid comprises a nucleotide sequence encoding a Smyd1 polypeptide, where in some embodiments, a suitable Smyd1 polypeptide comprises an amino acid sequence having at least about 80%, at least about 85%, at least about 90%, at least about 95%, at least about 98%, at least about 99%, or 100%, amino acid sequence identity to a contiguous stretch of from about 400 amino acids (aa) to about 450 aa, or from about 450 aa to 490 aa, of the amino acid sequence depicted in SEQ ID NO:45. The encoded Smyd1 polypeptide is biologically active.

Srf

In some embodiments, a suitable Srf nucleic acid comprises a nucleotide sequence having at least about 80%, at least about 85%, at least about 90%, at least about 95%, at least about 98%, at least about 99%, or 100%, nucleotide sequence identity to a contiguous stretch of from about 1450 nucleotides to about 1500 nucleotides (nt), or from about 1500 nt to 1527 nt, of the nucleotide sequence depicted in SEQ ID NO:48.

A suitable Srf nucleic acid comprises a nucleotide sequence encoding a Srf polypeptide, where in some embodiments, a suitable Srf polypeptide comprises an amino acid sequence having at least about 80%, at least about 85%, at least about 90%, at least about 95%, at least about 98%, at least about 99%, or 100%, amino acid sequence identity to a contiguous stretch of from about 450 amino acids (aa) to about 500 aa, or from about 500 aa to 508 aa, of the amino acid sequence depicted in SEQ ID NO:47. The encoded Srf polypeptide is biologically active.

It has been found that introduction of one or more nucleic acids comprising nucleotide sequences encoding one or more reprogramming factors (e.g., one or more of Gata4, Mef2c, Tbx5, Mesp1, Nkx2-5, Isl-1, Myocd, Smyd1, and Srf; or a subset of reprogramming factors comprising Gata4, Mef2c, and Tbx5 polypeptides) is sufficient to reprogram a post-natal fibroblast into a cardiomyocyte. Thus, a post-natal fibroblast can be reprogrammed to become a cardiomyocyte without the need for introducing an induction factor (e.g., any other exogenous polypeptide; any other nucleic acid encoding any other exogenous polypeptide) that would reprogram a fibroblast into a stem cell or progenitor cell into the post-natal fibroblast. For example, a subject method does not require and does not involve introducing into a post-natal fibroblast any of an exogenous Sox2 polypeptide, an exogenous Oct-3/4 polypeptide, an exogenous c-Myc polypeptide, an exogenous Klf4 polypeptide, an exogenous Nanog polypeptide, or an exogenous Lin28 polypeptide. A subject method does not require and does not involve introducing into a post-natal fibroblast a nucleic acid(s) comprising nucleotide sequences encoding any of Sox2, Oct-3/4, c-Myc, Klf4, Nanog, or any other polypeptide that would reprogram a fibroblast into a stem cell or progenitor cell.

As noted above, to generate an induced cardiomyocyte, a post-natal fibroblast is genetically modified with one or more nucleic acids comprising nucleotide sequences encoding one or more reprogramming factors (e.g., one or more of Gata4, Mef2c, Tbx5, Mesp1, Nkx2-5, Isl-1, Myocd, Smyd1, and Srf; or a subset of reprogramming factors comprising Gata4, Mef2c, and Tbx5 polypeptides). Induced cardiomyocytes express one or more cardiomyocyte-specific markers, where cardiomyocyte-specific markers include, but are not limited to, cardiac troponin I, cardiac troponin-C, tropomyosin, caveolin-3, myosin heavy chain, myosin light chain-2a, myosin light chain-2v, ryanodine receptor, sarcomeric α-actinin, Nkx2.5, connexin 43, and atrial natriuretic factor. Induced cardiomyocytes can also exhibit sarcomeric structures. Induced cardiomyocytes exhibit increased expression of cardiomyocyte-specific genes Actc1 (cardiac α-actin), Myh6 (α-myosin heavy chain), Ryr2 (ryanodine receptor 2), and Gja1 (connexin43). Expression of fibroblasts markers such as Col1a2 (collagen 1a2) is downregulated in induced cardiomyocytes, compared to fibroblasts from which the iCM is derived.

The expression of various markers specific to cardiomyocytes is detected by conventional biochemical or immunochemical methods (e.g., enzyme-linked immunosorbent assay; immunohistochemical assay; and the like). Alternatively, expression of nucleic acid encoding a cardiomyocyte-specific marker can be assessed. Expression of cardiomyocyte-specific marker-encoding nucleic acids in a cell can be confirmed by reverse transcriptase polymerase chain reaction (RT-PCR) or hybridization analysis, molecular biological methods which have been commonly used in the past for amplifying, detecting and analyzing mRNA coding for any marker proteins. Nucleic acid sequences coding for markers specific to cardiomyocytes are known and are available through public data bases such as GenBank; thus, marker-specific sequences needed for use as primers or probes is easily determined.

Induced cardiomyocytes can also exhibit spontaneous contraction. Whether an induced cardiomyocyte exhibits spontaneous contraction can be determined using standard electrophysiological methods (e.g., patch clamp); a suitable method is described in the Examples.

Induced cardiomyocytes can also exhibit spontaneous $Ca^{2+}$ oscillations. $Ca^{2+}$ oscillations can be detected using standard methods, e.g., using any of a variety of calcium-sensitive dyes. intracellular $Ca^{2+}$ ion-detecting dyes include, but are not limited to, fura-2, bis-fura 2, indo-1, Quin-2, Quin-2 AM, Benzothiaza-1, Benzothiaza-2, indo-5F, Fura-FF, BTC, Mag-Fura-2, Mag-Fura-5, Mag-Indo-1, fluo-3, rhod-2, rhod-3, fura-4F, fura-5F, fura-6F, fluo-4, fluo-5F, fluo-5N, Oregon Green 488 BAPTA, Calcium Green, Calcein, Fura-C18, Calcium Green-C18, Calcium Orange, Calcium Crimson, Calcium Green-5N, Magnesium Green, Oregon Green 488 BAPTA-1, Oregon Green 488 BAPTA-2, X-rhod-1, Fura Red, Rhod-5F, Rhod-5N, X-Rhod-5N, Mag-Rhod-2, Mag-X-Rhod-1, Fluo-5N, Fluo-5F, Fluo-4FF, Mag-Fluo-4, Aequorin, dextran conjugates or any other derivatives of any of these dyes, and others (see, e.g., the catalog or Internet site for Molecular Probes, Eugene, see, also, Nuccitelli, ed., *Methods in Cell Biology, Volume 40: A Practical Guide to the Study of Calcium in Living Cells*, Academic Press (1994); Lambert, ed., *Calcium Signaling Protocols* (Methods in Molecular Biology Volume 114), Humana Press (1999); W. T. Mason, ed., *Fluorescent and Luminescent Probes for Biological Activity. A Practical Guide to Technology for Quantitative Real-Time Analysis*, Second Ed, Academic Press (1999); *Calcium Signaling Protocols* (Methods in Molecular Biology), 2005, D. G. Lamber, ed., Humana Press).

Introduction of Exogenous Re-Programming Factor Polypeptide into a Post-Natal Fibroblast In some embodiments, introduction of exogenous reprogramming factor polypeptides (e.g., one or more of Gata4, Mef2c, Tbx5, Mesp1, Nkx2-5, Isl-1, Myocd, Smyd1, and Srf; or a subset of reprogramming factors comprising Gata4, Mef2c, and Tbx5 polypeptides) into a post-natal fibroblast is achieved by contacting the post-natal fibroblast with exogenous reprogramming factor polypeptides, wherein the exogenous reprogramming factor polypeptides are taken up into the cell.

In some embodiments, each of an exogenous reprogramming factor polypeptides comprises a protein transduction domain. As a non-limiting example, an exogenous Gata4 polypeptide, an exogenous Mef2C polypeptide, and a Tbx4 polypeptide is linked, covalently or non-covalently, to a protein transduction domain.

"Protein Transduction Domain" or PTD refers to a polypeptide, polynucleotide, carbohydrate, or organic or inorganic compound that facilitates traversing a lipid bilayer, micelle, cell membrane, organelle membrane, or vesicle membrane. A PTD attached to another molecule facilitates the molecule traversing a membrane, for example going from extracellular space to intracellular space, or cytosol to within an organelle. In some embodiments, a PTD is covalently linked to the amino terminus of a reprogramming factor polypeptide (e.g., a Gata4 polypeptide, a Mef2c polypeptide, or a Tbx5 polypeptide). In some embodiments, a PTD is covalently linked to the carboxyl terminus of a reprogramming factor polypeptide (e.g., a Gata4 polypeptide, a Mef2c polypeptide, or a Tbx5 polypeptide).

Exemplary protein transduction domains include but are not limited to a minimal undecapeptide protein transduction domain (corresponding to residues 47-57 of HIV-1 TAT comprising YGRKKRRQRRR; SEQ ID NO:1); a polyarginine sequence comprising a number of arginines sufficient to direct entry into a cell (e.g., 3, 4, 5, 6, 7, 8, 9, 10, or 10-50 arginines); a VP22 domain (Zender et al., Cancer Gene Ther. 2002 June; 9(6):489-96); an *Drosophila* Antennapedia protein transduction domain (Noguchi et al., Diabetes 2003; 52(7):1732-1737); a truncated human calcitonin peptide (Trehin et al. Pharm. Research, 21:1248-1256, 2004); polylysine (Wender et al., PNAS, Vol. 97:13003-13008); RRQRRTSKLMKR (SEQ ID NO:2); Transportan GWTLN-SAGYLLGKINLKALAALAKKIL (SEQ ID NO:3); KALAWEAKLAKALAKALAKHLAKALAKALKCEA (SEQ ID NO:4); and RQIKIWFQNRRMKWKK (SEQ ID NO:5). Exemplary PTDs include but are not limited to, YGRKKRRQRRR (SEQ ID NO:1), RKKRRQRRR (SEQ ID NO:6); an arginine homopolymer of from 3 arginine residues to 50 arginine residues; Exemplary PTD domain amino acid sequences include, but are not limited to, any of the following: YGRKKRRQRRR (SEQ ID NO:1); RKKRRQRR (SEQ ID NO:6); YARAAARQARA (SEQ ID NO:7); THRLPRRRRRR (SEQ ID NO:8); and GGRRARRRRRR (SEQ ID NO:9).

In some embodiments, an exogenous reprogramming factor polypeptide (e.g., one or more of Gata4, Mef2c, Tbx5, Mesp1, Nkx2-5, Isl-1, Myocd, Smyd1, and Srf; or a subset of reprogramming factors comprising Gata4, Mef2c, and Tbx5 polypeptides) comprises an arginine homopolymer of from 3 arginine residues to 50 arginine residues, e.g., from 3 to 6 arginine residues, from 6 to 10 arginine residues, from 10 to 20 arginine residues, from 20 to 30 arginine residues, from 30 to 40 arginine residues, or from 40 to 50 arginine residues. In some embodiments, an exogenous reprogramming factor polypeptide (e.g., one or more of Gata4, Mef2c, Tbx5, Mesp1, Nkx2-5, Isl-1, Myocd, Smyd1, and Srf; or a subset of reprogramming factors comprising Gata4, Mef2c, and Tbx5 polypeptides) comprises six Arg residues covalently linked (e.g., by a peptide bond) at the amino terminus of the reprogramming factor polypeptide. In some embodiments, an exogenous reprogramming factor polypeptide comprises six Arg residues covalently linked (e.g., by a peptide bond) at the carboxyl terminus of the reprogramming factor polypeptide.

Exogenous reprogramming factor polypeptides (e.g., one or more of Gata4, Mef2c, Tbx5, Mesp1, Nkx2-5, Isl-1, Myocd, Smyd1, and Srf; or a subset of reprogramming factors comprising Gata4, Mef2c, and Tbx5 polypeptides) that are introduced into a host post-natal fibroblast can be purified, e.g., at least about 75% pure, at least about 80% pure, at least about 85% pure, at least about 90% pure, at least about 95% pure, at least about 98% pure, at least about 99% pure, or more than 99% pure, e.g., free of proteins other than reprogramming factor(s) being introduced into the cell and free of macromolecules other than the reprogramming factor(s) being introduced into the cell.

Genetic Modification of a Post-Natal Fibroblast

In some embodiments, introduction of exogenous reprogramming factor polypeptides (e.g., one or more of Gata4, Mef2c, Tbx5, Mesp1, Nkx2-5, Isl-1, Myocd, Smyd1, and Srf; or a subset of reprogramming factors comprising Gata4, Mef2c, and Tbx5 polypeptides) into a post-natal fibroblast is achieved by genetic modification of the post-natal fibroblast with one or more exogenous nucleic acids comprising nucleotide sequences encoding reprogramming factor polypeptides (e.g., one or more of Gata4, Mef2c, Tbx5, Mesp1, Nkx2-5, Isl-1, Myocd, Smyd1, and Srf; or a subset of reprogramming factors comprising Gata4, Mef2c, and Tbx5 polypeptides). In the following discussion, one or more exogenous nucleic acids comprising nucleotide sequences encoding one or more of Gata4, Mef2c, Tbx5, Mesp1, Nkx2-5, Isl-1, Myocd, Smyd1, and Srf (or a subset of reprogramming factors comprising Gata4, Mef2c, and Tbx5 polypeptides) are referred to generically as "one or more exogenous nucleic acids."

The one or more exogenous nucleic acids comprising nucleotide sequences encoding the above-noted exogenous reprogramming factor polypeptides can be a recombinant expression vector, where suitable vectors include, e.g., recombinant retroviruses, lentiviruses, and adenoviruses; retroviral expression vectors, lentiviral expression vectors, nucleic acid expression vectors, and plasmid expression vectors. In some cases, the one or more exogenous nucleic acids is integrated into the genome of a host post-natal fibroblast and its progeny. In other cases, the one or more exogenous nucleic acids persists in an episomal state in the host post-natal fibroblast and its progeny. In some cases, an endogenous, natural version of the reprogramming factor-encoding nucleic acid may already exist in the cell but an additional "exogenous gene" is added to the host post-natal fibroblast to increase expression of the reprogramming factor. In other cases, the exogenous reprogramming factor-encoding nucleic acid encodes a reprogramming factor polypeptide having an amino acid sequence that differs by one or more amino acids from a polypeptide encoded by an endogenous reprogramming factor-encoding nucleic acid within the host post-natal fibroblast.

In some embodiments, a post-natal fibroblast is genetically modified with three separate expression constructs (expression vectors), each comprising a nucleotide sequence encoding one of Gata4, Mef2c, Tbx5, Mesp1, Nkx2-5, Isl-1, Myocd, Smyd1, and Srf. In some embodiments, an expression construct will comprise nucleotide sequences encoding two or more of Gata4, Mef2c, Tbx5, Mesp1, Nkx2-5, Isl-1, Myocd, Smyd1, and Srf.

In some embodiments, a post-natal fibroblast is genetically modified with three separate expression constructs (expression vectors), each comprising a nucleotide sequence encoding one of Gata4, Mef2c, and Tbx5. In some embodiments, an expression construct will comprise nucleotide sequences encoding both Gata4 and Mef2c, both Gata4 and Tbx5, or both Mef2c and Tbx5. In some embodiments, an expression construct will comprise nucleotide sequences encoding Gata4, Mef2c, and Tbx5.

In some embodiments, one or more exogenous nucleic acids comprising nucleotide sequences encoding one or more of Gata4, Mef2c, Tbx5, Mesp1, Nkx2-5, Isl-1, Myocd, Smyd1, and Srf (or a subset, e.g., Gata4, Mef2c, and Tbx5) polypeptides is introduced into a single post-natal fibroblast (e.g., a single post-natal fibroblast host cell) in vitro. In other embodiments, one or more exogenous nucleic acids comprising nucleotide sequences encoding Gata4, Mef2c, Tbx5, Mesp1, Nkx2-5, Isl-1, Myocd, Smyd1, and Srf (or a subset, e.g., Gata4, Mef2c, and Tbx5) polypeptides is introduced into a population of post-natal fibroblasts (e.g., a population of host post-natal fibroblasts) in vitro. In some embodiments, one or more exogenous nucleic acids comprising nucleotide sequences encoding one or more of Gata4, Mef2c, Tbx5, Mesp1, Nkx2-5, Isl-1, Myocd, Smyd1, and Srf (or a subset, e.g., Gata4, Mef2c, and Tbx5) polypeptides is introduced into a post-natal fibroblast (e.g., a single post-natal fibroblast or a population of post-natal fibroblasts) in vivo.

Where a population of post-natal fibroblasts is genetically modified (in vitro or in vivo) with one or more exogenous nucleic acids comprising nucleotide sequences encoding one or more of Gata4, Mef2c, Tbx5, Mesp1, Nkx2-5, Isl-1, Myocd, Smyd1, and Srf (or a subset, e.g., Gata4, Mef2c, and Tbx5) polypeptides, the one or more exogenous nucleic acids can be introduced into greater than 20% of the total population of post-natal fibroblasts, e.g., 25%, 30%, 35%, 40%, 44%, 50%, 57%, 62%, 70%, 74%, 75%, 80%, 90%, or other percent of cells greater than 20%.

In some embodiments, the one or more nucleic acids comprising nucleotide sequences encoding one or more of Gata4, Mef2c, Tbx5, Mesp1, Nkx2-5, Isl-1, Myocd, Smyd1, and Srf (or a subset, e.g., Gata4, Mef2c, and Tbx5) polypeptides is/are an expression construct that provides for production of the one or more reprogramming factor polypeptides in the genetically modified host post-natal fibroblast cell. In some embodiments, the expression construct is a viral construct, e.g., a recombinant adeno-associated virus construct (see, e.g., U.S. Pat. No. 7,078,387), a recombinant adenoviral construct, a recombinant lentiviral construct, etc.

Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:8186, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like.

Numerous suitable expression vectors are known to those of skill in the art, and many are commercially available. The following vectors are provided by way of example; for eukaryotic host cells: pXT1, pSG5 (Stratagene), pSVK3, pBPV, pMSG, and pSVLSV40 (Pharmacia). However, any other vector may be used so long as it is compatible with the host cell.

Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) *Methods in Enzymology*, 153:516-544).

In some embodiments, a reprogramming factor-encoding nucleotide sequence (e.g., a Gata4-encoding nucleotide sequence, an Mef2c-encoding nucleotide sequence, a Tbx5-encoding nucleotide sequence) is operably linked to a control element, e.g., a transcriptional control element, such as a promoter. The transcriptional control element is functional in a eukaryotic cell, e.g., a mammalian cell. Suitable transcriptional control elements include promoters and enhancers. In some embodiments, the promoter is constitutively active. In other embodiments, the promoter is inducible.

Non-limiting examples of suitable eukaryotic promoters (promoters functional in a eukaryotic cell) include CMV immediate early, HSV thymidine kinase, early and late SV40, long terminal repeats (LTRs) from retrovirus, and mouse metallothionein-I.

In some embodiments, a reprogramming factor-encoding nucleotide sequence is operably linked to a cardiac-specific transcriptional regulator element (TRE), where TREs include promoters and enhancers. Suitable TREs include, but are not limited to, TREs derived from the following genes: myosin light chain-2, α-myosin heavy chain, AE3, cardiac troponin C, and cardiac actin. Franz et al. (1997) Cardiovasc. Res. 35:560-566; Robbins et al. (1995) Ann. N.Y. Acad. Sci. 752:492-505; Linn et al. (1995) Circ. Res. 76:584-591; Parmacek et al. (1994) Mol. Cell. Biol. 14:1870-1885; Hunter et al. (1993) Hypertension 22:608-617; and Sartorelli et al. (1992) Proc. Natl. Acad. Sci. USA 89:4047-4051.

Selection of the appropriate vector and promoter is well within the level of ordinary skill in the art. The expression vector may also contain a ribosome binding site for translation initiation and a transcription terminator. The expression vector may also include appropriate sequences for amplifying expression.

Examples of suitable mammalian expression vectors (expression vectors suitable for use in mammalian host cells) include, but are not limited to: recombinant viruses, nucleic acid vectors, such as plasmids, bacterial artificial chromosomes, yeast artificial chromosomes, human artificial chromosomes, cDNA, cRNA, and polymerase chain reaction (PCR) product expression cassettes. Examples of suitable promoters for driving expression of a Gata4-, Mef2c-, or Tbx5-encoding nucleotide sequence include, but are not limited to, retroviral long terminal repeat (LTR) elements; constitutive promoters such as CMV, HSV1-TK, SV40, EF-1α, β-actin; phosphoglycerol kinase (PGK), and inducible promoters, such as those containing Tet-operator elements. In some cases, the mammalian expression vector(s) encodes, in addition to exogenous Gata4, Mef2c, and Tbx5 polypeptides, a marker gene that facilitates identification or selection of cells that have been transfected or infected. Examples of marker genes include, but are not limited to, genes encoding fluorescent proteins, e.g., enhanced green fluorescent protein, Ds-Red (DsRed: *Discosoma* sp. red fluorescent protein (RFP); Bevis and Glick (2002) *Nat. Biotechnol.* 20:83), yellow fluorescent protein, and cyano-fluorescent protein; and genes encoding proteins conferring resistance to a selection agent, e.g., a neomycin resistance gene, a puromycin resistance gene, a blasticidin resistance gene, and the like.

Examples of suitable viral vectors include, but are not limited, viral vectors based on retroviruses (including lentiviruses); adenoviruses; and adeno-associated viruses. An example of a suitable retrovirus-based vector is a vector based on murine moloney leukemia virus (MMLV); however, other recombinant retroviruses may also be used, e.g., Avian Leukosis Virus, Bovine Leukemia Virus, Murine Leukemia Virus (MLV), Mink-Cell focus-Inducing Virus, Murine Sarcoma Virus, Reticuloendotheliosis virus, Gibbon Abe Leukemia Virus, Mason Pfizer Monkey Virus, or Rous Sarcoma Virus, see, e.g., U.S. Pat. No. 6,333,195.

In other cases, the retrovirus-based vector is a lentivirus-based vector, (e.g., Human Immunodeficiency Virus-1 (HIV-1); Simian Immunodeficiency Virus (SIV); or Feline Immunodeficiency Virus (FIV)), See, e.g., Johnston et al., (1999), Journal of Virology, 73(6):4991-5000 (FIV); Negre D et al., (2002), Current Topics in Microbiology and Immunology, 261:53-74 (SIV); Naldini et al., (1996), Science, 272:263-267 (HIV).

The recombinant retrovirus may comprise a viral polypeptide (e.g., retroviral env) to aid entry into the target cell. Such viral polypeptides are well-established in the art, see, e.g., U.S. Pat. No. 5,449,614. The viral polypeptide may be an amphotropic viral polypeptide, e.g., amphotropic env, which aids entry into cells derived from multiple species, including cells outside of the original host species. The viral polypeptide may be a xenotropic viral polypeptide that aids entry into cells outside of the original host species. In some embodiments, the viral polypeptide is an ecotropic viral polypeptide, e.g., ecotropic env, which aids entry into cells of the original host species.

Examples of viral polypeptides capable of aiding entry of retroviruses into cells include but are not limited to: MMLV amphotropic env, MMLV ecotropic env, MMLV xenotropic env, vesicular stomatitis virus-g protein (VSV-g), HIV-1 env, Gibbon Ape Leukemia Virus (GALV) env, RD114, FeLV-C, FeLV-B, MLV 10A1 env gene, and variants thereof, including chimeras. See e.g., Yee et al., (1994), Methods Cell Biol., Pt A:99-112 (VSV-G); U.S. Pat. No. 5,449,614. In some cases, the viral polypeptide is genetically modified to promote expression or enhanced binding to a receptor.

In general, a recombinant virus is produced by introducing a viral DNA or RNA construct into a producer cell. In some cases, the producer cell does not express exogenous genes. In other cases, the producer cell is a "packaging cell" comprising one or more exogenous genes, e.g., genes encoding one or more gag, pol, or env polypeptides and/or one or more retroviral gag, pol, or env polypeptides. The retroviral packaging cell may comprise a gene encoding a viral polypeptide, e.g., VSV-g that aids entry into target cells. In some cases, the packaging cell comprises genes encoding one or more lentiviral proteins, e.g., gag, pol, env, vpr, vpu, vpx, vif, tat, rev, or nef. In some cases, the packaging cell comprises genes encoding adenovirus proteins such as E1A or E1B or other adenoviral proteins. For example, proteins supplied by packaging cells may be retrovirus-derived proteins such as gag, pol, and env; lentivirus-derived proteins such as gag, pol, env, vpr, vpu, vpx, vif, tat, rev, and nef; and adenovirus-derived proteins such as E1A and E1B. In many examples, the packaging cells supply proteins derived from a virus that differs from the virus from which the viral vector derives.

Packaging cell lines include but are not limited to any easily-transfectable cell line. Packaging cell lines can be based on 293T cells, NIH3T3, COS or HeLa cell lines. Packaging cells are often used to package virus vector plasmids deficient in at least one gene encoding a protein required for virus packaging. Any cells that can supply a protein or polypeptide lacking from the proteins encoded by such virus vector plasmid may be used as packaging cells. Examples of packaging cell lines include but are not limited to: Platinum-E (Plat-E); Platinum-A (Plat-A); BOSC 23 (ATCC CRL 11554); and Bing (ATCC CRL 11270), see, e.g., Morita et al., (2000), Gene Therapy, 7:1063-1066; Onishi et al., (1996), Experimental Hematology, 24:324-329; U.S. Pat. No. 6,995,009. Commercial packaging lines are also useful, e.g., Ampho-Pak 293 cell line, Eco-Pak 2-293 cell line, RetroPack PT67 cell line, and Retro-X Universal Packaging System (all available from Clontech).

The retroviral construct may be derived from a range of retroviruses, e.g., MMLV, HIV-1, SIV, FIV, or other retrovirus described herein. The retroviral construct may encode all viral polypeptides necessary for more than one cycle of replication of a specific virus. In some cases, the efficiency of viral entry is improved by the addition of other factors or other viral polypeptides. In other cases, the viral polypeptides encoded by the retroviral construct do not support more than one cycle of replication, e.g., U.S. Pat. No. 6,872,528. In such circumstances, the addition of other factors or other viral polypeptides can help facilitate viral entry. In an exemplary embodiment, the recombinant retrovirus is HIV-1 virus comprising a VSV-g polypeptide but not comprising a HIV-1 env polypeptide.

The retroviral construct may comprise: a promoter, a multi-cloning site, and/or a resistance gene. Examples of promoters include but are not limited to CMV, SV40, EF1α, β-actin; retroviral LTR promoters, and inducible promoters. The retroviral construct may also comprise a packaging signal (e.g., a packaging signal derived from the MFG vector; a psi packaging signal). Examples of some retroviral constructs known in the art include but are not limited to: pMX, pBabeX or derivatives thereof. See e.g., Onishi et al., (1996), Experimental Hematology, 24:324-329. In some cases, the retroviral construct is a self-inactivating lentiviral vector (SIN) vector, see, e.g., Miyoshi et al., (1998), J. Virol., 72(10):8150-8157. In some cases, the retroviral construct is LL-CG, LS-CG, CL-CG, CS-CG, CLG or MFG. Miyoshi et al., (1998), J. Virol., 72(10):8150-8157; Onishi et al., (1996), Experimental Hematology, 24:324-329; Riviere et al., (1995), PNAS, 92:6733-6737. Virus vector plasmids (or constructs), include: pMXs, pMxs-IB, pMXs-puro, pMXs-neo (pMXs-IB is a vector carrying the blasticidin-resistant gene in stead of the puromycin-resistant gene of pMXs-puro) Kimatura et al., (2003), Experimental Hematology, 31: 1007-1014; MFG Riviere et al., (1995), Proc. Natl. Acad. Sci. U.S.A., 92:6733-6737; pBabePuro; Morgenstern et al., (1990), Nucleic Acids Research, 18:3587-3596; LL-CG, CL-CG, CS-CG, CLG Miyoshi et al., (1998), Journal of Virology, 72:8150-8157 and the like as the retrovirus system, and pAdex1 Kanegae et al., (1995), Nucleic Acids Research, 23:3816-3821 and the like as the adenovirus system. In exemplary embodiments, the retroviral construct comprises blasticidin (e.g., pMXs-IB), puromycin (e.g., pMXs-puro, pBabePuro); or neomycin (e.g., pMXs-neo). See, e.g., Morgenstern et al., (1990), Nucleic Acids Research, 18:3587-3596.

Methods of producing recombinant viruses from packaging cells and their uses are well established; see, e.g., U.S. Pat. Nos. 5,834,256; 6,910,434; 5,591,624; 5,817,491; 7,070,994; and 6,995,009. Many methods begin with the introduction of a viral construct into a packaging cell line. The viral construct may be introduced into a host fibroblast by any method known in the art, including but not limited to: a calcium phosphate method, a lipofection method (Felgner et al. (1987) Proc. Natl. Acad. Sci. U.S.A. 84:7413-7417), an electroporation method, microinjection, Fugene transfection, and the like, and any method described herein.

A nucleic acid construct can be introduced into a host cell using a variety of well known techniques, such as non-viral based transfection of the cell. In an exemplary aspect the construct is incorporated into a vector and introduced into a host cell. Introduction into the cell may be performed by any non-viral based transfection known in the art, such as, but not limited to, electroporation, calcium phosphate mediated transfer, nucleofection, sonoporation, heat shock, magnetofection, liposome mediated transfer, microinjection, microprojectile mediated transfer (nanoparticles), cationic polymer mediated transfer (DEAE-dextran, polyethylenimine, polyethylene glycol (PEG) and the like) or cell fusion. Other methods of transfection include transfection reagents such as Lipofectamine™, Dojindo Hilymax™, Fugene™, jetPEI™ Effectene™, and DreamFect™

Additional Polypeptides

In some embodiments, a subject method does not require and does not involve introducing into a post-natal fibroblast any of an exogenous Hopx polypeptide, an exogenous Nkx2-5 polypeptide, an exogenous Hrt2 polypeptide, an exogenous Pitx2 polypeptide, an exogenous Smyd1 polypeptide, an exogenous Myocd polypeptide, an exogenous Baf60c polypeptide, an exogenous Srf polypeptide, an exogenous Isl1 polypeptide, an exogenous Hand2 polypeptide, or an exogenous Mesp1 polypeptide. In some embodiments, a subject method does not require and does not involve introducing into a post-natal fibroblast a nucleic acid(s) comprising nucleotide sequences encoding any of Hopx, Nkx2-5, Hrt2, Pitx2, Smyd1, Myocd, Baf60c, Srf, Isl1, Hand2, or Mesp1. However, in other embodiments, a subject method can involve use of Gata4, Mef2c, and Tbx5; and one or more additional polypeptides that can contribute to the reprogramming of a post-natal fibroblast directly into a cardiomyocyte.

A post-natal fibroblast can be modified (by introduction into the post-natal fibroblast of a polypeptide), or genetically modified as described above, where the post-natal fibroblast is modified with a Gata4 polypeptide, an Mef2c polypeptide, and a Tbx5 polypeptide, or where the post-natal fibroblast is genetically modified with one or more nucleic acids comprising nucleotide sequences encoding a Gata4 polypeptide, an Mef2c polypeptide, and a Tbx5 polypeptide. In some embodiments, one or more additional polypeptides (or nucleic acids comprising nucleotide sequences encoding same) are introduced into a post-natal fibroblast, where the one or more additional polypeptides is selected from Mesp1, Isl1, Myocd, Smyd1, Srf, Baf60c, Hand2, Hopx, Hrt2, Pitx2c, and Nkx2-5.

Thus, in some embodiments, a post-natal fibroblast is modified by introduction into the post-natal fibroblast of a Gata4 polypeptide, an Mef2c polypeptide, and a Tbx5 polypeptide; and 1, 2, 3, 4, 5, 6, 7, 8, 9, 10, or 11, of a Mesp1 polypeptide, a Isl1 polypeptide, a Myocd polypeptide, a Smyd1 polypeptide, a Srf polypeptide, a Baf60c polypeptide, a Hand2 polypeptide, a Hopx polypeptide, a Hrt2 polypeptide, a Pitx2c polypeptide, and an Nkx2-5 polypeptide. In some embodiments, a post-natal fibroblast is genetically modified with one or more nucleic acids comprising nucleotide sequences encoding a Gata4 polypeptide, an Mef2c polypeptide, and a Tbx5 polypeptide; and 1, 2, 3, 4, 5, 6, 7, 8, 9, 10, or 11, of a Mesp1 polypeptide, a Isl1 polypeptide, a Myocd polypeptide, a Smyd1 polypeptide, a Srf polypeptide, a Baf60c polypeptide, a Hand2 polypeptide, a Hopx polypeptide, a Hrt2 polypeptide, a Pitx2c polypeptide, and an Nkx2-5 polypeptide. The following are exemplary, non-limiting combinations.

In some embodiments, a post-natal fibroblast is modified by introduction into the post-natal fibroblast of a Gata4 polypeptide, an Mef2c polypeptide, a Tbx5 polypeptide, a Isl1 polypeptide, an Mesp1 polypeptide, a Myocd polypeptide, an Nkx2.5 polypeptide, a Smyd1 polypeptide, and a Srf polypeptide. In some embodiments, a post-natal fibroblast is genetically modified with one or more nucleic acids comprising nucleotide sequences encoding a Gata4 polypeptide, an Mef2c polypeptide, a Tbx5 polypeptide, a Isl1 polypeptide, an Mesp1 polypeptide, a Myocd polypeptide, an Nkx2.5 polypeptide, a Smyd1 polypeptide, and a Srf polypeptide.

In some embodiments, a post-natal fibroblast is modified by introduction into the post-natal fibroblast of a Gata4 polypeptide, an Mef2c polypeptide, a Tbx5 polypeptide, an Mesp1 polypeptide, a Myocd polypeptide, and an Nkx2.5 polypeptide. In some embodiments, a post-natal fibroblast is genetically modified with one or more nucleic acids comprising nucleotide sequences encoding a Gata4 polypeptide, an Mef2c polypeptide, a Tbx5 polypeptide, a Mesp1 polypeptide, a Myocd polypeptide, and an Nkx2.5 polypeptide.

In some embodiments, a post-natal fibroblast is modified by introduction into the post-natal fibroblast of a Gata4 polypeptide, an Mef2c polypeptide, a Tbx5 polypeptide, an Mesp1 polypeptide, and a Myocd polypeptide. In some embodiments, a post-natal fibroblast is genetically modified with one or more nucleic acids comprising nucleotide sequences encoding a Gata4 polypeptide, an Mef2c polypeptide, a Tbx5 polypeptide, an Mesp1 polypeptide, and a Myocd polypeptide.

In some embodiments, a post-natal fibroblast is modified by introduction into the post-natal fibroblast of a Gata4 polypeptide, an Mef2c polypeptide, a Tbx5 polypeptide, and an Mesp1 polypeptide. In some embodiments, a post-natal fibroblast is genetically modified with one or more nucleic acids comprising nucleotide sequences encoding a Gata4 polypeptide, an Mef2c polypeptide, a Tbx5 polypeptide, and an Mesp1 polypeptide.

Amino acid sequences of Mesp1, Isl1, Myocd, Smyd1, Srf, Baf60c, Hand2, Hopx, Hrt2, Pitx2c, and Nkx2-5 polypeptides are known in the art, as are nucleotide sequences encoding the polypeptides. See, e.g., GenBank Accession Nos: 1) AAR88511.1 (*Homo sapiens* BAF60c; amino acid sequence), and AY450431 (nucleotide sequence encoding the AAR88511.1 amino acid sequence); 2) AAR88510.1 (*Homo sapiens* BAF60c; amino acid sequence), and AY450430 (nucleotide sequence encoding the AAR88510.1 amino acid sequence); 3) NP_068808 (*Homo sapiens* Hand2 amino acid sequence), and NM_021973 (nucleotide sequence encoding the NP_068808 amino acid sequence); 4) NP_115884.4 (*Homo sapiens* Hopx amino acid sequence), and NM_032495 (nucleotide sequence encoding the NP_115884.4 amino acid sequence); 5) NP_631958.1 (*Homo sapiens* Hopx amino acid sequence), and NM_139212 (nucleotide sequence encoding the NP_631958.1 amino acid sequence); 6) AAG31157 (*Homo sapiens* Hrt2 amino acid sequence), and AF311884 (nucleotide sequence encoding the AAG31157 amino acid sequence; 7) NP_000316 (*Homo sapiens* Pitx2c amino acid sequence), and NM_000325 (nucleotide sequence encoding the NP_000316 amino acid sequence); 8) NP_061140.1 (*Homo sapiens* Mesp1 amino acid sequence), and NM_018670.3 (nucleotide sequence encoding the NP_061140.1 amino acid sequence); 9) XP_523151.2 (*Pan troglodytes* Mesp1 amino acid sequence), and XM_523151 (nucleotide sequence encoding the XP_523151.2 amino acid sequence; 10) BAA12041.1 (*Mus musculus* Mesp1 amino acid sequence), and BAA12041 (nucleotide sequence encoding the BAA12041.1 amino acid sequence); 11) NP_001101001.1 (*Rattus norvegicus* Mesp1 amino acid sequence), and NM_001107531 (nucleotide sequence encoding the NP_001101001.1 amino acid sequence; 12) NP_004378.1 (*Homo sapiens* NKX2-5 amino acid sequence), and NM_004387 (nucleotide sequence encoding the NP_004378.1 amino acid sequence; 13) NP_001159648.1 (*Homo sapiens* NKX2-5 amino acid sequence), and NM_001166176 (nucleotide sequence encoding the NP_001159648.1 amino acid sequence; 14) NP_001159647.1 (*Homo sapiens* Nkx2-5 amino acid sequence), and NM_001166175 (nucleotide sequence encoding the NP_001159647.1 amino acid sequence; 15) NP_002193.2 (*Homo sapiens* Isl1 amino acid sequence), and NM_002202 (nucleotide sequence encoding the NP_002193.2 amino acid sequence); 16) NP_059035 (*Rattus norvegicus* Isl1 amino acid), and NM_017339 (nucleotide sequence encoding the NP_059035 amino acid sequence); 17) BAC41153 (*Mus musculus* Isl1 amino acid sequence), and AK090263 (nucleotide sequence encoding the BAC41153 amino acid sequence); 18) NP_001139785.1 (*Homo sapiens* Myocd amino acid sequence), and NM_001146313 (nucleotide sequence encoding the NP_001139785.1 amino acid sequence); 19) NP_001139784.1 (*Homo sapiens* Myocd amino acid sequence), and NM_001146312 (nucleotide sequence encoding the NP_001139784.1 amino acid sequence); 20) NP_705832.1 (*Homo sapiens* Myocd amino acid sequence), and NM_153604 (nucleotide sequence encoding the NP_705832.1 amino acid sequence); 21) NP_938015.1 (*Homo sapiens* Smyd1 amino acid sequence), and NM_198274 (nucleotide sequence encoding the NP_938015.1 amino acid sequence); 22) NP_001100065.1 (*Rattus norvegicus* Smyd1 amino acid sequence), and NM_001106595 (nucleotide sequence encoding the NP_001100065.1 amino acid sequence); 23) NP_001153599.1 (*Mus musculus* Smyd1 amino acid sequence), and NM_001160127 (nucleotide sequence encoding the NP_001153599.1 amino acid sequence); 24) NP_003122.1 (*Homo sapiens* Srf amino acid sequence), and NM_003131 (nucleotide sequence encoding the NP_003122.1 amino acid sequence; 25) XP_518487.2 (*Pan troglodytes* Srf amino acid sequence), and XM_518487 (nucleotide sequence encoding the XP_518487.2 amino acid sequence; 26) NP_001102772.1 (*Rattus norvegicus* Srf amino acid sequence), and NM_001109302 (nucleotide sequence encoding the NP_001102772.1 amino acid sequence).

Suitable mino acid sequences of Mesp1, Isl1, Myocd, Smyd1, Srf, Baf60c, Hand2, Hopx, Hrt2, Pitx2c, and Nkx2-5 polypeptides include amino acid sequences having at least about 85%, at least about 90%, at least about 95%, at least about 98%, at least about 99%, or 100%, amino acid sequence identity to an amino acid sequence set forth in one of the aforementioned GenBank entries.

Suitable nucleotide sequences encoding Mesp1, Isl1, Myocd, Smyd1, Srf, Baf60c, Hand2, Hopx, Hrt2, Pitx2c, and Nkx2-5 polypeptides include nucleotide sequences having at least about 85%, at least about 90%, at least about 95%, at least about 98%, at least about 99%, or 100%, nucleotide sequence identity to a nucleotide sequence set forth in one of the aforementioned GenBank entries.

Additional Factors

A post-natal fibroblast can be modified or genetically modified as described above; and can also be contacted with one or more additional factors which can be added to the culture system, e.g., the one or more additional factors can be included as additives in the culture medium. Examples of such additional factors include, but are not limited to: histone deacetylase (HDAC) inhibitors, see, e.g. Huangfu et al. (2008) Nature Biotechnol. 26:795-797; Huangfu et al. (2008) Nature Biotechnol. 26: 1269-1275; DNA demethylating agents, see, e.g., Mikkelson et al (2008) Nature 454, 49-55; histone methyltransferase inhibitors, see, e.g., Shi et al. (2008) Cell Stem Cell 2:525-528; L-type calcium channel agonists, see, e.g., Shi et al. (2008) 3:568-574; Wnt3a, see, e.g., Marson et al. (2008) Cell 134:521-533; siRNA, see, e.g., Zhao et al. (2008) Cell Stem Cell 3: 475-479.

Histone deacetylases (HDAC) are a class of enzymes that remove acetyl groups from an [epsilon]-N-acetyl lysine amino acid on a histone. Exemplary HDACs include those Class I HDAC: HDAC1, HDAC2, HDAC3, HDAC8; and Class II HDACs: HDAC4, HDAC5, HDAC6, HDAC7A, HDAC9, HDAC10. Type I mammalian HDACs include: HDAC1, HDAC2, HDAC3, HDAC8, and HDACI1. Type II mammalian HDACs include: HDAC4, HDAC5, HDAC6, HDAC7, HDAC9, and HDAC1. In some embodiments, an HDAC inhibitor selectively inhibits a Class I or a Class II HDAC.

Suitable concentrations of an HDAC inhibitor range from about 0.001 nM to about 10 mM, depending on the particular HDAC inhibitor to be used. The HDAC concentration can range from 0.01 nM to 1000 nM.

Suitable HDAC inhibitors include any agent that inhibits HDAC enzymatic activity in deacetylation of histone. Suitable HDAC inhibitors include, but are not limited to, carboxylate HDAC inhibitors; hydroxamic acid HDAC inhibitors; peptide (e.g., cyclic tetrapeptide) HDAC inhibitors; benzamide HDAC inhibitors; electrophilic ketone HDAC inhibitors; hybrid polar HDAC inhibitors; and short chain fatty acid HDAC inhibitors.

Suitable HDAC inhibitors include trichostatin A and its analogs, for example: trichostatin A (TSA); and trichostatin C (Koghe et al., (1998), Biochem. Pharmacol, 56:1359-1364).

Suitable peptide HDAC inhibitors include, for example: oxamflatin [(2E)-5-[3-[(phenylsulfonyl)aminophenyl]-pent-2-ene-4-inohydroxamic acid (Kim et al., (1999), Oncogene, 18:2461-2470); Trapoxin A (cyclo-(L-phenylalanyl-L-phenylalanyl-D-pipecolinyl-L-2-amino-8-oxo-9,10-epoxy-decanoyl) (Kijima et al., (1993), J. Biol. Chem. 268:22429-22435); FR901228, depsipeptide ((1S,4S,7Z,10S,16E,21R)-7-ethylidene-4,21-diisopropyl-2-oxa-12,13-dithia-5,8,20,23-tetrazabicyclo[8.7.6]tricos-[6-ene-3,6,9,19,22-pentone) (Nakajima et al., (1998). Ex. Cell Res., 241:126-133); apicidin, cyclic tetrapeptide [cyclo-(N—O-methyl-L-tryptophanyl-L-isoleucinyl-D-pipecolinyl-L-2-amino-8-oxodecanoyl)] (Darkin-Rattray et al., (1996), Proc. Natl. Acad. Sci. U.S.A., 93:13143-13147; apicidin Ia, apicidin Ib, apicidin Ic, apicidin IIa, and apicidin IIb (WO 97/11366); HC-toxin, cyclic tetrapeptide (Bosch et al. (1995), Plant Cell, 7:1941-1950); and chlamydocin (Bosch et al., supra).

Suitable HDAC inhibitors include hybrid polar compounds (HPC) based on hydroxamic acid, for example: salicyl hydroxamic acid (SBHA) (Andrews et al., (2000), International J. Parasitology, 30:761-8); suberoylanilide hydroxamic acid (SAHA) (Richon et al., (1998), Proc. Natl. Acad. Sci. U.S.A., 95: 3003-7); azelaic bishydroxamic acid (ABHA) (Andrews et al., supra); azelaic-1-hydroxamate-9-anilide (AAHA) (Qiu et al., (2000), Mol. Biol. Cell, 11:2069-83); M-carboxy cinnamic acid bishydroxamide (CBHA) (Richon et al., supra); 6-(3-chlorophenylureido) carpoic hydroxamic acid, 3-Cl-UCHA) (Richon et al., supra); MW2796 (Andrews et al., supra); MW2996 (Andrews et al., supra); the hydroxamic acid derivative NVP-LAQ-824 (Catley et al. (2003) *Blood* 102:2615; and Atadja et al. (2004) *Cancer Res.* 64:689); and CBHA (m-carboxycinnaminic acid bishydroxamic acid).

Suitable HDAC inhibitors include short chain fatty acid (SCFA) compounds, for example: sodium butyrate (Cousens et al., (1979), J. Biol. Chem., 254:1716-23); isovalerate (McBain et al., (1997), Biochem. Pharm., 53:1357-68); valproic acid; valerate (McBain et al., supra); 4-phenyl butyric acid (4-PBA) (Lea and Tulsyan, (1995), Anticancer Research, 15:879-3); phenyl butyric acid (PB) (Wang et al., (1999), Cancer Research 59: 2766-99); propinate (McBain et al., supra); butylamide (Lea and Tulsyan, supra); isobutylamide (Lea and Tulsyan, supra); phenyl acetate (Lea and Tulsyan, supra); 3-bromopropionate (Lea and Tulsyan, supra); tributyrin (Guan et al., (2000), Cancer Research, 60:749-55); arginine butyrate; isobutyl amide; and valproate.

Suitable HDAC inhibitors include benzamide derivatives, for example: MS-275 [N-(2-aminophenyl)-4-[N-(pyridine-3-yl-methoxycarbonyl)aminomethyl]benzam-ide] (Saito et al., (1999), Proc. Natl. Acad. Sci. U.S.A., 96:4592-7); and a 3'-amino derivative of MS-275 (Saito et al., supra); and CI-994.

Additional suitable HDAC inhibitors include: BML-210 (N-(2-aminophenyl)-N'-phenyl-octanediamide); Depudecin (e.g., (−)-Depudecin); Nullscript (4-(1,3-Dioxo-1H,3H-benzo[de]isoquinolin-2-yl)-N-hydroxybutanamide); Scriptaid; Suramin Sodium; pivaloyloxymethyl butyrate (Pivanex, AN-9), Trapoxin B; CI-994 (i.e., N-acetyl dinaline); MGCD0103 (N-(2-Aminophenyl)-4-[[(4-pyridin-3-ylpyrimidin-2-yl)amino]methyl]benzamide); JNJ16241199 (R-306465; see, e.g., Arts et al. (2007) *Br. J. Cancer* 97:1344); Tubacin; A-161906; proxamide; oxamflatin; 3-C1-UCHA (6-(3-chlorophenylureido)caproic hydroxamic acid); and AOE (2-amino-8-oxo-9,10-epoxydecanoic acid).

Suitable DNA methylation inhibitors are inhibitors of DNA methyltransferase, and include, but are not limited to, 5-deoxy-azacytidine (DAC); 5-azacytidine (5-aza-CR) (Vidaza); 5-aza-2'-deoxycytidine (5-aza-CdR; decitabine); 1-[beta]-D-arabinofuranosyl-5-azacytosine; dihydro-5-azacytidine; zebularine ((1-(β-D-ribofuranosyl)-1,2-dihydropyrimidin-2-one); Sinefungin (e.g., InSolution™ Sinefungin), and 5-fluoro-2'-deoxycyticine (FdCyd). Examples of suitable non-nucleoside DNA methyltransferse inhibitors (e.g., other than procaine) include: (−)-epigallocatechin-3-gallate (EGCG); hydralazine; procainamide; psammaplin A (N,N"-(dithiodi-2,1-ethanediyl)bis[3-bromo-4-hydroxy-a-(hydroxyimino)-benzenepropanamide); and RG108 (2-(1,3-Dioxo-1,3-dihydro-2H-isoindol-2-yl)-3-(1H-indol-3-yl) propionic acid).

Suitable histone methyltransferase (HMT) inhibitors include, but are not limited to, SC-202651 (2-(Hexahydro-4-methyl-1H-1,4-diazepin-1-yl)-6,7-dimethoxy-N-(1-(phenylmethyl)-4-piperidinyl)-4-quinazolinamine); chaetocin (Grainer et al. (2005) *Nature Chem. Biol.* 1:143); BIX-01294 (2-(Hexahydro-4-methyl-1H-1,4-diazepin-1-yl)-6,7-dimethoxy-N-[1-(phenylmethyl)-4-piperidinyl]-4-quinazolinamine trihydrochloride); 3-deazaneplanocin (Glazer et al. (1986) *BBRC* 135:688); and the like.

Genetically Modified Host Cells

The present disclosure provides genetically modified host cells, including isolated genetically modified host cells, where a subject genetically modified host cell comprises (has been genetically modified with) one or more exogenous nucleic acids comprising nucleotide sequences encoding one or more of Gata4, Mef2c, Tbx5, Mesp1, Nkx2-5, Isl-1, Myocd, Smyd1, and Srf polypeptides. In some embodiments, a subject genetically modified host cell is in vitro. In some embodiments, a subject genetically modified host cell is a human cell or is derived from a human cell. In some embodiments, a subject genetically modified host cell is a rodent cell or is derived from a rodent cell. The present disclosure further provides progeny of a subject genetically modified host cell, where the progeny can comprise the same exogenous nucleic acid as the subject genetically modified host cell from which it was derived. The present disclosure further provides a composition comprising a subject genetically modified host cell.

The present disclosure provides genetically modified host cells, including isolated genetically modified host cells, where a subject genetically modified host cell comprises (has been genetically modified with) one or more exogenous nucleic acids comprising nucleotide sequences encoding Gata4, Mef2c, and Tbx5 polypeptides. In some embodiments, a subject genetically modified host cell is in vitro. In some embodiments, a subject genetically modified host cell is a human cell or is derived from a human cell. In some embodiments, a subject genetically modified host cell is a rodent cell or is derived from a rodent cell. The present disclosure further provides progeny of a subject genetically modified host cell, where the progeny can comprise the same exogenous nucleic acid as the subject genetically modified host cell from which it was derived. The present disclosure further provides a composition comprising a subject genetically modified host cell.

Genetically Modified Post-Natal Fibroblasts

In some embodiments, a subject genetically modified host cell is a genetically modified post-natal fibroblast. Thus, the present disclosure provides a genetically modified post-natal fibroblast that comprises (has been genetically modified with) one or more exogenous nucleic acids comprising nucleotide sequences encoding one or more of Gata4, Mef2c, Tbx5, Mesp1, Nkx2-5, Isl-1, Myocd, Smyd1, and Srf polypeptides, or a subset (e.g., Gata4, Mef2c, and Tbx5 polypeptides). In some embodiments, a subject genetically modified post-natal fibroblast is in vitro. In some embodiments, a subject genetically modified post-natal fibroblast is a human cell or is derived from a human cell. In some embodiments, a subject genetically modified post-natal fibroblast is a rodent cell or is derived from a rodent cell. The present disclosure further provides progeny of a subject genetically modified post-natal fibroblast, where the progeny can comprise the same exogenous nucleic acid as the subject genetically modified post-natal fibroblast from which it was derived. The present disclosure further provides a composition comprising a subject genetically modified post-natal fibroblast.

Genetically Modified Induced Cardiomyocytes

The present disclosure further provides cardiomyocytes ("induced cardiomyocytes") derived from a subject genetically modified host cell. Because a subject induced cardiomyocyte is derived from a subject genetically modified post-natal fibroblast, a subject induced cardiomyocyte is also genetically modified. Thus, the present disclosure provides a genetically modified cardiomyocyte that comprises one or more exogenous nucleic acids comprising nucleotide sequences encoding one or more of Gata4, Mef2c, Tbx5, Mesp1, Nkx2-5, Isl-1, Myocd, Smyd1, and Srf polypeptides, or a subset (e.g., Gata4, Mef2c, and Tbx5 polypeptides). In some embodiments, a subject genetically modified cardiomyocyte is in vitro. In some embodiments, a subject genetically modified cardiomyocyte is a human cell or is derived from a human cell. In some embodiments, a subject genetically modified cardiomyocyte is a rodent cell or is derived from a rodent cell. The present disclosure further provides progeny of a subject genetically modified cardiomyocyte, where the progeny can comprise the same exogenous nucleic acid as the subject genetically modified cardiomyocyte from which it was derived. The present disclosure further provides a composition comprising a subject genetically modified cardiomyocyte.

Compositions

The present disclosure provides a composition comprising a subject genetically modified host cell (e.g., a subject genetically modified post-natal fibroblast; progeny of a subject genetically modified post-natal fibroblast; a subject induced cardiomyocyte; progeny of a subject induced cardiomyocyte). A subject composition comprises a subject genetically modified host cell; and will in some embodiments comprise one or more further components, which components are selected based in part on the intended use of the genetically modified host cell. Suitable components include, but are not limited to, salts; buffers; stabilizers; protease-inhibiting agents; cell membrane- and/or cell wall-preserving compounds, e.g., glycerol, dimethylsulfoxide, etc.; nutritional media appropriate to the cell; and the like.

In some embodiments, a subject composition comprises a subject genetically modified host cell and a matrix (a "subject genetically modified cell/matrix composition"), where a subject genetically modified host cell is associated with the matrix. The term "matrix" refers to any suitable carrier material to which the genetically modified cells are able to attach themselves or adhere in order to form a cell composite. In some embodiments, the matrix or carrier material is present already in a three-dimensional form desired for later application. For example, bovine pericardial tissue is used as matrix which is crosslinked with collagen, decellularized and photofixed.

For example, a matrix (also referred to as a "biocompatible substrate") is a material that is suitable for implantation into a subject. A biocompatible substrate does not cause toxic or injurious effects once implanted in the subject. In one embodiment, the biocompatible substrate is a polymer with a surface that can be shaped into the desired structure that requires repairing or replacing. The polymer can also be shaped into a part of a structure that requires repairing or replacing. The biocompatible substrate can provide the supportive framework that allows cells to attach to it and grow on it.

Suitable matrix components include, e.g., collagen; gelatin; fibrin; fibrinogen; laminin; a glycosaminoglycan; elastin; hyaluronic acid; a proteoglycan; a glycan; poly(lactic acid); poly(vinyl alcohol); poly(vinyl pyrrolidone); poly(ethylene oxide); cellulose; a cellulose derivative; starch; a starch derivative; poly(caprolactone); poly(hydroxy butyric acid); mucin; and the like. In some embodiments, the matrix comprises one or more of collagen, gelatin, fibrin, fibrinogen, laminin, and elastin; and can further comprise a non-proteinaceous polymer, e.g., can further comprise one or more of poly(lactic acid), poly(vinyl alcohol), poly(vinyl pyrrolidone), poly(ethylene oxide), poly(caprolactone), poly(hydroxy butyric acid), cellulose, a cellulose derivative, starch, and a starch derivative. In some embodiments, the matrix comprises one or more of collagen, gelatin, fibrin, fibrinogen, laminin, and elastin; and can further comprise hyaluronic acid, a proteoglycan, a glycosaminoglycan, or a glycan. Where the matrix comprises collagen, the collagen can comprise type I collagen, type II collagen, type III collagen, type V collagen, type XI collagen, and combinations thereof.

The matrix can be a hydrogel. A suitable hydrogel is a polymer of two or more monomers, e.g., a homopolymer or a heteropolymer comprising multiple monomers. Suitable hydrogel monomers include the following: lactic acid, glycolic acid, acrylic acid, 1-hydroxyethyl methacrylate (HEMA), ethyl methacrylate (EMA), propylene glycol methacrylate (PEMA), acrylamide (AAM), N-vinylpyrrolidone, methyl methacrylate (MMA), glycidyl methacrylate (GDMA), glycol methacrylate (GMA), ethylene glycol, fumaric acid, and the like. Common cross linking agents include tetraethylene glycol dimethacrylate (TEGDMA) and N,N'-methylenebisacrylamide. The hydrogel can be homopolymeric, or can comprise co-polymers of two or more of the aforementioned polymers. Exemplary hydrogels include, but are not limited to, a copolymer of poly(ethylene oxide) (PEO) and poly(propylene oxide) (PPO); Pluronic™ F-127 (a difunctional block copolymer of PEO and PPO of the nominal formula $EO_{100}$-$PO_{65}$-$EO_{100}$, where EO is ethylene oxide and PO is propylene oxide); poloxamer 407 (a tri-block copolymer consisting of a central block of poly(propylene glycol) flanked by two hydrophilic blocks of poly(ethylene glycol)); a poly(ethylene oxide)-poly(propylene oxide)-poly(ethylene oxide) co-polymer with a nominal molecular weight of 12,500 Daltons and a PEO:PPO ratio of 2:1); a poly(N-isopropylacrylamide)-base hydrogel (a PNIPAAm-based hydrogel); a PNIPAAm-acrylic acid co-polymer (PNIPAAm-co-AAc); poly(2-hydroxyethyl methacrylate); poly(vinyl pyrrolidone); and the like.

A subject genetically modified cell/matrix composition can further comprise one or more additional components, where suitable additional components include, e.g., a growth factor; an antioxidant; a nutritional transporter (e.g., transferrin); a polyamine (e.g., glutathione, spermidine, etc.); and the like.

The cell density in a subject genetically modified cell/matrix composition can range from about $10^2$ cells/mm$^3$ to about $10^9$ cells/mm$^3$, e.g., from about $10^2$ cells/mm$^3$ to about $10^4$ cells/mm$^3$, from about $10^4$ cells/mm$^3$ to about $10^6$ cells/mm$^3$, from about $10^6$ cells/mm$^3$ to about $10^7$ cells/mm$^3$, from about $10^7$ cells/mm$^3$ to about $10^8$ cells/mm$^3$, or from about $10^8$ cells/mm$^3$ to about $10^9$ cells/mm$^3$.

The matrix can take any of a variety of forms, or can be relatively amorphous. For example, the matrix can be in the form of a sheet, a cylinder, a sphere, etc.

Implantable Devices

The present disclosure provides an implantable device (such as an intravascular stent, a scaffold, a graft (e.g., an aortic graft), an artificial heart valve, a coronary shunt, a pacemaker electrode, an endocardial lead, etc.) that comprises a reprogramming composition comprising one or more of Gata4, Mef2c, Tbx5, Mesp1, Nkx2-5, Isl-1, Myocd, Smyd1, and Srf polypeptides. The present disclosure further provides an implantable device that comprises a reprogramming composition comprising one or more nucleic acids comprising nucleotide sequences encoding one or more of Gata4, Mef2c, Tbx5, Mesp1, Nkx2-5, Isl-1, Myocd, Smyd1, and Srf polypeptides. The reprogramming composition (comprising one or more of Gata4, Mef2c, Tbx5, Mesp1, Nkx2-5, Isl-1, Myocd, Smyd1, and Srf polypeptides, or comprising one or more nucleic acids comprising nucleotide sequences encoding one or more of Gata4, Mef2c, Tbx5, Mesp1, Nkx2-5, Isl-1, Myocd, Smyd1, and Srf polypeptides) can be coated onto a surface of the implantable device, or can be contained within a reservoir in the implantable device. Where the reprogramming composition is contained within a reservoir in the implantable device, the reservoir is structured so as to allow the reprogramming composition to elute from the device.

The present disclosure provides an implantable device (such as an intravascular stent, a scaffold, a graft (e.g., an aortic graft), an artificial heart valve, a coronary shunt, a pacemaker electrode, an endocardial lead, etc.) that comprises a reprogramming composition comprising a Gata4 polypeptide, a Mef2c polypeptide, and a Tbx5 polypeptide. The present disclosure further provides an implantable device that comprises a reprogramming composition comprising one or more nucleic acids comprising nucleotide sequences encoding Gata4, Mef2c, and Tbx5 polypeptides. The reprogramming composition (comprising Gata4, Mef2c, and Tbx5 polypeptides, or comprising one or more nucleic acids comprising nucleotide sequences encoding Gata4, Mef2c, and Tbx5 polypeptides) can be coated onto a surface of the implantable device, or can be contained within a reservoir in the implantable device. Where the reprogramming composition is contained within a reservoir in the implantable device, the reservoir is structured so as to allow the reprogramming composition to elute from the device.

When the implantable device is at a site in an individual, the nucleic acids or the polypeptides in the reprogramming composition leave the implantable device, and the polypeptides or the nucleic acids enter into a fibroblast at or near the site of the implantable device. Thus, a subject implantable device, when implanted in an individual, can provide for introduction of reprogramming factors, or nucleic acids encoding same, into a fibroblast at or near the site of implant, and can thereby provide for reprogramming of the fibroblast into a cardiomyocyte. For example, where a subject implantable device is a stent, the stent can be implanted into a coronary artery, where the reprogramming factors, or nucleic acids encoding same, elute from the stent, enter fibroblasts in the coronary vascular bed, and reprogram the fibroblasts into cardiomyocytes.

The present disclosure provides a stent comprising a reprogramming composition. Intravascular stents include, e.g., self-expandable stents, balloon-expandable stents, and stent-grafts.

In some instances, a subject implantable device comprises: a reprogramming composition incorporated within a first polymeric material (a first layer) that is affixed to the surface of an implantable device (e.g., a stent); and a second polymeric material (e.g., a barrier layer) is affixed to the first polymeric material, where the second polymeric material controls the elution rate of the polypeptides or the nucleic acids present in the reprogramming composition. As an example, the first polymeric material can comprise a fluoropolymer; and the second polymeric material can comprise an acrylic.

In some instances, a subject implantable device comprises: a reprogramming composition incorporated into a polymeric layer (a first layer) that is coated onto a surface of an implantable device (e.g., a stent); and a barrier layer over at least a portion of the polymeric layer to reduce the rate of release of the polypeptides or nucleic acids contained within the reprogramming composition from the implantable device. The polymeric layer can comprise poly(methylmethacrylate) or poly(butylmethacrylate), and can further include poly(ethylene co-vinyl acetate). The barrier can comprise a polymer or an inorganic material.

Suitable polymer materials for first layer include, but are not limited to, polyurethanes, polyesterurethanes, silicone, fluoropolymers, ethylene vinyl acetate, polyethylene, polypropylene, polycarbonates, trimethylenecarbonate, polyphosphazene, polyhydroxybutyrate, polyhydroxyvalerate, polydioxanone, polyiminocarbonates, polyorthoesters, ethylene vinyl alcohol copolymer, L-polylactide, D,L-polylactide, polyglycolide, polycaprolactone, copolymers of lactide and glycolide, polymethylmethacrylate, poly(n-butyl)methacrylate, polyacrylates, polymethacrylates, elastomers, and mixtures thereof.

Representative elastomers include, but are not limited to, a thermoplastic elastomer material, polyether-amide thermoplastic elastomer, fluoroelastomers, fluorosilicone elastomer, sytrene-butadiene rubber, butadiene-styrene rubber, polyisoprene, neoprene (polychloroprene), ethylene-propylene elastomer, chloro-sulfonated polyethylene elastomer, butyl rubber, polysulfide elastomer, polyacrylate elastomer, nitrile, rubber, polyester, styrene, ethylene, propylene, butadiene and isoprene, polyester thermoplastic elastomer, and mixtures thereof.

The barrier layer is biocompatible (i.e., its presence does not elicit an adverse response from the body). The barrier layer can have a thickness ranging from about 50 angstroms to about 20,000 angstroms. The barrier can comprise mostly inorganic material. However, some organic compounds (e.g., polyacrylonitrile, polyvinylidene chloride, nylon 6-6, perfluoropolymers, polyethylene terephthalate, polyethylene 2,6-napthalene dicarboxylate, and polycarbonate) may be incorporated in the barrier. Suitable inorganic materials for use within the barrier include, but are not limited to, inorganic elements, such as pure metals including aluminum, chromium, gold, hafnium, iridium, niobium, palladium, platinum, tantalum, titanium, tungsten, zirconium, and alloys of these metals, and inorganic compounds, such as inorganic silicides, oxides, nitrides, and carbides. Generally, the solubility of the drug in the material of the barrier is significantly less than the solubility of the drug in the polymer carrier. Also, generally, the diffusivity of the drug in the material of the barrier is significantly lower than the diffusivity of the drug in the polymer carrier.

The barrier may or may not be biodegradable (i.e., capable of being broken down into harmless compounds by the action of the body). While non-biodegradable barrier materials may be used, some biodegradable materials may be used as barriers. For example, calcium phosphates such as hydroxyapatite, carbonated hydroxyapatite, tricalcium phosphate, beta-tricalcium phosphate, octacalcium phosphate, amorphous calcium phosphate, and calcium orthophosphate may be used. Certain calcium salts such as calcium phosphate (plaster of paris) may also be used. The biodegradability of the barrier may act as an additional mechanism for controlling drug release from the underlying first layer.

Methods of affixing the first layer onto the surface of an implantable device, and methods of affixing a barrier layer on the first layer, are known in the art. See, e.g., U.S. Pat. Nos. 7,695,731 and 7,691,401.

As noted above, in some embodiments, a subject implantable device comprises a reservoir comprising a reprogramming composition. For example, in some embodiments, a subject implantable device has at least one surface for contacting a bodily tissue, organ or fluid, where the implantable device comprises: a substrate having a contacting surface; and a drug-eluting coating on at least a portion of the contacting surface, where the coating is comprised of a polymer having zeolites dispersed through the polymer, and where a porous structure of the zeolites includes reservoirs containing a release agent and a reprogramming composition. The release agent prevents the therapeutic material from exiting the reservoir until a triggering condition is met. A triggering condition can be contact of the release agent with a bodily fluid; a change in pH proximate to the release agent; and the like.

Biodegradable polymers, suitable for use alone or in combination, include, but are not limited to: poly(α-hydroxy acids), such as, polycapro lactone (PCL), poly(lactide-co-glycolide) (PLGA), polylactide (PLA), and polyglycolide (PGA), and combinations and blends thereof above at different ratios to fine-tune release rates, PLGA-PEG (polyethylene glycol), PLA-PEG, PLA-PEG-PLA, polyanhydrides, trimethylene carbonates, polyorthoesters, polyaspirins, polyphosphagenes, and tyrozine polycarbonates; natural and synthetic hydrogel materials, e.g., collagen, starch, chitosans, gelatin, alginates, dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, and PLGA-PEO-PLGA. Polymer matrices according to embodiments of the present invention may include any of the following biostable polymers, alone or in combination: polyurethanes, polymethylmethacrylates copolymers, polyvinyl acetate (PVA), polyamides, and copolymers of polyurethane and silicone.

Reprogramming Composition

The present disclosure provides reprogramming compositions.

In some embodiments, a subject reprogramming composition comprises either: 1) a mixture of two or more of Gata4, Mef2c, Tbx5, Mesp1, Nkx2-5, Isl-1, Myocd, Smyd1, and Srf polypeptides; or 2) one or more nucleic acids comprising nucleotide sequences encoding two or more of Gata4, Mef2c, Tbx5, Mesp1, Nkx2-5, Isl-1, Myocd, Smyd1, and Srf polypeptides. The reprogramming composition can comprise, in addition to the polypeptides or the nucleic acids, one or more of: a salt, e.g., NaCl, MgCl, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino) ethanesulfonic acid sodium salt (MES), 3-(N-Morpholino) propanesulfonic acid (MOPS), N-tris[Hydroxymethyl] methyl-3-aminopropanesulfonic acid (TAPS), etc.; a solubilizing agent; a detergent, e.g., a non-ionic detergent such as Tween-20, etc.; a protease inhibitor; glycerol; and the like.

In some embodiments, a subject reprogramming composition comprises either: 1) a mixture of Gata4, Mef2c, and Tbx5 polypeptides; or 2) one or more nucleic acids comprising nucleotide sequences encoding Gata4, Mef2c, and Tbx5 polypeptides. The reprogramming composition can comprise, in addition to the polypeptides or the nucleic acids, one or more of: a salt, e.g., NaCl, MgCl, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino) ethanesulfonic acid sodium salt (MES), 3-(N-Morpholino) propanesulfonic acid (MOPS), N-tris[Hydroxymethyl] methyl-3-aminopropanesulfonic acid (TAPS), etc.; a solubilizing agent; a detergent, e.g., a non-ionic detergent such as Tween-20, etc.; a protease inhibitor; glycerol; and the like.

A subject reprogramming composition can be included in a subject implantable device, as described above. A subject reprogramming composition can be administered directly into an individual. A subject reprogramming composition is useful for reprogramming a post-natal fibroblast into a cardiomyocyte, which reprogramming can be carried out in vitro or in vivo. Reprogramming a post-natal fibroblast into a cardiomyocyte can be used to treat various cardiac disorders, as described below.

A subject reprogramming composition can include a pharmaceutically acceptable excipient. Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of a subject antibody adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some embodiments, a subject reprogramming composition is formulated as a controlled release formulation. Sustained-release preparations may be prepared using methods well known in the art. Suitable examples of sustained-release preparations include semipermeable matrices of solid hydrophobic polymers containing the antibody in which the matrices are in the form of shaped articles, e.g. films or microcapsules. Examples of sustained-release matrices include polyesters, copolymers of L-glutamic acid and ethyl-L-glutamate, non-degradable ethylene-vinyl acetate, hydrogels, polylactides, degradable lactic acid-glycolic acid copolymers and poly-D-(−)-3-hydroxybutyric acid. Possible loss of biological activity and possible changes in activity of a polypeptide or a nucleic acid comprised in sustained-release preparations may be prevented by using appropriate additives, by controlling moisture content and by developing specific polymer matrix compositions.

A subject reprogramming composition can further comprise one or more therapeutic agents. Therapeutic agents that can be included in a subject reprogramming composition can include, e.g., digitalis, a statin, an anti-platelet agent, an anti-coagulant, a calcium channel blocker, an angiotensin-converting enzyme inhibitor, a vasodilator, an angiotensin II receptor blocker, a beta blocker, and the like.

Utility

A subject method of reprogramming a post-natal fibroblast is useful for generating a population of induced cardiomyocytes, which induced cardiomyocytes can be used in analytical assays, for generating artificial heart tissue, and in treatment methods.

Analytical Assays

A subject method can be used to generate cardiomyocytes for analytical assays. Analytical assays include, e.g., introduction of the cardiomyocytes into a non-human animal model of a disease (e.g., a cardiac disease) to determine efficacy of the cardiomyocytes in the treatment of the disease; use of the cardiomyocytes in screening methods to identify candidate agents suitable for use in treating cardiac disorders; and the like. In some cases, a cardiomyocyte generated using a subject method can be used to assess the toxicity of a test agent or for drug optimization.

Animal Models

In some embodiments, a cardiomyocyte generated using a subject method can be introduced into a non-human animal model of a cardiac disorder, and the effect of the cardiomyocyte on ameliorating the disorder can be tested in the non-human animal model (e.g., a rodent model such as a rat model, a guinea pig model, a mouse model, etc.; a non-human primate model; a lagomorph model; and the like). For example, the effect of a cardiomyocyte generated using a subject method on a cardiac disorder in a non-human animal model of the disorder can be tested by introducing the cardiomyocyte into, near, or around diseased cardiac tissue in the non-human animal model; and the effect, if any, of the introduced cardiomyocyte on cardiac function can be assessed. Methods of assessing cardiac function are well known in the art; and any such method can be used.

Drug/Agent Screening or Identification

Cardiomyocytes generated using a subject method may be used to screen for drugs or test agents (e.g., solvents, small molecule drugs, peptides, oligonucleotides) or environmental conditions (e.g., culture conditions or manipulation) that affect the characteristics of such cells and/or their various progeny. See, e.g., U.S. Pat. No. 7,425,448. Drugs or test agents may be individual small molecules of choice (e.g., a lead compound from a previous drug screen) or in some cases, the drugs or test agents to be screened come from a combinatorial library, e.g., a collection of diverse chemical compounds generated by either chemical synthesis or biological synthesis by combining a number of chemical "building blocks." For example, a linear combinatorial chemical library such as a polypeptide library is formed by combining a set of amino acids in every possible way for a given compound length (e.g., the number of amino acids in a polypeptide compound). Millions of test agents (e.g., chemical compounds) can be synthesized through such combinatorial mixing of chemical building blocks. Indeed, theoretically, the systematic, combinatorial mixing of 100 interchangeable chemical building blocks results in the synthesis of 100 million tetrameric compounds or 10 billion pentameric compounds. See, e.g., Gallop et al. (1994), J. Med. Chem 37(9), 1233. Preparation and screening of combinatorial chemical libraries are well known in the art. Combinatorial chemical libraries include, but are not limited to: diversomers such as hydantoins, benzodiazepines, and dipeptides, as described in, e.g., Hobbs et al. (1993), Proc. Natl. Acad. Sci. U.S.A. 90, 6909; analogous organic syntheses of small compound libraries, as described in Chen et al. (1994), J. Amer. Chem. Soc., 116: 2661; Oligocarbamates, as described in Cho, et al. (1993), Science 261, 1303; peptidyl phosphonates, as described in Campbell et al. (1994), J. Org. Chem., 59: 658; and small organic molecule libraries containing, e.g., thiazolidinones and metathiazanones (U.S. Pat. No. 5,549,974), pyrrolidines (U.S. Pat. Nos. 5,525,735 and 5,519,134), benzodiazepines (U.S. Pat. No. 5,288,514).

Numerous combinatorial libraries are commercially available from, e.g., ComGenex (Princeton, N.J.); Asinex (Moscow, Russia); Tripos, Inc. (St. Louis, Mo.); ChemStar, Ltd. (Moscow, Russia); 3D Pharmaceuticals (Exton, Pa.); and Martek Biosciences (Columbia, Md.).

In some embodiments, a cardiomyocyte generated using a subject method is contacted with a test agent, and the effect, if any, of the test agent on a biological activity of the cardiomyocyte is assessed, where a test agent that has an effect on a biological activity of the cardiomyocyte is a candidate agent for treating a cardiac disorder or condition. For example, a test agent of interest is one that increases a biological activity of the cardiomyocyte by at least about 5%, at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared to the biological activity in the absence of the test agent. A test agent of interest is a candidate agent for treating a cardiac disorder or condition. In some embodiments, the contacting is carried out in vitro. In other embodiments, the contacting is carried out in vivo, e.g, in a non-human animal.

A "biological activity" includes, e.g., one or more of marker expression (e.g., cardiomyocyte-specific marker expression), receptor binding, ion channel activity, contractile activity, and electrophysiological activity.

For example, in some embodiments, the effect, if any, of the test agent on expression of a cardiomyocyte marker is assessed. Cardiomyocyte markers include, e.g., cardiac troponin I (cTnI), cardiac troponin T (cTnT), sarcomeric myosin heavy chain (MHC), GATA-4, Nkx2.5, N-cadherin, β-adrenoceptor (β1-AR), a member of the MEF-2 family of transcription factors, creatine kinase MB (CK-MB), myoglobin, and atrial natriuretic factor (ANF).

As another example, the effect, if any, of the test agent on electrophysiology of the cardiomyocyte is assessed. Electrophysiology can be studied by patch clamp analysis for cardiomyocyte-like action potentials. See Igelmund et al., Pflugers Arch. 437:669, 1999; Wobus et al., Ann. N.Y. Acad. Sci. 27:752, 1995; and Doevendans et al., J. Mol. Cell Cardiol. 32:839, 2000.

As another example, in some embodiments, the effect, if any, of the test agent on ligand-gated ion channel activity is assessed. As another example, in some embodiments, the effect, if any, of the test agent on voltage-gated ion channel activity is assessed. The effect of a test agent on ion channel activity is readily assessed using standard assays, e.g., by measuring the level of an intracellular ion (e.g., $Na^+$, $Ca^{2+}$, $K^+$, etc.). A change in the intracellular concentration of an ion can be detected using an indicator appropriate to the ion whose influx is controlled by the channel. For example, where the ion channel is a potassium ion channel, a potassium-detecting dye is used; where the ion channel is a calcium ion channel, a calcium-detecting dye is used; etc.

Suitable intracellular $K^+$ ion-detecting dyes include, but are not limited to, $K^+$-binding benzofuran isophthalate and the like. Suitable intracellular $Ca^{2+}$ ion-detecting dyes are listed above.

The effect of a test agent in the assays described herein can be assessed using any standard assay to observe phenotype or activity of cardiomyocytes generated using a subject method, such as marker expression, receptor binding, contractile activity, or electrophysiology—either in in vitro cell culture or in vivo. See, e.g., U.S. Pat. No. 7,425,448. For example, pharmaceutical candidates are tested for their effect on contractile activity—such as whether they increase or decrease the extent or frequency of contraction, using any methods known in the art. Where an effect is observed, the concentration of the compound can be titrated to determine the median effective dose (ED50).

Test Agent/Drug Toxicity

A cardiomyocyte generated using a subject method can be used to assess the toxicity of a test agent, or drug, e.g., a test agent or drug designed to have a pharmacological effect on cardiomyocytes, e.g., a test agent or drug designed to have effects on cells other than cardiomyocytes but potentially affecting cardiomyocytes as an unintended consequence. In some embodiments, the disclosure provides methods for evaluating the toxic effects of a drug, test agent, or other factor, in a human or non-human (e.g., murine; lagomorph; non-human primate) subject, comprising contacting one or more cardiomyocytes generated using a subject method with a dose of a drug, test agent, or other factor and assaying the contacted cardiomyocytes for markers of toxicity or cardiotoxicity.

Any method known in the art may be used to evaluate the toxicity or adverse effects of a test agent or drug on cardiomyocytes generated using a subject method. Cytotoxicity or cardiotoxicity can be determined, e.g., by the effect on cell viability, survival, morphology, and the expression of certain markers and receptors. For example, biochemical markers of myocardial cell necrosis (e.g., cardiac troponin T and I (cTnT, cTnI)) may be used to assess drug-induced toxicity or adverse reactions in cardiomyocytes generated using a subject method, where the presence of such markers in extracellular fluid (e.g., cell culture medium) can indicate necrosis. See, e.g., Gaze and Collinson (2005) Expert Opin Drug Metab Toxicol 1(4):715-725. In another example, lactate dehydrogenase is used to assess drug-induced toxicity or adverse reactions in cardiomyocytes generated using a subject method. See, e.g., Inoue et al. (2007) AATEX 14, Special Issue: 457-462. In another example, the effects of a drug on chromosomal DNA can be determined by measuring DNA synthesis or repair and used to assess drug-induced toxicity or adverse reactions in cardiomyocytes generated using a subject method. In still another example, the rate, degree, and/or timing of [$^3$H]-thymidine or BrdU incorporation may be evaluated to assess drug-induced toxicity or adverse reactions in cardiomyocytes generated using a subject method. In yet another example, evaluating the rate or nature of sister chromatid exchange, determined by metaphase spread, can be used to assess drug-induced toxicity or adverse reactions in cardiomyocytes generated using a subject method. See, e.g., A. Vickers (pp 375-410 in In vitro Methods in Pharmaceutical Research, Academic Press, 1997). In yet another example, assays to measure electrophysiology or activity of ion-gated channels (e.g., Calcium-gated channels) can be used to assess drug-induced toxicity or adverse reactions in cardiomyocytes generated using a subject method. In still another example, contractile activity (e.g., frequency of contraction) can be used to assess drug-induced toxicity or adverse reactions in cardiomyocytes generated using a subject method.

In some embodiments, the present disclosure provides methods for reducing the risk of drug toxicity in a human or murine subject, comprising contacting one or more cardiomyocytes generated using a subject method with a dose of a drug, test agent, or pharmacological agent, assaying the contacted one or more differentiated cells for toxicity, and prescribing or administering the pharmacological agent to the subject if the assay is negative for toxicity in the contacted cells. In some embodiments, the present disclosure provides methods for reducing the risk of drug toxicity in a human or murine subject, comprising contacting one or more cardiomyocytes generated using a subject method with a dose of a pharmacological agent, assaying the contacted one or more differentiated cells for toxicity, and prescribing or administering the pharmacological agent to the subject if the assay indicates a low risk or no risk for toxicity in the contacted cells.

Treatment Methods Using Cells

A subject modified or genetically modified fibroblast can be used to treat an individual in need of such treatment. Similarly, a subject induced cardiomyocyte can be used to treat an individual in need of such treatment. A subject modified or genetically modified fibroblast, or a subject induced cardiomyocyte, can be introduced into a recipient individual (an individual in need of treatment), where introduction into the recipient individual of a subject modified or genetically modified fibroblast, or a subject induced cardiomyocyte, treats a condition or disorder in the individual. Thus, in some embodiments, a subject treatment method involves administering to an individual in need thereof a population of subject modified or genetically modified fibroblasts. In some embodiments, a subject treatment method involves administering to an individual in need thereof a population of subject induced cardiomyocytes.

In some embodiments, the present disclosure provides a method for performing cell transplantation in a recipient individual in need thereof, the method generally involving: (i) generating an induced cardiomyocyte from a fibroblast obtained from a donor individual, wherein the donor individual is immunocompatible with the recipient individual; and (ii) transplanting one or more of the induced cardiomyocytes into the recipient individual. In some embodiments, the recipient individual and the donor individual are the same individual. In some embodiments, the recipient individual and the donor individual are not the same individuals.

In some embodiments, the present disclosure provides a method for performing cell transplantation in a recipient individual in need thereof, the method generally involving: (i) genetically modifying a host post-natal fibroblast with one or more nucleic acids comprising nucleotide sequences encoding Gata4, Mef2c, and Tbx5 polypeptides, where the host post-natal fibroblasts are obtained from a donor individual, wherein the donor individual is immunocompatible with the recipient individual; and (ii) transplanting one or more of the genetically modified post-natal fibroblasts into the recipient individual. In some embodiments, the recipient individual and the donor individual are the same individual. In some embodiments, the recipient individual and the donor individual are not the same individuals.

In some embodiments, the present disclosure provides a method for performing cell transplantation in a recipient individual in need thereof, the method generally involving: (i) modifying a host post-natal fibroblast by introducing into the host post-natal fibroblast one or more of Gata4, Mef2c, Tbx5, Mesp1, Nkx2-5, Isl-1, Myocd, Smyd1, and Srf polypeptides, or a subset (e.g., Gata4, Mef2c, and Tbx5 polypeptides), where the host post-natal fibroblasts are obtained from a donor individual, wherein the donor individual is immunocompatible with the recipient individual; and (ii) transplanting one or more of the modified post-natal fibroblasts into the recipient individual. In some embodiments, the recipient individual and the donor individual are the same individual. In some embodiments, the recipient individual and the donor individual are not the same individuals.

A subject method of generating induced cardiomyocytes is useful for generating artificial heart tissue, e.g., for implanting into a mammalian subject in need thereof. In some embodiments, a subject treatment method involves administering to an individual in need thereof a subject artificial heart tissue.

A subject treatment method is useful for replacing damaged heart tissue (e.g., ischemic heart tissue). Where a subject method involves introducing (implanting) an induced cardiomyocyte into an individual, allogeneic or autologous transplantation can be carried out.

The present disclosure provides methods of treating a cardiac disorder in an individual, the method generally involving administering to an individual in need thereof a therapeutically effective amount of: a) a population of induced cardiomyocytes prepared using a subject method; b) a population of genetically modified post-natal fibroblasts prepared using a subject method; c) a population of modified post-natal fibroblasts prepared using a subject method; or d) an artificial heart tissue prepared using a subject method.

For example, in some embodiments, a subject method comprises: i) generating an induced cardiomyocyte in vitro, as described above; and ii) introducing the induced cardiomyocyte into an individual in need thereof. In other embodiments, a subject method comprises: i) genetically modifying a host post-natal fibroblast with one or more nucleic acids comprising nucleotide sequences encoding one or more of Gata4, Mef2c, Tbx5, Mesp1, Nkx2-5, Isl-1, Myocd, Smyd1, and Srf polypeptides, or a subset (e.g., Gata4, Mef2c, and Tbx5 polypeptides); and ii) introducing the genetically modified post-natal fibroblasts into an individual in need thereof.

In other embodiments, a subject method comprises: i) modifying a host post-natal fibroblast by introducing into the host post-natal fibroblast one or more of Gata4, Mef2c, Tbx5, Mesp1, Nkx2-5, Isl-1, Myocd, Smyd1, and Srf polypeptides, or a subset (e.g., Gata4, Mef2c, and Tbx5 polypeptides); and ii) introducing the modified post-natal fibroblasts into an individual in need thereof.

In other embodiments, a subject method comprises: i) generating artificial heart tissue by: a) generating an induced cardiomyocyte, as described above; and b) associating the induced cardiomyocyte with a matrix, to form artificial heart tissue; and ii) introducing the artificial heart tissue into an individual in need thereof. In other embodiments, a subject comprises: i) generating artificial heart tissue by: a) genetically modifying a host post-natal fibroblast with one or more nucleic acids comprising nucleotide sequences encoding one or more of Gata4, Mef2c, Tbx5, Mesp1, Nkx2-5, Isl-1, Myocd, Smyd1, and Srf polypeptides, or a subset (e.g., Gata4, Mef2c, and Tbx5 polypeptides); and b) associating the genetically modified post-natal fibroblasts with a matrix, to form artificial heart tissue; and ii) introducing the artificial heart tissue into an individual in need thereof. In other embodiments, a subject comprises: i) generating artificial heart tissue by: a) modifying a host post-natal fibroblast by introducing into the host post-natal fibroblast one or more of Gata4, Mef2c, Tbx5, Mesp1, Nkx2-5, Isl-1, Myocd, Smyd1, and Srf polypeptides, or a subset (e.g., Gata4, Mef2c, and Tbx5 polypeptides); and b) associating the modified post-natal fibroblasts with a matrix, to form artificial heart tissue; and ii) introducing the artificial heart tissue into an individual in need thereof. The artificial heart tissue can be introduced into, on, or around existing heart tissue in the individual.

Individuals in need of treatment using a subject method and/or donor individuals include, but are not limited to, individuals having a congenital heart defect; individuals suffering from a degenerative muscle disease; individuals suffering from a condition that results in ischemic heart tissue, e.g., individuals with coronary artery disease; and the like. In some examples, a subject method is useful to treat a degenerative muscle disease or condition, e.g., familial cardiomyopathy, dilated cardiomyopathy, hypertrophic cardiomyopathy, restrictive cardiomyopathy, or coronary artery disease with resultant ischemic cardiomyopathy. In some examples, a subject method is useful to treat individuals having a cardiac or cardiovascular disease or disorder, e.g., cardiovascular disease, aneurysm, angina, arrhythmia, atherosclerosis, cerebrovascular accident (stroke), cerebrovascular disease, congenital heart disease, congestive heart failure, myocarditis, valve disease coronary, artery disease dilated, diastolic dysfunction, endocarditis, high blood pressure (hypertension), cardiomyopathy, hypertrophic cardiomyopathy, restrictive cardiomyopathy, coronary artery disease with resultant ischemic cardiomyopathy, mitral valve prolapse, myocardial infarction (heart attack), or venous thromboembolism.

Individuals who are suitable for treatment with a subject method include individuals (e.g., mammalian subjects, such as humans; non-human primates; experimental non-human mammalian subjects such as mice, rats, etc.) having a cardiac condition including but limited to a condition that results in ischemic heart tissue, e.g., individuals with coronary artery disease; and the like. In some examples, an individual suitable for treatment suffers from a cardiac or cardiovascular disease or condition, e.g., cardiovascular disease, aneurysm, angina, arrhythmia, atherosclerosis, cerebrovascular accident (stroke), cerebrovascular disease, congenital heart disease, congestive heart failure, myocarditis, valve disease coronary, artery disease dilated, diastolic dysfunction, endocarditis, high blood pressure (hypertension), cardiomyopathy, hypertrophic cardiomyopathy, restrictive cardiomyopathy, coronary artery disease with resultant ischemic cardiomyopathy, mitral valve prolapse, myocardial infarction (heart attack), or venous thromboembolism. In some examples, individuals suitable for treatment with a subject method include individuals who have a degenerative muscle disease, e.g., familial cardiomyopathy, dilated cardiomyopathy, hypertrophic cardiomyopathy, restrictive cardiomyopathy, or coronary artery disease with resultant ischemic cardiomyopathy.

For administration to a mammalian host, a population of induced cardiomyocytes, or a population of genetically modified post-natal fibroblasts, generated using a subject method can be formulated as a pharmaceutical composition. A pharmaceutical composition can be a sterile aqueous or non-aqueous solution, suspension or emulsion, which additionally comprises a physiologically acceptable carrier (i.e., a non-toxic material that does not interfere with the activity of the cardiomyocytes). Any suitable carrier known to those of ordinary skill in the art may be employed in a subject pharmaceutical composition. The selection of a carrier will depend, in part, on the nature of the substance (i.e., cells or chemical compounds) being administered. Representative carriers include physiological saline solutions, gelatin, water, alcohols, natural or synthetic oils, saccharide solutions, glycols, injectable organic esters such as ethyl oleate or a combination of such materials. Optionally, a pharmaceutical composition may additionally contain preservatives and/or other additives such as, for example, antimicrobial agents, anti-oxidants, chelating agents and/or inert gases, and/or other active ingredients.

In some embodiments, an induced cardiomyocyte population, a population of modified post-natal fibroblasts, or a population of genetically modified post-natal fibroblasts, is encapsulated, according to known encapsulation technologies, including microencapsulation (see, e.g., U.S. Pat. Nos. 4,352,883; 4,353,888; and 5,084,350). Where the cardiomyocytes, the modified post-natal fibroblasts, or the genetically modified post-natal fibroblasts are encapsulated, in some embodiments the cardiomyocytes, the modified post-natal fibroblasts, or the genetically modified post-natal fibroblasts are encapsulated by macroencapsulation, as described in U.S. Pat. Nos. 5,284,761; 5,158,881; 4,976,859; 4,968,733; 5,800,828 and published PCT patent application WO 95/05452.

In some embodiments, an induced cardiomyocyte population, a population of modified post-natal fibroblasts, or a population of genetically modified post-natal fibroblasts, is present in a matrix, as described below.

A unit dosage form of an induced cardiomyocyte population, a population of modified post-natal fibroblasts, or a population of genetically modified post-natal fibroblasts, can contain from about $10^3$ cells to about $10^9$ cells, e.g., from about $10^3$ cells to about $10^4$ cells, from about $10^4$ cells to about $10^5$ cells, from about $10^5$ cells to about $10^6$ cells, from about $10^6$ cells to about $10^7$ cells, from about $10^7$ cells to about $10^8$ cells, or from about $10^8$ cells to about $10^9$ cells.

An induced cardiomyocyte population, a population of modified post-natal fibroblasts, or a population of genetically modified post-natal fibroblasts, can be cryopreserved according to routine procedures. For example, cryopreservation can be carried out on from about one to ten million cells in "freeze" medium which can include a suitable proliferation medium, 10% BSA and 7.5% dimethylsulfoxide. Cells are centrifuged. Growth medium is aspirated and replaced with freeze medium. Cells are resuspended as spheres. Cells are slowly frozen, by, e.g., placing in a container at −80° C. Cells are thawed by swirling in a 37° C. bath, resuspended in fresh proliferation medium, and grown as described above.

Artificial Heart Tissue

In some embodiments, a subject method comprises: a) reprogramming a population of post-natal fibroblasts into cardiomyocytes in vitro, e.g., where the post-natal fibroblasts are present in a matrix, wherein a population of induced cardiomyocytes is generated; and b) implanting the population of induced cardiomyocytes into or on an existing heart tissue in an individual. Thus, the present disclosure provides a method for generating artificial heart tissue in vitro; and implanting the artificial heart tissue in vivo. In some embodiments, a subject method comprises: a) reprogramming a population of post-natal fibroblasts into cardiomyocytes in vitro, generating a population of induced cardiomyocytes; b) associating the induced cardiomyocytes with a matrix, forming an artificial heart tissue; and c) implanting the artificial heart tissue into or on an existing heart tissue in an individual.

The artificial heart tissue can be used for allogeneic or autologous transplantation into an individual in need thereof. To produce artificial heart tissue, a matrix can be provided which is brought into contact with the post-natal fibroblasts, where the post-natal fibroblasts are reprogrammed into cardiomyocytes using a subject method, as described above. This means that this matrix is transferred into a suitable vessel and a layer of the cell-containing culture medium is placed on top (before or during the reprogramming of the post-natal fibroblasts). The term "matrix" should be understood in this connection to mean any suitable carrier material to which the cells are able to attach themselves or adhere in order to form the corresponding cell composite, i.e. the artificial tissue. In some embodiments, the matrix or carrier material, respectively, is present already in a three-dimensional form desired for later application. For example, bovine pericardial tissue is used as matrix which is crosslinked with collagen, decellularized and photofixed.

For example, a matrix (also referred to as a "biocompatible substrate") is a material that is suitable for implantation into a subject onto which a cell population can be deposited. A biocompatible substrate does not cause toxic or injurious effects once implanted in the subject. In one embodiment, the biocompatible substrate is a polymer with a surface that can be shaped into the desired structure that requires repairing or replacing. The polymer can also be shaped into a part of a structure that requires repairing or replacing. The biocompatible substrate provides the supportive framework that allows cells to attach to it, and grow on it. Cultured populations of cells can then be grown on the biocompatible substrate, which provides the appropriate interstitial distances required for cell-cell interaction.

Treatment Methods Using Polypeptides or Nucleic Acids

The present disclosure provides methods of reprogramming a fibroblast into a cardiomyocyte in vivo.

In some embodiments, the methods generally involve contacting a fibroblast in vivo with a reprogramming composition. As discussed above, a reprogramming composition comprises either: 1) two or more of Gata4, Mef2c, Tbx5, Mesp1, Nkx2-5, Isl-1, Myocd, Smyd1, and Srf polypeptides; or 2) one or more nucleic acids comprising nucleotide sequences encoding two or more of Gata4, Mef2c, Tbx5, Mesp1, Nkx2-5, Isl-1, Myocd, Smyd1, and Srf polypeptides. As described above, a subject reprogramming composition can comprise one or more additional components. A subject reprogramming composition can be administered to an individual at or near a treatment site, e.g., in or around the heart.

In some embodiments, the methods generally involve contacting a fibroblast in vivo with a reprogramming composition. As discussed above, a reprogramming composition comprises either: 1) a mixture of Gata4, Mef2c, and Tbx5 polypeptides; or 2) one or more nucleic acids comprising nucleotide sequences encoding Gata4, Mef2c, and Tbx5 polypeptides. As described above, a subject reprogramming composition can comprise one or more additional components. A subject reprogramming composition can be administered to an individual at or near a treatment site, e.g., in or around the heart.

In some embodiments, a reprogramming composition is introduced into an individual in need thereof in association with an implantable device. Thus, in some embodiments, the present disclosure provides methods of reprogramming a fibroblast into a cardiomyocyte in vivo, the methods generally involving introducing a subject implantable device (comprising a subject reprogramming composition) into an individual in need thereof, where the implantable device is introduced at or near a treatment site, e.g., in or around the heart.

Individuals in need of treatment using a subject method and/or donor individuals include, but are not limited to, individuals having a congenital heart defect; individuals suffering from a degenerative muscle disease; individuals suffering from a condition that results in ischemic heart tissue, e.g., individuals with coronary artery disease; and the like. In some examples, a subject method is useful to treat a degenerative muscle disease or condition, e.g., familial cardiomyopathy, dilated cardiomyopathy, hypertrophic cardiomyopathy, restrictive cardiomyopathy, or coronary artery disease with resultant ischemic cardiomyopathy. In some examples, a subject method is useful to treat individuals having a cardiac or cardiovascular disease or disorder, e.g., cardiovascular disease, aneurysm, angina, arrhythmia, atherosclerosis, cerebrovascular accident (stroke), cerebrovascular disease, congenital heart disease, congestive heart failure, myocarditis, valve disease coronary, artery disease dilated, diastolic dysfunction, endocarditis, high blood pressure (hypertension), cardiomyopathy, hypertrophic cardiomyopathy, restrictive cardiomyopathy, coronary artery disease with resultant ischemic cardiomyopathy, mitral valve prolapse, myocardial infarction (heart attack), or venous thromboembolism.

Individuals who are suitable for treatment with a subject method include individuals (e.g., mammalian subjects, such as humans; non-human primates; experimental non-human mammalian subjects such as mice, rats, etc.) having a cardiac condition including but limited to a condition that results in ischemic heart tissue, e.g., individuals with coronary artery disease; and the like. In some examples, an individual suitable for treatment suffers from a cardiac or cardiovascular disease or condition, e.g., cardiovascular disease, aneurysm, angina, arrhythmia, atherosclerosis, cerebrovascular accident (stroke), cerebrovascular disease, congenital heart disease, congestive heart failure, myocarditis, valve disease coronary, artery disease dilated, diastolic dysfunction, endocarditis, high blood pressure (hypertension), cardiomyopathy, hypertrophic cardiomyopathy, restrictive cardiomyopathy, coronary artery disease with resultant ischemic cardiomyopathy, mitral valve prolapse, myocardial infarction (heart attack), or venous thromboembolism. In some examples, individuals suitable for treatment with a subject method include individuals who have a degenerative muscle disease, e.g., familial cardiomyopathy, dilated cardiomyopathy, hypertrophic cardiomyopathy, restrictive cardiomyopathy, or coronary artery disease with resultant ischemic cardiomyopathy.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

Direct Reprogramming of Cardiac Fibroblasts into Functional Cardiomyocytes by Defined Factors Materials and Methods
Generation of αMHC-GFP and Isl1-YFP Mice To generate α-myosin heavy chain-green fluorescent protein (αMHC-GFP) mice, enhanced green fluorescent protein-internal ribosome binding site-puromycin$^R$ (EGFP-IRES-Puromycin) cDNA were subcloned into the expression vector containing α-myosin heavy chain (α-MHC) promoter (Gulick et al. (1991) J Biol Chem 266, 9180-9185). Pronuclear microinjection and other procedures were performed according to the standard protocols (Ieda et al. (2007) Nat Med 13, 604-612. The transgene was identified by polymerase chain reaction (PCR) analysis (the forward primer, 5'-ATGACAGACAGATCCCTCCT-3' (SEQ ID NO:11); the reverse primer, 5'-AAGTCGTGCT-GCTTCATGTG-3' (SEQ ID NO:12)). Isl1-yellow fluorescent protein (Isl1-YFP) mice were obtained by crossing Isl1-Cre mice and R26R-enhanced yellow fluorescent protein (R26R-EYFP) mice (Srinivas et al. (2001) BMC Dev Biol 1, 4).

Cell Culture

For explant culture, isolated neonatal or adult mouse hearts were minced into small pieces less than 1 mm$^3$ in size. The explants were plated on gelatin-coated dishes, and cultured for 7 days in explant medium (IMDM/20% FBS) (Andersen et al. (2009) Stem Cells 27, 1571-1581). Migrated cells were harvested and filtered with 40-μm cell strainers (BD) to avoid contamination of heart tissue fragments. αMHC-GFP$^-$/Thy1$^+$, Isl1-YFP$^-$/Thy1$^+$, αMHC-GFP$^-$/Thy1$^+$/c-kit$^-$ or αMHC-GFP$^-$/Thy1$^+$/c-kit$^+$ live cells (as defined by the lack of propidium iodine staining) were isolated using fluorescence-activated cell sorting (FACS) Aria 2 (BD Biosciences). For conventional isolation of neonatal cardiac fibroblasts, hearts were digested with 0.1% trypsin and plated on plastic dishes (Ieda et al., (2009) Dev Cell 16:233). Attached fibroblasts were cultured for 7 days and sorted αMHC-GFP$^-$/Thy1$^+$ cells. Sorted cells were cultured in DMEM/M199 medium containing 10% fetal bovine serum (FBS) at a density of 10$^4$/cm$^2$. Cells were transduced by retroviruses after 24 h.

Isolation of Cardiomyocytes

To isolate cardiomyocytes, neonatal αMHC-GFP$^+$ ventricles were cut into small pieces and digested with collagenase type II solution (Ieda et al., (2009) supra). A single-cell suspension was obtained by gentle triturating and passing through a 40-μm cell strainer. αMHC-GFP$^+$ live cells were isolated by FACS Aria 2.

Molecular Cloning and Retroviral Infection

Retroviruses were generated as described (Kitamura et al., (2003) Exp. Hematol. 31:1007; Takahashi and Yamanaka, (2006) Cell 126:663). Briefly, to construct pMXs retroviral vectors, the coding regions of candidate genes were amplified by polymerase chain reaction (PCR) and subcloned into pMXs vector. The pMXs retroviral vectors were transfected into Plat-E cells with Fugene 6 (Roche) to generate viruses. Pool of virus-containing supernatants was used for transduction. After 24 h, the medium was replaced with DMEM/M199 medium and changed every 2-3 days. The pMXs-DsRed Express retrovirus infection in cardiac fibroblasts resulted in >95% transfection efficiency (Hong et al., (2009) Nature 460:1132).

Mouse nucleotide sequences of Mef2c, Tbx5, and Gata4 used in the constructs are set forth in SEQ ID NOs:23, 25, and 27, respectively. Amino acid sequences of the encoded Mef2c, Tbx5, and Gata4 polypeptides are set forth in SEQ ID NOs:24, 26, and 28, respectively.

FACS Analyses and Sorting

For green fluorescent protein (GFP) expression analyses, cells were harvested from cultured dishes and analyzed on a FACS Calibur (BD Biosciences) with FlowJo software. For αMHC-GFP/cTnT expression, cells were fixed with 4% PFA for 15 min, permealized with Saponin, and stained with anti-cTnT and anti-GFP antibodies, followed by secondary antibodies conjugated with Alexa 488 and 647 (Kattman et al., (2006) Dev. Cell 11:723).

For αMHC-GFP$^-$/Thy1$^+$ and Isl1-YFP$^-$/Thy1$^+$ cell sorting, cells were incubated with PECy7-conjugated anti-Thy1 antibody (eBioscience) and sorted by FACS Aria 2 (Ieda et al., (2009) supra). For αMHC-GFP$^-$/Thy1$^+$/c-kit$^-$ and αMHC-GFP$^-$/Thy1$^+$/c-kit$^+$ cell sorting, PECy7-conjugated anti-Thy1 and allophycocyanin (APC)-conjugated anti-c-kit antibodies (BD) were used. Bone marrow cells were used as a positive control for c-kit staining. PECy7 is a conjugate of phycoerythrin and Cy7 fluorescent dyes.

Cell Transplantation

Fibroblasts were harvested the next day after retroviral infection. A left thoracotomy was carried out in non-obese diabetic-severe combined immunodeficiency (NOD-SCID) mice, and $10^6$ cultured cells were injected into the left ventricle. After 1-2 weeks, the hearts were excised for immunohistochemistry.

Immunocytochemistry

Cells were fixed in 4% paraformaldehyde for 15 min at room temperature, blocked, and incubated with primary antibodies against sarcomeric α-actinin (Sigma Aldrich), vimentin (Progen), GFP (Invitrogen), Thy-1 (BD Biosciences), cardiac troponin T (cTnT) (Thermo Scientific), Nppa (Chemicon), RFP (Rockland), Nkx2.5 (Santa Cruz), with secondary antibodies conjugated with Alexa 488 or 594 (Molecular Probes), and DAPI (Invitrogen).

Histology

For immunohistochemical studies in cell-injected hearts, hearts were fixed in 0.4% paraformaldehyde overnight, embedded in OCT compound, and frozen in liquid nitrogen (Ieda et al., (2007) supra; Ieda et al., (2009) supra). Hearts were cut vertically in 7-μm sections to show both ventricles. Sections were stained with primary antibodies against actinin, red fluorescent protein (RFP), green fluorescent protein (GFP), with secondary antibodies conjugated with Alexa 488 or 594, and 4',6'-diamino-2-phenylindole (DAPI). To analyze GFP expression pattern in αMHC-GFP hearts, hearts were cut longitudinally and stained with actinin, GFP and vimentin.

Quantitative RT-PCR

Total RNA was isolated from cells, and quantitative reverse transcription-polymerase chain reaction (qRT-PCR) was performed on an ABI 7900HT (Applied Biosystems) with TaqMan probes (Applied Biosystems): Actc1 (Mm01333821_m1), Col1a2 (Mm00483888_m1), Myh6 (Mm00440354_m1), Ryr2 (Mm00465877_m1), Gja1 (Mm00439105_m1), Tbx5 (Mm00803521_m1). The mRNA levels were normalized by comparison to Gapdh mRNA.

Microarray Analyses

Mouse genome-wide gene expression analyses were performed using Affymetrix Mouse Gene 1.0 ST Array. αMHC-GFP$^+$ cardiomyocytes were collected by FACS. Three-factor transduced GFP$^+$ cells and GFP$^-$ cells were collected by FACS after 4 weeks of culture. Cardiac fibroblasts were also collected after 4 weeks of culture. RNA was extracted using PicoPure RNA Isolation (Arcturus). Microarray analyses were performed in triplicate from independent biologic samples, according to the standard Affymetrix Genechip protocol. Data were analyzed using the Affymetrix Power Tool (APT, version 1.8.5). Linear models were fitted for each gene on the sample group to derive estimated group effects and their associated significance with the limma package (Smyth, 2004) in R/Bioconductor. Moderated t-statistics and the associated p-values were calculated. P-values were adjusted for multiple testing by controlling for false-discovery rate by the Benjamini-Hochberg method. Gene annotations were retrieved from Affymetrix (version Nov. 12, 2007). Differential gene expression was defined using the statistics/threshold combination.

Ca$^{2+}$ Imaging

Ca$^{2+}$ imaging was performed according to the standard protocol. Briefly, cells were labeled with Rhod-3 (Invitrogen) for 1 h at room temperature, washed, and incubated for an additional 1 h to allow de-esterification of the dye. Rhod-3 labeled cells were analyzed by Axio Observer (Zeiss) with MiCAM02 (SciMedia).

Electrophysiology

After 4-week transduction with three factors, the electrophysiological activities of induced cardiomyocytes were performed using extracellular electrode recording with an Axopatch 700B amplifier and the pClamp9.2 software (Axon Instruments). Induced cardiomyocytes were visually identified by GFP expression and spontaneous contraction. Glass patch pipettes, with typical resistances of 2-4 Mω, were directly attached on single GFP$^+$ cells for extracellular recording in Tyrode's bath solution.

Statistical Analyses

Differences between groups were examined for statistical significance using Student's t-test or ANOVA. P values of <0.05 were regarded as significant.

Results

Screening for Cardiomyocyte Inducing Factors

An assay system was developed in which the induction of mature cardiomyocytes from fibroblasts could be analyzed quantitatively by reporter-based fluorescence-activated cell sorting (FACS) (FIG. 1A). To accomplish this, αMHC promoter-driven EGFP-IRES-Puromycin transgenic mice (αMHC-GFP) were generated, in which only mature cardiomyocytes expressed the green fluorescent protein (GFP) (Gulick et al., (1991) supra). It was confirmed that only cardiomyocytes, but not other cell types including cardiac fibroblasts, expressed GFP in the transgenic mouse hearts.

To have enough cardiac fibroblasts for FACS screening, GFP$^-$ cardiac fibroblasts were obtained from neonatal αMHC-GFP hearts by explant culture. Fibroblast-like cells migrated out from the explants after 2 days and were confluent after 1 week. The migrating cells did not express GFP, but expressed Thy1 and Vimentin, markers of cardiac fibroblasts (FIG. 1B) (Hudon-David et al., (2007) J. Mol. Cell. Cardiol. 42:991; Ieda et al., (2009) supra). To avoid contamination of cardiomyocytes, the cells were filtered by cell strainers to remove heart tissue fragments and isolated Thy1$^+$/GFP$^-$ cells by FACS (FIG. 1C). The purity of cardiac fibroblasts with Thy1 as a marker for FACS was previously shown (Ieda et al., (2009) supra). Using these procedures, no cardiomyocyte contamination was found in the fibroblast culture, and greater than twice the number of cardiac fibroblasts could be generated than by conventional fibroblast isolation techniques (Ieda et al., (2009) supra).

To select potential cardiac reprogramming factors, microarray analyses were used to identify transcription factors and epigenetic remodeling factors with greater expression in mouse cardiomyocytes (CM) than in cardiac fibroblasts (CF) at embryonic day 12.5 (Ieda et al., (2009) supra). Among them, 13 factors were selected that exhibited severe developmental cardiac defects and embryonic lethality when mutated (Table).

TABLE

Table. Transcription factors upregulated in embryonic cardiomyocytes compared to cardiac fibroblasts by microarray are listed along with their fold enrichment (n = 3).

| Gene | Relative expression CM vs. CF (E12) |
|---|---|
| Hopx | 33.1 |
| Nkx2-5 | 30.7 |
| Hrt2 | 29.6 |
| Pitx2 | 24.1 |
| Smyd1 | 20.6 |
| Myocd | 7.5 |
| Baf60c | 3.9 |
| Tbx5 | 3.0 |
| Srf | 2.5 |
| Gata4 | 2.2 |
| Isl1 | 2.1 |
| Mef2c | 2.0 |

TABLE-continued

Table. Transcription factors upregulated in embryonic cardiomyocytes compared to cardiac fibroblasts by microarray are listed along with their fold enrichment (n = 3).

| Gene | Relative expression CM vs. CF (E12) |
|---|---|
| Hand2 | 1.8 |
| Mesp1 | ND |

Mesp1 expression was not detected (ND) in either cell type.

The cardiovascular mesoderm-specific transcription factor Mesp1 was also included because of its cardiac trans-differentiation effect in *Xenopus* (David et al., (2008) Nat. Cell Biol. 10:338). Individual retroviruses were generated, to efficiently express each gene in cardiac fibroblasts.

Thy1$^+$/GFP$^-$ neonatal mouse cardiac fibroblasts were transduced with a mixture of retroviruses expressing all 14 factors or with DsRed retrovirus (negative control) (Hong et al., (2009) supra). No GFP$^+$ cells in cardiac fibroblasts were observed 1 week after Ds-Red retrovirus infection or 1 week of culture without any viral infection. In contrast, transduction of all 14 factors into fibroblast cells resulted in the generation of a small number of GFP$^+$ cells (1.7%), indicating the successful activation of the cardiac-enriched αMHC gene in some cells (FIGS. 1D and E).

To determine which of the 14 factors were critical for activating cardiac gene expression, individual factors were serially removed from the pool of 14. Pools lacking five factors (Baf60c, Hand2, Hopx, Hrt2, and Pitx2c) produced an increased number of GFP$^+$ cells, suggesting they are dispensable (FIGS. 1D and E). Of note, removal of Gata4 decreased the percentage of GFP$^+$ cells to 0.5%, while removal of Pitx2c increased it to 5%. Three further rounds of single factor withdrawal were conducted from nine-, six-, and five-factor pools; it was found that four factors (Gata4, Mef2c, Mesp1, and Tbx5) were sufficient for efficient GFP$^+$ cell induction from cardiac fibroblasts (FIG. 1F-H). The combination of these four factors dramatically increased the number of fibroblasts activating the αMHC-GFP reporter to over 20% (FIG. 1I).

FIGS. 1A-I. Screening for Cardiomyocyte Inducing Factors (A) Schematic representation of the strategy to test candidate factors. (B) Morphology and characterization of fibroblast-like cells migrating from αMHC-GFP heart explants. Phase contrast (left), GFP (middle), and Thy-1 immunostaining (right). Insets are high-magnification views. (C) Thy-1$^+$/GFP$^-$ cells were FACS sorted from explant culture for reprogramming after filtration with cell strainers to remove myocytes. (D) Summary of FACS analyses for GFP$^+$ cells. Effect on GFP$^+$ cell induction with 14 factors or the removal of individual factors from the pool of 14 factors (n=3). (E) FACS plots for analyses of GFP$^+$ cells. GFP$^+$ cells were analyzed 1 week after 14-factor transduction. The number of GFP$^+$ cells were reduced by removal of Gata4, but increased by removal of Pitx2c from 14 factors. (F-H) Effect on GFP$^+$ cell induction of the removal of individual factors from the pool of 9 (F), 6 (G), or 5 (H) factors (n=3 in each case). (I) GFP$^+$ cells were induced from fibroblasts by the combination of four factors, Gata4, Mef2c, Mesp1, and Tbx5. Representative data are shown in each panel. All data are presented as means±SD. PI, propidium iodine. *, P<0.01; **, P<0.05 vs relative control. Scale bars, 100 μm.

Gata4, Mef2c, and Tbx5 are Necessary and Sufficient for Cardiomyocyte Induction

Figure 2:
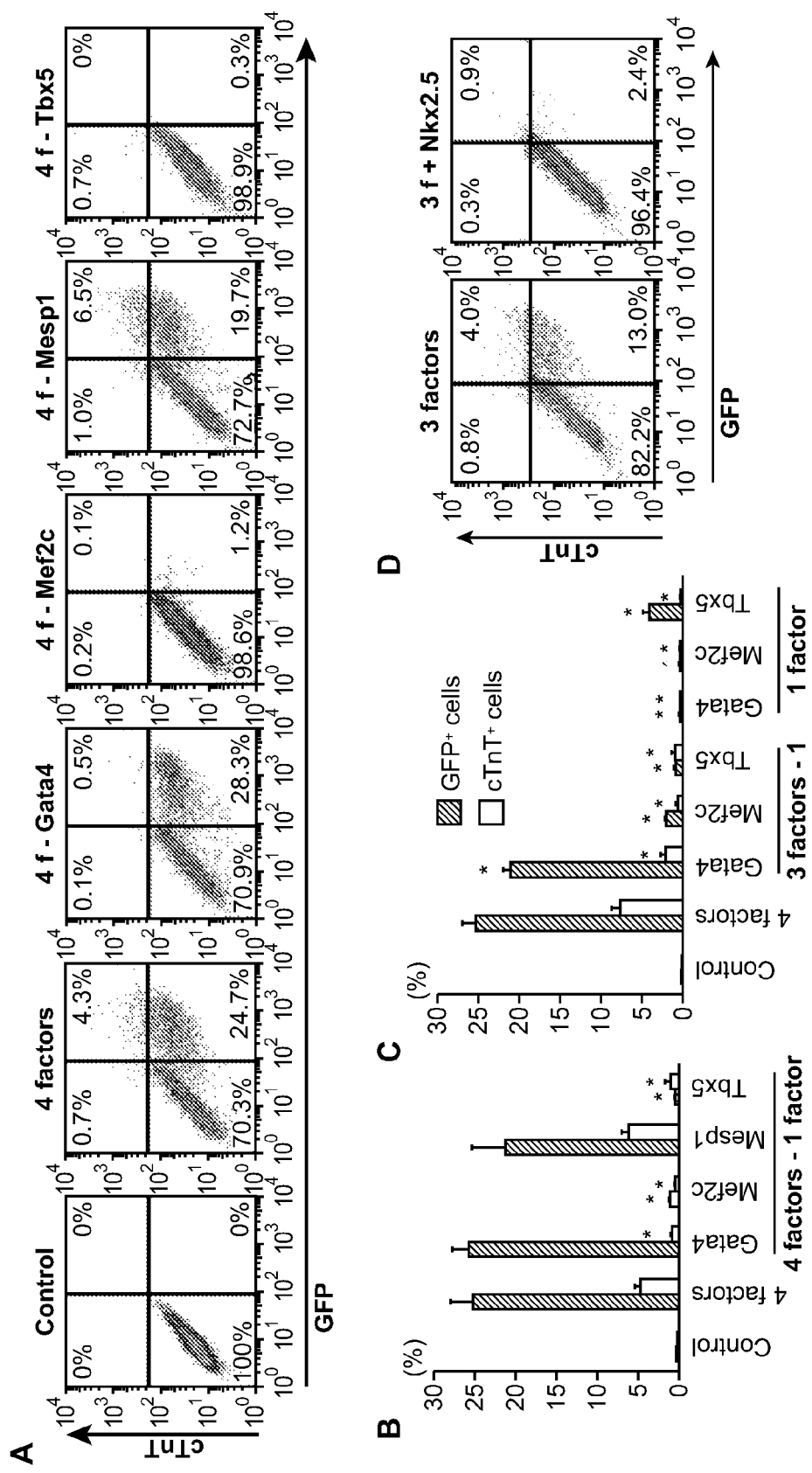
FIGS. 2A-F depict the effect of various factors on cardiac gene expression in fibroblasts.
Figure 2:
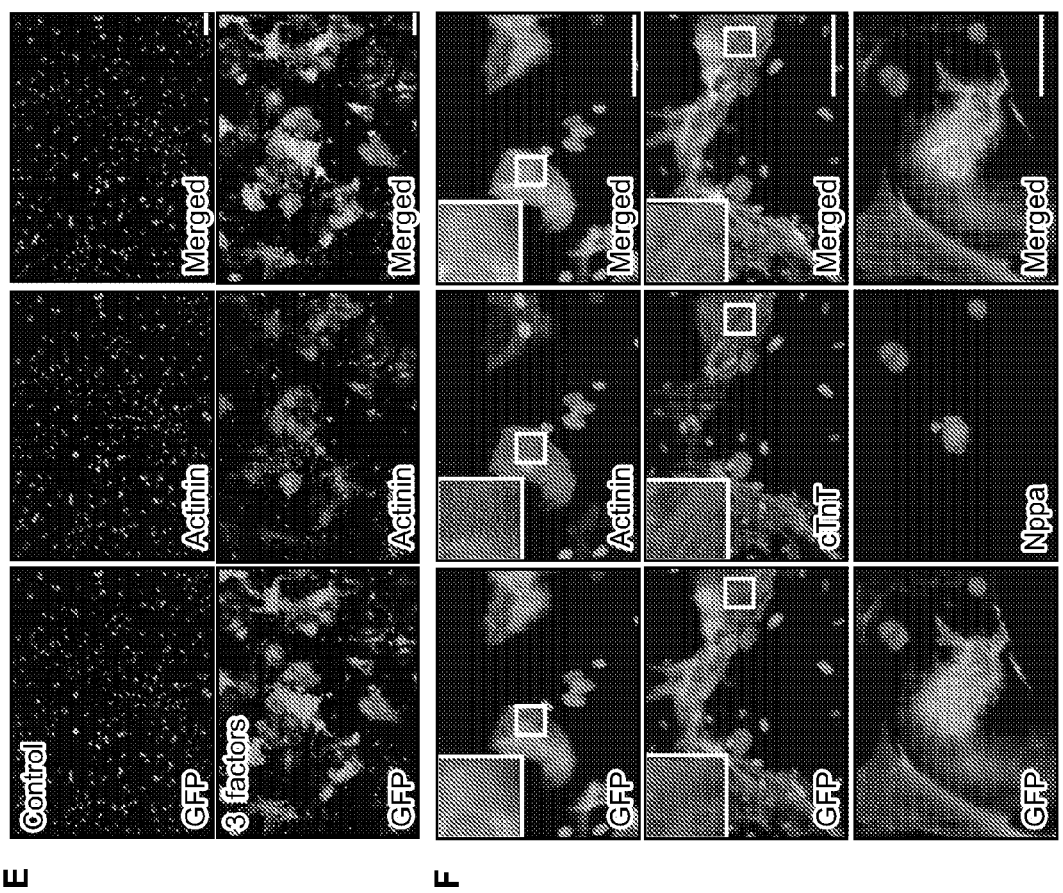

Next, expression of cardiac troponin T (cTnT), a specific sarcomeric marker of differentiated cardiomyocytes (Kattman et al., (2006) supra), was examined. It was found that 20% of GFP$^+$ cells expressed cTnT 1 week after the four-factor transduction. Again removing individual factors from the four-factor pool in transduction, it was found that Mesp1 was dispensable for cTnT expression (FIGS. 2A and B). In contrast, cTnT$^+$ or GFP$^+$ cells were not observed, when either Mef2c or Tbx5 was removed. Removal of Gata4 did not significantly affect the number of GFP$^+$ cells, but cTnT expression was completely abolished, suggesting Gata4 was also required. The combination of two factors, Mef2c and Tbx5, induced GFP expression but not cTnT. No other combination of two factors or single factor induced both GFP and cTnT expression in cardiac fibroblasts (FIG. 2C). These data suggested that the combination of three factors, Gata4, Mef2c, and Tbx5, is necessary and sufficient to induce cardiac gene expression. To confirm the screening results, cardiac fibroblasts were transduced with three factors (Gata4, Mef2c, and Tbx5) plus Nkx2-5, a critical factor for cardiogenesis but excluded by the initial screening. Surprisingly, adding Nkx2-5 dramatically inhibited the expression of GFP and cTnT in cardiac fibroblasts, confirming the screening results (FIG. 2D).

Next, immunocytochemistry was used to determine if other cardiac markers were expressed in GFP$^+$ cells. Most GFP$^+$ cells induced with the three factors expressed sarcomeric α-actinin (actinin) and had well-defined sarcomeric structures (FIGS. 2E and F). GFP$^+$ cells also expressed cTnT and ANF (atrial natriuretic factor), indicating GFP$^+$ cells expressed several cardiomyocyte-specific markers (FIG. 2F).

FIGS. 2A-F. Combination of Three Transcription Factors Induces Cardiac Gene Expression in Fibroblasts (A) FACS analyses for α-MHC-GFP and cardiac Troponin T (cTnT) expression. Effects of the removal of individual factors from the pool of four factors on GFP$^+$ and cTnT$^+$ cell induction. Note that removal of Gata4 did not affect GFP$^+$, but cTnT expression was strongly inhibited. (B) Quantitative data of GFP$^+$ cells and cTnT$^+$ cells in (A) (n=3). (C) Effect of the transduction of pools of three, two, and one factors on GFP$^+$ and cTnT$^+$ cell induction (n=3). (D) FACS plot showing that Nkx2-5 inhibited reprogramming induced with three (GMT; Gata4, Mef2c and Tbx5) factors. (E) Immunofluorescent staining for GFP (green), actinin (red) and DAPI (blue). The combination of three factors, Gata4, Mef2c and Tbx5, induced abundant GFP expression in cardiac fibroblasts 2 weeks after transduction. Note that the majority of GFP$^+$ cells were positive for actinin. (F) Induced cardiomyocytes expressed several cardiac markers by immunocytochemistry with clear sarcomeric organization (actinin and Nppa, 2 weeks after transduction; cTnT, 4 weeks after transduction). Insets are high-magnification views. All data are presented as means±SD. *, P<0.01 vs relative control. Scale bars, 100 μm.

Induced Cardiomyocytes are Directly Differentiated from Cardiac Fibroblasts

Figure 3:
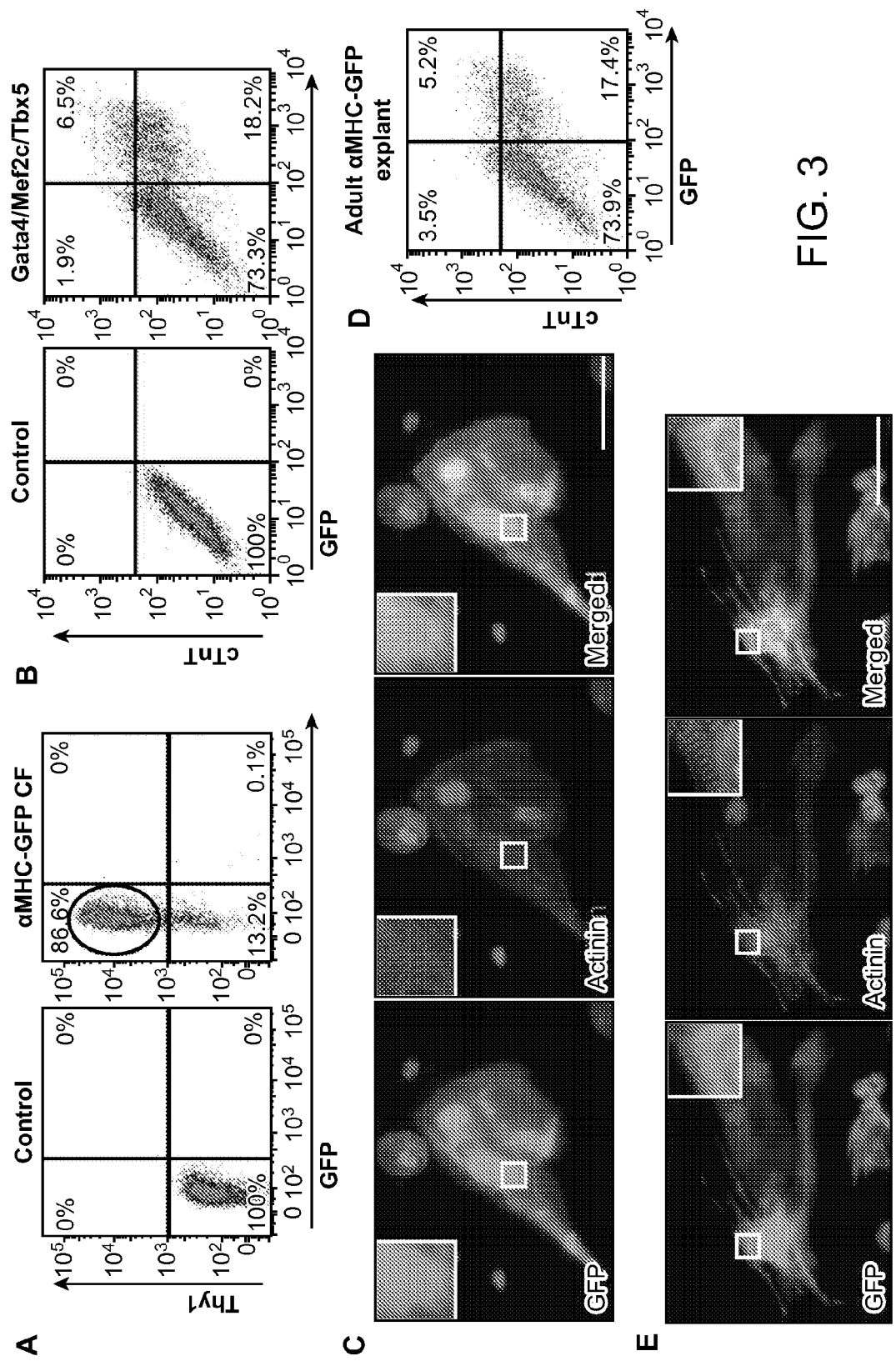
FIGS. 3A-J depict reprogramming of cardiac fibroblasts directly into cardiomyocytes.
Figure 3:
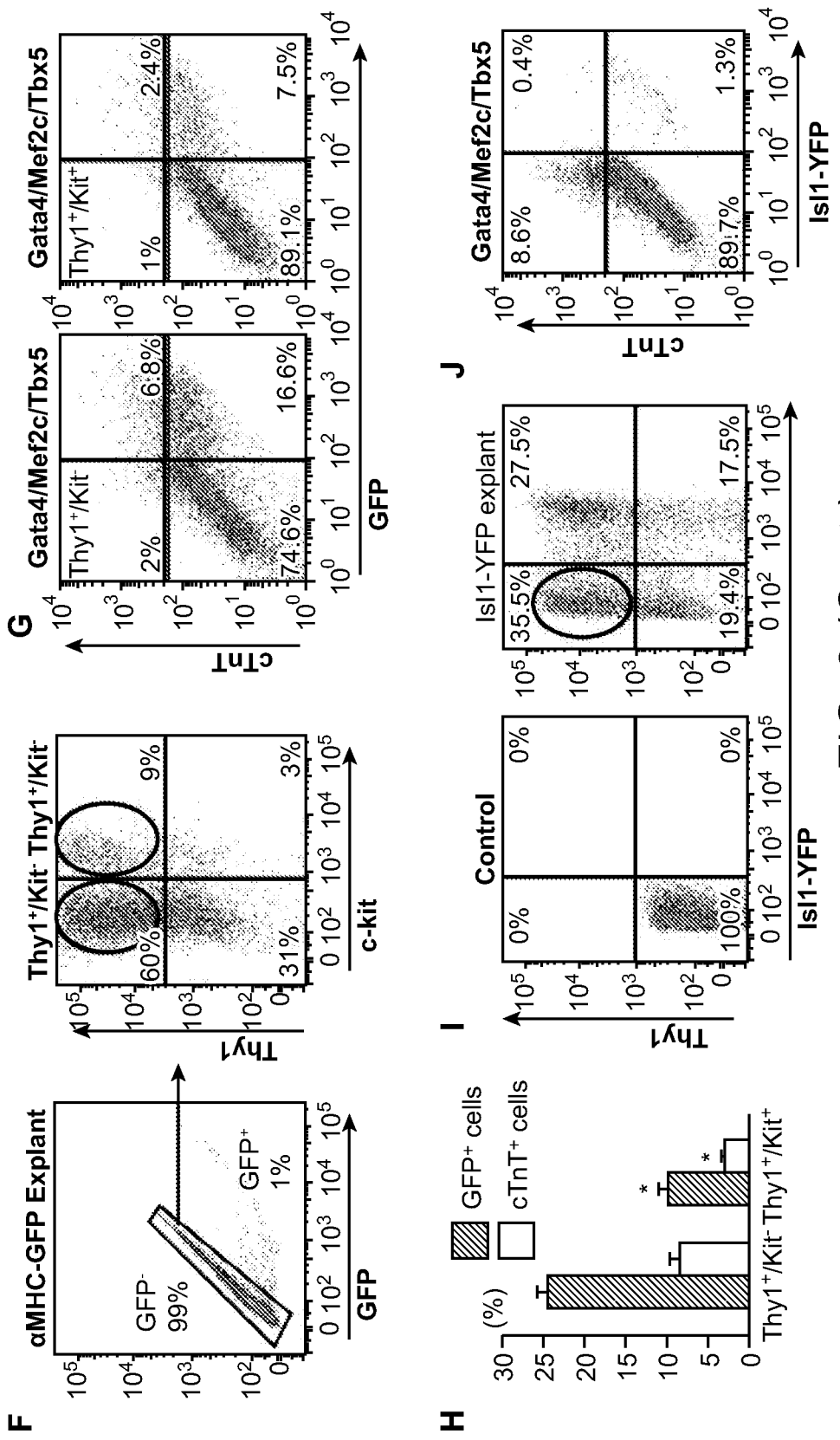

Next, neonatal cardiac fibroblasts were isolated by the conventional fibroblast isolation method in which hearts were digested with trypsin and plated on plastic dishes (Ieda et al., (2009) supra). More than 80% of the cells expressed Thy1, and Thy1$^+$/GFP$^-$ cells were isolated by FACS to exclude cardiomyocyte contamination (FIG. 3A). Fibroblasts transduced with Gata4/Mef2c/Tbx5, hereafter referred to as GMT, expressed GFP, cTnT and actinin after 1 week at the same level as fibroblasts isolated from explant cultures (FIGS. 3B and C). Similar results were obtained upon introduction of GMT into adult cardiac fibroblasts, with full formation of sarcomeric structures (FIGS. 3D and E).

To determine if the induced cardiomyocytes were arising from a subpopulation of stem-like cells, c-kit expression (Beltrami et al., (2003) Cell 114:763; Wu et al., (2006) Cell 127:1137) was analyzed in the Thy1$^+$/GFP$^-$ cells. Most c-kit$^+$ cells co-expressed Thy1, while 15% of Thy1$^+$ cells expressed c-kit. GFP$^-$/Thy1$^+$/c-kit$^+$ cells and GFP$^-$/Thy1$^+$/c-kit$^-$ cells were isolated by FACS and transduced each population of cells with the three factors. The results showed 2-3-fold more cardiomyocyte induction from GFP$^-$/Thy1$^+$/c-kit$^-$ cells than from GFP$^-$/Thy1$^+$/c-kit$^+$ cells (FIG. 3F-H). These results suggest that most of the induced cardiomyocytes originated from a c-kit negative population.

Next, it was investigated whether the reprogramming of cardiac fibroblasts to differentiated cardiomyocytes was a direct event or if the fibroblasts first passed through a cardiac progenitor cell fate before further differentiation. To distinguish between these two possibilities, Isl1-YFP mice were used, which were obtained by crossing Isl1-Cre mice and R26R-EYFP mice (Srinivas et al., (2001) supra). Isl1 is an early cardiac progenitor marker that is transiently expressed before cardiac differentiation. If cardiomyocytes generated from fibroblasts passed through a cardiac progenitor state, they and their descendents should permanently express YFP (Laugwitz et al., (2005) Nature 433:647). Isl1-YFP$^-$/Thy1$^+$ cells were isolated from Isl1-YFP heart explants by FACS and transduced the cells with Gata4, Mef2c, and Tbx5. The resulting cTnT$^+$ cells did not express YFP, suggesting that the induced cardiomyocytes (iCMs) were not first reprogrammed into cardiac progenitor cells. Moreover, these results indicated that iCMs did not originate from a rare population of cardiac progenitor cells, which might exist in neonatal hearts (FIGS. 3I and J).

FIGS. 3A-J. Induced Cardiomyocytes Originate from Differentiated Cardiac Fibroblasts and are Directly Reprogrammed (A) Cardiac fibroblasts isolated by the conventional isolation method. Most cells were positive for Thy1, and Thy-1$^+$/GFP$^-$ cells were sorted by FACS for transduction. (B) FACS analyses for GFP and cTnT expression in cardiac fibroblasts isolated in (A) one week after transduction by three factors (GMT). (C) Immunofluorescent staining for GFP (green), actinin (red) and DAPI (blue) in the three-factor induced cardiomyocytes originated from (A). (D) Cardiac fibroblasts isolated from adult αMHC-GFP hearts were transduced with three factors. (E) Immunofluorescent staining for GFP, actinin and DAPI in the induced cardiomyocytes originated from adult cardiac fibroblasts indicated in (D). (F) GFP$^-$/Thy1$^+$/c-kit$^+$ cells and GFP$^-$/Thy1$^+$/c-kit$^-$ cells were isolated by FACS, and transduced with 3 factors. (G) GFP$^-$/Thy1$^+$/c-kit$^-$ cells expressed more GFP and cTnT than GFP$^-$/Thy1$^+$/c-kit$^+$ cells by three-factor transduction. (H) Quantitative data of GFP$^+$ cells and cTnT$^+$ cells in (G) (n=3). (I) Isl1-YFP$^-$/Thy1$^+$ cells were sorted from Isl1-YFP heart explants and transduced with three factors. (J) The vast majority of cTnT$^+$ cells induced from Isl1-YFP$^-$/Thy1$^+$ cells were negative for YFP. All data are presented as means±SD. *, P<0.01 vs relative control. Scale bars, 100 µm.

Figure 4:
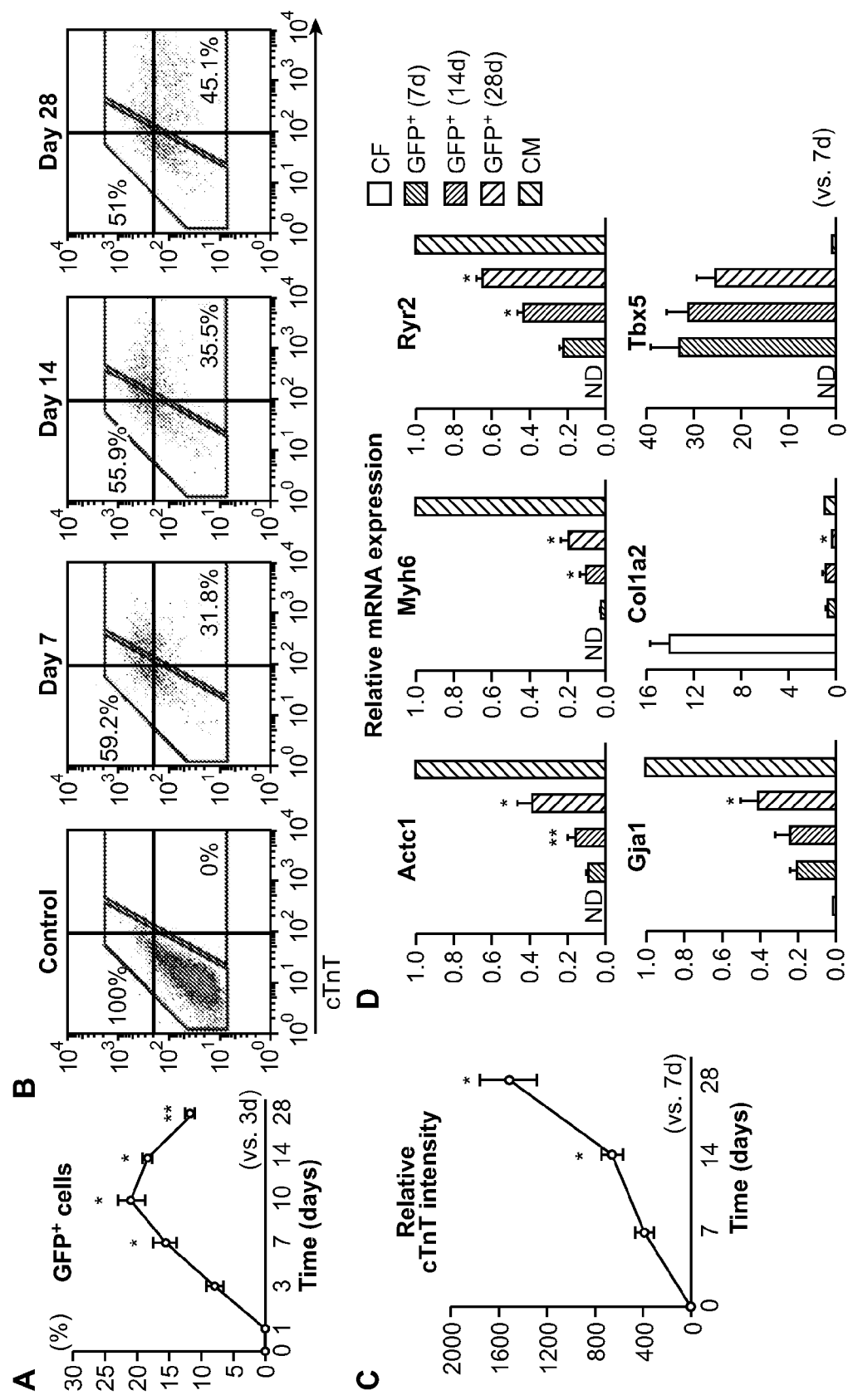
FIGS. 4A-D depict reprogramming of gene expression in induced cardiomyocytes (iCMs).

Induced Cardiomyocytes Resemble Neonatal Cardiomyocytes in Global Gene Expression The time course of cardiomyocyte induction was analyzed. GFP$^+$ cells were detected 3 days after induction and gradually increased in number up to 20% at day 10, and were still present after 4 weeks (FIG. 4A). Importantly, the percentage of cTnT$^+$ cells and the intensity of cTnT expression in GFP$^+$ cells increased significantly over time (FIGS. 4B and C). GFP$^+$ cells were sorted at 7, 14, and 28 days after transduction with GMT and compared candidate gene expression with cardiac fibroblasts and neonatal cardiomyocytes. The cardiomyocyte-specific genes, Actc1 (cardiac α-actin), Myh6 (α-myosin heavy chain), Ryr2 (ryanodine receptor 2), and Gja1 (connexin43), were significantly upregulated in a time-dependent manner in GFP$^+$ cells, but were not detected in cardiac fibroblasts by quantitative RT-PCR (qPCR). Col1a2 (collagen 1a2), a marker of fibroblasts, was dramatically downregulated in GFP$^+$ cells from 7-day culture to the same level as in cardiomyocytes. Expression of the three transduced genes was strongly upregulated in induced cardiomyocytes up to 4 weeks later, suggesting they were not silenced (FIG. 4D). These data indicated that the three factors induced direct conversion of cardiac fibroblasts to cardiomyocytes rapidly and efficiently, but full maturation was a slow process.

The global gene expression pattern of iCMs, neonatal cardiomyocytes, and cardiac fibroblasts was compared by mRNA microarray analyses. GFP$^+$ cells and GFP$^-$ cells were sorted 28 days after GMT transduction. The induced GFP$^+$ cells were strikingly similar to neonatal cardiomyocytes, but were distinct from GFP$^-$ cells and cardiac fibroblasts in global gene expression pattern. These results demonstrate that iCMs are highly similar to neonatal cardiomyocytes, indicating that the reprogramming event was broadly reflected in global gene expression.

FIGS. 4A-D. Gene Expression of Induced Cardiomyocytes is Globally Reprogrammed (A) The percent of GFP$^+$ cells compared to the number of plated cells (n=3). The number of GFP$^+$ cells was counted by FACS sorting at each time point. (B) FACS analyses of cTnT expression in GFP$^+$ cells. Note that cTnT$^+$ cell number and cTnT intensity were both increased over time (n=3). (C) Quantitative data of cTnT intensity in (B) (n=4). (D) Actc1, Myh6, Ryr2, Gja1, Col1a2 and Tbx5 mRNA expression in cardiac fibroblasts (CF), induced cardiomyocytes (GFP$^+$, 7 d, 14 d, 28 d after transduction) and neonatal cardiomyocytes (CM), determined by qPCR (n=3).

Induced Cardiomyocytes Exhibit Spontaneous Contraction

Figure 5:
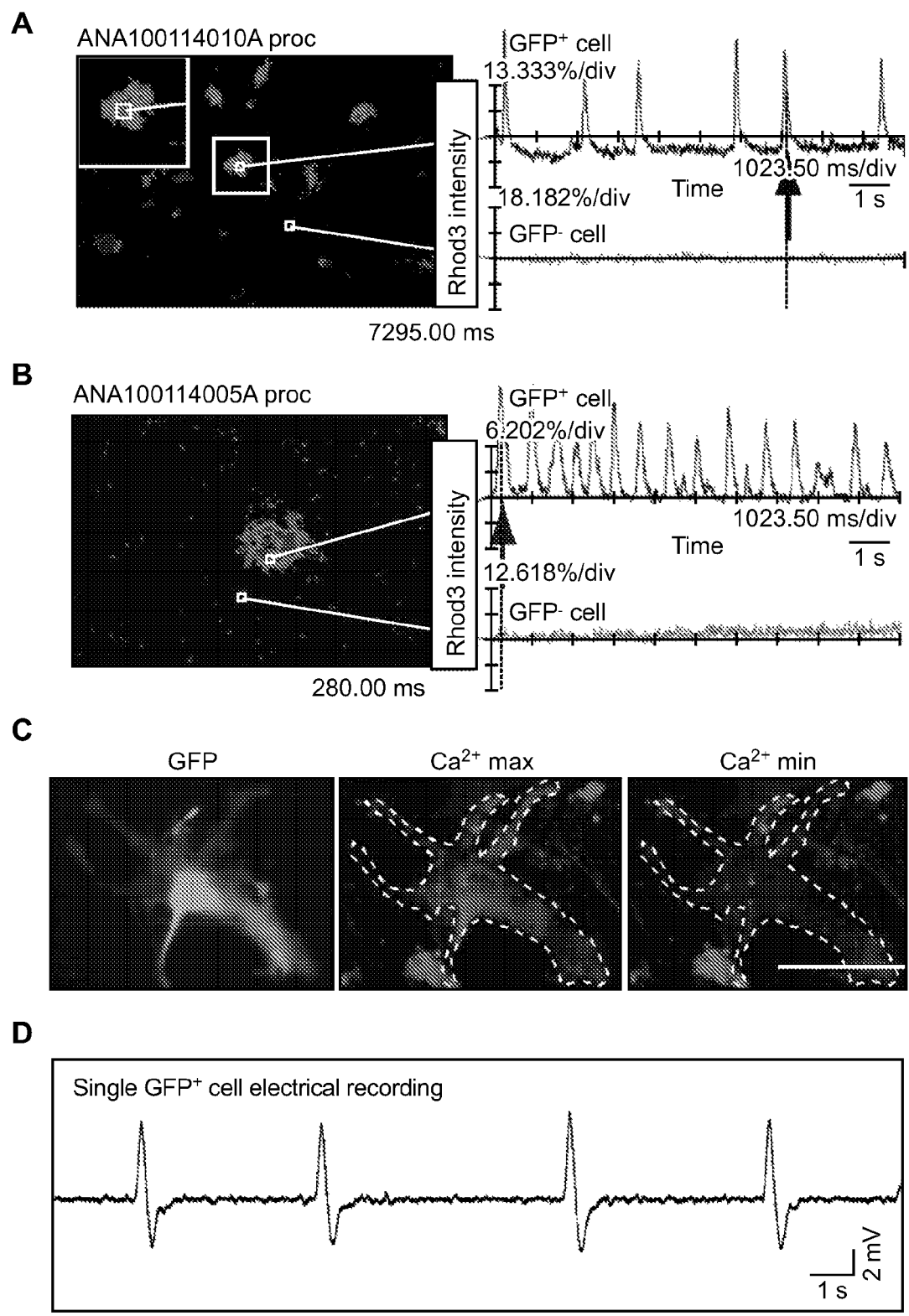
FIGS. 5A-D depict spontaneous $Ca^{2+}$ flux, electrical activity, and beating in iCMs.

To determine if iCMs possessed the functional properties characteristic of cardiomyocytes, intracellular Ca$^{2+}$ flux was analyzed in iCMs after 4 weeks of culture. Around 30% of iCMs showed spontaneous Ca$^{2+}$ oscillations that resembled those of neonatal cardiomyocytes (FIG. 5A). Ca$^{2+}$ oscillation frequency was variable among the cells (FIG. 5B). In addition, spontaneous Ca$^{2+}$ waves were observed in iCMs, similar to neonatal cardiomyocytes (FIG. 5C).

In addition to the characteristic Ca$^{2+}$ flux, iCMs showed spontaneous contractile activity after 4-5 weeks in culture. Single cell extracellular recording of electrical activity in beating cells revealed tracings similar to neonatal cardiomyocytes (FIG. 5D) (Yeung et al., 2001). Thus, the reprogramming of cardiac fibroblast to iCMs was associated with global changes in gene expression and the functional properties characteristic of cardiomyocytes.

FIGS. 5A-D. Induced Cardiomyocytes Exhibit Spontaneous Ca$^{2+}$ Flux, Electrical Activity and Beating (A) α-MHC-GFP$^+$ cells showed spontaneous Ca$^{2+}$ oscillation. The pseudo-color image shows Rhod-3 fluorescence intensity in cells. Small squares indicate the Ca$^{2+}$ measuring areas, and the inset is a high-magnification view (left panel). The Rhod-3 intensity trace (right panel) corresponds to the left panel. The arrow indicates the time point corresponding to the image on the left. (B) High frequency of $Ca^{2+}$ oscillation was observed in induced cardiomyocytes. The arrow indicates the time point corresponding to the image on the left. (C) Spontaneous $Ca^{2+}$ waves observed in the induced cardiomyocyte. GFP and Rhod-3 at $Ca^{2+}$ max and min, are shown. The $GFP^+$ cell is outlined in white dots. (D) Spontaneously contracting cells had electrical activity measured by single cell extracellular electrodes. Representative data are shown in each panel (n=10).

Figure 6:
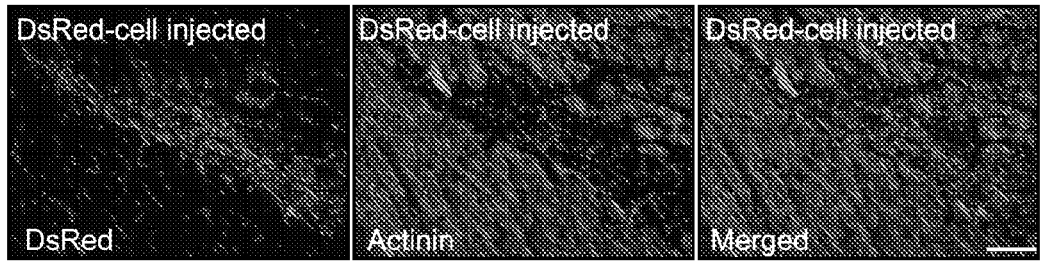
FIGS. 6A-C depict in vivo reprogramming of cardiac fibroblasts into cardiomyocytes.
Figure 6:
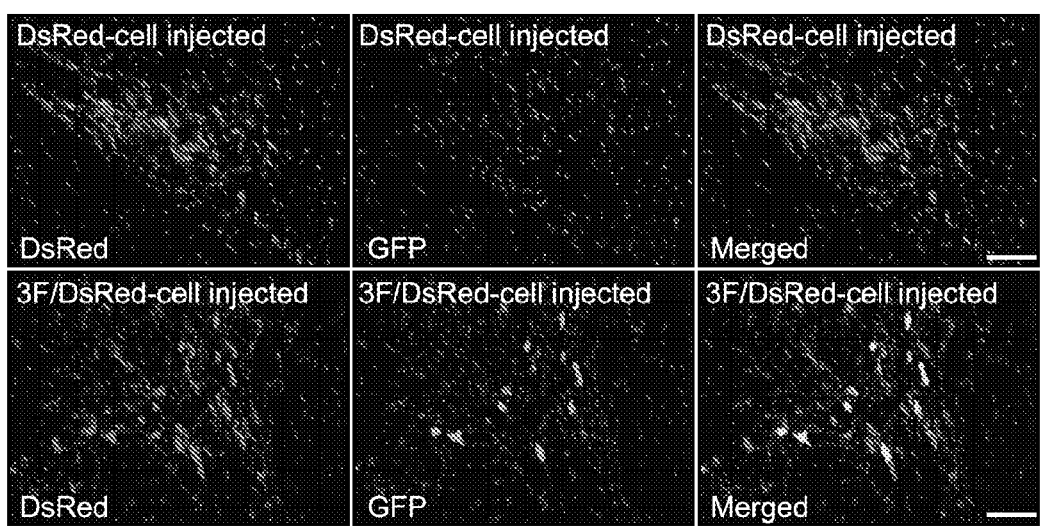
Figure 6:
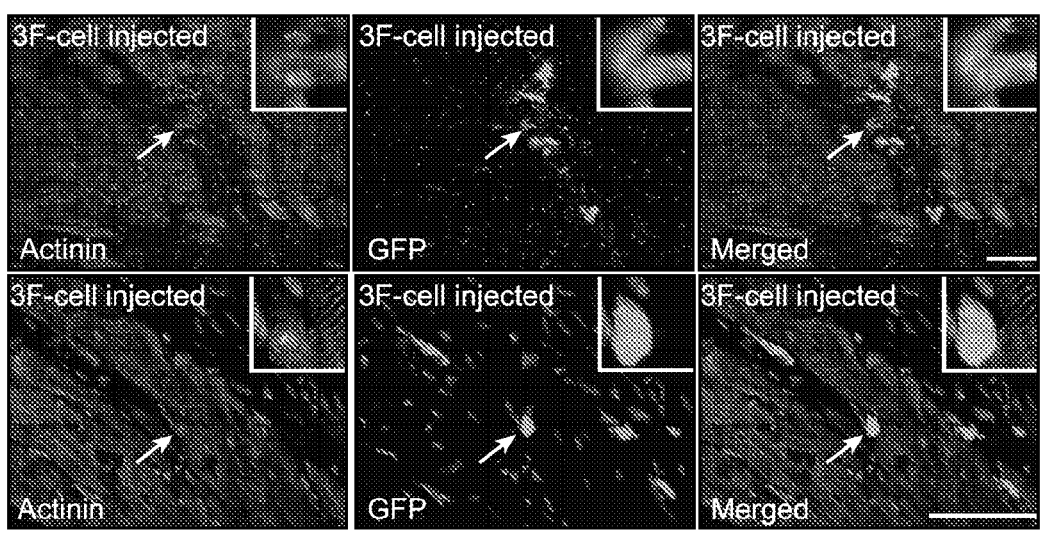

Cardiac Fibroblasts Convert to Cardiomyocytes by Three-Factor Transduction In Vivo Next, to investigate whether Gata4+ Mef2c+Tbx5 (GMT)-transduced cardiac fibroblasts can be reprogrammed to cardiomyocytes in vivo, $GFP^-/Thy1^+$ cardiac fibroblasts were harvested at day 1 after viral transduction and injected them into non-obese diabetic-severe combined immunodeficiency (NOD-SCID) mouse hearts. GMT-infected cells did not express GFP at day 1 after transduction (FIG. 4A). Cardiac fibroblasts were infected with either the mixture of the three factors and DsRed retroviruses or DsRed retrovirus (negative control) to be readily identified by fluorescence. Cardiac fibroblasts infected with DsRed did not express actinin or GFP, confirming cardiomyocyte conversion did not happen in the negative control (FIGS. 6A and B). Despite being injected into the heart only 1 day after viral infection, a subset of cardiac fibroblasts transduced with the three factors (GMT) and DsRed expressed GFP in the mouse heart within 2 weeks (FIG. 6B). The $GFP^+$ cells expressed actinin and had clear sarcomeric structures (FIG. 6C). These results suggested that Gata4, Mef2c, and Tbx5 were sufficient to convert cardiac fibroblasts to cardiomyocytes within two weeks in vivo.

FIGS. 6A-C. Cardiac Fibroblasts can be Reprogrammed to Cardiomyocytes In Vivo (A) DsRed infected cardiac fibroblasts (DsRed-cell) were transplanted into NOD-SCID mouse hearts 1 day after infection and sections of hearts analyzed by immunocytochemistry after 2 weeks. Transplanted fibroblasts marked with DsRed did not express actinin (green). (B) Cardiac fibroblasts infected with DsRed or Gata4/Mef2c/Tbx5 with DsRed (3F/DsRed-cell) were transplanted into NOD-SCID mouse hearts 1 day after infection. Note that a subset of 3F/DsRed cells (red) expressed α-MHC-GFP (green). Data were analyzed two weeks after transplantation. (C) Gata4/Mef2c/Tbx5-transduced cardiac fibroblasts (3F-cell) were transplanted into mouse hearts. A subset of induced $GFP^+$ cells expressed actinin (red) and had sarcomeric structures. Insets are high-magnification views (arrows). Data were analyzed two weeks after transplantation. Representative data are shown in each panel (n=4 in each group). Scale bars, 100 µm.

Example 2

Direct Reprogramming of Cardiac Fibroblasts into Functional Cardiomyocytes

Using methods essentially as described in Example 1, exogenous Gata4, Tbx5, and Mef2c were introduced into mouse post-natal tail tip fibroblasts. About 20% to 30% of the post-natal tail tip fibroblasts were reprogrammed to myosin heavy chain-$GFP^+$ cells (cardiomyocytes) following introduction of Gata4, Tbx5, and Mef2c (where Gata4, Tbx5, and Mef2c are collectively referred to as GMT).

Example 3

In Vivo Reprogramming of Murine Cardiac Fibroblasts into Cardiomyocytes

Materials and Methods

Retrovirus Generation, Concentration and Titration.

Retroviruses were generated as described in Example 1. The pMXs retroviral vectors containing coding regions of Gata4, Mef2c, Tbx5, and dsRed were transfected into Plat-E cells with Fugene 6 (Roche) to generate viruses. Ultra-high titer virus ($>1 \times 10^{10}$ plaque-forming units (p.f.u) per ml) was obtained by standard ultracentrifugation. Retroviral titration was performed using Retro-X qRT-PCR Titration Kit (Clontech).

Animals, Surgery, Echocardiography and Electrocardiography.

Postn-Cre; R26R-lacZ mice were obtained by crossing Periostin-Cre mice (Snider et al. (2009) Circulation Res. 105:934) and Rosa26-lacZ mice (Soriano (1999) Nat. Genet. 21:70). Postn-Cre; R26R-EYFP mice were obtained by crossing Periostin-Cre mice and Rosa26-EYFP mice (Srinivas et al. (2001) supra). All surgeries and subsequent analyses were performed in a blinded fashion for genotype and intervention. Myocardial infarction (MI) was induced by permanent ligation of the left anterior descending artery (LAD) as described (Qian et al. (2011) J. Exp. Med. 208: 549). A pool of concentrated virus (GMT (Gata-4, Mef2c, Tbx5); or GMTR (GMT plus DsRed)) was mixed, and 10 µl of mixed virus plus 10 µl of PBS or 40 ng/µl Thymosin β4 was injected along the boundary between infarct zone and border zone (based on the blanched infarct area) after coronary artery occlusion. Mouse echocardiography and surface electrocardiography were performed as described (Qian et al. (2011) supra).

Immunohistochemistry and Immunocytochemistry.

Immunohistochemistry and immunocytochemistry were performed as described (Qian et al. (2011) supra). Scar size was determined by Masson-Trichrome staining (Bock-Marquette et al. (2004) Nature 432:466; and Qian et al. (2011) supra). The area at risk (AAR) and myocardial infarct size were determined by Evans Blue/triphenyltetrazolium chloride labeling technique (Kurrelmeyer et al. (2000) Proc. Natl. Acad. Sci. USA 97:5456).

Isolation of Adult Cardiomyocytes, Single Cell Patch Clamp, and Cardiac Fibroblast Migration Assay.

Adult cardiomyocyte isolation was performed as described with minor modifications (Xu et al. (1999) J. Gen. Physiol. 113:661). Single cell patch clamp recordings were performed as described (Knollmann et al. (2003) Circulation Res. 92:428; Le Guennec et al. (1994) J. Physiol. 478 Pt 3:493; Spencer et al. (2003) Am. J. Physiol. Heart Circ. Physiol. 285:H2552). Migration assay was performed according to the published explant culture protocol (Example 1; Bock-Marquette et al. (2004) supra; and Andersen et al. (2009) supra). In brief, isolated adult mouse hearts were minced into small pieces less than 1 $mm^3$ in size. The explants were plated on gelatin-coated dishes and cultured in explant medium (IMDM/20% FBS) until fibroblasts migrated out from minced tissue. The number of days when 10 heart pieces were identified with migratory fibroblasts was recorded.

FACS and Quantitative RT-PCR.

Dissociated cardiac cells from mouse hearts were stained with APC-conjugated anti-Thy1 antibody (eBioscience) for 30 minutes at room temperature. After washing with PBS twice, stained cells were sorted by FACSAria2 (BD). RNA was extracted by TRizol method (Invitrogen). RT-PCR was performed using the Superscript III first-strand synthesis system (Invitrogen). qPCR was performed using the ABI 7900HT (TaqMan, Applied Biosystems), per the manufacturer's protocols. Optimized primers from Taqman Gene Expression Array were used.

Statistics.

Differences between groups were examined for statistical significance using unpaired student's t-test or ANOVA. $p<0.05$ was regarded as significant.

Results

Example 1 describes direct reprogramming of fibroblasts into cardiomyocyte-like cells in vitro upon expression of the three transcription factors, Gata4, Mef2c, and Tbx5 (GMT). As observed in reprogramming to iPS cells, the percentage of fibroblast cells that became fully reprogrammed to beating cardiomyocytes in vitro was small, but far more were partially reprogrammed, much like pre-iPS cells that have potential to become fully pluripotent with additional stimuli. It was posited that cardiac fibroblasts may reprogram more fully in vivo in their native environment, which might promote their survival, maturation, and coupling with neighboring cells. If so, the vast endogenous pool of cardiac fibroblasts could serve as a potential source of new cardiomyocytes for regenerative therapy.

To efficiently deliver GMT at high levels in vivo, a retroviral system was used to express GMT, or dsRed as a marker, into hearts of 2-month-old male mice. 10 µl of ultra-high-titer retrovirus ($\sim 10^{10}$ copies/ml) that expressed each transcription factor and dsRed control was injected into the myocardial wall as a mixture. Two days after retrovirus injection, transverse sections across the injected area were prepared and co-stained for dsRed, the cardiomyocyte marker, α-Actinin, and Vimentin, which is enriched in the fibroblast population. While no markers are completely specific to cardiac fibroblasts, fibroblasts are characterized by expression of Vimentin and the surface markers Thy1 and DDR2 (Ieda et al. (2009) supra). At baseline, it was difficult to detect any α-Actinin- or Vimentin-positive cells that also expressed dsRed, suggesting minimal viral uptake. This was consistent with the observation that retroviruses only infect cells that are actively dividing (Byun et al. (2000) *J. Gene Med.* 2:2).

Figure 7:
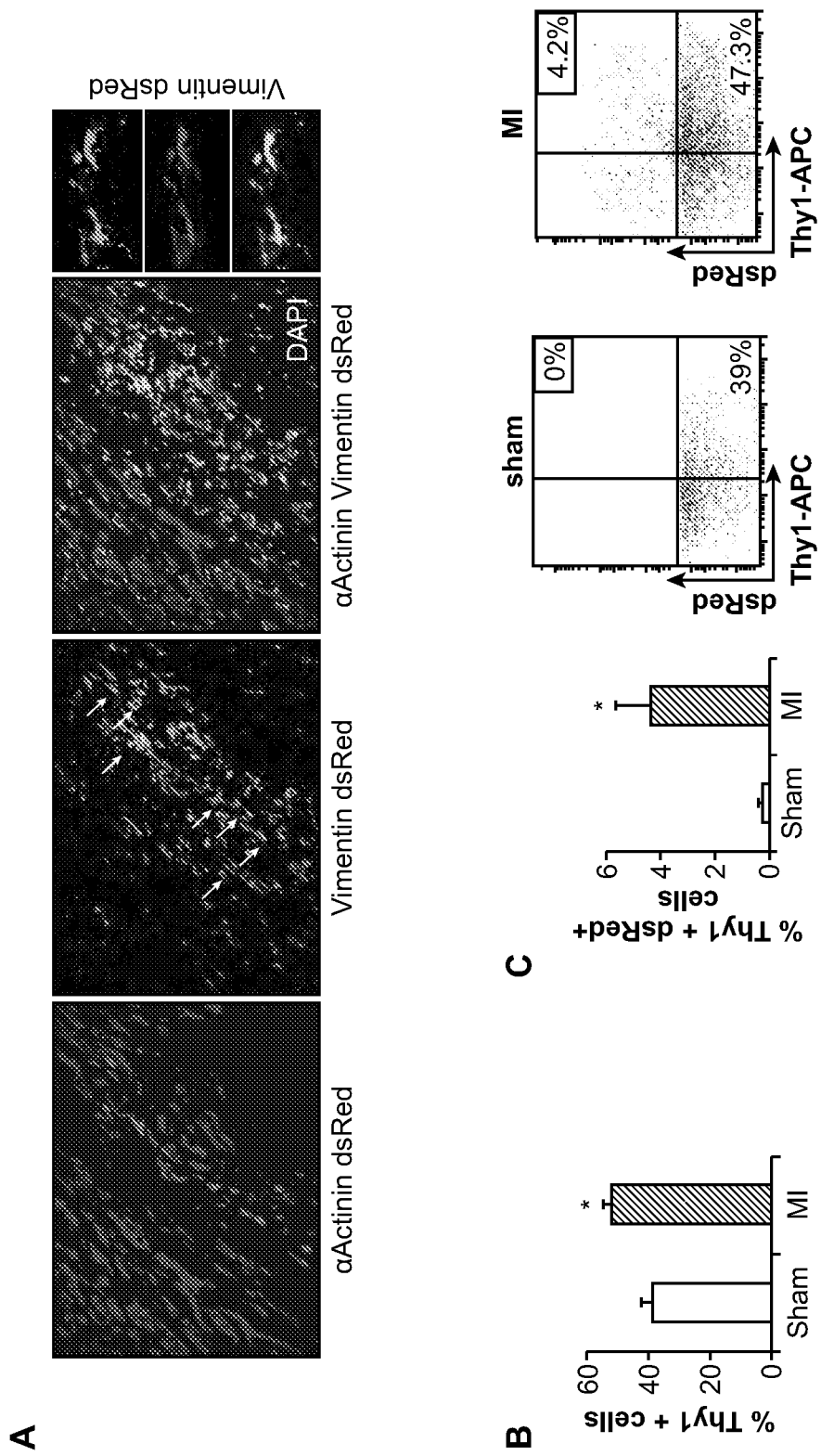
FIGS. 7A-G depict in vivo reprogramming of cardiac fibroblasts to cardiomyocyte-like cells.
Figure 7:
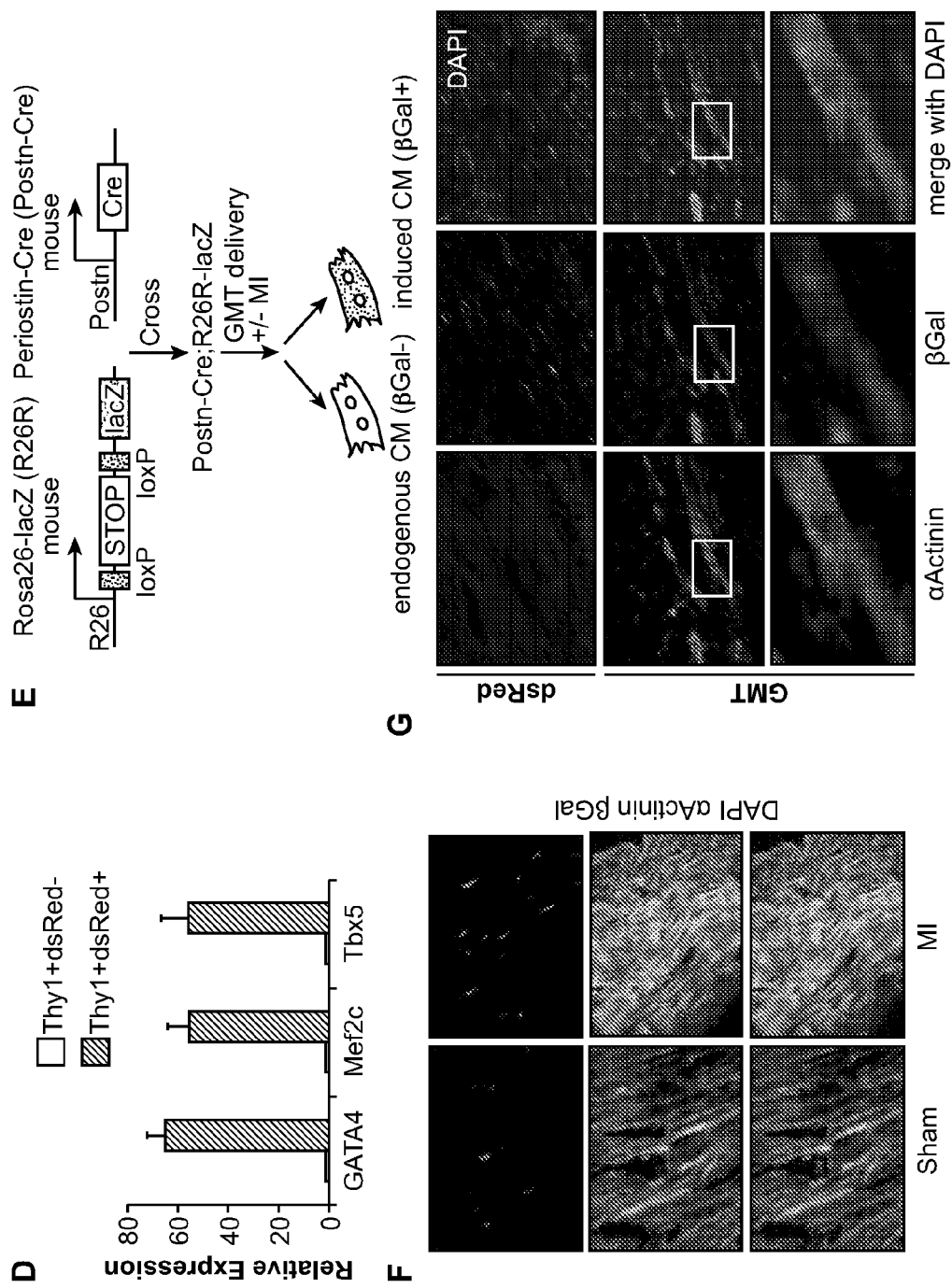

Fibroblasts, which have an embryologic origin distinct from cardiomyocytes, become activated after cardiac injury, such as myocardial infarction (MI), and migrate to the site of injury and proliferate. Cardiac injury was induced by coronary artery ligation and injected dsRed retrovirus into the myocardium bordering the infarct zone. While cells co-expressing dsRed and α-Actinin were still undetectable, many Vimentin-positive cells, that were also positive for dsRed, were found (FIG. 7A). To quantify the percentage of heart cells that took up the virus, fluorescence activated cell sorting (FACS) was used to analyze cells dissociated from the infarct/border zone of injected hearts two days after injury. Cells stained with Thy1, a surface marker enriched in fibroblasts, were increased upon surgery, suggesting successful activation of cardiac fibroblasts (FIG. 7B). Rare dsRed$^+$Thy1$^+$ cells were detected by FACS from sham-operated mice; however, 4.2% of cells from the infarct/border zone of mice with MI were dsRed$^+$Thy1$^+$, suggesting successful delivery of virus into cardiac fibroblasts upon injury (FIG. 7C). In agreement with this, dsRed$^+$Thy1$^+$ sorted cells expressed 60 fold higher levels of Gata4, Mef2c, and Tbx5 than dsRed$^-$Thy1$^+$ cells by quantitative PCR (qPCR) (FIG. 7D).

To determine if cardiomyocyte conversion from a non-myocyte pool was occurring in vivo, lineage-tracing experiments were used to track the origin of putative induced cardiomyocytes. Cardiac fibroblasts were genetically labeled with a mouse line that expresses Cre-recombinase under the promoter of the fibroblast-enriched gene, Periostin (Snider et al. (2009) supra; and Snider et al. (2008) *Circulation Res.* 102:752). When intercrossed with the R26R-lacZ reporter line (Soriano et al. (1999) supra), which results in activation of β-galactosidase in Periostin-expressing cells and all their progeny (FIG. 7E), β-galactosidase activity was found in the majority of cardiac fibroblasts and some endocardial and endothelial cells, as reported (Snider et al. (2009) supra; Snider et al. (2008) supra; and Takeda et al. (2010) *J. Clin. Invest.* 120:254). Most importantly, β-galactosidase activity was not detected in any cardiomyocytes, even after injury by coronary ligation, in agreement with reports (FIG. 7F) (Snider et al. (2009) supra; Snider et al. (2008) supra; and Takeda et al. (2010) supra). However, 4 weeks after MI and retroviral delivery of GMT, many β-galactosidase$^+$ cells that were also α-Actinin$^+$ were found in the injured area of the heart, suggesting that they may be descendants of cells that once expressed Periostin (FIG. 7G). These cells had well-formed sarcomeres and were shaped similar to β-galactosidase$^-$ myocytes (FIG. 7G).

FIGS. 7A-G. Genetic Lineage Tracing Demonstrates In Vivo Reprogramming of Cardiac Fibroblasts to Cardiomyocyte-Like Cells.

a, Confocal images of immunofluourescent staining on hearts showing the integration of dsRed control virus (red) into Vimentin$^+$ cells (green) but not into αActinin$^+$ cells (blue) 2 days after MI. Arrows point to dsRed$^+$Vimentin$^+$ cells (yellow), two of which were scanned under high magnification and shown in the right three panels, with merged image at bottom. b, Quantification by FACS analyses of Thy-1 positive cells from hearts 2 days after sham-operation or myocardial infarction (MI). n=3, *p<0.05. c, FACS analyses of Thy-1$^+$dsRed$^+$ cells from sham-operated or MI mice with quantification (left) and representative FACS plots (right). n=3, *p<0.05. d, qPCR of Gata4, Mef2c and Tbx5 in Thy-1$^+$dsRed$^+$ cells compared to Thy-1$^+$dsRed$^-$ cells sorted two days after GMTR (Gata4, Mef2c, Tbx5 and dsRed) was injected into hearts post-MI. n=3 with technical quadruplicates. e, Schematic diagram showing the genetic fate mapping method to lineage trace cardiomyocyte-like cells reprogrammed from Postn-Cre; R26R-lacZ cells. f, Immunofluorescent staining for αActinin (green), βGal (red), and DAPI (blue) on Postn-Cre; R26R-lacZ mouse heart sections 4 weeks after sham operation or MI. Note absence of αActinin$^+$ βGal$^+$ double-positive cells even after MI. g, Immunofluorescent staining for αActinin (green), βGal (red), and DAPI (blue) on dsRed- or GMT-injected Postn-Cre; R26R-lacZ heart sections from border zone of mice 4 weeks post MI. The lowest panels are magnified pictures of boxed areas in the middle panels.

The extent and spectrum to which the β-galactosidase$^+$ α-Actinin$^+$ cells had been reprogrammed was determined. To avoid the potential for false positive signals from overlaying cells due to the thickness of heart sections, adult cardiomyocytes were isolated at the single-cell level from the infarct/border zone of Periostin-Cre; R26R-lacZ hearts 4 weeks after coronary ligation and injection with GMT or dsRed control. No cardiomyocytes isolated from dsRed-injected hearts were β-galactosidase$^+$ by immunostaining (FIG. 8A, n=6 animals, 4~6 slides/animal); similar cells isolated from Periostin-Cre; R26R-EYFP mice showed no YFP$^+$ cardiomyocytes among thousands of cells visualized.

Figure 8:
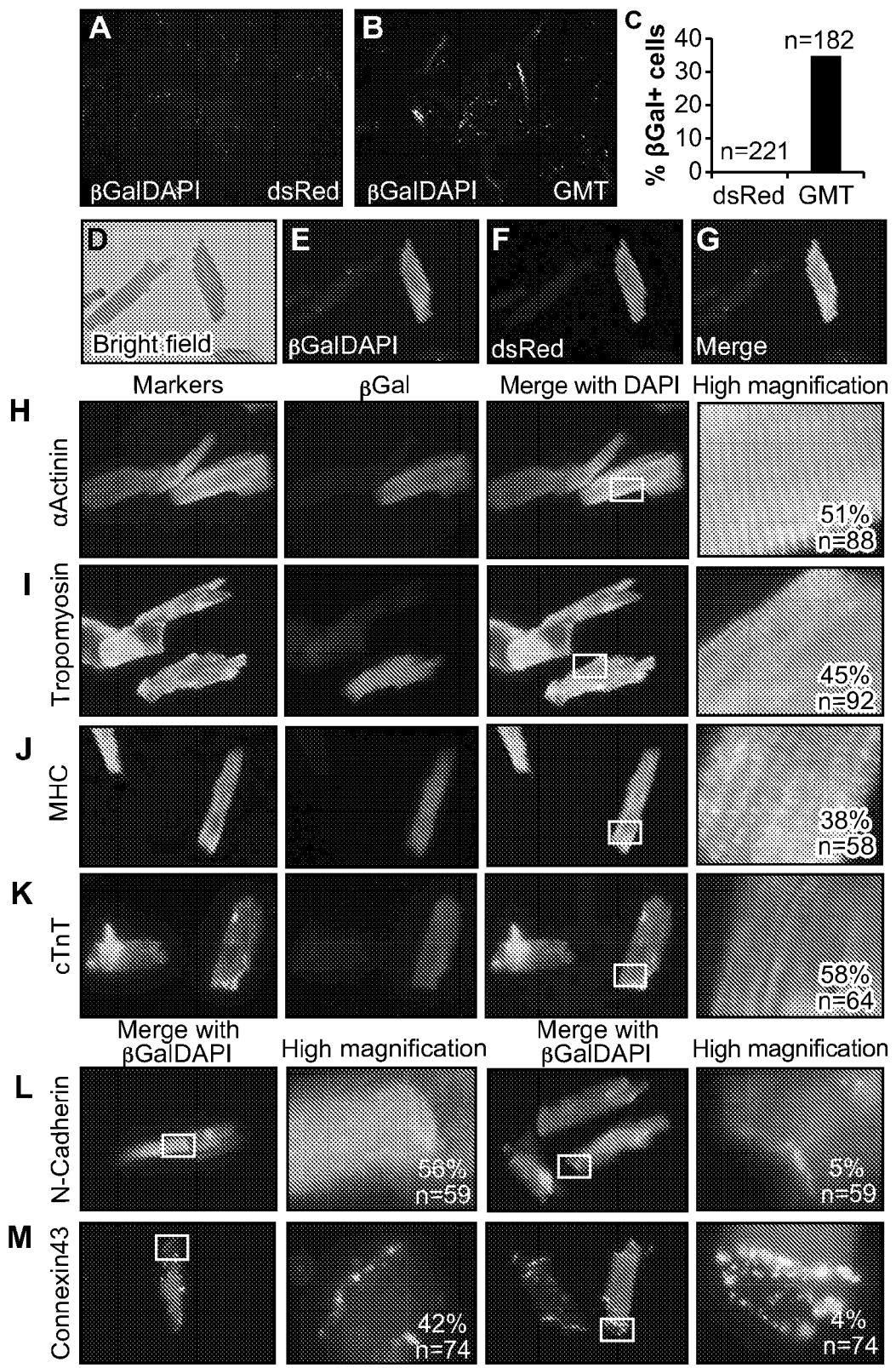
FIGS. 8A-N depict single-cell analysis of cardiac reprogramming in vivo.
Figure 8:
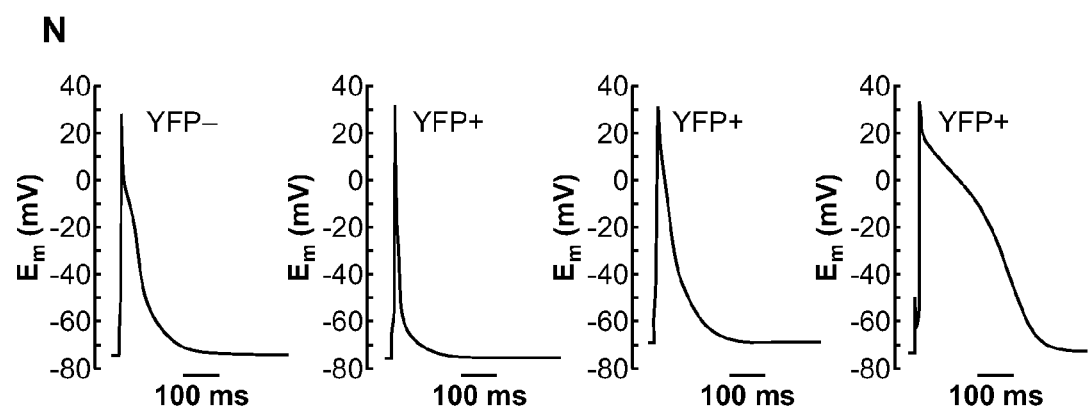

In contrast, 35% of cells isolated in the cardiomyocyte preparation from the border/infarct zone were β-galactosidase$^+$ after GMT injection (FIGS. 8B and 8C). Among the β-galactosidase$^+$ cells, 98% were α-Actinin+. To address the possibility that the β-galactosidase$^+$ cells might represent leaky expression of Periostin-Cre or ectopic activation of Cre in cardiomyocytes, hearts were co-injected with pooled retrovirus for GMT and dsRed (GMTR), providing a marker for non-myocyte cells that took up GMT retrovirus. It was found that the β-galactosidase$^+$ cells were also positive for dsRed, indicating they were infected by virus, consistent with their non-cardiomyocyte origin (FIGS. 8D-G).

Morphologically, the majority of β-galactosidase$^+$ cells were large with a rod-shaped appearance and were binucleated, closely resembling endogenous cardiomyocytes that were β-galactosidase negative from the same isolation (FIGS. 8D-G). Further analyses revealed that, in addition to α-Actinin (FIG. 8H), the β-galactosidase$^+$ cells expressed multiple sarcomeric markers, including Tropomyosin (FIG. 8I), cardiac muscle heavy chain (MHC) (FIG. 8J), and cardiac TroponinT (cTnT) (FIG. 8K). Examples of cells that showed nearly normal sarcomeric structures throughout the cell, representing ~50% of cells, are shown (FIGS. 8H-K). The cells did not express Vimentin, smooth muscle α-actin, or SM22, suggesting the cells were no longer cardiac fibroblasts, nor did they become myofibroblasts or vascular smooth muscle cells. For simplicity, the β-galactosidase$^+$α-Actinin$^+$ cardiomyocyte-like cells are referred to as in vivo induced cardiomyocytes (iCMs), at least based on distinctive morphology, gene expression and sarcomeric structure.

To determine if the iCMs expressed proteins involved in cell-cell communication with endogenous cardiomyocytes, the expression level and pattern of N-Cadherin, a cell-surface Ca$^{2+}$-dependent adhesion molecule that is located in intercalated disks in the myocardium, was examined. Over 90% of iCMs expressed N-Cadherin; 61% had localized N-Cadherin at the cell border; and 5% fully resembled the endogenous cardiomyocyte localization (FIG. 8L). Expression of Connexin 43 (Cx43), the major gap junction protein in the heart that promotes electrical coupling of cells and synchronized contraction of myocytes throughout the ventricle, was also examined. About 90% of iCMs expressed Cx43, with half of those expressing Cx43 at high levels and in a pattern similar to endogenous cardiomyocytes with cell border localization (FIG. 8M); in 4%, Cx43 was localized in a pattern almost indistinguishable from that of an endogenous cardiomyocyte (FIG. 8M).

Figure 9:
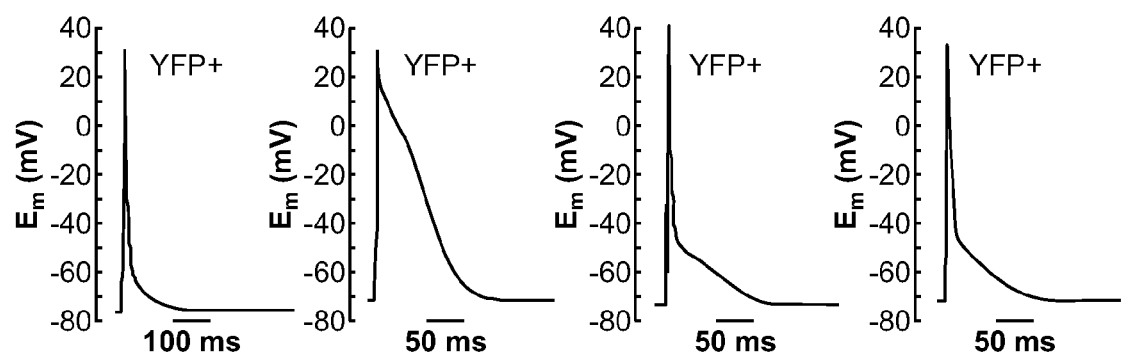
FIG. 9 depicts intracellular recordings showing action potentials for additional in vivo reprogrammed iCMs.
Figure 10:
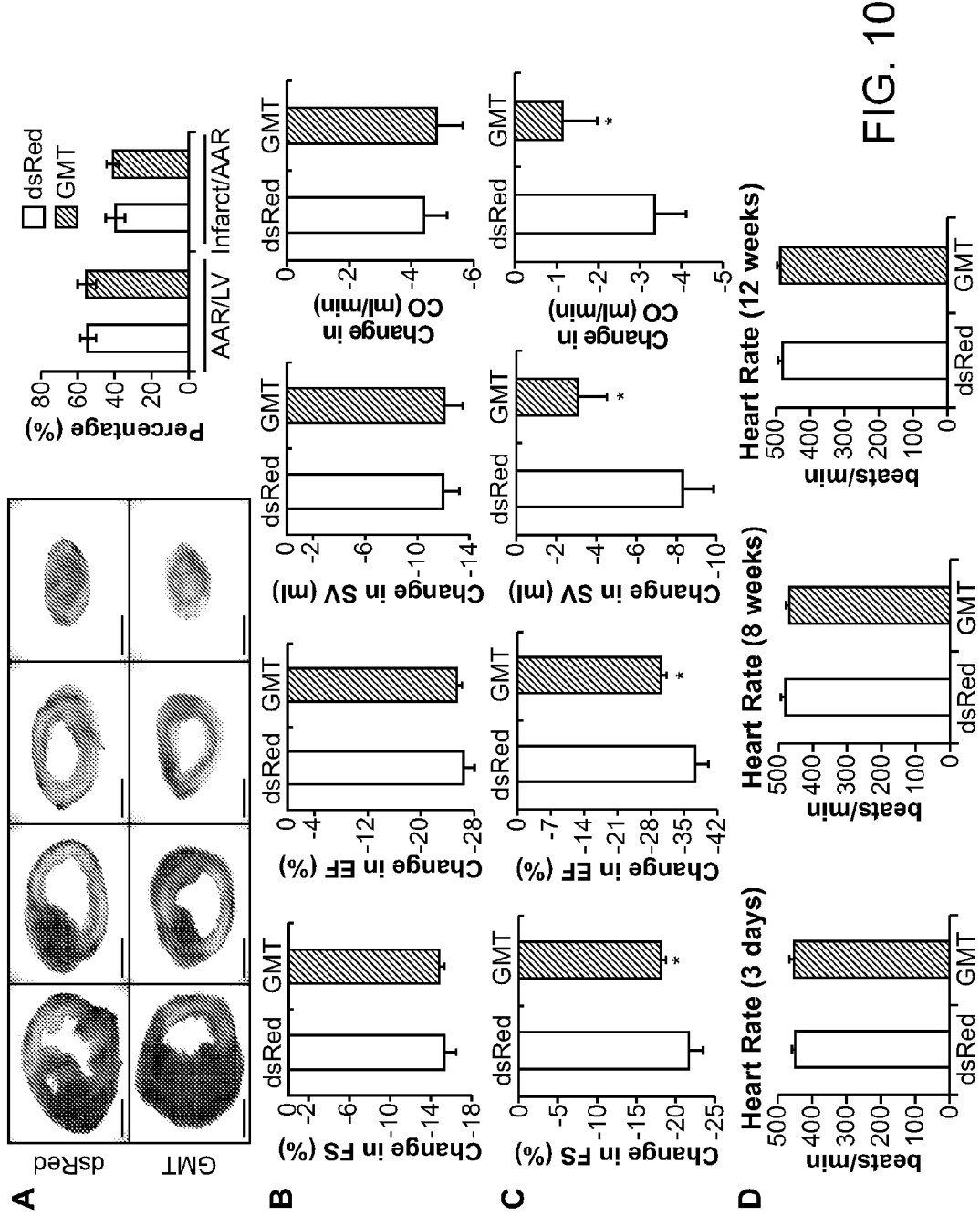
FIGS. 10A-D depict determination of area at risk (AAR) and infarct size for dsRed or GMT (expression vector encoding three factors: Gata4-Mef2c-Tbx-5) injected hearts after coronary ligation and echocardiography data.

To determine if iCMs possessed the typical electrophysiological properties of mature cardiomyocytes, intracellular electrical recording was performed by standard patch clamp techniques. Recording from a single-cell suspension of cardiomyocytes from the border/infarct zone of Periostin-Cre; R26R-EYFP mice transduced with GMT, action potentials of YFP$^+$ cells (iCMs) and endogenous cardiomyocytes that were YFP$^-$ were compared (FIG. 8N; and FIG. 9). Many reprogrammed cells had a physiological resting membrane potential (−70 mV or less) and exhibited contraction in response to electrical stimulation but not at rest, similar to adult ventricular cardiomyocytes, which are normally quiescent in the absence of stimulation. Varying action potential morphologies were identified (FIG. 8N; and FIG. 9), and some spontaneously contracting cells were observed, but these had resting potentials around −50 mV. Taken together, many in vivo reprogrammed cardiomyocytes closely resembled adult ventricular cardiomyocytes 4 weeks after introduction of GMT, while others were broadly similar, differing mainly in their ability to maintain a hyperpolarized resting potential when evaluated as single cells in culture.

FIGS. 8A-N. Single-Cell Analysis of Cardiac Reprogramming In Vivo.

a-c, Immunofluorescent staining for βGal and DAPI on isolated cardiomyocytes from the infarct/border zone of Postn-Cre; R26R-lacZ hearts 4 weeks after dsRed (a) or GMT (b) injection with quantification in (c). d-g, Brightfield image of CMs isolated from GMTR-injected Postn-Cre; R26R-lacZ hearts 4 weeks after MI (d). Of these, (e) is βGal positive and (f,g) are co-stained with dsRed. h-k, Immunofluorescent staining for cardiac markers including αActinin, Tropomyosin, cardiac myosin heavy chain (MHC), and cardiac Troponin T (cTnT) co-labeled with βGal and DAPI, on isolated cardiomyocytes from the infarct/border zone of Postn-Cre; R26R-lacZ hearts 4 weeks after GMT injection. The pictures are representative examples of the induced cardiomyocytes next to an endogenous cardiomyocyte from the same preparation with quantification and sample size. High magnification images of boxed areas are shown in the far right panels. l-m, Immunofluorescent staining for N-Cadherin, or Connexin 43 co-labeled with βGal and DAPI, on isolated cardiomyocytes from the infarct/border zone of Postn-Cre; R26R-lacZ hearts 4 weeks after GMT injection. Left two panels are representative images with quantification and sample size; right two panels represent examples of the best-reprogrammed induced cardiomyocytes next to an endogenous cardiomyocyte from the same preparation with quantification and sample size. High magnification images of boxed areas are shown next to the merge pictures. n, Intracellular current clamp recording of multiple cardiomyocytes isolated from Postn-Cre; R26R-EYFP hearts 4 weeks after MI. iCMs that were YFP$^+$ displayed action potentials that resembled those of endogenous cardiomyocytes that were YFP$^-$ from the same preparation. Cells were isolated from Postn-Cre; Rosa-EYFP mice 8 weeks post MI and virus transduction.

FIG. 9. Intracellular recordings showing action potentials for additional in vivo reprogrammed iCMs (YFP$^+$ cells isolated from Postn-Cre; Rosa-EYFP hearts 8 weeks after MI and infection with Gata4, Mef2c, and Tbx5).

Figure 11:
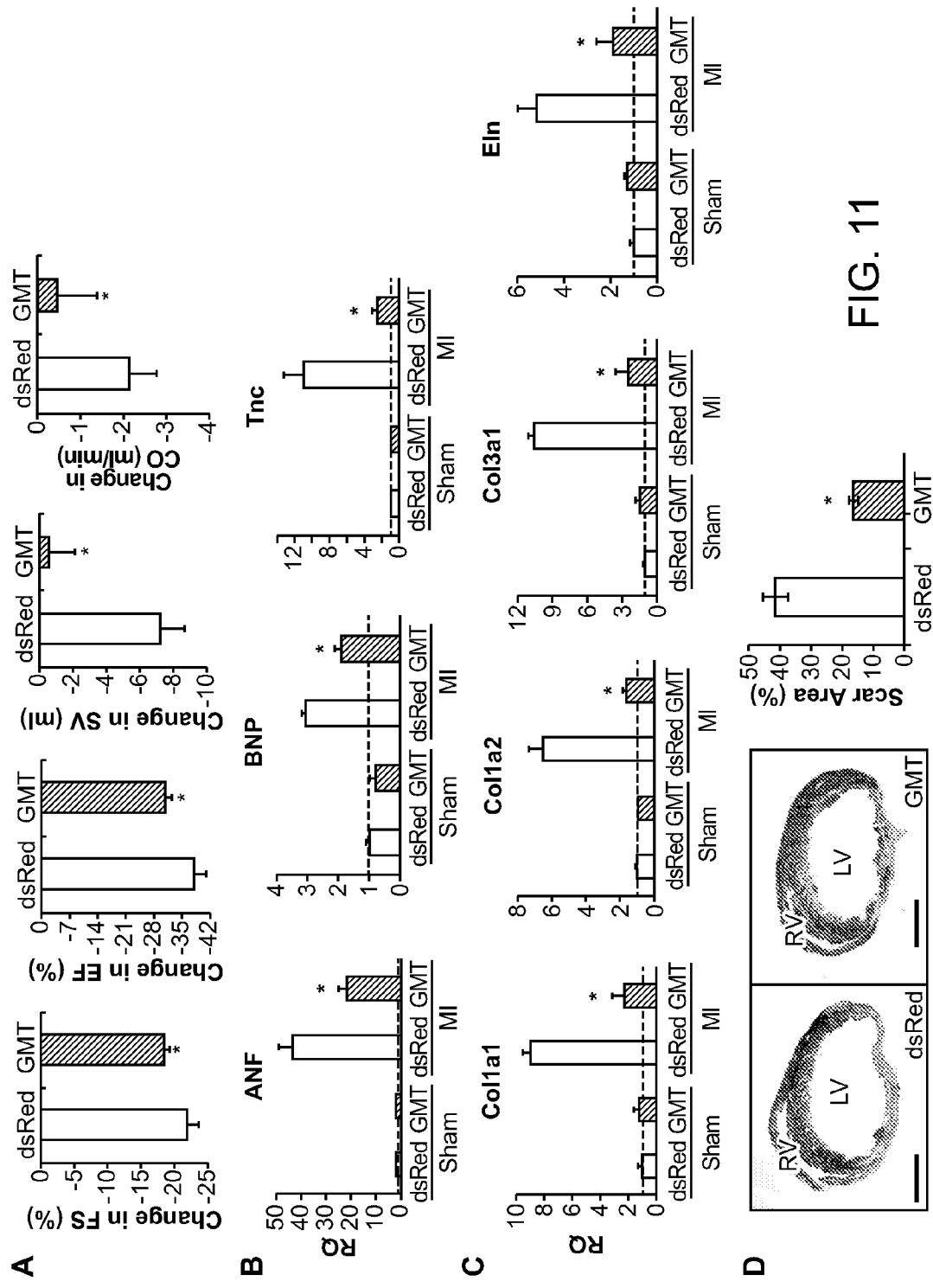
FIGS. 11A-D depict the effect of in vivo delivery of cardiac reprogramming factors on cardiac function after myocardial infarction.

Since in vivo reprogrammed iCMs had contractile potential and may electrically couple with viable endogenous cardiomyocytes, it was determined if converting endogenous cardiac fibroblasts into myocytes translates into partial restoration of heart function after MI. All studies were performed in blinded fashion, including retroviral injection, and de-coded after completion of measurements. Mice injected with GMT or dsRed alone underwent serial high-resolution echocardiography 1 day before and 3 days and 1, 4, 8, and 12 weeks after MI. Using Evans blue/TTC double staining, the area at risk (AAR), and the infarct size of myocardium 48 hours after coronary ligation, were assessed. GMT- and dsRed-injected mice showed no differences in AAR or infarct size (FIG. 10A), suggesting that the extent of initial cardiac injury post-MI was not significantly affected by GMT induction. All mice showed a reduction in left ventricular function after coronary artery ligation (FIG. 11; and FIG. 10B). 8 and 12 weeks after injection, the fraction of blood ejected from the left ventricle with each contraction (ejection fraction) and the fractional shortening of the ventricular chamber was significantly improved in mice injected with GMT, compared to controls injected with dsRed (FIG. 11B; and FIGS. 10B-D). Stroke volume (volume of blood ejected with each heart beat) and cardiac output were improved after 8 weeks (FIG. 10C) and were close to normal after 12 weeks (FIG. 11A).

As a molecular readout of cardiac dysfunction, qPCR was performed to monitor the expression levels of atrial natriuretic factor (ANF), brain natriuretic peptide (BNP) and tenascin C (Tnc) from GMT-injected and control hearts in the area of injury. All were up-regulated after MI, as expected, but this upregulation was attenuated by injection of GMT in infarcted hearts (FIG. 11B). It was also found that the expression level of collagen genes, which was increased upon MI, was partially restored by injecting GMT (FIG. 11C). In agreement with the improvement of cardiac function, injection of GMT resulted in a smaller scar size 8 weeks after MI (FIG. 11D). ECG studies did not indicate evidence for arrhythmias with GMT injection compared to control dsRed injection, and no mice suffered sudden death.

FIGS. 10A-D. Determination of Area at Risk (AAR) and Infarct Size for dsRed or GMT Injected Hearts after Coronary Ligation and Additional Echocardiography Data.

a, Representative pictures of Evans blue TTC staining on four continuous slices of left ventricle from representative hearts of dsRed or GMT injected hearts 48 hours after myocardial infarction (MI). Scale bars: 500 μm. Histogram is the blinded quantification of the area at risk (AAR) and infarct size as described in Methods. There was no statistical difference between dsRed and GMT injected MI hearts. b-c, Fractional shortening (FS), ejection fraction (EF), stroke volume (SV), and cardiac output (CO) of the left ventricle are shown using high-resolution echocardiography on hearts injected with dsRed or GMT. Changes in these parameters 3 days (b) and 8 weeks (c) after MI are shown. d, Heart rate during echocardiography is shown for each time point showing no difference between dsRed and GMT cohorts. All echo data in (b, c, d) were collected in blinded fashion. dsRed, n=9; GMT, n=10. *p<0.05.

FIGS. 11A-D. In Vivo Delivery of Cardiac Reprogramming Factors Improves Cardiac Function after Myocardial Infarction.

a, Fractional shortening (FS), ejection fraction (EF), stroke volume (SV), and cardiac output (CO) of the left ventricle were measured using high-resolution echocardiography. Changes in these parameters before and 12 weeks after MI were calculated. Data were collected in blinded fashion. dsRed, n=9; GMT (Gata4, Mef2c, Tbx5), n=10. *p<0.05. b, qPCR of ANF (Atrial Natriuretic Factor), BNP (Brain Natriuretic Peptide) and Tnc (Tenascin C) on RNA extracted from the border zone of hearts 4 weeks after MI and injection of dsRed or GMT. c, qPCR of collagen type I alpha 1 (Col1a1), collagen type I alpha 2 (Col1a2), collagen type III alpha 1(Col3a1), elastin (Eln) on RNA extracted from the border zone of hearts 4 weeks after MI and injection of dsRed or GMT. Data in (b) and (c) are shown relative to dsRed injected sham-operated mice, indicated by dashed line. n=3 for each genotype with technical quadruplicates. d, Masson-Trichrome staining of heart sections 8 weeks post-MI injected with dsRed or GMT. Scale bars: 500 μm. Quantification of scar size was calculated by measurement of scar area in four sections for each heart in blinded fashion. dsRed, n=8; GMT, n=9. *p<0.05.

Figure 12:
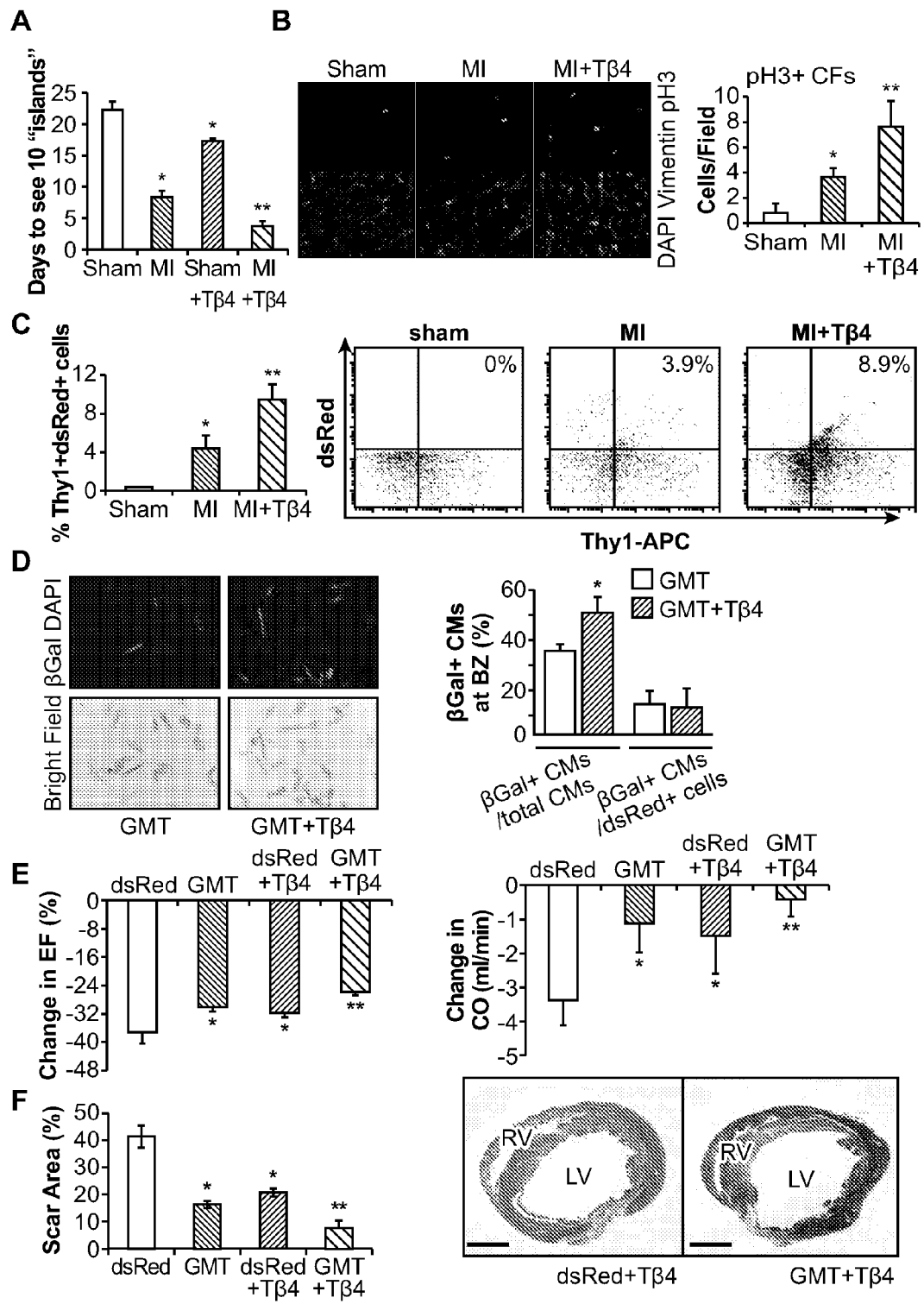
FIGS. 12A-F and FIGS. 13A-E depict the effect of thymosin β4 on cardiac fibroblasts upon injury and on in vivo reprogramming.
Figure 13:
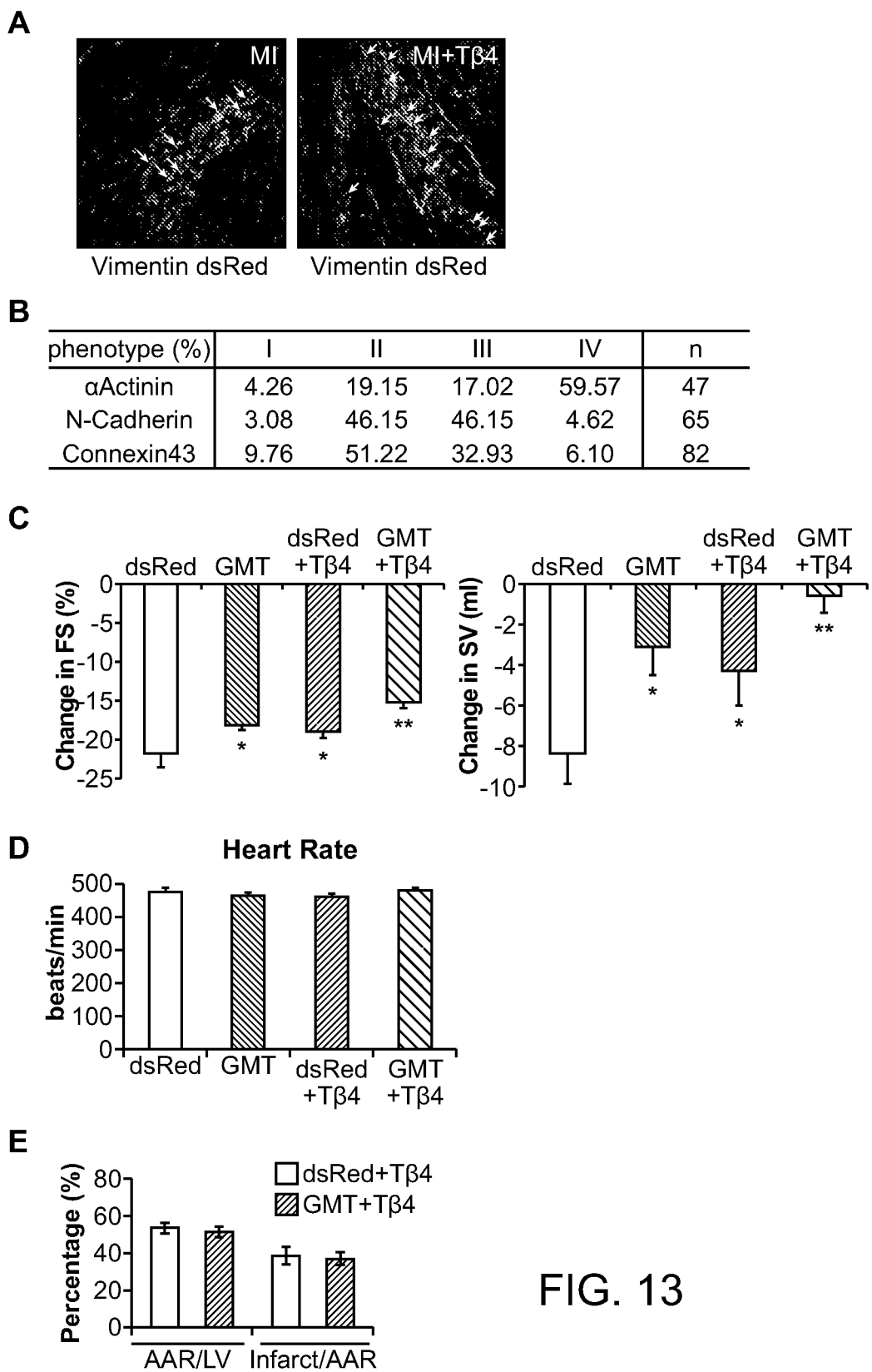

While GMT delivery significantly affected cardiac repair after MI, it was hypothesized that increasing the number of Thy1$^+$ cells that were infected by the retrovirus might lead to an even greater functional improvement. Thymosin β4, a 43-amino-acid G-actin monomer-binding protein, promotes cell migration, cardiac cell survival and can activate epicardial cells to become more proliferative and give rise to more cardiac fibroblasts and endothelial cells. It was previously reported that Thymosin β4 improves cardiac function and decreases scar size after MI. To test the effects of Thymosin β4 on cardiac fibroblast migration, a cardiac explant migration assay was used. The average time for fibroblasts to migrate from adult heart explants was approximately 3 weeks; however, with Thymosin β4, equivalent fibroblast migration was observed after only 2 weeks and was even more accelerated after MI (FIG. 12A). Similarly, the proliferation of Vimentin$^+$ cells increased after MI, and increased even further with Thymosin β4, as marked by phosphohistone H3 (FIG. 12B). Consistent with the activation of fibroblasts by Thymosin β4, the percent of Thy1$^+$ (FIG. 12C) or Vimentin$^+$ (FIG. 13A) cells infected by retrovirus in the setting of MI more than doubled upon intramyocardial injection of Thymosin β4 (FIG. 12C). The improved delivery of GMT-expressing retrovirus by Thymosin β4 resulted in an increase in the percent of βGal$^+$ iCMs, compared to total cardiomyocytes, in single-cell cardiomyocyte culture from the infarct/border zone of Periostin-Cre; R26R-lacZ hearts (51% vs. 35%, p<0.05) (FIG. 12D). However, no change was observed in the in vivo reprogramming efficiency (iCMs/total cells infected with GMT virus), which remained ~12% (FIG. 12D), or the degree of reprogramming (FIG. 13B).

Injection of Thymosin β4 immediately after coronary ligation resulted in functional improvement of cardiac function, as reported. Co-injection of Thymosin β4 and GMT yielded further functional improvement in ejection fraction and cardiac output 8 weeks after infarction (FIG. 13E; and FIGS. 12C and 12D). In agreement with this, co-injection of Thymosin β4 and GMT caused a greater reduction in scar size than either Thymosin β4 or GMT injection alone (FIG. 12F), despite the area at risk and initial infarct size being similar in both groups (FIG. 13E).

FIGS. 12A-F. Thymosin β4 Activates Cardiac Fibroblasts Upon Injury and Enhances In Vivo Reprogramming.

a, Quantification for cardiac fibroblast migration assay performed on sham-operated or post-MI hearts with or without Tβ4 injection. Days when 10 minced cardiac tissues were surrounded by migratory fibroblasts ("islands") were averaged from three injected hearts. b, Immunofluorescent staining for phosphohistone H3 (pH3, red), Vimentin (green) and DAPI (blue) on heart sections 48 hours after sham-operation, MI or MI with injection of Tβ4. At right, quantification for pH3$^+$ Vimentin$^+$ cells. n=3 for each genotype. c, FACS analyses of Thy-1$^+$dsRed$^+$ cells from hearts 2 days after sham-operation, MI, or MI with injection of Tβ4 with quantification (left) and representative FACS plots (right). n=3. d, Upper panels show immunofluorescent staining for βGal and DAPI on isolated CMs from infarct/border zone of Postn-Cre; R26R-lacZ hearts 4 weeks after MI and GMT injection with or without Tβ4. Lower panels are bright field pictures for the same cells. Quantification of βGal$^+$ cardiomyocyte (CM)-like cells compared to total CMs or total dsRed$^+$ cells (virus-infected) from the border zone of hearts 4 weeks after MI and injection of GMT with or without Tβ4. n=3. e, Changes in ejection fraction (EF) and cardiac output (CO) of the left ventricle were determined using high-resolution echocardiography 8 weeks post-surgery. dsRed, n=9; GMT, n=10; dsRed+Tβ4, n=10; GMT+Tβ4, n=8. f, Scar area calculated in blinded fashion from multiple heart sections 8 weeks post-MI after dsRed (n=8), GMT (n=9), dsRed+Tβ4 (n=7) or GMT+Tβ4 (n=8) injection. Representative Masson-Trichrome staining on heart sections is shown. Scale bars: 500 μm. Quantification of scar size was calculated by measurement of scar area in blinded fashion. *p<0.05; **p<0.01.

FIGS. 13A-E. Thymosin β4 Activates Cardiac Fibroblasts Upon Injury and Enhances In Vivo Reprogramming.

a, Confocal images showing the integration of dsRed control virus into Vimentin+ cells in hearts with or without Thymosin β4 (Tβ4) injection after myocardial infarction (MI). Arrows point to dsRed+Vimentin+ cells. b, Quantification of iCM phenotypes after single cell isolation from hearts injected with Tβ4 and GMT. c, Blinded quantification of the area at risk (AAR) and infarct size of hearts co-injected with Thymosin β4 and dsRed or GMT 48 hours after MI. d, Changes in fractional shortening (FS) and stroke volume (SV) of the left ventricle 8 weeks after MI using high-resolution echocardiography. dsRed, n=9; GMT, n=10; dsRed+Tβ4, n=10; GMT+Tβ4, n=8. *p<0.05, **p<0.01. e, Heart rate was measured during echocardiography and no difference was found among the four groups. Echo data in (d, e) were collected in blinded fashion.

The above-described experiments show that resident cardiac fibroblasts can be converted into cardiomyocyte-like cells in vivo by local delivery of Gata4, Mef2c, and Tbx5 using retroviral-mediated gene transfer upon cardiac injury. Compared to in vitro conversion, in vivo cardiac reprogramming occurred with similar initial efficiency. Reprogrammed cells more closely resembled endogenous cardiomyocytes and were more fully reprogrammed.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An in vitro method of generating an induced cardiomyocyte, the method consisting of:
genetically modifying a rodent post-natal fibroblast with one or more nucleic acids encoding only three reprogramming factor polypeptides, wherein the three reprogramming factor polypeptides consist of Gata4, Mef2c, and Tbx5, and wherein said genetic modification results in direct reprogramming of the rodent post-natal fibroblast into a cardiomyocyte, thereby generating an induced cardiomyocyte.

2. The method of claim 1, wherein the post-natal fibroblast is a mouse cell or a rat cell.

3. The method of claim 1, wherein the three reprogramming factor polypeptides are encoded on a single nucleic acid.

4. The method of claim 1, wherein said one or more nucleic acids is a recombinant vector.

5. The method of claim 1, wherein said one or more nucleic acids are operably linked to a transcription regulatory element.

6. The method of claim 5, wherein the transcription regulatory element is a constitutive promoter functional in the post-natal fibroblast.

7. An in vitro method of generating an induced cardiomyocyte, the method consisting of:
   genetically modifying a rodent post-natal fibroblast with one or more nucleic acids encoding only three reprogramming factor polypeptides, wherein the three reprogramming factor polypeptides consist of Gata4, Mef2c, and Tbx5, and wherein said genetic modification results in direct reprogramming of the rodent post-natal fibroblast into a cardiomyocyte, thereby generating an induced cardiomyocyte; and
   isolating the induced cardiomyocyte.

8. A method for performing cell transplantation in a rodent recipient, the method comprising:
   (i) generating an induced cardiomyocyte from a post-natal fibroblast of a rodent donor according to the method of claim 7; and
   (ii) transplanting the induced cardiomyocyte into a rodent recipient that is immunocompatible with the donor.

9. The method of claim 8, wherein said recipient and said donor are the same individual.

10. The method of claim 8, wherein said recipient and said donor are different individuals.

* * * * *

```
                        SEQUENCE LISTING

<160> NUMBER OF SEQ ID NOS: 48

<210> SEQ ID NO 1
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 1

Tyr Gly Arg Lys Lys Arg Arg Gln Arg Arg Arg
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 2

Arg Arg Gln Arg Arg Thr Ser Lys Leu Met Lys Arg
1               5                   10

<210> SEQ ID NO 3
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 3

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 4
<211> LENGTH: 33
<212> TYPE: PRT
<213> ORGANISM: Artificial Sequence
<220> FEATURE:
<223> OTHER INFORMATION: Synthetic polypeptide

<400> SEQUENCE: 4

Lys Ala Leu Ala Trp Glu Ala Lys Leu Ala Lys Ala Leu Ala Lys Ala
1               5                   10                  15
```

```
Leu Ala Lys His Leu Ala Lys Ala Leu Ala Lys Ala Leu Lys Cys Glu
            20                  25                  30

Ala

<210> SEQ ID NO 5
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 5

Arg Gln Ile Lys Ile Trp Phe Gln Asn Arg Arg Met Lys Trp Lys Lys
1               5                   10                  15

<210> SEQ ID NO 6
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 6

Arg Lys Lys Arg Arg Gln Arg Arg Arg
1               5

<210> SEQ ID NO 7
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 7

Tyr Ala Arg Ala Ala Ala Arg Gln Ala Arg Ala
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 8

Thr His Arg Leu Pro Arg Arg Arg Arg Arg
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 9

Gly Gly Arg Arg Ala Arg Arg Arg Arg Arg
1               5                   10

<210> SEQ ID NO 10
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
```

```
<221> NAME/KEY: misc_difference
<222> LOCATION: 3, 4
<223> OTHER INFORMATION: n =a or t

<400> SEQUENCE: 10 ctnnaaatag                                                                  10

<210> SEQ ID NO 11
<211> LENGTH: 20
<212> TYPE: DNA
<213> ORGANISM: Artificial Sequence
<220> FEATURE:
<223> OTHER INFORMATION: Synthetic primer

<400> SEQUENCE: 11
atgacagaca gatccctcct                                                       20

<210> SEQ ID NO 12
<211> LENGTH: 20
<212> TYPE: DNA
<213> ORGANISM: Artificial Sequence
<220> FEATURE:
<223> OTHER INFORMATION: Synthetic primer

<400> SEQUENCE: 12
aagtcgtgct gcttcatgtg                                                       20

<210> SEQ ID NO 13
<211> LENGTH: 442
<212> TYPE: PRT
<213> ORGANISM: Homo sapiens

<400> SEQUENCE: 13
```

Met Tyr Gln Ser Leu Ala Met Ala Ala Asn His Gly Pro Pro Pro Gly
  1               5                  10                  15

Ala Tyr Glu Ala Gly Gly Pro Gly Ala Phe Met His Gly Ala Gly Ala
             20                  25                  30

Ala Ser Ser Pro Val Tyr Val Pro Thr Pro Arg Val Pro Ser Ser Val
         35                  40                  45

Leu Gly Leu Ser Tyr Leu Gln Gly Gly Ala Gly Ser Ala Ser Gly
     50                  55                  60

Gly Ala Ser Gly Gly Ser Ser Gly Gly Ala Ser Gly Ala Gly Pro
 65                  70                  75                  80

Gly Thr Gln Gln Gly Ser Pro Gly Trp Ser Gln Ala Gly Ala Asp Gly
                 85                  90                  95

Ala Ala Tyr Thr Pro Pro Pro Val Ser Pro Arg Phe Ser Phe Pro Gly
            100                 105                 110

Thr Thr Gly Ser Leu Ala Ala Ala Ala Ala Ala Ala Ala Ala Arg Glu
        115                 120                 125

Ala Ala Ala Tyr Ser Ser Gly Gly Gly Ala Ala Gly Ala Gly Leu Ala
    130                 135                 140

Gly Arg Glu Gln Tyr Gly Arg Ala Gly Phe Ala Gly Ser Tyr Ser Ser
145                 150                 155                 160

Pro Tyr Pro Ala Tyr Met Ala Asp Val Gly Ala Ser Trp Ala Ala Ala
                165                 170                 175

Ala Ala Ala Ser Ala Gly Pro Phe Asp Ser Pro Val Leu His Ser Leu
            180                 185                 190

Pro Gly Arg Ala Asn Pro Ala Ala Arg His Pro Asn Leu Asp Met Phe
        195                 200                 205

```
Asp Asp Phe Ser Glu Gly Arg Glu Cys Val Asn Cys Gly Ala Met Ser
    210                 215                 220
Thr Pro Leu Trp Arg Arg Asp Gly Thr Gly His Tyr Leu Cys Asn Ala
225                 230                 235                 240
Cys Gly Leu Tyr His Lys Met Asn Gly Ile Asn Arg Pro Leu Ile Lys
                245                 250                 255
Pro Gln Arg Arg Leu Ser Ala Ser Arg Arg Val Gly Leu Ser Cys Ala
            260                 265                 270
Asn Cys Gln Thr Thr Thr Thr Thr Leu Trp Arg Arg Asn Ala Glu Gly
        275                 280                 285
Glu Pro Val Cys Asn Ala Cys Gly Leu Tyr Met Lys Leu His Gly Val
    290                 295                 300
Pro Arg Pro Leu Ala Met Arg Lys Glu Gly Ile Gln Thr Arg Lys Arg
305                 310                 315                 320
Lys Pro Lys Asn Leu Asn Lys Ser Lys Thr Pro Ala Ala Pro Ser Gly
                325                 330                 335
Ser Glu Ser Leu Pro Pro Ala Ser Gly Ala Ser Ser Asn Ser Ser Asn
            340                 345                 350
Ala Thr Thr Ser Ser Ser Glu Glu Met Arg Pro Ile Lys Thr Glu Pro
        355                 360                 365
Gly Leu Ser Ser His Tyr Gly His Ser Ser Val Ser Gln Thr Phe
    370                 375                 380
Ser Val Ser Ala Met Ser Gly His Gly Pro Ser Ile His Pro Val Leu
385                 390                 395                 400
Ser Ala Leu Lys Leu Ser Pro Gln Gly Tyr Ala Ser Pro Val Ser Gln
                405                 410                 415
Ser Pro Gln Thr Ser Ser Lys Gln Asp Ser Trp Asn Ser Leu Val Leu
            420                 425                 430
Ala Asp Ser His Gly Asp Ile Ile Thr Ala
        435                 440

<210> SEQ ID NO 14
<211> LENGTH: 1329
<212> TYPE: DNA
<213> ORGANISM: Homo sapiens

<400> SEQUENCE: 14
atgtatcaga gcttggccat ggccgccaac cacgggccgc cccccggtgc ctacgaggcg      60
ggcggccccg cgccttcat gcacggcgcg ggcgccgcgt cctcgccagt ctacgtgccc      120
acaccgcggg tgccctcctc cgtgctgggc ctgtcctacc tccagggcgg aggcgcgggc     180
tctgcgtccg gaggcgcctc gggcggcagc tccggtgggg ccgcgtctgg tgcggggccc     240
gggacccagc agggcagccc gggatggagc caggcgggag ccgacggagc cgcttacacc     300
ccgccgccgg tgtcgccgcg cttctccttc ccggggacca ccgggtccct ggcggccgcc     360
gccgccgctg ccgcggcccg ggaagctgcg gcctacagca gtggcggcgg agcggcgggt     420
gcgggcctgg cgggccgcga gcagtacggg gcgccggct tcgcgggctc ctactccagc      480
ccctacccgg cttacatggc cgacgtgggc gcgtcctggg ccgcagccgc cgccgcctcc     540
gccgccccct cgacagcccc ggtcctgcac agcctgcccg ccgggccaa ccggccgcc      600 cgacacccca atctcgatat gtttgacgac ttctcagaag gcagagagtg tgtcaactgt     660
ggggctatgt ccaccccgct ctggaggcga gatgggacgg gtcactatct gtgcaacgcc     720
tgcggcctct accacaagat gaacggcatc aaccggccgc tcatcaagcc tcagcgccgg     780
```

```
ctgtccgcct cccgccgagt gggcctctcc tgtgccaact gccagaccac caccaccacg    840
ctgtggcgcc gcaatgcgga gggcgagcct gtgtgcaatg cctgcggcct ctacatgaag    900
ctccacgggg tccccaggcc tcttgcaatg cggaaagagg ggatccaaac cagaaaacgg    960
aagcccaaga acctgaataa atctaagaca ccagcagctc cttcaggcag tgagagcctt   1020
cctcccgcca gcggtgcttc cagcaactcc agcaacgcca ccaccagcag cagcgaggag   1080
atgcgtccca tcaagacgga gcctggcctg tcatctcact acgggcacag cagctccgtg   1140
tcccagacgt tctcagtcag tgcgatgtct ggccatgggc cctccatcca ccctgtcctc   1200
tcggccctga agctctcccc acaaggctat gcgtctcccg tcagccagtc tccacagacc   1260
agctccaagc aggactcttg gaacagcctg gtcttggccg acagtcacgg ggacataatc   1320
actgcgtaa                                                           1329
```

<210> SEQ ID NO 15
<211> LENGTH: 463
<212> TYPE: PRT
<213> ORGANISM: Homo sapiens

<400> SEQUENCE: 15

```
Met Gly Arg Lys Lys Ile Gln Ile Thr Arg Ile Met Asp Glu Arg Asn
 1               5                  10                  15

Arg Gln Val Thr Phe Thr Lys Arg Lys Phe Gly Leu Met Lys Lys Ala
            20                  25                  30

Tyr Glu Leu Ser Val Leu Cys Asp Cys Glu Ile Ala Leu Ile Ile Phe
        35                  40                  45

Asn Ser Thr Asn Lys Leu Phe Gln Tyr Ala Ser Thr Asp Met Asp Lys
    50                  55                  60

Val Leu Leu Lys Tyr Thr Glu Tyr Asn Glu Pro His Glu Ser Arg Thr
65                  70                  75                  80

Asn Ser Asp Ile Val Glu Ala Leu Asn Lys Lys Glu Asn Lys Gly Cys
                85                  90                  95

Glu Ser Pro Asp Pro Asp Ser Ser Tyr Ala Leu Thr Pro Arg Thr Glu
           100                 105                 110

Glu Lys Tyr Lys Lys Ile Asn Glu Glu Phe Asp Asn Met Ile Lys Ser
       115                 120                 125

His Lys Ile Pro Ala Val Pro Pro Asn Phe Glu Met Pro Val Ser
   130                 135                 140

Ile Pro Val Ser Ser His Asn Ser Leu Val Tyr Ser Asn Pro Val Ser
145                 150                 155                 160

Ser Leu Gly Asn Pro Asn Leu Leu Pro Leu Ala His Pro Ser Leu Gln
                165                 170                 175

Arg Asn Ser Met Ser Pro Gly Val Thr His Arg Pro Pro Ser Ala Gly
           180                 185                 190

Asn Thr Gly Gly Leu Met Gly Gly Asp Leu Thr Ser Gly Ala Gly Thr
       195                 200                 205

Ser Ala Gly Asn Gly Tyr Gly Asn Pro Arg Asn Ser Pro Gly Leu Leu
   210                 215                 220

Val Ser Pro Gly Asn Leu Asn Lys Asn Met Gln Ala Lys Ser Pro Pro
225                 230                 235                 240

Pro Met Asn Leu Gly Met Asn Asn Arg Lys Pro Asp Leu Arg Val Leu
                245                 250                 255

Ile Pro Pro Gly Ser Lys Asn Thr Met Pro Ser Val Asn Gln Arg Ile
           260                 265                 270
```

```
Asn Asn Ser Gln Ser Ala Gln Ser Leu Ala Thr Pro Val Ser Val
            275                 280                 285

Ala Thr Pro Thr Leu Pro Gly Gln Gly Met Gly Tyr Pro Ser Ala
    290                 295                 300

Ile Ser Thr Thr Tyr Gly Thr Glu Tyr Ser Leu Ser Ser Ala Asp Leu
305                 310                 315                 320

Ser Ser Leu Ser Gly Phe Asn Thr Ala Ser Ala Leu His Leu Gly Ser
                325                 330                 335

Val Thr Gly Trp Gln Gln Gln His Leu His Asn Met Pro Pro Ser Ala
            340                 345                 350

Leu Ser Gln Leu Gly Ala Cys Thr Ser Thr His Leu Ser Gln Ser Ser
            355                 360                 365

Asn Leu Ser Leu Pro Ser Thr Gln Ser Leu Asn Ile Lys Ser Glu Pro
            370                 375                 380

Val Ser Pro Pro Arg Asp Arg Thr Thr Thr Pro Ser Arg Tyr Pro Gln
385                 390                 395                 400

His Thr Arg His Glu Ala Gly Arg Ser Pro Val Asp Ser Leu Ser Ser
                405                 410                 415

Cys Ser Ser Ser Tyr Asp Gly Ser Asp Arg Glu Asp His Arg Asn Glu
                420                 425                 430

Phe His Ser Pro Ile Gly Leu Thr Arg Pro Ser Pro Asp Glu Arg Glu
            435                 440                 445

Ser Pro Ser Val Lys Arg Met Arg Leu Ser Glu Gly Trp Ala Thr
            450                 455                 460

<210> SEQ ID NO 16
<211> LENGTH: 1392
<212> TYPE: DNA
<213> ORGANISM: Homo sapiens

<400> SEQUENCE: 16
atggggagaa aaaagattca gattacgagg attatggatg aacgtaacag acaggtgaca     60
tttacaaaga ggaaatttgg gttgatgaag aaggcttatg agctgagcgt gctgtgtgac    120
tgtgagattg cgctgatcat cttcaacagc accaacaagc tgttccagta tgccagcacc    180
gacatggaca aagtgcttct caagtacacg gagtacaacg agccgcatga gagccggaca    240
aactcagaca tcgtggaggc attgaacaag aaagaaaaca aaggctgtga agccccgat     300 cccgactcct cttatgcact cacccccacgc actgaagaaa atacaaaaa aattaatgaa    360 gaatttgata tatgatcaa gagtcataaa attcctgctg ttccacctcc caacttcgag    420
atgccagtct ccatcccagt gtccagccac aacagtttgg tgtacagcaa ccctgtcagc    480
tcactgggaa accccaacct attgccactg gctcacccct tctctgcagag gaatagtatg    540 tctcctggtg taacacatcg acctccaagt gcaggtaaca caggtggtct gatgggtgga    600
gacctcacgt ctggtgcagg caccagtgca gggaacgggt atggcaatcc ccgaaactca    660
ccaggtctgc tggtctcacc tggtaacttg aacaagaata tgcaagcaaa atctcctccc    720
ccaatgaatt taggaatgaa taaccgtaaa ccagatctcc gagttcttat tccaccaggc    780
agcaagaata cgatgccatc agtgaatcaa aggataaata ctcccagtc ggctcagtca    840 ttggctaccc cagtggtttc cgtagcaact cctactttac aggacaagg aatgggagga    900 tatccatcag ccatttcaac aacatatggt accgagtact ctctgagtag tgcagacctg    960
tcatctctgt ctgggtttaa caccgccagc gctcttcacc ttggttcagt aactggctgg   1020
caacagcaac acctacataa catgccacca tctgccctca gtcagttggg agcttgcact   1080
```

```
agcactcatt tatctcagag ttcaaatctc tccctgcctt ctactcaaag cctcaacatc    1140
aagtcagaac ctgtttctcc tcctagagac cgtaccacca ccccttcgag atacccacaa    1200
cacacgcgcc acgaggcggg gagatctcct gttgacagct tgagcagctg tagcagttcg    1260
tacgacggga gcgaccgaga ggatcaccgg aacgaattcc actcccccat ggactcacc     1320 agaccttcgc cggacgaaag ggaaagtccc tcagtcaagc gcatgcgact ttctgaagga    1380
tgggcaacat ga                                                        1392
```

<210> SEQ ID NO 17
<211> LENGTH: 473
<212> TYPE: PRT
<213> ORGANISM: Homo sapiens

<400> SEQUENCE: 17

```
Met Gly Arg Lys Lys Ile Gln Ile Thr Arg Ile Met Asp Glu Arg Asn
 1               5                  10                  15

Arg Gln Val Thr Phe Thr Lys Arg Lys Phe Gly Leu Met Lys Lys Ala
             20                  25                  30

Tyr Glu Leu Ser Val Leu Cys Asp Cys Glu Ile Ala Leu Ile Ile Phe
         35                  40                  45

Asn Ser Thr Asn Lys Leu Phe Gln Tyr Ala Ser Thr Asp Met Asp Lys
     50                  55                  60

Val Leu Leu Lys Tyr Thr Glu Tyr Asn Glu Pro His Glu Ser Arg Thr
 65                  70                  75                  80

Asn Ser Asp Ile Val Glu Thr Leu Arg Lys Lys Gly Leu Asn Gly Cys
                 85                  90                  95

Asp Ser Pro Asp Pro Asp Ala Asp Asp Ser Val Gly His Ser Pro Glu
            100                 105                 110

Ser Glu Asp Lys Tyr Arg Lys Ile Asn Glu Asp Ile Asp Leu Met Ile
        115                 120                 125

Ser Arg Gln Arg Leu Cys Ala Val Pro Pro Asn Phe Glu Met Pro
    130                 135                 140

Val Ser Ile Pro Val Ser Ser His Asn Ser Leu Val Tyr Ser Asn Pro
145                 150                 155                 160

Val Ser Ser Leu Gly Asn Pro Asn Leu Leu Pro Leu Ala His Pro Ser
                165                 170                 175

Leu Gln Arg Asn Ser Met Ser Pro Gly Val Thr His Arg Pro Pro Ser
            180                 185                 190

Ala Gly Asn Thr Gly Gly Leu Met Gly Gly Asp Leu Thr Ser Gly Ala
        195                 200                 205

Gly Thr Ser Ala Gly Asn Gly Tyr Gly Asn Pro Arg Asn Ser Pro Gly
    210                 215                 220

Leu Leu Val Ser Pro Gly Asn Leu Asn Lys Asn Met Gln Ala Lys Ser
225                 230                 235                 240

Pro Pro Pro Met Asn Leu Gly Met Asn Asn Arg Lys Pro Asp Leu Arg
                245                 250                 255

Val Leu Ile Pro Pro Gly Ser Lys Asn Thr Met Pro Ser Val Ser Glu
            260                 265                 270

Asp Val Asp Leu Leu Leu Asn Gln Arg Ile Asn Asn Ser Gln Ser Ala
        275                 280                 285

Gln Ser Leu Ala Thr Pro Val Val Ser Val Ala Thr Pro Thr Leu Pro
    290                 295                 300

Gly Gln Gly Met Gly Gly Tyr Pro Ser Ala Ile Ser Thr Thr Tyr Gly
```

```
                305                 310                 315                 320
            Thr Glu Tyr Ser Leu Ser Ser Ala Asp Leu Ser Ser Leu Ser Gly Phe
                        325                 330                 335

Asn Thr Ala Ser Ala Leu His Leu Gly Ser Val Thr Gly Trp Gln Gln
                        340                 345                 350

Gln His Leu His Asn Met Pro Pro Ser Ala Leu Ser Gln Leu Gly Ala
                        355                 360                 365

Cys Thr Ser Thr His Leu Ser Gln Ser Ser Asn Leu Ser Leu Pro Ser
                        370                 375                 380

Thr Gln Ser Leu Asn Ile Lys Ser Glu Pro Val Ser Pro Arg Asp
            385                 390                 395                 400

Arg Thr Thr Thr Pro Ser Arg Tyr Pro Gln His Thr Arg His Glu Ala
                        405                 410                 415

Gly Arg Ser Pro Val Asp Ser Leu Ser Ser Cys Ser Ser Ser Tyr Asp
                        420                 425                 430

Gly Ser Asp Arg Glu Asp His Arg Asn Glu Phe His Ser Pro Ile Gly
                        435                 440                 445

Leu Thr Arg Pro Ser Pro Asp Glu Arg Glu Ser Pro Ser Val Lys Arg
                        450                 455                 460

Met Arg Leu Ser Glu Gly Trp Ala Thr
            465                 470

<210> SEQ ID NO 18
<211> LENGTH: 1422
<212> TYPE: DNA
<213> ORGANISM: Homo sapiens

<400> SEQUENCE: 18 atgggagaa aaagattca gattacgagg attatggatg aacgtaacag acaggtgaca      60
tttacaaaga ggaaatttgg gttgatgaag aaggcttatg agctgagcgt gctgtgtgac     120
tgtgagattg cgctgatcat cttcaacagc accaacaagc tgttccagta tgccagcacc     180
gacatggaca agtgcttct caagtacacg gagtacaacg agccgcatga gagccggaca      240
aactcagaca tcgtgggagac gttgagaaag aagggcctta atggctgtga cagcccagac     300
cccgatgcgg acgattccgt aggtcacagc cctgagtctg aggacaagta caggaaaatt     360
aacgaagata ttgatctaat gatcagcagg caaagattgt gtgctgttcc acctcccaac     420
ttcgagatgc cagtctccat cccagtgtcc agccacaaca gtttggtgta cagcaaccct     480
gtcagctcac tgggaaaccc caacctattg ccactggctc acccttctct gcagaggaat     540
agtatgtctc ctggtgtaac acatcgacct ccaagtgcag gtaacacagg tggtctgatg     600
ggtggagacc tcacgtctgg tgcaggcacc agtgcaggga cgggtatgg caatccccga      660 aactcaccag gtctgctggt ctcacctggt aacttgaaca gaatatgca gcaaaatct      720 cctccccca tgaatttagg aatgaataac cgtaaaccag atctccgagt tcttattcca     780
ccaggcagca agaatacgat gccatcagtg tctgaggatg tcgacctgct tttgaatcaa     840
aggataaata actcccagtc ggctcagtca ttggctaccc cagtggtttc cgtagcaact     900
cctactttac caggacaagg aatgggagga tatccatcag ccatttcaac acatatggt     960 accgagtact ctctgagtag tgcagacctg tcatctctgt ctgggtttaa caccgccagc    1020
gctcttcacc ttggttcagt aactggctgg caacagcaac acctacataa catgccacca    1080
tctgccctca gtcagttggg agcttgcact agcactcatt tatctcagag ttcaaatctc    1140
tccctgcctt ctactcaaag cctcaacatc aagtcagaac ctgtttctcc tcctagagac    1200
```
cgtaccacca ccccttcgag atacccacaa cacacgcgcc acgaggcggg gagatctcct    1260
gttgacagct tgagcagctg tagcagttcg tacgacggga gcgaccgaga ggatcaccgg    1320
aacgaattcc actcccccat tggactcacc agaccttcgc cggacgaaag ggaaagtccc    1380
tcagtcaagc gcatgcgact ttctgaagga tgggcaacat ga                       1422

<210> SEQ ID NO 19
<211> LENGTH: 513
<212> TYPE: PRT
<213> ORGANISM: Homo sapiens

<400> SEQUENCE: 19

Met Ala Asp Ala Asp Glu Ala Leu Ala Gly Ala His Leu Trp Ser Leu
 1               5                  10                  15

Thr Gln Lys Thr Cys Leu Arg Phe Glu Pro Arg Ala Arg Ser Gly Pro
            20                  25                  30

Pro Ala Ser Pro Pro Gly Arg Pro Arg Ser Arg Leu His Pro Ala Gly
        35                  40                  45

Met Glu Gly Ile Lys Val Phe Leu His Glu Arg Glu Leu Trp Leu Lys
    50                  55                  60

Phe His Glu Val Thr Glu Met Ile Ile Thr Lys Ala Gly Arg Arg Met
65                  70                  75                  80

Phe Pro Ser Tyr Lys Val Lys Val Thr Gly Ile Asn Pro Lys Thr Lys
                85                  90                  95

Tyr Ile Leu Leu Met Asp Ile Val Pro Ala Asp Asp His Arg Tyr Lys
            100                 105                 110

Phe Ala Asp Asn Lys Trp Cys Val Thr Gly Lys Ala Glu Pro Ala Met
        115                 120                 125

Ala Gly Arg Leu Tyr Val His Pro Asp Ser Pro Ala Thr Gly Ala His
    130                 135                 140

Trp Met Arg Gln Leu Val Ser Phe Gln Lys Leu Lys Leu Thr Asn Asn
145                 150                 155                 160

His Leu Asp Pro Phe Gly His Ile Ile Leu Asn Ser Met His Lys Tyr
                165                 170                 175

Gln Pro Arg Leu His Ile Val Lys Ala Asp Glu Asn Asn Gly Phe Gly
            180                 185                 190

Ser Lys Asn Thr Ala Phe Cys Thr His Val Phe Pro Glu Thr Ala Phe
        195                 200                 205

Ile Ala Val Thr Ser Tyr Gln Asn His Lys Ile Thr Gln Leu Lys Ile
    210                 215                 220

Glu Asn Asn Pro Phe Ala Lys Gly Phe Arg Gly Ser Asp Asp Met Glu
225                 230                 235                 240

Leu His Arg Met Ser Arg Met Gln Ser Lys Glu Tyr Pro Val Val Pro
                245                 250                 255

Arg Ser Thr Val Arg Gln Lys Val Ala Ser Asn His Ser Pro Phe Ser
            260                 265                 270

Ser Glu Ser Arg Ala Leu Ser Thr Ser Ser Asn Leu Gly Ser Gln Tyr
        275                 280                 285

Gln Cys Glu Asn Gly Val Ser Gly Pro Ser Gln Asp Leu Leu Pro Pro
    290                 295                 300

Pro Asn Pro Tyr Pro Leu Pro Gln Glu His Ser Gln Ile Tyr His Cys
305                 310                 315                 320

Thr Lys Arg Lys Glu Glu Glu Cys Ser Thr Thr Asp His Pro Tyr Lys
                325                 330                 335

```
Lys Pro Tyr Met Glu Thr Ser Pro Ser Glu Glu Asp Ser Phe Tyr Arg
            340                 345                 350

Ser Ser Tyr Pro Gln Gln Gln Gly Leu Gly Ala Ser Tyr Arg Thr Glu
            355                 360                 365

Ser Ala Gln Arg Gln Ala Cys Met Tyr Ala Ser Ser Ala Pro Pro Ser
        370                 375                 380

Glu Pro Val Pro Ser Leu Glu Asp Ile Ser Cys Asn Thr Trp Pro Ser
385                 390                 395                 400

Met Pro Ser Tyr Ser Ser Cys Thr Val Thr Val Gln Pro Trp Thr
                405                 410                 415

Gly Tyr Pro Thr Ser Thr Ser Pro Leu Thr Ser Pro Arg Gly Pro Trp
            420                 425                 430

Ser Leu Gly Trp Leu Ala Trp Gln Pro Trp Leu Pro Thr Ala Gly Arg
        435                 440                 445

Gly Asn Val Pro Ser Thr Arg Pro Val Ala His Gln Pro Val Val
450                 455                 460

Ser Ser Val Gly Pro Gln Thr Gly Leu Gln Ser Pro Gly Thr Leu Gln
465                 470                 475                 480

Pro Pro Glu Phe Leu Tyr Ser His Gly Val Gln Gly Leu Tyr Pro Leu
                485                 490                 495

Ile Ser Thr Thr Leu Cys Thr Glu Leu Ala Trp Cys Arg Val Glu Arg
            500                 505                 510
Gln

<210> SEQ ID NO 20
<211> LENGTH: 1542
<212> TYPE: DNA
<213> ORGANISM: Homo sapiens

<400> SEQUENCE: 20
atggccgacg cagacgaggc tttggctggc gcacacctct ggagcctgac gcaaaagacc      60
tgcctgcgat cgaaccgag agcgcgctcg ggcccccag caagtccccc cggtcgtccc      120
cgcagccgcc ttcacccagc aggcatggag ggaatcaaag tgtttctcca tgaaagagaa      180
ctgtggctaa aattccacga agtcacggaa atgatcataa ccaaggctgg aaggcggatg      240
tttcccagtt acaaagtgaa ggtgacgggc attaatccca aaacgaagta cattcttctc      300
atggacattg tacctgcgga cgatcacaga tacaaattcg cagataataa atggtgtgtg      360
acgggcaaag ctgagcccgc catggctggc cgcctgtacg tgcacccaga ctcccccgcc      420
accggggcgc attggatgag gcagctcgtc tccttccaga aactcaagct caccaacaac      480
cacctggacc catttgggca tattattcta aattccatgc acaaatacca gcctagatta      540
cacatcgtga agcggatgaa aataatggat tttggctcaa aaaatacagc gttctgcact      600
cacgtctttc ctgagactgc gtttatagca gtgacttcct accagaacca caagatcacg      660
caattaaaga ttgagaataa tccctttgcc aaaggatttc ggggcagtga tgacatggag      720
ctgcacagaa tgtcaagaat gcaaagtaaa gaatatcccg tggtcccag gagcaccgtg      780 aggcaaaaag tggcctccaa ccacagtcct ttcagcagcg agtctcgagc tctctccacc      840
tcatccaatt tggggtccca ataccagtgt gagaatggtg tttccggccc ctcccaggac      900
ctcctgcctc cacccaaccc atacccactg ccccaggagc atagccaaat ttaccattgt      960
accaagagga agaggaaga atgttccacc acagaccatc cctataagaa gccctacatg     1020
gagacatcac ccagtgaaga agattccttc taccgctcta gctatccaca gcagcagggc     1080
```

-continued

```
ctgggtgcct cctacaggac agagtcggca cagcggcaag cttgcatgta tgccagctct   1140 gcgccccca gcgagcctgt gcccagccta gaggacatca gctgcaacac gtggccaagc   1200
atgccttcct acagcagctg caccgtcacc accgtgcagc catggacagg ctaccctacc   1260
agcacttctc cgctcacttc acctcggggc ccctggtccc tcggctggct ggcatggcaa   1320
ccatggctcc ccacagctgg gagagggaat gttcccagca ccagacctcc cgtggcccac   1380
cagcctgtgg tcagcagtgt ggggccccaa actggcctgc agtcccctgg cacccttcag   1440 cccctgagt tcctctactc tcatggcgtg caaggactct atccctcat cagtaccact    1500 ctgtgcacgg agttggcatg gtgcagagtg gagcgacaat ag                    1542
```

<210> SEQ ID NO 21
<211> LENGTH: 518
<212> TYPE: PRT
<213> ORGANISM: Homo sapiens

<400> SEQUENCE: 21

```
Met Ala Asp Ala Asp Glu Gly Phe Gly Leu Ala His Thr Pro Leu Glu
  1               5                  10                  15

Pro Asp Ala Lys Asp Leu Pro Cys Asp Ser Lys Pro Glu Ser Ala Leu
             20                  25                  30

Gly Ala Pro Ser Lys Ser Pro Ser Pro Gln Ala Ala Phe Thr Gln
         35                  40                  45

Gln Gly Met Glu Gly Ile Lys Val Phe Leu His Glu Arg Glu Leu Trp
     50                  55                  60

Leu Lys Phe His Glu Val Gly Thr Glu Met Ile Ile Thr Lys Ala Gly
 65                  70                  75                  80

Arg Arg Met Phe Pro Ser Tyr Lys Val Lys Val Thr Gly Leu Asn Pro
                 85                  90                  95

Lys Thr Lys Tyr Ile Leu Leu Met Asp Ile Val Pro Ala Asp Asp His
            100                 105                 110

Arg Tyr Lys Phe Ala Asp Asn Lys Trp Ser Val Thr Gly Lys Ala Glu
        115                 120                 125

Pro Ala Met Pro Gly Arg Leu Tyr Val His Pro Asp Ser Pro Ala Thr
    130                 135                 140

Gly Ala His Trp Met Arg Gln Leu Val Ser Phe Gln Lys Leu Lys Leu
145                 150                 155                 160

Thr Asn Asn His Leu Asp Pro Phe Gly His Ile Ile Leu Asn Ser Met
                165                 170                 175

His Lys Tyr Gln Pro Arg Leu His Ile Val Lys Ala Asp Glu Asn Asn
            180                 185                 190

Gly Phe Gly Ser Lys Asn Thr Ala Phe Cys Thr His Val Phe Pro Glu
        195                 200                 205

Thr Ala Phe Ile Ala Val Thr Ser Tyr Gln Asn His Lys Ile Thr Gln
    210                 215                 220

Leu Lys Ile Glu Asn Asn Pro Phe Ala Lys Gly Phe Arg Gly Ser Asp
225                 230                 235                 240

Asp Met Glu Leu His Arg Met Ser Arg Met Gln Ser Lys Glu Tyr Pro
                245                 250                 255

Val Val Pro Arg Ser Thr Val Arg Gln Lys Val Ala Ser Asn His Ser
            260                 265                 270

Pro Phe Ser Ser Glu Ser Arg Ala Leu Ser Thr Ser Ser Asn Leu Gly
        275                 280                 285
```

```
Ser Gln Tyr Gln Cys Glu Asn Gly Val Ser Gly Pro Ser Gln Asp Leu
    290                 295                 300

Leu Pro Pro Asn Pro Tyr Pro Leu Pro Gln Glu His Ser Gln Ile
305                 310                 315                 320

Tyr His Cys Thr Lys Arg Lys Glu Glu Cys Ser Thr Thr Asp His
                325                 330                 335

Pro Tyr Lys Lys Pro Tyr Met Glu Thr Ser Pro Ser Glu Glu Asp Ser
            340                 345                 350

Phe Tyr Arg Ser Ser Tyr Pro Gln Gln Gly Leu Gly Ala Ser Tyr
                355                 360                 365

Arg Thr Glu Ser Ala Gln Arg Gln Ala Cys Met Tyr Ala Ser Ser Ala
370                 375                 380

Pro Pro Ser Glu Pro Val Pro Ser Leu Glu Asp Ile Ser Cys Asn Thr
385                 390                 395                 400

Trp Pro Ser Met Pro Ser Tyr Ser Ser Cys Thr Val Thr Val Gln
                405                 410                 415

Pro Met Asp Arg Leu Pro Tyr Gln His Phe Ser Ala His Phe Thr Ser
            420                 425                 430

Gly Pro Leu Val Pro Arg Leu Ala Gly Met Ala Asn His Gly Ser Pro
            435                 440                 445

Gln Leu Gly Glu Gly Met Phe Gln His Gln Thr Ser Val Ala His Gln
450                 455                 460

Pro Val Val Arg Gln Cys Gly Pro Gln Thr Gly Leu Gln Ser Pro Gly
465                 470                 475                 480

Thr Leu Gln Pro Pro Glu Phe Leu Tyr Ser His Gly Val Pro Arg Thr
                485                 490                 495

Leu Ser Pro His Gln Tyr His Ser Val His Gly Val Gly Met Val Pro
            500                 505                 510

Glu Trp Ser Asp Asn Ser
        515

<210> SEQ ID NO 22
<211> LENGTH: 1557
<212> TYPE: DNA
<213> ORGANISM: Homo sapiens

<400> SEQUENCE: 22
atggccgacg cagacgaggg ctttggcctg gcgcacacgc tctggagcc tgacgcaaaa      60 gacctgccct gcgattcgaa acccgagagc gcgctcgggg cccccagcaa gtccccgtcg     120
tccccgcagg ccgccttcac ccagcagggc atggagggaa tcaaagtgtt tctccatgaa     180
agagaactgt ggctaaaatt ccacgaagtg ggcacggaaa tgatcataac caaggctgga     240
aggcggatgt ttcccagtta caaagtgaag gtgacgggcc ttaatcccaa acgaagtac      300 attcttctca tggacattgt acctgccgac gatcacagat acaaattcgc agataataaa     360
tggtctgtga cgggcaaagc tgagcccgcc atgcctggcc gcctgtacgt gcacccagac     420
tcccccgcca ccggggcgca ttggatgagg cagctcgtct ccttccagaa actcaagctc     480
accaacaacc acctggaccc atttgggcat attattctaa attccatgca caaataccag     540
cctagattac acatcgtgaa agcggatgaa ataatggatt ttggctcaaa aaatacagcg     600
ttctgcactc acgtctttcc tgagactgcg tttatagcag tgacttccta ccagaaccac     660
aagatcacgc aattaaagat tgagaataat cctttgccaa aggatttcg gggcagtgat     720 gacatggagc tgcacagaat gtcaagaatg caaagtaaag aatatcccgt ggtccccagg     780
```

| | |
|---|---|
| agcaccgtga ggcaaaaagt ggcctccaac cacagtcctt tcagcagcga gtctcgagct | 840 |
| ctctccacct catccaattt ggggtcccaa taccagtgtg agaatggtgt ttccggcccc | 900 |
| tcccaggacc tcctgcctcc acccaaccca tacccactgc cccaggagca tagccaaatt | 960 |
| taccattgta ccaagaggaa agaggaagaa tgttccacca cagaccatcc ctataagaag | 1020 |
| ccctacatgg agacatcacc cagtgaagaa gattccttct accgctctag ctatccacag | 1080 |
| cagcagggcc tgggtgcctc ctacaggaca gagtcggcac agcggcaagc ttgcatgtat | 1140 |
| gccagctctg cgcccccag cgagcctgtg cccagcctag aggacatcag ctgcaacacg | 1200 |
| tggccaagca tgccttccta cagcagctgc accgtcacca ccgtgcagcc catggacagg | 1260 |
| ctaccctacc agcacttctc cgctcacttc acctcggggc ccctggtccc tcggctggct | 1320 |
| ggcatggcca accatggctc cccacagctg ggagagggaa tgttccagca ccagacctcc | 1380 |
| gtggcccacc agcctgtggt caggcagtgt gggcctcaga ctggcctgca gtccctggc | 1440 |
| acccttcagc ccctgagtt cctctactct catggcgtgc caaggactct atcccctcat | 1500 |
| cagtaccact ctgtgcacgg agttggcatg gtgccagagt ggagcgacaa tagctaa | 1557 |

<210> SEQ ID NO 23
<211> LENGTH: 1302
<212> TYPE: DNA
<213> ORGANISM: Mus musculus

<400> SEQUENCE: 23

| | |
|---|---|
| actatgggga gaaaaagat tcagattacg aggataatgg atgagcgtaa cagacaggtg | 60 |
| acttttacga agaggaaatt tggattgatg aagaaggctt atgagctgag cgtgctgtgc | 120 |
| gactgtgaga ttgcactgat catcttcaac agcaccaaca agctgttcca gtacgccagc | 180 |
| actgacatgg ataaggtgtt gctcaagtac accgagtaca cgagccgca cgagagccgg | 240 |
| acaaactcag acattgtgga ggcattgaac aagaagaaa acaaaggctc tgaaagcccc | 300 |
| gatcctgact cctcttatgc actcaccca cgcactgaag aaaaatacaa aaaaattaat | 360 |
| gaagaatttg ataatatgat caagagtcat aaaaattcctg ctgttccacc tcccagcttt | 420 |
| gagatgccag ttaccatccc agtgtccagc cataacagtt tggtgtacag caatcctgtc | 480 |
| agcacactgg gaaaccccaa tcttctgcca ctggcccacc cgtctctgca gaggaatagt | 540 |
| atgtctcctg gtgtaacaca tagacctcca agtgcaggta cacacaggcgg tctgatgggc | 600 |
| ggagatctga catccggtgc aggcaccagc gcagggaatg gatacggcaa ccccccggaac | 660 |
| tcaccaggcc tgctggtctc acctggtaac ctgaacaaga atatacaagc caaatctcct | 720 |
| cccccctatga atctaggaat gaataatcgt aagccagatc tccgcgttct tatcccacct | 780 |
| ggcagcaaga acacgatgcc atcagtgaat caaaggataa ataactccca gtcggctcag | 840 |
| tcattggcta ccccggtggt ttccgtagca actcctactt taccaggaca aggaatggga | 900 |
| ggatatccat cagccatttc aacaacatat ggtactgagt actctctgag tagcgcagat | 960 |
| ctgtcatctc tgtctggctt caacactgcc agtgcgctcc acctcggctc tgtaactggc | 1020 |
| tggcagcagc agcacctaca taacatgccg ccatctgccc tcagtcagtt gggagaccgt | 1080 |
| accaccaccc cttcgagata cccacaacac accacgcgcc acgaggcggg gaggtctcct | 1140 |
| gttgacagct tgagcagctg tagcagttcc tacgatggga gcgaccgaga ggatcaccgg | 1200 |
| aacgaattcc actcccccat tggactcacc agaccttcgc cggacgaaag ggaaagtcct | 1260 |
| tcagtcaagc gcatgcgact ctctgaagga tgggcaacat ga | 1302 |

```
<210> SEQ ID NO 24
<211> LENGTH: 432
<212> TYPE: PRT
<213> ORGANISM: Mus musculus

<400> SEQUENCE: 24
```

| | | | | | | | | | | | | | | | |
|---|---|---|---|---|---|---|---|---|---|---|---|---|---|---|---|
| Met | Gly | Arg | Lys | Lys | Ile | Gln | Ile | Thr | Arg | Ile | Met | Asp | Glu | Arg | Asn |
| 1 | | | | 5 | | | | | 10 | | | | | 15 | |
| Arg | Gln | Val | Thr | Phe | Thr | Lys | Arg | Lys | Phe | Gly | Leu | Met | Lys | Lys | Ala |
| | | | 20 | | | | | 25 | | | | | 30 | | |
| Tyr | Glu | Leu | Ser | Val | Leu | Cys | Asp | Cys | Glu | Ile | Ala | Leu | Ile | Ile | Phe |
| | | | 35 | | | | | 40 | | | | | 45 | | |
| Asn | Ser | Thr | Asn | Lys | Leu | Phe | Gln | Tyr | Ala | Ser | Thr | Asp | Met | Asp | Lys |
| | 50 | | | | | 55 | | | | | 60 | | | | |
| Val | Leu | Leu | Lys | Tyr | Thr | Glu | Tyr | Asn | Glu | Pro | His | Glu | Ser | Arg | Thr |
| 65 | | | | | 70 | | | | | 75 | | | | | 80 |
| Asn | Ser | Asp | Ile | Val | Glu | Ala | Leu | Asn | Lys | Lys | Glu | Asn | Lys | Gly | Ser |
| | | | | 85 | | | | | 90 | | | | | 95 | |
| Glu | Ser | Pro | Asp | Pro | Asp | Ser | Ser | Tyr | Ala | Leu | Thr | Pro | Arg | Thr | Glu |
| | | | 100 | | | | | 105 | | | | | 110 | | |
| Glu | Lys | Tyr | Lys | Lys | Ile | Asn | Glu | Glu | Phe | Asp | Asn | Met | Ile | Lys | Ser |
| | | | 115 | | | | | 120 | | | | | 125 | | |
| His | Lys | Ile | Pro | Ala | Val | Pro | Pro | Pro | Ser | Phe | Glu | Met | Pro | Val | Thr |
| | 130 | | | | | 135 | | | | | 140 | | | | |
| Ile | Pro | Val | Ser | Ser | His | Asn | Ser | Leu | Val | Tyr | Ser | Asn | Pro | Val | Ser |
| 145 | | | | | 150 | | | | | 155 | | | | | 160 |
| Thr | Leu | Gly | Asn | Pro | Asn | Leu | Leu | Pro | Leu | Ala | His | Pro | Ser | Leu | Gln |
| | | | | 165 | | | | | 170 | | | | | 175 | |
| Arg | Asn | Ser | Met | Ser | Pro | Gly | Val | Thr | His | Arg | Pro | Pro | Ser | Ala | Gly |
| | | | 180 | | | | | 185 | | | | | 190 | | |
| Asn | Thr | Gly | Gly | Leu | Met | Gly | Gly | Asp | Leu | Thr | Ser | Gly | Ala | Gly | Thr |
| | | | 195 | | | | | 200 | | | | | 205 | | |
| Ser | Ala | Gly | Asn | Gly | Tyr | Gly | Asn | Pro | Arg | Asn | Ser | Pro | Gly | Leu | Leu |
| | 210 | | | | | 215 | | | | | 220 | | | | |
| Val | Ser | Pro | Gly | Asn | Leu | Asn | Lys | Asn | Ile | Gln | Ala | Lys | Ser | Pro | Pro |
| 225 | | | | | 230 | | | | | 235 | | | | | 240 |
| Pro | Met | Asn | Leu | Gly | Met | Asn | Asn | Arg | Lys | Pro | Asp | Leu | Arg | Val | Leu |
| | | | | 245 | | | | | 250 | | | | | 255 | |
| Ile | Pro | Pro | Gly | Ser | Lys | Asn | Thr | Met | Pro | Ser | Val | Asn | Gln | Arg | Ile |
| | | | 260 | | | | | 265 | | | | | 270 | | |
| Asn | Asn | Ser | Gln | Ser | Ala | Gln | Ser | Leu | Ala | Thr | Pro | Val | Val | Ser | Val |
| | | | 275 | | | | | 280 | | | | | 285 | | |
| Ala | Thr | Pro | Thr | Leu | Pro | Gly | Gln | Gly | Met | Gly | Gly | Tyr | Pro | Ser | Ala |
| | 290 | | | | | 295 | | | | | 300 | | | | |
| Ile | Ser | Thr | Thr | Tyr | Gly | Thr | Glu | Tyr | Ser | Leu | Ser | Ser | Ala | Asp | Leu |
| 305 | | | | | 310 | | | | | 315 | | | | | 320 |
| Ser | Ser | Leu | Ser | Gly | Phe | Asn | Thr | Ala | Ser | Ala | Leu | His | Leu | Gly | Ser |
| | | | | 325 | | | | | 330 | | | | | 335 | |
| Val | Thr | Gly | Trp | Gln | Gln | Gln | His | Leu | His | Asn | Met | Pro | Pro | Ser | Ala |
| | | | 340 | | | | | 345 | | | | | 350 | | |
| Leu | Ser | Gln | Leu | Gly | Asp | Arg | Thr | Thr | Thr | Pro | Ser | Arg | Tyr | Pro | Gln |
| | | | 355 | | | | | 360 | | | | | 365 | | |
| His | Thr | Thr | Arg | His | Glu | Ala | Gly | Arg | Ser | Pro | Val | Asp | Ser | Leu | Ser |
| | 370 | | | | | 375 | | | | | 380 | | | | |

Ser Cys Ser Ser Ser Tyr Asp Gly Ser Asp Arg Glu Asp His Arg Asn
385             390             395             400

Glu Phe His Ser Pro Ile Gly Leu Thr Arg Pro Ser Pro Asp Glu Arg
        405             410             415

Glu Ser Pro Ser Val Lys Arg Met Arg Leu Ser Glu Gly Trp Ala Thr
        420             425             430

<210> SEQ ID NO 25
<211> LENGTH: 1560
<212> TYPE: DNA
<213> ORGANISM: Mus musculus

<400> SEQUENCE: 25

```
accatggccg atacagatga gggctttggc ctggcgcgca cgcctctgga gcctgattcc      60
aaagacaggt cttgcgattc gaaacctgag agtgctctgg gggctcccag caagtctcca     120
tcatccccgc aggctgcctt cacccagcag ggcatggaag aatcaaggt gtttcttcat      180
gaacgtgaac tgtggctgaa gttccacgaa gtgggcacag atgatcat caccaaggca      240
gggaggagaa tgtttcctag ttacaaagtg aaggtgactg cccttaatcc caaaacgaag     300
tatattcttc tcatggatat tgttcccgca gacgaccaca gatataaatt tgctgataac     360
aaatggtccg taactggcaa agcagagcct gccatgccgg ggcgccttta cgtgcacccg     420
gactccccag caaccggagc ccactggatg cgacaacttg tctccttcca gaagctcaaa     480
ctcaccaaca accacctgga cccgtttgga cacattatcc tgaactccat gcacaaatac     540
cagcccccgat tacacatcgt gaaagcagac gaaataatg ggttcggttc aaagaacact      600
gcgttttgca cccacgtctt cccggagaca gcttttatcg ctgtgacttc gtaccagaat     660
cacaagatca cacagctgaa aattgagaac aacccttcg ccaaaggctt tcggggcagt      720
gatgacctgg agttacacag gatgtctcgg atgcaaagta aagagtatcc tgtggttccc     780
aggagcacag tgaggcacaa agtcacctcc aaccacagcc ccttcagcag cgagacccga     840
gctctctcca cctcatccaa tttagggtcc cagtaccagt gtgagaatgg tgtctctggc     900
ccctcccagg accttctgcc cccacctaac ccatacccac tggcccagga gcacagccaa     960
atttaccact gtaccaagag gaaagatgag gaatgttcca gcacggagca cccctataag    1020
aagccgtaca tggagacatc ccccagcgag gaagacacct tctatcgctc gggctacccc    1080
cagcagcagg gcctgagtac ctcttacagg acagagtcgg cccagcggca ggcctgcatg    1140
tatgccagct ccgctccccc cagcgagccc gtgcctagcc tggaggacat cagctgtaac    1200
acatggccca gcatgccctc ctatagcagc tgtaccgtca ccaccgtgca gcccatggac    1260
cgtcttccct accagcactt ctccgctcat ttcacctcgg ggcccctggt ccctcggttg    1320
gctggcatgg ccaaccatgg ttctccccag ctcggcgaag gatgtttca gcaccagacc    1380
tcagtggccc atcagcctgt ggtcaggcag tgcgggcctc agactggcct tcagtctccg    1440
ggcggcctcc agccccagga gtttctctac actcacggcg tgcccaggac cctgtccccc    1500
catcagtatc actcggtaca cggcgtcggc atggtgccag agtggagtga aatagctaa    1560
```

<210> SEQ ID NO 26
<211> LENGTH: 518
<212> TYPE: PRT
<213> ORGANISM: Mus musculus

<400> SEQUENCE: 26

Met Ala Asp Thr Asp Glu Gly Phe Gly Leu Ala Arg Thr Pro Leu Glu
1               5                   10                  15

-continued

```
Pro Asp Ser Lys Asp Arg Ser Cys Asp Ser Lys Pro Glu Ser Ala Leu
            20                  25                  30

Gly Ala Pro Ser Lys Ser Pro Ser Ser Pro Gln Ala Ala Phe Thr Gln
        35                  40                  45

Gln Gly Met Glu Gly Ile Lys Val Phe Leu His Glu Arg Glu Leu Trp
 50                  55                  60

Leu Lys Phe His Glu Val Gly Thr Glu Met Ile Ile Thr Lys Ala Gly
 65                  70                  75                  80

Arg Arg Met Phe Pro Ser Tyr Lys Val Lys Val Thr Gly Leu Asn Pro
                85                  90                  95

Lys Thr Lys Tyr Ile Leu Leu Met Asp Ile Val Pro Ala Asp Asp His
            100                 105                 110

Arg Tyr Lys Phe Ala Asp Asn Lys Trp Ser Val Thr Gly Lys Ala Glu
        115                 120                 125

Pro Ala Met Pro Gly Arg Leu Tyr Val His Pro Asp Ser Pro Ala Thr
130                 135                 140

Gly Ala His Trp Met Arg Gln Leu Val Ser Phe Gln Lys Leu Lys Leu
145                 150                 155                 160

Thr Asn Asn His Leu Asp Pro Phe Gly His Ile Ile Leu Asn Ser Met
                165                 170                 175

His Lys Tyr Gln Pro Arg Leu His Ile Val Lys Ala Asp Glu Asn Asn
            180                 185                 190

Gly Phe Gly Ser Lys Asn Thr Ala Phe Cys Thr His Val Phe Pro Glu
        195                 200                 205

Thr Ala Phe Ile Ala Val Thr Ser Tyr Gln Asn His Lys Ile Thr Gln
210                 215                 220

Leu Lys Ile Glu Asn Asn Pro Phe Ala Lys Gly Phe Arg Gly Ser Asp
225                 230                 235                 240

Asp Leu Glu Leu His Arg Met Ser Arg Met Gln Ser Lys Glu Tyr Pro
                245                 250                 255

Val Val Pro Arg Ser Thr Val Arg His Lys Val Thr Ser Asn His Ser
            260                 265                 270

Pro Phe Ser Ser Glu Thr Arg Ala Leu Ser Thr Ser Ser Asn Leu Gly
        275                 280                 285

Ser Gln Tyr Gln Cys Glu Asn Gly Val Ser Gly Pro Ser Gln Asp Leu
290                 295                 300

Leu Pro Pro Pro Asn Pro Tyr Pro Leu Ala Gln Glu His Ser Gln Ile
305                 310                 315                 320

Tyr His Cys Thr Lys Arg Lys Asp Glu Glu Cys Ser Ser Thr Glu His
                325                 330                 335

Pro Tyr Lys Lys Pro Tyr Met Glu Thr Ser Pro Ser Glu Glu Asp Thr
            340                 345                 350

Phe Tyr Arg Ser Gly Tyr Pro Gln Gln Gln Gly Leu Ser Thr Ser Tyr
        355                 360                 365

Arg Thr Glu Ser Ala Gln Arg Gln Ala Cys Met Tyr Ala Ser Ser Ala
370                 375                 380

Pro Pro Ser Glu Pro Val Pro Ser Leu Glu Asp Ile Ser Cys Asn Thr
385                 390                 395                 400

Trp Pro Ser Met Pro Ser Tyr Ser Ser Cys Thr Val Thr Thr Val Gln
                405                 410                 415

Pro Met Asp Arg Leu Pro Tyr Gln His Phe Ser Ala His Phe Thr Ser
            420                 425                 430
```

-continued

Gly Pro Leu Val Pro Arg Leu Ala Gly Met Ala Asn His Gly Ser Pro
           435                 440                 445

Gln Leu Gly Glu Gly Met Phe Gln His Gln Thr Ser Val Ala His Gln
    450                 455                 460

Pro Val Val Arg Gln Cys Gly Pro Gln Thr Gly Leu Gln Ser Pro Gly
465                 470                 475                 480

Gly Leu Gln Pro Pro Glu Phe Leu Tyr Thr His Gly Val Pro Arg Thr
                485                 490                 495

Leu Ser Pro His Gln Tyr His Ser Val His Gly Val Gly Met Val Pro
            500                 505                 510

Glu Trp Ser Glu Asn Ser
        515

<210> SEQ ID NO 27
<211> LENGTH: 1329
<212> TYPE: DNA
<213> ORGANISM: Mus musculus

<400> SEQUENCE: 27

| | |
|---|---|
| gcgatgtacc aaagcctggc catggccgcc aaccacggcc cccgcccgg cgcctacgaa | 60 |
| gcaggtggcc ctggcgcctt catgcacagc gcgggcgccg cgtcctcgcc cgtctacgtg | 120 |
| cccactccgc gggtgccgtc ctctgtgctg ggcctgtcct acctgcaggg cggtggcagt | 180 |
| gccgctgcag ctggaaccac ctcgggtggc agctccgggg ccggcccgtc gggtgcaggg | 240 |
| cctgggaccc agcagggtag ccctggctgg agccaagctg agccgaggg agccgcctac | 300 |
| accccgccgc ccgtgtcccc gcgcttctct ttcccgggga ctactgggtc cctggcggcc | 360 |
| gctgccgccg ctgccgcagc ccgggaagct gcagcctacg gcagtggcgg cggggcggcg | 420 |
| ggcgctggtc tggctggccg agagcagtac gggcgtccgg gcttcgccgg ctcctactcc | 480 |
| agcccctacc cagcctacat ggccgacgtg ggagcatcct gggccgcagc cgctgccgcc | 540 |
| tctgccggcc ccttcgacag cccagtcctg cacagcctgc ctggacgggc aaccctgga | 600 |
| agacacccca atctcgatat gtttgatgac ttctcagaag gcagagagtg tgtcaattgt | 660 |
| ggggccatgt ccacccact ctggaggcga gatgggacgg acactacct gtgcaatgcc | 720 |
| tgtggcctct atcacaagat gaacggcatc aaccggcccc tcattaagcc tcagcgccgc | 780 |
| ctgtccgctt cccgccgggt aggcctctcc tgtgccaact gccagactac caccaccacg | 840 |
| ctgtggcgtc gtaatgccga gggtgagcct gtatgtaatg cctgcggcct ctacatgaag | 900 |
| ctccatgggg ttcccaggcc tcttgcaatg cggaaggagg ggattcaaac cagaaaacgg | 960 |
| aagcccaaga acctgaataa atctaagacg ccagcaggtc ctgctggtga ccctccct | 1020 |
| ccctccagtg gtgcctccag cggtaactcc agcaatgcca ctagcagcag cagcagcagt | 1080 |
| gaagagatgc gccccatcaa gacagagccc ggctgtcat ctcactatgg cacagcagc | 1140 |
| tccatgtccc agacattcag tactgtgtcc ggccacgggc cctccatcca tccagtgctg | 1200 |
| tctgctctga agctgtcccc acaaggctat gcatctcctg tcactcagac atcgcaggcc | 1260 |
| agctccaagc aggactcttg aacagcctg gtcctggctg acagtcatgg ggacataatc | 1320 |
| accgcgtaa | 1329 |

<210> SEQ ID NO 28
<211> LENGTH: 441
<212> TYPE: PRT
<213> ORGANISM: Mus musculus

<400> SEQUENCE: 28

```
Met Tyr Gln Ser Leu Ala Met Ala Ala Asn His Gly Pro Pro Gly
  1               5                  10                 15

Ala Tyr Glu Ala Gly Gly Pro Gly Ala Phe Met His Ser Ala Gly Ala
            20                  25                  30

Ala Ser Ser Pro Val Tyr Val Pro Thr Pro Arg Val Pro Ser Ser Val
            35                  40                  45

Leu Gly Leu Ser Tyr Leu Gln Gly Gly Ser Ala Ala Ala Gly
         50                  55                  60

Thr Thr Ser Gly Gly Ser Ser Gly Ala Gly Pro Ser Gly Ala Gly Pro
65                   70                  75                  80

Gly Thr Gln Gln Gly Ser Pro Gly Trp Ser Gln Ala Gly Ala Glu Gly
             85                  90                  95

Ala Ala Tyr Thr Pro Pro Pro Val Ser Pro Arg Phe Ser Phe Pro Gly
             100                 105                 110

Thr Thr Gly Ser Leu Ala Ala Ala Ala Ala Ala Ala Ala Arg Glu
             115                 120                 125

Ala Ala Ala Tyr Gly Ser Gly Gly Ala Gly Ala Gly Leu Ala
             130                 135                 140

Gly Arg Glu Gln Tyr Gly Arg Pro Gly Phe Ala Gly Ser Tyr Ser Ser
145                 150                 155                 160

Pro Tyr Pro Ala Tyr Met Ala Asp Val Gly Ala Ser Trp Ala Ala Ala
             165                 170                 175

Ala Ala Ala Ser Ala Gly Pro Phe Asp Ser Pro Val Leu His Ser Leu
             180                 185                 190

Pro Gly Arg Ala Asn Pro Gly Arg His Pro Asn Leu Asp Met Phe Asp
             195                 200                 205

Asp Phe Ser Glu Gly Arg Glu Cys Val Asn Cys Gly Ala Met Ser Thr
             210                 215                 220

Pro Leu Trp Arg Arg Asp Gly Thr Gly His Tyr Leu Cys Asn Ala Cys
225                 230                 235                 240

Gly Leu Tyr His Lys Met Asn Gly Ile Asn Arg Pro Leu Ile Lys Pro
             245                 250                 255

Gln Arg Arg Leu Ser Ala Ser Arg Arg Val Gly Leu Ser Cys Ala Asn
             260                 265                 270

Cys Gln Thr Thr Thr Thr Thr Leu Trp Arg Arg Asn Ala Glu Gly Glu
             275                 280                 285

Pro Val Cys Asn Ala Cys Gly Leu Tyr Met Lys Leu His Gly Val Pro
             290                 295                 300

Arg Pro Leu Ala Met Arg Lys Glu Gly Ile Gln Thr Arg Lys Arg Lys
305                 310                 315                 320

Pro Lys Asn Leu Asn Lys Ser Lys Thr Pro Ala Gly Pro Ala Gly Glu
             325                 330                 335

Thr Leu Pro Pro Ser Ser Gly Ala Ser Ser Gly Asn Ser Ser Asn Ala
             340                 345                 350

Thr Ser Ser Ser Ser Ser Ser Glu Glu Met Arg Pro Ile Lys Thr Glu
             355                 360                 365

Pro Gly Leu Ser Ser His Tyr Gly His Ser Ser Met Ser Gln Thr
             370                 375                 380

Phe Ser Thr Val Ser Gly His Gly Pro Ser Ile His Pro Val Leu Ser
385                 390                 395                 400

Ala Leu Lys Leu Ser Pro Gln Gly Tyr Ala Ser Pro Val Thr Gln Thr
             405                 410                 415
```

```
Ser Gln Ala Ser Ser Lys Gln Asp Ser Trp Asn Ser Leu Val Leu Ala
            420                 425                 430

Asp Ser His Gly Asp Ile Ile Thr Ala
        435                 440

<210> SEQ ID NO 29
<211> LENGTH: 268
<212> TYPE: PRT
<213> ORGANISM: Homo sapiens

<400> SEQUENCE: 29

Met Ala Gln Pro Leu Cys Pro Pro Leu Ser Glu Ser Trp Met Leu Ser
  1               5                  10                  15

Ala Ala Trp Gly Pro Thr Arg Arg Pro Pro Ser Asp Lys Asp Cys
             20                  25                  30

Gly Arg Ser Leu Val Ser Ser Pro Asp Ser Trp Gly Ser Thr Pro Ala
             35                  40                  45

Asp Ser Pro Val Ala Ser Pro Ala Arg Pro Gly Thr Leu Arg Asp Pro
         50                  55                  60

Arg Ala Pro Ser Val Gly Arg Arg Gly Ala Arg Ser Ser Arg Leu Gly
 65                  70                  75                  80

Ser Gly Gln Arg Gln Ser Ala Ser Glu Arg Glu Lys Leu Arg Met Arg
                 85                  90                  95

Thr Leu Ala Arg Ala Leu His Glu Leu Arg Arg Phe Leu Pro Pro Ser
            100                 105                 110

Val Ala Pro Ala Gly Gln Ser Leu Thr Lys Ile Glu Thr Leu Arg Leu
            115                 120                 125

Ala Ile Arg Tyr Ile Gly His Leu Ser Ala Val Leu Gly Leu Ser Glu
        130                 135                 140

Glu Ser Leu Gln Arg Arg Cys Arg Gln Arg Gly Asp Ala Gly Ser Pro
145                 150                 155                 160

Arg Gly Cys Pro Leu Cys Pro Asp Asp Cys Pro Ala Gln Met Gln Thr
                165                 170                 175

Arg Thr Gln Ala Glu Gly Gln Gly Gln Gly Arg Gly Leu Gly Leu Val
            180                 185                 190

Ser Ala Val Arg Ala Gly Ala Ser Trp Gly Ser Pro Pro Ala Cys Pro
        195                 200                 205

Gly Ala Arg Ala Ala Pro Glu Pro Arg Asp Pro Ala Leu Phe Ala
    210                 215                 220

Glu Ala Ala Cys Pro Glu Gly Gln Ala Met Glu Pro Ser Pro Ser
225                 230                 235                 240

Pro Leu Leu Pro Gly Asp Val Leu Ala Leu Leu Glu Thr Trp Met Pro
                245                 250                 255

Leu Ser Pro Leu Glu Trp Leu Pro Glu Glu Pro Lys
            260                 265

<210> SEQ ID NO 30
<211> LENGTH: 807
<212> TYPE: DNA
<213> ORGANISM: Homo sapiens

<400> SEQUENCE: 30
atggcccagc ccctgtgccc gccgctctcc gagtcctgga tgctctctgc ggcctggggc      60
ccaactcggc ggccgccgcc ctccgacaag gactgcggcc gctccctcgt ctcgtcccca     120
gactcatggg gcagcacccc agccgacagc cccgtggcga gccccgcgcg gccaggcacc     180
```

```
ctccgggacc  cccgcgcccc  ctccgtaggt  aggcgcggcg  cgcgcagcag  ccgcctgggc    240
agcgggcaga  ggcagagcgc  cagtgagcgg  gagaaactgc  gcatgcgcac  gctggcccgc    300
gccctgcacg  agctgcgccg  ctttctaccg  ccgtccgtgg  cgcccgcggg  ccagagcctg    360
accaagatcg  agacgctgcg  cctggctatc  cgctatatcg  gccacctgtc  ggccgtgcta    420
ggcctcagcg  aggagagtct  ccagcgccgg  tgccggcagc  gcggtgacgc  ggggtcccct    480
cggggctgcc  cgctgtgccc  cgacgactgc  cccgcgcaga  tgcagacacg  gacgcaggct    540
gaggggcagg  ggcaggggcg  cgggctgggc  ctggtatccg  ccgtccgcgc  cggggcgtcc    600
tggggatccc  cgcctgcctg  ccccggagcc  cgagctgcac  ccgagccgcg  cgacccgcct    660
gcgctgttcg  ccgaggcggc  gtgccctgaa  gggcaggcga  tggagccaag  cccaccgtcc    720
ccgctccttc  cgggcgacgt  gctggctctg  ttggagacct  ggatgcccct  ctcgcctctg    780
gagtggctgc  ctgaggagcc  caagtga                                           807
```

<210> SEQ ID NO 31
<211> LENGTH: 149
<212> TYPE: PRT
<213> ORGANISM: Homo sapiens

<400> SEQUENCE: 31

```
Met Phe Pro Ser Pro Ala Leu Thr Pro Thr Pro Phe Ser Val Lys Asp
 1               5                  10                  15

Ile Leu Asn Leu Glu Gln Gln Gln Arg Ser Leu Ala Ala Ala Gly Glu
            20                  25                  30

Leu Ser Ala Arg Leu Glu Ala Thr Ala Pro Ser Ser Cys Met Leu Ala
        35                  40                  45

Ala Lys Pro Glu Ala Tyr Ala Gly Pro Glu Ala Ala Pro Gly Leu
    50                  55                  60

Pro Glu Leu Arg Ala Glu Leu Gly Arg Ala Pro Ser Pro Ala Lys Cys
65                  70                  75                  80

Ala Ser Ala Phe Pro Ala Ala Pro Ala Phe Tyr Pro Arg Ala Tyr Ser
                85                  90                  95

Asp Pro Asp Pro Ala Lys Asp Pro Arg Ala Glu Lys Lys Gly Cys Glu
            100                 105                 110

Leu Pro Arg Gly Gln Arg Pro Val Leu Phe Ser Ser Ala Leu Ser
        115                 120                 125

Gln Pro Asp Phe Leu Gln Met Leu Ser Glu Thr Cys Arg Trp Leu Pro
    130                 135                 140

Val His Leu Ala Glu
145
```

<210> SEQ ID NO 32
<211> LENGTH: 456
<212> TYPE: DNA
<213> ORGANISM: Homo sapiens

<400> SEQUENCE: 32

```
atgttcccca  gcctgctctc  cacgcccacg  cccttctcag  tcaaagacat  cctaaacctg     60
gaacagcagc  agcgcagcct  ggctgccgcc  ggagagctct  gcccgcct    ggaggcgacc    120 ctggcgccct  cctcctgcat  gctggccgcc  ttcaagccag  aggcctacgc  tgggcccgag    180
gcggctgcgc  cgggcctccc  agagctgcgc  gcagagctgg  gccgcgcgcc  ttcaccggcc    240
aagtgtgcgt  ctgcctttcc  cgccgccccc  gccttctatc  cacgtgccta  cagcgacccc    300
gacccagcca  aggaccctag  agccgaaaag  aaagggtgtg  aactgccccg  agggcagaga    360
```

```
cctcccgttt tgttctccag cgccttgagc cagcctgact ttctacaaat gctgagtgag    420
acgtgtcggt ggctcccagt gcacttggca gagtga                              456
```

<210> SEQ ID NO 33
<211> LENGTH: 324
<212> TYPE: PRT
<213> ORGANISM: Homo sapiens

<400> SEQUENCE: 33

```
Met Phe Pro Ser Pro Ala Leu Thr Pro Thr Pro Phe Ser Val Lys Asp
 1               5                  10                  15

Ile Leu Asn Leu Glu Gln Gln Gln Arg Ser Leu Ala Ala Ala Gly Glu
            20                  25                  30

Leu Ser Ala Arg Leu Glu Ala Thr Leu Ala Pro Ser Ser Cys Met Leu
        35                  40                  45

Ala Ala Phe Lys Pro Glu Ala Tyr Ala Gly Pro Glu Ala Ala Ala Pro
    50                  55                  60

Gly Leu Pro Glu Leu Arg Ala Glu Leu Gly Arg Ala Pro Ser Pro Ala
65                  70                  75                  80

Lys Cys Ala Ser Ala Phe Pro Ala Pro Ala Phe Tyr Pro Arg Ala
                85                  90                  95

Tyr Ser Asp Pro Asp Pro Ala Lys Asp Pro Arg Ala Glu Lys Lys Glu
            100                 105                 110

Leu Cys Ala Leu Gln Lys Ala Val Glu Leu Glu Lys Thr Glu Ala Asp
        115                 120                 125

Asn Ala Glu Arg Pro Arg Ala Arg Arg Arg Lys Pro Arg Val Leu
    130                 135                 140

Phe Ser Gln Ala Gln Val Tyr Glu Leu Glu Arg Arg Phe Lys Gln Gln
145                 150                 155                 160

Arg Tyr Leu Ser Ala Pro Glu Arg Asp Gln Leu Ala Ser Val Leu Lys
                165                 170                 175

Leu Thr Ser Thr Gln Val Lys Ile Trp Phe Gln Asn Arg Arg Tyr Lys
            180                 185                 190

Cys Lys Arg Gln Arg Gln Asp Gln Thr Leu Glu Leu Val Gly Leu Pro
        195                 200                 205

Pro Pro Pro Pro Pro Ala Arg Arg Ile Ala Val Pro Val Leu Val
    210                 215                 220

Arg Asp Gly Lys Pro Cys Leu Gly Asp Ser Ala Pro Tyr Ala Pro Ala
225                 230                 235                 240

Tyr Gly Val Gly Leu Asn Pro Tyr Gly Tyr Asn Ala Tyr Pro Ala Tyr
                245                 250                 255

Pro Gly Tyr Gly Gly Ala Ala Cys Ser Pro Gly Tyr Ser Cys Thr Ala
            260                 265                 270

Ala Tyr Pro Ala Gly Pro Ser Pro Ala Gln Pro Ala Thr Ala Ala Ala
        275                 280                 285

Asn Asn Asn Phe Val Asn Phe Gly Val Gly Asp Leu Asn Ala Val Gln
    290                 295                 300

Ser Pro Gly Ile Pro Gln Ser Asn Ser Gly Val Ser Thr Leu His Gly
305                 310                 315                 320

Ile Arg Ala Trp
```

<210> SEQ ID NO 34
<211> LENGTH: 975
<212> TYPE: DNA

<213> ORGANISM: Homo sapiens

<400> SEQUENCE: 34

| | |
|---|---|
| atgttcccca gccctgctct cacgcccacg cccttctcag tcaaagacat cctaaacctg | 60 |
| gaacagcagc agcgcagcct ggctgccgcc ggagagctct ctgcccgcct ggaggcgacc | 120 |
| ctggcgccct cctcctgcat gctggccgcc ttcaagccag aggcctacgc tgggcccgag | 180 |
| gcggctgcgc cgggcctccc agagctgcgc gcagagctgg gccgcgcgcc ttcaccggcc | 240 |
| aagtgtgcgt ctgcctttcc cgccgccccc gccttctatc cacgtgccta cagcgacccc | 300 |
| gacccagcca aggaccctag agccgaaaag aaagagctgt gcgcgctgca gaaggcggtg | 360 |
| gagctggaga agacagaggc ggacaacgcg gagcggcccc gggcgcgacg gcggaggaag | 420 |
| ccgcgcgtgc tcttctcgca ggcgcaggtc tatgagctgg agcggcgctt caagcagcag | 480 |
| cggtacctgt cggcccccga acgcgaccag ctggccagcg tgctgaaact cacgtccacg | 540 |
| caggtcaaga tctggttcca gaaccggcgc tacaagtgca gcggcagcg caggaccag | 600 |
| actctggagc tggtggggct gccccgcg ccgccgccgc ctgcccgcag gatcgcggtg | 660 |
| ccagtgctgg tgcgcgatgg caagccatgc ctaggggact cggcgcccta cgcgcctgcc | 720 |
| tacgcgtgg gcctcaatcc ctacggttat aacgcctacc ccgcctatcc gggttacggc | 780 |
| ggcgcggcct gcagccctgg ctacagctgc actgccgctt accccgccgg gccttcccca | 840 |
| gcgcagccgg ccactgccgc cgccaacaac aacttcgtga acttcggcgt cggggacttg | 900 |
| aatgcggttc agagccccgg gattccgcag agcaactcgg gagtgtccac gctgcatggt | 960 |
| atccgagcct ggtag | 975 |

<210> SEQ ID NO 35
<211> LENGTH: 112
<212> TYPE: PRT
<213> ORGANISM: Homo sapiens

<400> SEQUENCE: 35

Met Phe Pro Ser Pro Ala Leu Thr Pro Thr Pro Phe Ser Val Lys Asp
1               5                   10                  15

Ile Leu Asn Leu Glu Gln Gln Gln Arg Ser Leu Ala Ala Ala Gly Glu
            20                  25                  30

Leu Ser Ala Arg Leu Glu Ala Thr Leu Ala Pro Ser Ser Cys Met Leu
        35                  40                  45

Ala Ala Phe Lys Pro Glu Ala Tyr Ala Gly Pro Glu Ala Ala Pro
    50                  55                  60

Gly Leu Pro Glu Leu Arg Ala Glu Leu Gly Arg Ala Pro Ser Pro Ala
65                  70                  75                  80

Lys Cys Ala Ser Ala Phe Pro Ala Ala Pro Ala Phe Tyr Pro Arg Ala
                85                  90                  95

Tyr Ser Asp Pro Asp Pro Ala Lys Asp Pro Arg Ala Glu Lys Lys Ala
            100                 105                 110

<210> SEQ ID NO 36
<211> LENGTH: 339
<212> TYPE: DNA
<213> ORGANISM: Homo sapiens

<400> SEQUENCE: 36

| | |
|---|---|
| atgttcccca gccctgctct cacgcccacg cccttctcag tcaaagacat cctaaacctg | 60 |
| gaacagcagc agcgcagcct ggctgccgcc ggagagctct ctgcccgcct ggaggcgacc | 120 |

```
ctggcgccct cctcctgcat gctggccgcc ttcaagccag aggcctacgc tgggcccgag    180
gcggctgcgc cgggcctccc agagctgcgc gcagagctgg gccgcgcgcc ttcaccggcc    240
aagtgtgcgt ctgcctttcc cgccgccccc gccttctatc cacgtgccta cagcgacccc    300
gacccagcca aggaccctag agccgaaaag aaagcctga                           339
```

<210> SEQ ID NO 37
<211> LENGTH: 346
<212> TYPE: PRT
<213> ORGANISM: Homo sapiens

<400> SEQUENCE: 37

```
Met Gly Asp Pro Pro Lys Lys Arg Leu Ile Ser Leu Cys Val Gly
 1               5                  10                  15

Cys Gly Asn Gln Ile His Asp Gln Tyr Ile Leu Arg Val Ser Pro Asp
                20                  25                  30

Leu Glu Trp His Ala Ala Cys Leu Lys Cys Ala Glu Cys Asn Gln Tyr
                35                  40                  45

Leu Asp Glu Ser Cys Thr Cys Phe Val Arg Asp Gly Lys Thr Tyr Cys
            50                  55                  60

Lys Arg Asp Tyr Ile Arg Leu Tyr Gly Ile Lys Cys Ala Lys Cys Ser
65                  70                  75                  80

Ile Gly Phe Ser Lys Asn Asp Phe Val Met Arg Ala Arg Ser Lys Val
                85                  90                  95

Tyr His Ile Glu Cys Phe Arg Cys Val Ala Cys Ser Arg Gln Leu Ile
                100                 105                 110

Pro Gly Asp Glu Phe Ala Leu Arg Glu Asp Gly Leu Phe Cys Arg Ala
            115                 120                 125

Asp His Asp Val Val Glu Arg Ala Ser Leu Gly Ala Gly Asp Pro Leu
130                 135                 140

Ser Pro Leu His Pro Ala Arg Pro Leu Gln Met Ala Ala Glu Pro Ile
145                 150                 155                 160

Ser Ala Arg Gln Pro Ala Leu Arg Pro His Val His Lys Gln Pro Glu
                165                 170                 175

Lys Thr Thr Arg Val Arg Thr Val Leu Asn Glu Lys Gln Leu His Thr
                180                 185                 190

Leu Arg Thr Cys Tyr Ala Ala Asn Pro Arg Pro Asp Ala Leu Met Lys
            195                 200                 205

Glu Gln Leu Val Glu Met Thr Gly Leu Ser Pro Arg Val Ile Arg Val
210                 215                 220

Trp Phe Gln Asn Lys Arg Cys Lys Asp Lys Lys Arg Ser Ile Met Met
225                 230                 235                 240

Lys Gln Leu Gln Gln Gln Pro Asn Asp Lys Thr Asn Ile Gln Gly
                245                 250                 255

Met Thr Gly Thr Pro Met Val Ala Ala Ser Pro Glu Arg His Asp Gly
                260                 265                 270

Gly Leu Gln Ala Asn Pro Val Glu Val Gln Ser Tyr Gln Pro Pro Trp
            275                 280                 285

Lys Val Leu Ser Asp Phe Ala Leu Gln Ser Asp Ile Asp Gln Pro Ala
            290                 295                 300

Phe Gln Gln Leu Val Asn Phe Ser Glu Gly Gly Pro Gly Ser Asn Ser
305                 310                 315                 320

Thr Gly Ser Glu Val Ala Ser Met Ser Ser Gln Leu Pro Asp Thr Pro
                325                 330                 335
```

Asn Ser Met Val Ala Ser Pro Ile Glu Ala
            340                 345

<210> SEQ ID NO 38
<211> LENGTH: 1041
<212> TYPE: DNA
<213> ORGANISM: Homo sapiens

<400> SEQUENCE: 38

| | | | | | |
|---|---|---|---|---|---|
| atgggagatc | caccaaaaaa | aaaacgtctg | atttccctat | gtgttggttg | cggcaatcag | 60 |
| attcacgatc | agtatattct | gagggtttct | ccggatttgg | aatggcatgc | ggcatgtttg | 120 |
| aaatgtgcgg | agtgtaatca | gtatttggac | gagagctgta | catgctttgt | tagggatggg | 180 |
| aaaacctact | gtaaaagaga | ttatatcagg | ttgtacggga | tcaaatgcgc | caagtgcagc | 240 |
| atcggcttca | gcaagaacga | cttcgtgatg | cgtgcccgct | ccaaggtgta | tcacatcgag | 300 |
| tgtttccgct | gtgtggcctg | cagccgccag | ctcatccctg | ggacgaatt | gcgcttcgg | 360 |
| gaggacggtc | tcttctgccg | agcagaccac | gatgtggtgg | agagggccag | tctaggcgct | 420 |
| ggcgacccgc | tcagtcccct | gcatccagcg | cggccactgc | aaatggcagc | ggagcccatc | 480 |
| tccgccaggc | agccagccct | gcggccccac | gtccacaagc | agccggagaa | gaccacccgc | 540 |
| gtgcggactg | tgctgaacga | gaagcagctg | cacaccttgc | ggacctgcta | cgccgcaaac | 600 |
| ccgcggccag | atgcgctcat | gaaggagcaa | ctggtagaga | tgacgggcct | cagtccccgt | 660 |
| gtgatccggg | tctggtttca | aaacaagcgg | tgcaaggaca | gaagcgaag | catcatgatg | 720 |
| aagcaactcc | agcagcagca | gcccaatgac | aaaactaata | tccaggggat | gacaggaact | 780 |
| cccatggtgg | ctgccagtcc | agagagacac | gacggtggct | acaggctaa | cccagtggaa | 840 |
| gtacaaagtt | accagccacc | ttggaaagta | ctgagcgact | cgccttgca | gagtgacata | 900 |
| gatcagcctg | cttttcagca | actggtcaat | ttttcagaag | gaggaccggg | ctctaattcc | 960 |
| actggcagtg | aagtagcatc | aatgtcctct | caacttccag | atacacctaa | cagcatggta | 1020 |
| gccagtccta | ttgaggcatg | a | | | | 1041 |

<210> SEQ ID NO 39
<211> LENGTH: 684
<212> TYPE: PRT
<213> ORGANISM: Homo sapiens

<400> SEQUENCE: 39

Met Lys Leu Lys Arg Ala Arg Leu Ala Asp Asp Leu Asn Glu Lys Ile
1               5                   10                  15

Ala Leu Arg Pro Gly Pro Leu Glu Leu Val Glu Lys Asn Ile Leu Pro
            20                  25                  30

Val Asp Ser Ala Val Lys Glu Ala Ile Lys Gly Asn Gln Val Ser Phe
        35                  40                  45

Ser Lys Ser Thr Asp Ala Phe Ala Phe Glu Glu Asp Ser Ser Ser Asp
    50                  55                  60

Gly Leu Ser Pro Asp Gln Thr Arg Ser Glu Asp Pro Gln Asn Ser Ala
65                  70                  75                  80

Gly Ser Pro Pro Asp Ala Lys Ala Ser Asp Thr Pro Thr Gly Ser
            85                  90                  95

Leu Gly Thr Asn Gln Asp Leu Ala Ser Gly Ser Glu Asn Asp Arg Asn
            100                 105                 110

Asp Ser Ala Ser Gln Pro Ser His Gln Ser Asp Ala Gly Lys Gln Gly
        115                 120                 125

```
Leu Gly Pro Pro Ser Thr Pro Ile Ala Val His Ala Val Lys Ser
    130                 135                 140

Lys Ser Leu Gly Asp Ser Lys Asn Arg His Lys Lys Pro Lys Asp Pro
145                 150                 155                 160

Lys Pro Lys Val Lys Lys Leu Lys Tyr His Gln Tyr Ile Pro Pro Asp
                165                 170                 175

Gln Lys Ala Glu Lys Ser Pro Pro Met Asp Ser Ala Tyr Ala Arg
                180                 185                 190

Leu Leu Gln Gln Gln Leu Phe Leu Gln Leu Gln Ile Leu Ser Gln
                195                 200                 205

Gln Gln Gln Gln Gln His Arg Phe Ser Tyr Leu Gly Met His Gln
    210                 215                 220

Ala Gln Leu Lys Glu Pro Asn Glu Gln Met Val Arg Asn Pro Asn Ser
225                 230                 235                 240

Ser Ser Thr Pro Leu Ser Asn Thr Pro Leu Ser Pro Val Lys Asn Ser
                245                 250                 255

Phe Ser Gly Gln Thr Gly Val Ser Ser Phe Lys Pro Gly Pro Leu Pro
                260                 265                 270

Pro Asn Leu Asp Asp Leu Lys Val Ser Glu Leu Arg Gln Gln Leu Arg
                275                 280                 285

Ile Arg Gly Leu Pro Val Ser Gly Thr Lys Thr Ala Leu Met Asp Arg
                290                 295                 300

Leu Arg Pro Phe Gln Asp Cys Ser Gly Asn Pro Val Pro Asn Phe Gly
305                 310                 315                 320

Asp Ile Thr Thr Val Thr Phe Pro Val Thr Pro Asn Thr Leu Pro Asn
                325                 330                 335

Tyr Gln Ser Ser Ser Ser Thr Ser Ala Leu Ser Asn Gly Phe Tyr His
                340                 345                 350

Phe Gly Ser Thr Ser Ser Ser Pro Pro Ile Ser Pro Ala Ser Ser Asp
                355                 360                 365

Leu Ser Val Ala Gly Ser Leu Pro Asp Thr Phe Asn Asp Ala Ser Pro
                370                 375                 380

Ser Phe Gly Leu His Pro Ser Pro Val His Val Cys Thr Glu Glu Ser
385                 390                 395                 400

Leu Met Ser Ser Leu Asn Gly Gly Ser Val Pro Ser Glu Leu Asp Gly
                405                 410                 415

Leu Asp Ser Glu Lys Asp Lys Met Leu Val Glu Lys Gln Lys Val Ile
                420                 425                 430

Asn Glu Leu Thr Trp Lys Leu Gln Gln Glu Gln Arg Gln Val Glu Glu
                435                 440                 445

Leu Arg Met Gln Leu Gln Lys Gln Lys Arg Asn Asn Cys Ser Glu Lys
450                 455                 460

Lys Pro Leu Pro Phe Leu Ala Ala Ser Ile Lys Gln Glu Glu Ala Val
465                 470                 475                 480

Ser Ser Cys Pro Phe Ala Ser Gln Val Pro Val Lys Arg Gln Ser Ser
                485                 490                 495

Ser Ser Glu Cys His Pro Pro Ala Cys Glu Ala Ala Gln Leu Gln Pro
                500                 505                 510

Leu Gly Asn Ala His Cys Val Glu Ser Ser Asp Gln Thr Asn Val Leu
                515                 520                 525

Ser Ser Thr Phe Leu Ser Pro Gln Cys Ser Pro Gln His Ser Pro Leu
530                 535                 540

Gly Ala Val Lys Ser Pro Gln His Ile Ser Leu Pro Pro Ser Pro Asn
```

| | | | | | | | | | | | |
|---|---|---|---|---|---|---|---|---|---|---|---|
| | | 545 | | | 550 | | | 555 | | | 560 |

Asn Pro His Phe Leu Pro Ser Ser Ser Gly Ala Gln Gly Glu Gly His
                         565                      570                 575

Arg Val Ser Ser Pro Ile Ser Ser Gln Val Cys Thr Ala Gln Asn Ser
          580                      585                   590

Gly Ala His Asp Gly His Pro Pro Ser Phe Ser Pro His Ser Ser Ser
        595                     600                   605

Leu His Pro Pro Phe Ser Gly Ala Gln Ala Asp Ser Ser His Gly Ala
    610                      615                   620

Gly Gly Asn Pro Cys Pro Lys Ser Pro Cys Val Gln Gln Lys Met Ala
625                   630                      635               640

Gly Leu His Ser Ser Asp Lys Val Gly Pro Lys Phe Ser Ile Pro Ser
               645                   650               655

Pro Thr Phe Ser Lys Ser Ser Ser Ala Ile Ser Glu Val Thr Gln Pro
            660                   665              670

Pro Ser Tyr Glu Asp Ala Val Lys Gln Val Thr Met
         675                   680

<210> SEQ ID NO 40
<211> LENGTH: 2055
<212> TYPE: DNA
<213> ORGANISM: Homo sapiens

<400> SEQUENCE: 40

| | |
|---|---|
| atgaagctga aaagagcccg actcgccgat gatctcaatg aaaaaattgc tctacgacca | 60 |
| gggccactgg agctggtgga aaaaaacatt cttcctgtgg attctgctgt gaaagaggcc | 120 |
| ataaaggta accaggtgag tttctccaaa tccacggatg cttttgcctt tgaagaggac | 180 |
| agcagcagcg atgggctttc tccggatcag actcgaagtg aagaccccca aaactcagcg | 240 |
| ggatccccgc cagacgctaa agcctcagat acccccttcga caggttctct ggggacaaac | 300 |
| caggatcttg cttctggctc agaaaatgac agaaatgact cagcctcaca gcccagccac | 360 |
| cagtcagatg cggggaagca ggggcttggc ccccccagca cccccatagc cgtgcatgct | 420 |
| gctgtaaagt ccaaatcctt gggtgacagt aagaaccgcc acaaaaagcc caaggacccc | 480 |
| aagccaaagg tgaagaagct taaatatcac cagtacattc ccccagacca gaaggcagag | 540 |
| aagtcccctc cacctatgga ctcagcctac gctcggctgc tccagcaaca gcagctgttc | 600 |
| ctgcagctcc aaatcctcag ccagcagcag cagcagcagc aacaccgatt cagctaccta | 660 |
| gggatgcacc aagctcagct taaggaacca aatgaacaga tggtcagaaa tccaaactct | 720 |
| tcttcaacgc cactgagcaa taccccttg tctcctgtca aaaacagttt ttctggacaa | 780 |
| actggtgtct cttcttttcaa accaggccca ctcccaccta acctggatga tctgaaggtc | 840 |
| tctgaattaa gacaacagct tcgaattcgg ggcttgcctg tgtcaggcac aaaacggct | 900 |
| ctcatggacc ggcttcgacc cttccaggac tgctctggca cccagtgcc gaactttggg | 960 |
| gatataacga ctgtcacttt tcctgtcaca cccaacacgc tgcccaatta ccagtcttcc | 1020 |
| tcttctacca gtgccctgtc aacggcttc taccactttg gcagcaccag ctccagcccc | 1080 |
| ccgatctccc cagcctcctc tgacctgtca gtcgctgggt cctgccgga cccttcaat | 1140 |
| gatgcctccc cctccttcgg cctgcacccg tccccagtcc acgtgtgcac ggaggaaagt | 1200 |
| ctcatgagca gctgaatgg gggctctgtt ccttctgagc tggatgggct ggactccgag | 1260 |
| aaggacaaga tgctggtgga gaagcagaag gtgatcaatg aactcacctg gaaactccag | 1320 |
| caagagcaga ggcaggtgga ggagctgagg atgcagcttc agaagcagaa aggaataac | 1380 |

```
tgttcagaga agaagccgct gcctttcctg gctgcctcca tcaagcagga agaggctgtc    1440
tccagctgtc cttttgcatc ccaagtacct gtgaaaagac aaagcagcag ctcagagtgt    1500
cacccaccgg cttgtgaagc tgctcaactc cagcctcttg gaaatgctca ttgtgtggag    1560
tcctcagatc aaaccaatgt actttcttcc acatttctca gccccagtg ttcccctcag     1620 cattcaccgc tgggggctgt gaaaagccca gcacatca gtttgccccc atcacccaac      1680
aaccctcact ttctgccctc atcctccggg gcccagggag aagggcacag ggtctcctcg    1740
cccatcagca gccaggtgtg cactgcacag aactcaggag cacacgatgg ccatcctcca    1800
agcttctctc cccattcttc cagcctccac ccgcccttct ctggagccca agcagacagc    1860
agtcatggtg ccggggggaaa cccttgtccc aaaagcccat gtgtacagca aagatggct    1920 ggtttacact cttctgataa ggtggggcca aagttttcaa ttccatcccc aacttttct     1980 aagtcaagtt cagcaatttc agaggtaaca cagcctccat cctatgaaga tgccgtaaag   2040
caggtaacca tgtga                                                     2055
```

<210> SEQ ID NO 41
<211> LENGTH: 986
<212> TYPE: PRT
<213> ORGANISM: Homo sapiens

<400> SEQUENCE: 41

```
Met Thr Leu Leu Gly Ser Glu His Ser Leu Ile Arg Ser Lys Phe
 1               5                  10                  15

Arg Ser Val Leu Gln Leu Arg Leu Gln Gln Arg Thr Gln Glu Gln
            20                  25                  30

Leu Ala Asn Gln Gly Ile Ile Pro Pro Leu Lys Arg Pro Ala Glu Phe
            35                  40                  45

His Glu Gln Arg Lys His Leu Asp Ser Asp Lys Ala Lys Asn Ser Leu
        50                  55                  60

Lys Arg Lys Ala Arg Asn Arg Cys Asn Ser Ala Asp Leu Val Asn Met
65                  70                  75                  80

His Ile Leu Gln Ala Ser Thr Ala Glu Arg Ser Ile Pro Thr Ala Gln
                85                  90                  95

Met Lys Leu Lys Arg Ala Arg Leu Ala Asp Asp Leu Asn Glu Lys Ile
            100                 105                 110

Ala Leu Arg Pro Gly Pro Leu Glu Leu Val Glu Lys Asn Ile Leu Pro
        115                 120                 125

Val Asp Ser Ala Val Lys Glu Ala Ile Lys Gly Asn Gln Val Ser Phe
    130                 135                 140

Ser Lys Ser Thr Asp Ala Phe Ala Phe Glu Glu Asp Ser Ser Ser Asp
145                 150                 155                 160

Gly Leu Ser Pro Asp Gln Thr Arg Ser Glu Asp Pro Gln Asn Ser Ala
                165                 170                 175

Gly Ser Pro Pro Asp Ala Lys Ala Ser Asp Thr Pro Thr Gly Ser
            180                 185                 190

Leu Gly Thr Asn Gln Asp Leu Ala Ser Gly Ser Glu Asn Asp Arg Asn
        195                 200                 205

Asp Ser Ala Ser Gln Pro Ser His Gln Ser Asp Ala Gly Lys Gln Gly
    210                 215                 220

Leu Gly Pro Pro Ser Thr Pro Ile Ala Val His Ala Ala Val Lys Ser
225                 230                 235                 240

Lys Ser Leu Gly Asp Ser Lys Asn Arg His Lys Lys Pro Lys Asp Pro
```

```
                245                 250                 255
Lys Pro Lys Val Lys Lys Leu Lys Tyr His Gln Tyr Ile Pro Pro Asp
            260                 265                 270

Gln Lys Ala Glu Lys Ser Pro Pro Met Asp Ser Ala Tyr Ala Arg
            275                 280             285

Leu Leu Gln Gln Gln Gln Leu Phe Leu Gln Leu Gln Ile Leu Ser Gln
            290                 295                 300

Gln Gln Gln Gln Gln Gln His Arg Phe Ser Tyr Leu Gly Met His Gln
305                 310                 315                 320

Ala Gln Leu Lys Glu Pro Asn Glu Gln Met Val Arg Asn Pro Asn Ser
            325                 330                 335

Ser Ser Thr Pro Leu Ser Asn Thr Pro Leu Ser Pro Val Lys Asn Ser
            340                 345                 350

Phe Ser Gly Gln Thr Gly Val Ser Ser Phe Lys Pro Gly Pro Leu Pro
            355                 360                 365

Pro Asn Leu Asp Asp Leu Lys Val Ser Glu Leu Arg Gln Gln Leu Arg
            370                 375                 380

Ile Arg Gly Leu Pro Val Ser Gly Thr Lys Thr Ala Leu Met Asp Arg
385                 390                 395                 400

Leu Arg Pro Phe Gln Asp Cys Ser Gly Asn Pro Val Pro Asn Phe Gly
            405                 410                 415

Asp Ile Thr Thr Val Thr Phe Pro Val Thr Pro Asn Thr Leu Pro Asn
            420                 425                 430

Tyr Gln Ser Ser Ser Ser Thr Ser Ala Leu Ser Asn Gly Phe Tyr His
            435                 440                 445

Phe Gly Ser Thr Ser Ser Ser Pro Pro Ile Ser Pro Ala Ser Ser Asp
            450                 455                 460

Leu Ser Val Ala Gly Ser Leu Pro Asp Thr Phe Asn Asp Ala Ser Pro
465                 470                 475                 480

Ser Phe Gly Leu His Pro Ser Pro Val His Val Cys Thr Glu Glu Ser
            485                 490                 495

Leu Met Ser Ser Leu Asn Gly Gly Ser Val Pro Ser Glu Leu Asp Gly
            500                 505                 510

Leu Asp Ser Glu Lys Asp Lys Met Leu Val Glu Lys Gln Lys Val Ile
            515                 520                 525

Asn Glu Leu Thr Trp Lys Leu Gln Gln Glu Gln Arg Gln Val Glu Glu
            530                 535                 540

Leu Arg Met Gln Leu Gln Lys Gln Lys Arg Asn Asn Cys Ser Glu Lys
545                 550                 555                 560

Lys Pro Leu Pro Phe Leu Ala Ala Ser Ile Lys Gln Glu Glu Ala Val
            565                 570                 575

Ser Ser Cys Pro Phe Ala Ser Gln Val Pro Val Lys Arg Gln Ser Ser
            580                 585                 590

Ser Ser Glu Cys His Pro Pro Ala Cys Glu Ala Ala Gln Leu Gln Pro
            595                 600                 605

Leu Gly Asn Ala His Cys Val Glu Ser Ser Asp Gln Thr Asn Val Leu
            610                 615                 620

Ser Ser Thr Phe Leu Ser Pro Gln Cys Ser Pro Gln His Ser Pro Leu
625                 630                 635                 640

Gly Ala Val Lys Ser Pro Gln His Ile Ser Leu Pro Pro Ser Pro Asn
            645                 650                 655

Asn Pro His Phe Leu Pro Ser Ser Ser Gly Ala Gln Gly Glu Gly His
            660                 665                 670
```

| | | | | | | | | | | | |
|---|---|---|---|---|---|---|---|---|---|---|---|
|Arg|Val|Ser|Ser|Pro|Ile|Ser|Ser|Gln|Val|Cys|Thr|Ala|Gln|Asn|Ser|
| |675| | | |680| | | |685| | |

Arg Val Ser Ser Pro Ile Ser Ser Gln Val Cys Thr Ala Gln Asn Ser
            675                 680                 685

Gly Ala His Asp Gly His Pro Pro Ser Phe Ser Pro His Ser Ser Ser
690                 695                 700

Leu His Pro Pro Phe Ser Gly Ala Gln Ala Asp Ser Ser His Gly Ala
705                 710                 715                 720

Gly Gly Asn Pro Cys Pro Lys Ser Pro Cys Val Gln Gln Lys Met Ala
                725                 730                 735

Gly Leu His Ser Ser Asp Lys Val Gly Pro Lys Phe Ser Ile Pro Ser
                740                 745                 750

Pro Thr Phe Ser Lys Ser Ser Ala Ile Ser Glu Val Thr Gln Pro
            755                 760                 765

Pro Ser Tyr Glu Asp Ala Val Lys Gln Gln Met Thr Arg Ser Gln Gln
            770                 775                 780

Met Asp Glu Leu Leu Asp Val Leu Ile Glu Ser Gly Glu Met Pro Ala
785                 790                 795                 800

Asp Ala Arg Glu Asp His Ser Cys Leu Gln Lys Val Pro Lys Ile Pro
                805                 810                 815

Arg Ser Ser Arg Ser Pro Thr Ala Val Leu Thr Lys Pro Ser Ala Ser
                820                 825                 830

Phe Glu Gln Ala Ser Ser Gly Ser Gln Ile Pro Phe Asp Pro Tyr Ala
            835                 840                 845

Thr Asp Ser Asp Glu His Leu Glu Val Leu Leu Asn Ser Gln Ser Pro
850                 855                 860

Leu Gly Lys Met Ser Asp Val Thr Leu Leu Lys Ile Gly Ser Glu Glu
865                 870                 875                 880

Pro His Phe Asp Gly Ile Met Asp Gly Phe Ser Gly Lys Ala Ala Glu
                885                 890                 895

Asp Leu Phe Asn Ala His Glu Ile Leu Pro Gly Pro Leu Ser Pro Met
                900                 905                 910

Gln Thr Gln Phe Ser Pro Ser Ser Val Asp Ser Asn Gly Leu Gln Leu
            915                 920                 925

Ser Phe Thr Glu Ser Pro Trp Glu Thr Met Glu Trp Leu Asp Leu Thr
            930                 935                 940

Pro Pro Asn Ser Thr Pro Gly Phe Ser Ala Leu Thr Thr Ser Ser Pro
945                 950                 955                 960

Ser Ile Phe Asn Ile Asp Phe Leu Asp Val Thr Asp Leu Asn Leu Asn
                965                 970                 975

Ser Ser Met Asp Leu His Leu Gln Gln Trp
            980                 985

<210> SEQ ID NO 42
<211> LENGTH: 2961
<212> TYPE: DNA
<213> ORGANISM: Homo sapiens

<400> SEQUENCE: 42
atgacactcc tggggtctga gcattccttg ctgattagga gcaagttcag atcagtttta    60
cagttaagac ttcaacaaag aaggacccag gaacaactgg ctaaccaagg cataatacca   120
ccactgaaac gtccagctga attccatgag caaagaaaac atttggatag tgacaaggct   180
aaaaattccc tgaagcgcaa agccagaaac aggtgcaaca gtgccgactt ggttaatatg   240
cacatactcc aagcttccac tgcagagagg tccattccaa ctgctcagat gaagctgaaa   300

```
agagcccgac tcgccgatga tctcaatgaa aaaattgctc tacgaccagg gccactggag    360
ctggtggaaa aaaacattct tcctgtggat tctgctgtga agaggccat aaaaggtaac    420 caggtgagtt tctccaaatc cacggatgct tttgcctttg aagaggacag cagcagcgat    480
gggctttctc cggatcagac tcgaagtgaa gaccccaaa actcagcggg atccccgcca    540
gacgctaaag cctcagatac cccttcgaca ggttctctgg ggacaaacca ggatcttgct    600
tctggctcag aaaatgacag aaatgactca gcctcacagc ccagccacca gtcagatgcg    660
gggaagcagg ggcttggccc cccagcacc cccatagccg tgcatgctgc tgtaaagtcc    720
aaatccttgg gtgacagtaa gaaccgccac aaaaagccca aggaccccaa gccaaaggtg    780
aagaagctta aatatcacca gtacattccc ccagaccaga aggcagagaa gtcccctcca    840
cctatggact cagcctacgc tcggctgctc cagcaacagc agctgttcct gcagctccaa    900
atcctcagcc agcagcagca gcagcagcaa caccgattca gctacctagg gatgcaccaa    960
gctcagctta aggaaccaaa tgaacagatg gtcagaaatc caaactcttc ttcaacgcca    1020
ctgagcaata ccccttgtc tcctgtcaaa acagttttt ctggacaaac tggtgtctct    1080
tctttcaaac caggcccact cccacctaac ctggatgatc tgaaggtctc tgaattaaga    1140
caacagcttc gaattcgggg cttgcctgtg tcaggcacca aaacggctct catggaccgg    1200
cttcgaccct tccaggactg ctctggcaac ccagtgccga ctttgggga tataacgact    1260 gtcacttttc ctgtcacacc caacacgctg cccaattacc agtcttcctc ttctaccagt    1320
gccctgtcca acggcttcta ccactttggc agcaccagct ccagcccccc gatctcccca    1380
gcctcctctg acctgtcagt cgctgggtcc ctgccggaca ccttcaatga tgcctccccc    1440
tccttcggcc tgcacccgtc cccagtccac gtgtgcacgg aggaaagtct catgagcagc    1500
ctgaatgggg gctctgttcc ttctgagctg gatgggctgg actccgagaa ggacaagatg    1560
ctggtggaga agcagaaggt gatcaatgaa ctcacctgga aactccagca agagcagagg    1620
caggtggagg agctgaggat gcagcttcag aagcagaaaa ggaataactg ttcagagaag    1680
aagccgctgc ctttcctggc tgcctccatc aagcaggaag aggctgtctc cagctgtcct    1740
tttgcatccc aagtacctgt gaaaagacaa agcagcagct cagagtgtca cccaccggct    1800
tgtgaagctg ctcaactcca gcctcttgga aatgctcatt gtgtggagtc ctcagatcaa    1860
accaatgtac tttcttccac atttctcagc ccccagtgtt cccctcagca ttcaccgctg    1920
ggggctgtga aaagcccaca gcacatcagt ttgccccat cacccaacaa ccctcacttt    1980
ctgccctcat cctccggggc ccaggggaga gggcacaggg tctcctcgcc catcagcagc    2040
caggtgtgca ctgcacagaa ctcaggagca cacgatggcc atcctccaag cttctctccc    2100
cattcttcca gcctccaccc gcccttctct ggagcccaag cagacagcag tcatggtgcc    2160 gggggaaaacc cttgtcccaa aagcccatgt gtacagcaaa agatggctgg tttacactct    2220
tctgataagg tggggccaaa gttttcaatt ccatccccaa cttttttctaa gtcaagttca    2280 gcaatttcag aggtaacaca gcctccatcc tatgaagatg ccgtaaagca gcaaatgacc    2340
cggagtcagc agatggatga actcctggac gtgcttattg aaagcggaga aatgccagca    2400
gacgctagag aggatcactc atgtcttcaa aaagtcccaa agatacccag atcttcccga    2460
agtccaactg ctgtcctcac caagccctcg gcttcctttg aacaagcctc ttcaggcagc    2520
cagatcccct tgatcccta tgccaccgac agtgatgagc atcttgaagt cttattaaat    2580
tcccagagcc ccctaggaaa gatgagtgat gtcacccttc taaaaattgg gagcgaagag    2640
cctcactttg atgggataat ggatggattc tctgggaagg ctgcagaaga cctcttcaat    2700
```

-continued

```
gcacatgaga tcttgccagg cccctctct ccaatgcaga cacagttttc accctcttct    2760
gtggacagca atgggctgca gttaagcttc actgaatctc cctgggaaac catggagtgg    2820
ctggacctca ctccgccaaa ttccacacca ggctttagcg ccctcaccac cagcagcccc    2880
agcatcttca acatcgattt cctggatgtc actgatctca atttgaattc ttccatggac    2940
cttcacttgc agcagtggta g                                              2961
```

<210> SEQ ID NO 43
<211> LENGTH: 938
<212> TYPE: PRT
<213> ORGANISM: Homo sapiens

<400> SEQUENCE: 43

```
Met Thr Leu Leu Gly Ser Glu His Ser Leu Leu Ile Arg Ser Lys Phe
  1               5                  10                  15

Arg Ser Val Leu Gln Leu Arg Leu Gln Gln Arg Arg Thr Gln Glu Gln
             20                  25                  30

Leu Ala Asn Gln Gly Ile Ile Pro Pro Leu Lys Arg Pro Ala Glu Phe
         35                  40                  45

His Glu Gln Arg Lys His Leu Asp Ser Asp Lys Ala Lys Asn Ser Leu
     50                  55                  60

Lys Arg Lys Ala Arg Asn Arg Cys Asn Ser Ala Asp Leu Val Asn Met
 65                  70                  75                  80

His Ile Leu Gln Ala Ser Thr Ala Glu Arg Ser Ile Pro Thr Ala Gln
                 85                  90                  95

Met Lys Leu Lys Arg Ala Arg Leu Ala Asp Asp Leu Asn Glu Lys Ile
            100                 105                 110

Ala Leu Arg Pro Gly Pro Leu Glu Leu Val Glu Lys Asn Ile Leu Pro
        115                 120                 125

Val Asp Ser Ala Val Lys Glu Ala Ile Lys Gly Asn Gln Val Ser Phe
    130                 135                 140

Ser Lys Ser Thr Asp Ala Phe Ala Phe Glu Glu Asp Ser Ser Ser Asp
145                 150                 155                 160

Gly Leu Ser Pro Asp Gln Thr Arg Ser Glu Asp Pro Gln Asn Ser Ala
                165                 170                 175

Gly Ser Pro Pro Asp Ala Lys Ala Ser Asp Thr Pro Ser Thr Gly Ser
            180                 185                 190

Leu Gly Thr Asn Gln Asp Leu Ala Ser Gly Ser Glu Asn Asp Arg Asn
        195                 200                 205

Asp Ser Ala Ser Gln Pro Ser His Gln Ser Asp Ala Gly Lys Gln Gly
    210                 215                 220

Leu Gly Pro Pro Ser Thr Pro Ile Ala Val His Ala Ala Val Lys Ser
225                 230                 235                 240

Lys Ser Leu Gly Asp Ser Lys Asn Arg His Lys Lys Pro Lys Asp Pro
                245                 250                 255

Lys Pro Lys Val Lys Lys Leu Lys Tyr His Gln Tyr Ile Pro Pro Asp
            260                 265                 270

Gln Lys Ala Glu Lys Ser Pro Pro Pro Met Asp Ser Ala Tyr Ala Arg
        275                 280                 285

Leu Leu Gln Gln Gln Gln Leu Phe Leu Gln Leu Gln Ile Leu Ser Gln
    290                 295                 300

Gln Gln Gln Gln Gln Gln His Arg Phe Ser Tyr Leu Gly Met His Gln
305                 310                 315                 320
```

-continued

```
Ala Gln Leu Lys Glu Pro Asn Glu Gln Met Val Arg Asn Pro Asn Ser
            325                 330                 335

Ser Ser Thr Pro Leu Ser Asn Thr Pro Leu Ser Pro Val Lys Asn Ser
        340                 345                 350

Phe Ser Gly Gln Thr Gly Val Ser Ser Phe Lys Pro Gly Pro Leu Pro
        355                 360                 365

Pro Asn Leu Asp Asp Leu Lys Val Ser Glu Leu Arg Gln Gln Leu Arg
370                 375                 380

Ile Arg Gly Leu Pro Val Ser Gly Thr Lys Thr Ala Leu Met Asp Arg
385                 390                 395                 400

Leu Arg Pro Phe Gln Asp Cys Ser Gly Asn Pro Val Pro Asn Phe Gly
            405                 410                 415

Asp Ile Thr Thr Val Thr Phe Pro Val Thr Pro Asn Thr Leu Pro Asn
            420                 425                 430

Tyr Gln Ser Ser Ser Thr Ser Ala Leu Ser Asn Gly Phe Tyr His
            435                 440                 445

Phe Gly Ser Thr Ser Ser Pro Pro Ile Ser Pro Ala Ser Ser Asp
        450                 455                 460

Leu Ser Val Ala Gly Ser Leu Pro Asp Thr Phe Asn Asp Ala Ser Pro
465                 470                 475                 480

Ser Phe Gly Leu His Pro Ser Pro Val His Val Cys Thr Glu Glu Ser
            485                 490                 495

Leu Met Ser Ser Leu Asn Gly Gly Ser Val Pro Ser Glu Leu Asp Gly
        500                 505                 510

Leu Asp Ser Glu Lys Asp Lys Met Leu Val Glu Lys Gln Lys Val Ile
        515                 520                 525

Asn Glu Leu Thr Trp Lys Leu Gln Gln Glu Gln Arg Gln Val Glu Glu
        530                 535                 540

Leu Arg Met Gln Leu Gln Lys Gln Lys Arg Asn Asn Cys Ser Glu Lys
545                 550                 555                 560

Lys Pro Leu Pro Phe Leu Ala Ala Ser Ile Lys Gln Glu Glu Ala Val
            565                 570                 575

Ser Ser Cys Pro Phe Ala Ser Gln Val Pro Val Lys Arg Gln Ser Ser
        580                 585                 590

Ser Ser Glu Cys His Pro Pro Ala Cys Glu Ala Ala Gln Leu Gln Pro
        595                 600                 605

Leu Gly Asn Ala His Cys Val Glu Ser Ser Asp Gln Thr Asn Val Leu
        610                 615                 620

Ser Ser Thr Phe Leu Ser Pro Gln Cys Ser Pro Gln His Ser Pro Leu
625                 630                 635                 640

Gly Ala Val Lys Ser Pro Gln His Ile Ser Leu Pro Pro Ser Pro Asn
            645                 650                 655

Asn Pro His Phe Leu Pro Ser Ser Gly Ala Gln Gly Glu Gly His
            660                 665                 670

Arg Val Ser Ser Pro Ile Ser Ser Gln Val Cys Thr Ala Gln Met Ala
        675                 680                 685

Gly Leu His Ser Ser Asp Lys Val Gly Pro Lys Phe Ser Ile Pro Ser
        690                 695                 700

Pro Thr Phe Ser Lys Ser Ser Ser Ala Ile Glu Val Thr Gln Pro
705                 710                 715                 720

Pro Ser Tyr Glu Asp Ala Val Lys Gln Gln Met Thr Arg Ser Gln Gln
            725                 730                 735

Met Asp Glu Leu Leu Asp Val Leu Ile Glu Ser Gly Glu Met Pro Ala
```

```
                740                 745                 750
Asp Ala Arg Glu Asp His Ser Cys Leu Gln Lys Val Pro Lys Ile Pro
            755                 760                 765

Arg Ser Ser Arg Ser Pro Thr Ala Val Leu Thr Lys Pro Ser Ala Ser
770                 775                 780

Phe Glu Gln Ala Ser Ser Gly Ser Gln Ile Pro Phe Asp Pro Tyr Ala
785                 790                 795                 800

Thr Asp Ser Asp Glu His Leu Glu Val Leu Leu Asn Ser Gln Ser Pro
                805                 810                 815

Leu Gly Lys Met Ser Asp Val Thr Leu Leu Lys Ile Gly Ser Glu Glu
            820                 825                 830

Pro His Phe Asp Gly Ile Met Asp Gly Phe Ser Gly Lys Ala Ala Glu
        835                 840                 845

Asp Leu Phe Asn Ala His Glu Ile Leu Pro Gly Pro Leu Ser Pro Met
850                 855                 860

Gln Thr Gln Phe Ser Pro Ser Ser Val Asp Ser Asn Gly Leu Gln Leu
865                 870                 875                 880

Ser Phe Thr Glu Ser Pro Trp Glu Thr Met Glu Trp Leu Asp Leu Thr
                885                 890                 895

Pro Pro Asn Ser Thr Pro Gly Phe Ser Ala Leu Thr Thr Ser Ser Pro
            900                 905                 910

Ser Ile Phe Asn Ile Asp Phe Leu Asp Val Thr Asp Leu Asn Leu Asn
        915                 920                 925

Ser Ser Met Asp Leu His Leu Gln Gln Trp
930                 935

<210> SEQ ID NO 44
<211> LENGTH: 2817
<212> TYPE: DNA
<213> ORGANISM: Homo sapiens

<400> SEQUENCE: 44
atgacactcc tggggtctga gcattccttg ctgattagga gcaagttcag atcagttta      60 cagttaagac ttcaacaaag aaggacccag gaacaactgg ctaaccaagg cataatacca    120
ccactgaaac gtccagctga attccatgag caaagaaaac atttggatag tgacaaggct    180
aaaaattccc tgaagcgcaa agccagaaac aggtgcaaca gtgccgactt ggttaatatg    240
cacatactcc aagcttccac tgcagagagg tccattccaa ctgctcagat gaagctgaaa    300
agagcccgac tcgccgatga tctcaatgaa aaaattgctc tacgaccagg gccactggag    360
ctggtggaaa aaacattct tcctgtggat tctgctgtga agaggccat aaaaggtaac      420 caggtgagtt tctccaaatc cacggatgct tttgcctttg aagaggacag cagcagcgat    480
gggctttctc cggatcagac tcgaagtgaa gacccccaaa actcagcggg atccccgcca    540
gacgctaaag cctcagatac cccttcgaca ggttctctgg ggacaaacca ggatcttgct    600
tctggctcag aaaatgacag aaatgactca gcctcacagc ccagccacca gtcagatgcg    660
gggaagcagg ggcttggccc cccagcaccc ccatagccg tgcatgctgc tgtaaagtcc      720
aaatccttgg gtgacagtaa gaaccgccac aaaaagccca aggacccaa gccaaaggtg      780 aagaagctta atatcacca gtacattccc ccagaccaga aggcagagaa gtcccctcca      840
cctatggact cagcctacgc tcggctgctc cagcaacagc agctgttcct gcagctccaa    900
atcctcagcc agcagcagca gcagcagcaa caccgattca gctacctagg gatgcaccaa    960
gctcagctta aggaaccaaa tgaacagatg gtcagaaatc caaactcttc ttcaacgcca   1020
```

```
ctgagcaata ccccttgtc tcctgtcaaa acagttttt ctggacaaac tggtgtctct      1080
tctttcaaac caggcccact cccacctaac ctggatgatc tgaaggtctc tgaattaaga      1140
caacagcttc gaattcgggg cttgcctgtg tcaggcacca aaacggctct catggaccgg      1200
cttcgaccct tccaggactg ctctggcaac ccagtgccga actttgggga tataacgact      1260
gtcacttttc ctgtcacacc caacacgctg cccaattacc agtcttcctc ttctaccagt      1320
gccctgtcca acggcttcta ccactttggc agcaccagct ccagccccc gatcccccca      1380
gcctcctctg acctgtcagt cgctgggtcc ctgccggaca ccttcaatga tgcctccccc      1440
tccttcggcc tgcacccgtc cccagtccac gtgtgcacgg aggaaagtct catgagcagc      1500
ctgaatgggg gctctgttcc ttctgagctg gatgggctgg actccgagaa ggacaagatg      1560
ctggtggaga gcagaaggt gatcaatgaa ctcacctgga aactccagca agagcagagg      1620
caggtggagg agctgaggat gcagcttcag aagcagaaaa ggaataactg ttcagagaag      1680
aagccgctgc ctttcctggc tgcctccatc aagcaggaag aggctgtctc cagctgtcct      1740
tttgcatccc aagtacctgt gaaaagacaa agcagcagct cagagtgtca cccaccggct      1800
tgtgaagctg ctcaactcca gcctcttgga aatgctcatt gtgtggagtc ctcagatcaa      1860
accaatgtac tttcttccac atttctcagc ccccagtgtt ccctcagca ttcaccgctg      1920
ggggctgtga aaagcccaca gcacatcagt ttgcccccat cacccaacaa ccctcacttt      1980
ctgccctcat cctccggggc cagggagaa gggcacaggg tctcctcgcc catcagcagc      2040
caggtgtgca ctgcacagat ggctggttta cactcttctg ataaggtggg gccaaagttt      2100
tcaattccat ccccaacttt ttctaagtca agttcagcaa tttcagaggt aacacagcct      2160
ccatcctatg aagatgccgt aaagcagcaa atgacccgga gtcagcagat ggatgaactc      2220
ctggacgtgc ttattgaaag cggagaaatg ccagcagacg ctagagagga tcactcatgt      2280
cttcaaaaag tcccaaagat acccagatct ccccgaagtc caactgctgt cctcaccaag      2340
ccctcggctt cctttgaaca agcctcttca ggcagccaga tccccttga tccctatgcc      2400
accgacagtg atgagcatct tgaagtctta ttaaattccc agagccccct aggaaagatg      2460
agtgatgtca cccttctaaa aattgggagc gaagagcctc actttgatgg gataatggat      2520
ggattctctg ggaaggctgc agaagacctc ttcaatgcac atgagatctt gccaggcccc      2580
ctctctccaa tgcagacaca gttttcaccc tcttctgtgg acagcaatgg gctgcagtta      2640
agcttcactg aatctcccctg ggaaaccatg gagtggctgg acctcactcc gccaaattcc      2700
acaccaggct ttagcgccct caccaccagc agccccagca tcttcaacat cgatttcctg      2760
gatgtcactg atctcaattt gaattcttcc atggaccttc acttgcagca gtggtag        2817

<210> SEQ ID NO 45
<211> LENGTH: 490
<212> TYPE: PRT
<213> ORGANISM: Homo sapiens

<400> SEQUENCE: 45

Met Thr Ile Gly Arg Met Glu Asn Val Glu Val Phe Thr Ala Glu Gly
 1               5                  10                  15

Lys Gly Arg Gly Leu Lys Ala Thr Lys Glu Phe Trp Ala Ala Asp Ile
            20                  25                  30

Ile Phe Ala Glu Arg Ala Tyr Ser Ala Val Val Phe Asp Ser Leu Val
        35                  40                  45

Asn Phe Val Cys His Thr Cys Phe Lys Arg Gln Glu Lys Leu His Arg
```

```
                50                  55                  60
Cys Gly Gln Cys Lys Phe Ala His Tyr Cys Asp Arg Thr Cys Gln Lys
 65                  70                  75                  80

Asp Ala Trp Leu Asn His Lys Asn Glu Cys Ser Ala Ile Lys Arg Tyr
                 85                  90                  95

Gly Lys Val Pro Asn Glu Asn Ile Arg Leu Ala Ala Arg Ile Met Trp
                100                 105                 110

Arg Val Glu Arg Glu Gly Thr Gly Leu Thr Glu Gly Cys Leu Val Ser
                115                 120                 125

Val Asp Asp Leu Gln Asn His Val Glu His Phe Gly Glu Glu Glu Gln
130                 135                 140

Lys Asp Leu Arg Val Asp Val Asp Thr Phe Leu Gln Tyr Trp Pro Pro
145                 150                 155                 160

Gln Ser Gln Gln Phe Ser Met Gln Tyr Ile Ser His Ile Phe Gly Val
                165                 170                 175

Ile Asn Cys Asn Gly Phe Thr Leu Ser Asp Gln Arg Gly Leu Gln Ala
                180                 185                 190

Val Gly Val Gly Ile Phe Pro Asn Leu Gly Leu Val Asn His Asp Cys
                195                 200                 205

Trp Pro Asn Cys Thr Val Ile Phe Asn Asn Gly Asn His Glu Ala Val
210                 215                 220

Lys Ser Met Phe His Thr Gln Met Arg Ile Glu Leu Arg Ala Leu Gly
225                 230                 235                 240

Lys Ile Ser Glu Gly Glu Leu Thr Val Ser Tyr Ile Asp Phe Leu
                245                 250                 255

Asn Val Ser Glu Glu Arg Lys Arg Gln Leu Lys Lys Gln Tyr Tyr Phe
                260                 265                 270

Asp Cys Thr Cys Glu His Cys Gln Lys Leu Lys Asp Asp Leu Phe
                275                 280                 285

Leu Gly Val Lys Asp Asn Pro Lys Pro Ser Gln Glu Val Val Lys Glu
                290                 295                 300

Met Ile Gln Phe Ser Lys Asp Thr Leu Glu Lys Ile Asp Lys Ala Arg
305                 310                 315                 320

Ser Glu Gly Leu Tyr His Glu Val Val Lys Leu Cys Arg Glu Cys Leu
                325                 330                 335

Glu Lys Gln Glu Pro Val Phe Ala Asp Thr Asn Ile Tyr Met Leu Arg
                340                 345                 350

Met Leu Ser Ile Val Ser Glu Val Leu Ser Tyr Leu Gln Ala Phe Glu
                355                 360                 365

Glu Ala Ser Phe Tyr Ala Arg Arg Met Val Asp Gly Tyr Met Lys Leu
                370                 375                 380

Tyr His Pro Asn Asn Ala Gln Leu Gly Met Ala Val Met Arg Ala Gly
385                 390                 395                 400

Leu Thr Asn Trp His Ala Gly Asn Ile Glu Val Gly His Gly Met Ile
                405                 410                 415

Cys Lys Ala Tyr Ala Ile Leu Leu Val Thr His Gly Pro Ser His Pro
                420                 425                 430

Ile Thr Lys Asp Leu Glu Ala Met Arg Val Gln Thr Glu Met Glu Leu
                435                 440                 445

Arg Met Phe Arg Gln Asn Glu Phe Met Tyr Tyr Lys Met Arg Glu Ala
                450                 455                 460

Ala Leu Asn Asn Gln Pro Met Gln Val Met Ala Glu Pro Ser Asn Glu
465                 470                 475                 480
```

Pro Ser Pro Ala Leu Phe His Lys Lys Gln
                485                 490

<210> SEQ ID NO 46
<211> LENGTH: 1473
<212> TYPE: DNA
<213> ORGANISM: Homo sapiens

<400> SEQUENCE: 46

| | | | | | |
|---|---|---|---|---|---|
| atgacaatag | ggagaatgga | gaacgtggag | gtcttcaccg | ctgagggcaa | aggaaggggt | 60 |
| ctgaaggcca | ccaaggagtt | ctgggctgca | gatatcatct | ttgctgagcg | ggcttattcc | 120 |
| gcagtggttt | ttgacagcct | tgttaatttt | gtgtgccaca | cctgcttcaa | gaggcaggag | 180 |
| aagctccatc | gctgtgggca | gtgcaagttt | gcccattact | gcgaccgcac | ctgccagaag | 240 |
| gatgcttggc | tgaaccacaa | gaatgaatgt | tcggccatca | gagatatgg | gaaggtgccc | 300 |
| aatgagaaca | tcaggctggc | ggcgcgcatc | atgtggcggg | tggagagaga | aggcaccggg | 360 |
| ctcacggagg | gctgcctggt | gtccgtggac | gacttgcaga | accacgtgga | gcactttggg | 420 |
| gaggaggagc | agaaggacct | gcgggtggac | gtggacacat | tcttgcagta | ctggccgccg | 480 |
| cagagccagc | agttcagcat | gcagtacatc | tcgcacatct | tcggagtgat | taactgcaac | 540 |
| ggttttactc | tcagtgatca | gagaggcctg | caggccgtgg | gcgtaggcat | cttccccaac | 600 |
| ctgggcctgg | tgaaccatga | ctgttggccc | aactgtactg | tcatatttaa | caatggcaat | 660 |
| catgaggcag | tgaaatccat | gtttcatacc | cagatgagaa | ttgagctccg | ggccctaggc | 720 |
| aagatctcag | aaggagagga | gctgactgtg | tcctatattg | acttcctcaa | cgttagtgaa | 780 |
| gaacgcaaga | ggcagctgaa | gaagcagtac | tactttgact | gcacatgtga | acactgccag | 840 |
| aaaaaactga | aggatgacct | cttcctgggg | gtgaaagaca | accccaagcc | ctctcaggaa | 900 |
| gtggtgaagg | agatgataca | attctccaag | gatacattgg | aaaagataga | caaggctcgt | 960 |
| tccgagggtt | tgtatcatga | ggttgtgaaa | ttatgccggg | agtgcctgga | gaagcaggag | 1020 |
| ccagtgtttg | ctgacaccaa | catctacatg | ctgcggatgc | tgagcattgt | ttcggaggtc | 1080 |
| ctttcctacc | tccaggcctt | tgaggaggcc | tcgttctatg | ccaggaggat | ggtggacggc | 1140 |
| tatatgaagc | tctaccaccc | caacaatgcc | caactgggca | tggccgtgat | gcgggcaggg | 1200 |
| ctgaccaact | ggcatgctgg | taacattgag | gtggggcacg | ggatgatctg | caaagcctat | 1260 |
| gccattctcc | tggtgacaca | cggacccctcc | cacccatca | ctaaggactt | agaggccatg | 1320 |
| cgggtgcaga | cggagatgga | gctacgcatg | ttccgccaga | acgaattcat | gtactacaag | 1380 |
| atgcgcgagg | ctgccctgaa | caaccagccc | atgcaggtca | tggccgagcc | cagcaatgag | 1440 |
| ccatccccag | ctctgttcca | caagaagcaa | tga | | | 1473 |

<210> SEQ ID NO 47
<211> LENGTH: 508
<212> TYPE: PRT
<213> ORGANISM: Homo sapiens

<400> SEQUENCE: 47

Met Leu Pro Thr Gln Ala Gly Ala Ala Ala Leu Gly Arg Gly Ser
 1               5                  10                  15

Ala Leu Gly Gly Ser Leu Asn Arg Thr Pro Thr Gly Arg Pro Gly Gly
             20                  25                  30

Gly Gly Gly Thr Arg Gly Ala Asn Gly Gly Arg Val Pro Gly Asn Gly
         35                  40                  45

```
Ala Gly Leu Gly Pro Gly Arg Leu Glu Arg Glu Ala Ala Ala Ala
 50                  55                  60

Ala Thr Thr Pro Ala Pro Thr Ala Gly Ala Leu Tyr Ser Gly Ser Glu
 65                  70                  75                  80

Gly Asp Ser Glu Ser Gly Glu Glu Glu Leu Gly Ala Glu Arg Arg
                 85                  90                  95

Gly Leu Lys Arg Ser Leu Ser Glu Met Glu Ile Gly Met Val Val Gly
                100                 105                 110

Gly Pro Glu Ala Ser Ala Ala Ala Thr Gly Gly Tyr Gly Pro Val Ser
            115                 120                 125

Gly Ala Val Ser Gly Ala Lys Pro Gly Lys Lys Thr Arg Gly Arg Val
130                 135                 140

Lys Ile Lys Met Glu Phe Ile Asp Asn Lys Leu Arg Arg Tyr Thr Thr
145                 150                 155                 160

Phe Ser Lys Arg Lys Thr Gly Ile Met Lys Lys Ala Tyr Glu Leu Ser
                165                 170                 175

Thr Leu Thr Gly Thr Gln Val Leu Leu Leu Val Ala Ser Glu Thr Gly
                180                 185                 190

His Val Tyr Thr Phe Ala Thr Arg Lys Leu Gln Pro Met Ile Thr Ser
            195                 200                 205

Glu Thr Gly Lys Ala Leu Ile Gln Thr Cys Leu Asn Ser Pro Asp Ser
210                 215                 220

Pro Pro Arg Ser Asp Pro Thr Thr Asp Gln Arg Met Ser Ala Thr Gly
225                 230                 235                 240

Phe Glu Glu Thr Asp Leu Thr Tyr Gln Val Ser Glu Ser Asp Ser Ser
                245                 250                 255

Gly Glu Thr Lys Asp Thr Leu Lys Pro Ala Phe Thr Val Thr Asn Leu
                260                 265                 270

Pro Gly Thr Thr Ser Thr Ile Gln Thr Ala Pro Ser Thr Ser Thr Thr
            275                 280                 285

Met Gln Val Ser Ser Gly Pro Ser Phe Pro Ile Thr Asn Tyr Leu Ala
290                 295                 300

Pro Val Ser Ala Ser Val Ser Pro Ser Ala Val Ser Ser Ala Asn Gly
305                 310                 315                 320

Thr Val Leu Lys Ser Thr Gly Ser Gly Pro Val Ser Ser Gly Gly Leu
                325                 330                 335

Met Gln Leu Pro Thr Ser Phe Thr Leu Met Pro Gly Gly Ala Val Ala
                340                 345                 350

Gln Gln Val Pro Val Gln Ala Ile Gln Val His Gln Ala Pro Gln Gln
            355                 360                 365

Ala Ser Pro Ser Arg Asp Ser Ser Thr Asp Leu Thr Gln Thr Ser Ser
370                 375                 380

Ser Gly Thr Val Thr Leu Pro Ala Thr Ile Met Thr Ser Ser Val Pro
385                 390                 395                 400

Thr Thr Val Gly Gly His Met Met Tyr Pro Ser Pro His Ala Val Met
                405                 410                 415

Tyr Ala Pro Thr Ser Gly Leu Gly Asp Gly Ser Leu Thr Val Leu Asn
                420                 425                 430

Ala Phe Ser Gln Ala Pro Ser Thr Met Gln Val Ser His Ser Gln Val
            435                 440                 445

Gln Glu Pro Gly Gly Val Pro Gln Val Phe Leu Thr Ala Ser Ser Gly
450                 455                 460

Thr Val Gln Ile Pro Val Ser Ala Val Gln Leu His Gln Met Ala Val
```

```
                465             470             475             480
Ile Gly Gln Gln Ala Gly Ser Ser Ser Asn Leu Thr Glu Leu Gln Val
                    485                 490                 495

Val Asn Leu Asp Thr Ala His Ser Thr Lys Ser Glu
                500                 505

<210> SEQ ID NO 48
<211> LENGTH: 1527
<212> TYPE: DNA
<213> ORGANISM: Homo sapiens

<400> SEQUENCE: 48
atgttaccga cccaagctgg ggccgcggcg gctctgggcc ggggctcggc cctgggggc       60 agcctgaacc ggaccccgac ggggcggccg ggcggcggcg gcgggacacg cggggctaac    120
gggggccggg tccccgggaa tggcgcgggg ctcgggcccg gccgcctgga gcggggaggct   180 gcggcagcgg cggcaaccac cccggcgccc accgcggggg ccctctacag cggcagcgag    240
ggcgactcgg agtcgggcga ggaggaggag ctgggcgccg agcggcgcgg cctgaagcgg    300
agcctgagcg agatggagat cggtatggtg gtcggtgggc ccgaggcgtc ggcagcggcc    360
accgggggct acgggccggt gagcggcgcg gtgagcgggg ccaagccggg taagaagacc    420
cggggccgcg tgaagatcaa gatggagttc atcgacaaca agctgcggcg ctacacgacc    480
ttcagcaaga ggaagacggg catcatgaag aaggcctatg agctgtccac gctgacaggg    540
acacaggtgc tgttgctggt ggccagtgag acaggccatg tgtataccttg tgccacccga   600 aaactgcagc ccatgatcac cagtgagacc ggcaaggcac tgattcagac ctgcctcaac    660
tcgccagact ctccaccccg ttcagacccc acaacagacc agagaatgag tgccactggc    720
tttgaagaga cagatctcac ctaccaggtg tcggagtctg acagcagtgg ggagaccaag    780
gacacactga gccggcgtt cacagtcacc aacctgccgg gtacaacctc caccatccaa    840
acagcaccta gcacctctac caccatgcaa gtcagcagcg gcccctcctt tcccatcacc    900
aactacctgg caccagtgtc tgctagtgtc agccccagtg ctgtcagcag tgccaatggg    960
actgtgctga gagtacagg cagcggccct gtctcctctg ggggccttat gcagctgcct   1020
accagcttca ccctcatgcc tggtggggca gtggcccagc aggtcccagt gcaggccatt   1080
caagtgcacc aggccccaca gcaagcgtct ccctcccgtg acagcagcac agacctcacg   1140
cagacctcct ccagcgggac agtgacgctg cccgccacca tcatgacgtc atccgtgccc   1200
acaactgtgg gtggccacat gatgtaccct agcccgcatg cggtgatgta tgcccccacc   1260
tcgggcctgg gtgatggcag cctcaccgtg ctgaatgcct tctcccaggc accatccacc   1320
atgcaggtgt cacacagcca ggtccaggag ccaggtggcg tcccccaggt gttcctgaca   1380
gcatcatctg ggacagtgca gatccctgtt tcagcagttc agctccacca gatggctgtg   1440
atagggcagc aggccgggag cagcagcaac ctcaccgagc tacaggtggt gaacctggac   1500
accgcccaca gcaccaagag tgaatga                                       1527
```